United States Patent
Vasserot et al.

(10) Patent No.: US 10,279,018 B2
(45) Date of Patent: May 7, 2019

(54) IMMUNOGENIC COMPOSITIONS FOR INDUCING AN IMMUNE RESPONSE FOR ELIMINATION OF SENESCENT CELLS

(71) Applicants: UNITY BIOTECHNOLOGY, INC., San Francisco, CA (US); KYTHERA BIOPHARMACEUTICALS, INC., Calabasas (CA); BUCK INSTITUTE FOR RESEARCH ON AGING, Novato, CA (US)

(72) Inventors: Alain Philippe Vasserot, Carlsbad, CA (US); Serge Lichtsteiner, Westlake Village, CA (US); Judith Campisi, Berkeley, CA (US)

(73) Assignees: UNITY BIOTECHNOLOGY, INC., Brisbane, CA (US); BUCK INSTITUTE FOR RESEARCH ON AGING, Novato, CA (US); KYTHERA BIOPHARMACEUTICALS, INC., Westlake Village, CA (US)

( * ) Notice: Subject to any disclaimer, the term of this patent is extended or adjusted under 35 U.S.C. 154(b) by 471 days.

(21) Appl. No.: 14/649,022

(22) PCT Filed: Dec. 3, 2013

(86) PCT No.: PCT/US2013/072938
§ 371 (c)(1),
(2) Date: Sep. 21, 2015

(87) PCT Pub. No.: WO2014/089124
PCT Pub. Date: Jun. 12, 2014

(65) Prior Publication Data
US 2016/0038576 A1 Feb. 11, 2016

Related U.S. Application Data

(60) Provisional application No. 61/747,653, filed on Dec. 31, 2012, provisional application No. 61/732,746, filed on Dec. 3, 2012.

(51) Int. Cl.
| | |
|---|---|
| *C07K 16/28* | (2006.01) |
| *A61K 39/00* | (2006.01) |
| *A61K 39/39* | (2006.01) |
| *C07K 14/47* | (2006.01) |
| *C07K 16/18* | (2006.01) |

(52) U.S. Cl.
CPC .......... *A61K 39/0005* (2013.01); *A61K 39/39* (2013.01); *C07K 14/47* (2013.01); *C07K 16/18* (2013.01); *C07K 16/28* (2013.01); *A61K 2039/70* (2013.01); *C07K 2317/56* (2013.01); *C07K 2317/64* (2013.01)

(58) Field of Classification Search
None
See application file for complete search history.

(56) References Cited

U.S. PATENT DOCUMENTS

| | | | |
|---|---|---|---|
| 7,851,626 B2 | 12/2010 | Ding et al. | |
| 9,114,101 B2* | 8/2015 | Kloor | A61K 39/0011 |
| 2005/0019865 A1 | 1/2005 | Kihm et al. | |
| 2005/0181076 A1 | 8/2005 | Ziegler | |
| 2006/0134709 A1* | 6/2006 | Stavenhagen | C07K 16/00 435/7.23 |
| 2006/0210591 A1* | 9/2006 | Doeberitz et al. | A61K 48/00 424/277.1 |
| 2008/0108062 A1 | 5/2008 | Sharpless et al. | |
| 2008/0221132 A1 | 9/2008 | Cai et al. | |
| 2008/0234362 A1 | 9/2008 | Chandler | |
| 2009/0220465 A1 | 9/2009 | Scadden et al. | |
| 2010/0016218 A1 | 1/2010 | Lichter et al. | |
| 2010/0260733 A1 | 10/2010 | Qi | |
| 2010/0310504 A1 | 12/2010 | Lowe et al. | |
| 2011/0212909 A1 | 9/2011 | Wen et al. | |
| 2012/0156134 A1 | 6/2012 | Squires | |
| 2012/0183534 A1 | 7/2012 | Gruber | |
| 2013/0287763 A1 | 10/2013 | Sathyanarayanan, Sr. et al. | |

(Continued)

FOREIGN PATENT DOCUMENTS

| | | |
|---|---|---|
| EP | 2141241 A1 | 1/2010 |
| WO | WO-2006018632 A2 | 2/2006 |

(Continued)

OTHER PUBLICATIONS

Naylor et al (Clinical Pharmacology & Therapeutics, e-pub Dec. 5, 2012, vol. 93, pp. 105-113) (Year: 2012).*
Makkouk and Weiner, Cancer Research, 2015, vol. 75, pp. 5-10 (Year: 2015).*
Curigliano et al (The Breast, 2011, vol. 53, pp. 571-574) (Year: 2011).*
Slingluff et al (The Cancer Journal, 2011, vol. 17, pp. 343-350) (Year: 2011).*
Adams. Healing and hurting: molecular mechanisms, functions, and pathologies of cellular senescence. Mol Cell. Oct. 9, 2009;36(1):2-14. doi: 10.1016/j.molcel.2009.09.021.

(Continued)

*Primary Examiner* — Karen A. Canella
(74) *Attorney, Agent, or Firm* — Michael Schiff; Wilson Sonsini Goodrich & Rosati

(57) ABSTRACT

Provided herein are immunogenic compositions (vaccines) and methods for immunizing a subject with the immunogenic compositions for inducing an adaptive immune response directed specifically against senescent cells for treatment and prophylaxis of age-related diseases and disorders, and other diseases and disorders associated with or exacerbated by the presence of senescent cells. The immunogenic compositions provided herein comprise at least one or more senescent cell-associated antigens, polynucleotides encoding senescent cell-associated antigens, and recombinant expression vectors comprising the polynucleotides for use in administering to a subject in need thereof.

14 Claims, No Drawings

Specification includes a Sequence Listing.

(56) References Cited

U.S. PATENT DOCUMENTS

| | | | |
|---|---|---|---|
| 2013/0288980 | A1 | 10/2013 | De Keizer et al. |
| 2013/0302283 | A1 | 11/2013 | Kihm |
| 2014/0017341 | A1 | 1/2014 | Gourlaouen |
| 2015/0064137 | A1 | 3/2015 | Lichtsteiner et al. |
| 2015/0151001 | A1 | 6/2015 | Squires |

FOREIGN PATENT DOCUMENTS

| | | | |
|---|---|---|---|
| WO | WO-2009085216 | A2 | 7/2009 |
| WO | WO-2009105234 | A2 | 8/2009 |
| WO | WO-2010148447 | A1 | 12/2010 |
| WO | WO-2013152038 | A1 | 10/2013 |
| WO | WO-2013158664 | A2 | 10/2013 |
| WO | WO-2013170174 | A1 | 11/2013 |
| WO | WO-2014160661 | A2 | 10/2014 |
| WO | WO-2014174511 | A1 | 10/2014 |
| WO | WO-2014186878 | A1 | 11/2014 |
| WO | WO-2015066442 | A1 | 5/2015 |

OTHER PUBLICATIONS

Baker, et al. Clearance of p16lnk4a-positive senescent cells delays ageing-associated disorders. Nature. Nov. 2, 2011;479(7372):232-6. doi: 10.1038/nature10600.

Bennett et al., "SP600125, An Anthrapyrazolone Inhibitor of Jun N-Terminal Kinase", PNAS, vol. 98, No. 24, 20, 2001, pp. 13681-13686.

Braun, et al. Cellular senescence limits regenerative capacity and allograft survival.J Am Soc Nephrol. Sep. 2012;23(9):1467-73. doi: 10.1681/ASN.2011100967. Epub Jul. 12, 2012.

Campisi, et al. Cellular senescence: a link between cancer and age-related degenerative disease? Semin Cancer Biol. Dec. 2011;21(6):354-9. doi: 10.1016/j.semcancer.2011.09.001. Epub Sep. 10, 2011.

Campisi et al., "Cellular senescence: when bad things happen to good cells," Nature Reviews Molecular Cell Biology 8:729-740, 2007.

Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.

Campisi, J. Senescent cells, tumor suppression, and organismal aging: good citizens, bad neighbors. Cell. Feb. 25, 2005;120(4):513-22.

Chang et al., "Effects of p21 Waf1/Cip1/Sdil on cellular gene expression: Implications for carcinogenesis, senescence, and age-related diseases," PNAS 97(8):4291-4296, 2000.

Chistiakov. How to fight with senescent cells? Geriatr Gerontol Int. Apr. 2011;11(2):233-5. doi: 10.1111/j.1447-0594.2010.00654.x.

Chung, et al. Molecular inflammation: underpinnings of aging and age-related diseases. Ageing Res Rev. Jan. 2009;8(1):18-30. doi: 10.1016/j.arr.2008.07.002. Epub Jul. 18, 2008.

Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.

Davalos, et al. p53-dependent release of Alarmin HMGB1 is a central mediator of senescent phenotypes. J Cell Biol. May 13, 2013;201(4):613-29. doi: 10.1083/jcb.201206006. Epub May 6, 2013.

Davalos, et al. Senescent cells as a source of inflammatory factors for tumor progression. Cancer Metastasis Rev. Jun. 2010;29(2):273-83. doi: 10.1007/s10555-010-9220-9.

"Deursen. Clearance of senescent cells and adult aging phenotypes. Pitts. Jun. 2014. 15 pages.".

"Deursen, et al. Senescent cells have some nerve! Mayo Clinic. NCI. Mar. 2015. Rochester, MN. 15 pages.".

"Deursen, et al. Senescent cells shorten health and life span. Mayo Clinic. Berlin. Feb. 2015. 30 pages.".

"Deursen, et al. Senescent in aging and age-related disease: from mechanism to therapy. Mayo Clinic. ICSA Conference. Jul. 2015. Santiago de Compostela. 40 pages.".

"Deursen. Senescent Cells as Drivers of Cancer & Aging. Mayo Clinic. NYU Dec. 2014. 55 pages.".

"Deursen. The role of p16+ (senescent) cells in aging. Erice. Jun. 2015. 17 pages.".

"Deursen. Understanding Senescence and Chromosomal Instability in Cancer and Aging. Mayo Clinic. Ohio State. Jan. 2015. 49 pages.".

Efeyan, et al. Induction of p53-dependent senescence by the MDM2 antagonist nutlin-3a in mouse cells of fibroblast origin. Cancer Res. Aug. 1, 2007;67(15):7350-7.

Freund, et al. Inflammatory networks during cellular senescence: causes and consequences. Trends Mol Med. May 2010;16(5):238-46. doi: 10.1016/j.molmed.2010.03.003. Epub May 3, 2010.

Freund, et al. Lamin B1 loss is a senescence-associated biomarker. Mol Biol Cell. Jun. 2012;23(11):2066-75. doi: 10.1091/mbc.E11-10-0884. Epub Apr. 11, 2012.

Gorenne, et al. Vascular smooth muscle cell senescence in atherosclerosis. Cardiovasc Res. Oct. 1, 2006;72(1):9-17. Epub Jun. 6, 2006.

International Preliminary Report in International Application No. PCT/US2012/043613, dated Jan. 9, 2014, 5 pages.

International search report and written opinion dated Apr. 22, 2014 for PCT Application No. US2013/072938.

International search report and written opinion dated May 6, 2015 for PCT/US2015/013376.

"International search report and written opinion dated Jun. 29, 2015 for PCT/US2015/013387.".

International search report and written opinion dated Aug. 13, 2013 for PCT/US2013/035023.

International Search Report and Written Opinion in International Application No. PCT/US2012/043613, dated Nov. 29, 2012, 9 pages.

International Search Report and Written Opinion received for PCT Patent Application No. PCT/US2013/035020, dated Jul. 22, 2013, 11 pages.

Invitation to pay additional fees dated Apr. 20, 2015 for PCT/US2015/013387.

Kassem, et al. Senescence-associated intrinsic mechanisms of osteoblast dysfunctions. Aging Cell. Apr. 2011;10(2):191-7. doi: 10.1111/j.1474-9726.2011.00669.x. Epub Feb. 18, 2011.

Kim, et al. SP600125, an inhibitor of Jnk pathway, reduces viability of relatively resistant cancer cells to doxorubicin. Biochem Biophys Res Commun. Sep. 25, 2009;387(3):450-5. doi: 10.1016/j.bbrc.2009.07.036. Epub Jul. 14, 2009.

Krtolica, et al. Senescent fibroblasts promote epithelial cell growth and tumorigenesis: a link between cancer and aging. Proc Natl Acad Sci U S A. Oct. 9, 2001;98(21):12072-7. Epub Oct. 2, 2001.

Kuilman et al., "The essence of senescence," Genes Develop., 2010, 24:2463-2479.

Laberge et al., "Glucocorticoids suppress selected components of the senescence-associated secretory phenotype," Aging Cell 11(4):569-578, 2012.

Le, et al. Ionizing radiation-induced long-term expression of senescence markers in mice is independent of p53 and immune status. Aging Cell. Jun. 2010;9(3):398-409. doi: 10.1111/j.1474-9726.2010.00567.x. Epub Mar. 13, 2010.

Lessene; et al., "Structure-guided design of a selective BCL-X(L) inhibitor.", Jun. 2013, 9(6), 390-7.

Martin et al., "The Role of Chondrocyte Senescence in the Pathogenesis of Osteoarthritis and in Limiting Cartilage Repair", J Bone Joint Surg Am, vol. 85, Suppl 2, Apr. 2003, pp. 106-110.

Minamino et al., Vascular Cell Senescence: Contribution to Atherosclerosis. Journal of the American Heart Association, Circ Res. Jan. 5, 2007;100(1):15-26.

Nelson, et al. Expression of p16INK4a as a biomarker of T-cell aging in HIV-infected patients prior to and during antiretroviral therapy. Aging Cell, Oct. 2012, vol. 11, pp. 916-918.

Office action dated Jan. 9, 2015 for U.S. Appl. No. 12/809,952.

Office action dated Apr. 7, 2015 for U.S. Appl. No. 14/125,841.

Office action dated May 30, 2014 for U.S. Appl. No. 12/809,952.

(56) References Cited

OTHER PUBLICATIONS

Office action dated Nov. 25, 2014 for U.S. Appl. No. 13/830,790.
Prieur, et al. Cellular senescence in vivo: a barrier to tumorigenesis. Curr Opin Cell Biol. Apr. 2008;20(2):150-5. doi: 10.1016/j.ceb.2008.01.007. Epub Mar. 18, 2008.
Roberts, et al. Senescence in human intervertebral discs. Eur Spine J. Aug. 2006;15 Suppl 3:S312-6. Epub Jun. 14, 2006.
Rodier, et al. Persistent DNA damage signalling triggers senescence-associated inflammatory cytokine secretion. Nat Cell Biol. Aug. 2009;11(8):973-9. doi: 10.1038/ncb1909. Epub 2009 Jul. 13, 2009.
Roninson, "Tumor Cell Senescence in Cancer Treatment," Cancer Research 63(11):2705-2715, 2003.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Sharpless et al., "Telomeres, stem cells, senescence, and cancer," Journal of Clinical Investigation 113(2):160-168, 2004.
Sis, et al. Accelerated expression of senescence associated cell cycle inhibitor p16INK4A in kidneys with glomerular disease. Kidney Int. Feb. 2007;71(3):218-26. Epub Dec. 20, 2006.
Stanley et al. Senescence and the Healing Rates of Venous Ulcers. J Vasc Surg. Jun. 2001;33(6):1206-11.
Tchkonia, et al. Fat tissue, aging, and cellular senescence. Aging Cell. Oct. 2010;9(5):667-84.
Tsuji, et al. Alveolar cell senescence exacerbates pulmonary inflammation in patients with chronic obstructive pulmonary disease. Respiration. 2010;80(1):59-70. doi: 10.1159/000268287. Epub Dec. 17, 2009.
Zhao; et al., "Small molecule inhibitors of MDM2-p53 and MDMX-p53 interactions as new cancer therapeutics. BioDiscovery, 8.", 2013, 8(4), 15 pages.
Nielsen, K., et al. *Homo sapiens* cyclin-dependent kinase inhibitor 2A (melanoma, p16, inhibits CDK4) NM_000077 (Accessed: Jan. 9, 2018).
No Author. Overview-of-signal-transduction pathways involved in apoptosis. Wikipedia accessed Jan. 11, 2018.
Reuschebach, M. et al. A Phase 1/2a Study to Test the Safety and Immunogenicity of a p16$^{INK4a}$ Peptide Vaccine in Patients with Advanced Human Papillomavirus-Associated Cancers. Cancer 1:122(9):1425-1433 (May 1, 2016).
Seelig, Hans Peter et al. Interferon-y-Inducible Protein p16. Arthritis & Rheumatism, 37(11): 1672-1683 (Nov. 1994).
U.S. Appl. No. 61/732,746 Provisional Application filed Dec. 3, 2012.

* cited by examiner

IMMUNOGENIC COMPOSITIONS FOR INDUCING AN IMMUNE RESPONSE FOR ELIMINATION OF SENESCENT CELLS

CROSS REFERENCE TO RELATED APPLICATION

This application is a U.S. national stage entry under 35 USC § 371 of PCT/US2013/072938, filed Dec. 3, 2013, which claims the benefit of U.S. Provisional Application No. 61/747,653, filed Dec. 31, 2012, and U.S. Provisional Application No. 61/732,746, filed Dec. 3, 2012, the contents of which are herein incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200201_412WO_SEQUENCE_LISTING.txt. The text file is 1 KB, was created on Dec. 3, 2013 and is being submitted electronically via EFS-Web.

BACKGROUND

Technical Field

The disclosure herein relates generally to immunogenic compositions (e.g., vaccines) and methods for using the immunogenic compositions for inducing an immune response directed specifically against senescent cells for treatment and prophylaxis of age-related diseases and disorders, and other diseases and disorders associated or exacerbated by the presence of senescent cells.

Description of the Related Art

Senescent cells accumulate in tissues and organs of individuals as they age and are found at sites of age-related pathologies. While senescent cells are believed important to inhibiting proliferation of dysfunctional or damaged cells and particularly to constraining development of malignancy (see, e.g., Campisi, Curr. Opin. Genet. Dev. 21:107-12 (2011); Campisi, Trends Cell Biol. 11:S27-31 (2001); Prieur et al., Curr. Opin. Cell Biol. 20:150-55 (2008)), the presence of senescent cells in an aging individual may contribute to aging and aging-related dysfunction (see, e.g., Campisi, Cell 120:513-22 (2005)). Given that senescent cells have been causally implicated in certain aspects of age-related decline in health and may contribute to certain diseases, and are also induced as a result of necessary life-preserving chemotherapeutic and radiation treatments, the presence of senescent cells may have deleterious effects to millions of patients worldwide (e.g., fatigue, weakness, loss of physical agility, decrease in cognitive function). Accordingly, treatments aimed at clearing aging-induced and therapy-induced senescent cells and improving age-sensitive traits have the potential to markedly improve the health, lifespan, and quality of life for patients exposed to senescence-inducing stimuli. The present disclosure addresses these needs and offers numerous related advantages.

BRIEF SUMMARY

Disclosed herein are immunogenic compositions and methods of using the compositions for inducing an immune response that is specific for senescent cells (i.e., specific for senescent cell associated antigens expressed by the senescent cells) and that comprises clearance (i.e., removal, elimination) of senescent cells from the subject receiving the immunogenic composition. The methods include active and passive immunization. Provided herein are the following embodiments.

In one embodiment, a method is provided for evoking an immune response specific for a senescent cell in a subject, wherein the immune response comprises clearance of the senescent cell by the immune system of the subject, wherein the method comprises administering to the subject an immunogenic composition comprising: (a) a pharmaceutically acceptable excipient, and (b) an immunogen. In particular embodiments, the immunogen is selected from (i) an isolated senescent cell-associated antigen or an antigenic fragment thereof, wherein the senescent cell-associated antigen is selected from (A) p16INK4a, (B) a senescent cell-associated antigen selected from Table 1, and (C) a senescent cell-associated antigen that is encoded by a nucleic acid sequence selected from Table 2 or Table 3, and wherein the antigenic fragment comprises at least 20 contiguous amino acids of the senescent cell-associated antigen; (ii) an isolated polynucleotide encoding at least two senescent cell-associated antigens of (i) or antigenic fragments thereof; (iii) at least two isolated polynucleotides, wherein a first isolated polynucleotide encodes a first senescent cell-associated antigen or an antigenic fragment thereof, and wherein the first senescent cell-associated antigen is selected from (A) p16INK4a, (B) a senescent cell-associated antigen selected from Table 1, and (C) a senescent cell-associated antigen that is encoded by a nucleic acid sequence selected from Table 2 or Table 3, and wherein the antigenic fragment comprises at least 20 contiguous amino acids of the first senescent cell-associated antigen, and a second polynucleotide encodes a second senescent cell-associated antigen, wherein the second senescent cell-associated antigen is selected from (A) p16INK4a, (B) a senescent cell-associated antigen selected from Table 1, and (C) a senescent cell-associated antigen that is encoded by a nucleic acid sequence selected from Table 2 or Table 3, and wherein the antigenic fragment comprises at least 20 contiguous amino acids of the second senescent cell-associated antigen; (iv) a recombinant expression vector that is a viral vector comprising a polynucleotide that encodes the senescent cell-associate antigen or antigenic fragment thereof of (i); (v) a senescent cell membrane preparation, a senescent cell organelle preparation, or an exosome; (vi) a fusion polypeptide comprising at least two senescent cell-associated antigens, wherein each of the at least two senescent cell-associated antigens are different and each is selected from (A) p16INK4a, (B) a senescent cell-associated antigen selected from Table 1, and (C) a senescent cell-associated antigen that is encoded by a nucleic acid sequence selected from Table 2 or Table 3; (vii) a fusion polypeptide comprising at least two antigenic fragments wherein each of the at least two antigenic fragments comprises at least 20 contiguous amino acids of a senescent cell-associated antigen selected from (A) p16INK4a, (B) a senescent cell-associated antigen selected from Table 1, and (C) a senescent cell-associated antigen that is encoded by a nucleic acid sequence selected from Table 2 or Table 3; (viii) a fusion polypeptide comprising at least one senescent cell-associated antigen of (i) or an antigenic fragment thereof and a co-stimulatory polypeptide; and (ix) a modified dendritic cell wherein a dendritic cell is isolated from the subject and is modified by (A) introducing a senescent cell-associated antigen, or an antigenic fragment that comprises at least 20 contiguous amino acids of the senescent cell-associated antigen, wherein the senescent cell-associated antigen is selected from (A) p16INK4a, (B) a senescent cell-associated antigen selected from Table 1, and (C) a senescent cell-associated antigen that is encoded by a nucleic acid sequence selected from Table 2 or Table 3, or (B) introducing a polynucleotide encoding the senescent cell-associated antigen, or an antigenic fragment of (A), into the dendritic cell ex vivo to provide a modified dendritic cell, and wherein the modified dendritic cell is administered to the subject. In certain particular embodiments for use in the methods described above and herein, the senescent cell-associated antigen that is encoded by a nucleic acid sequence selected from Table 2 is any one of ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, or ZNF419 (see Table 2). In other more specific embodiments, the senescent cell-associated antigen that is encoded by a nucleic acid sequence selected from Table 2 is any one of NEU1, SELO, SERP1, SERPINE1, or SNX3. In other specific embodiments, the senescent cell-associated antigen is p16INK4a. In other particular embodiments, the at least first and the at least second senescent cell-associated antigen encoded by a nucleic acid sequence selected from Table 2 are different and selected from any one of ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419 (see Table 2). In other more specific embodiments, the at least first and the at least second senescent cell-associated antigens encoded by a nucleic acid sequence selected from Table 2 is selected from any one of NEU1, SELO, SERP1, SERPINE1, and SNX3. In still other particular embodiments, the at least first senescent cell-associated antigen or the at least second senescent cell-associated antigen is p16INK4a.

In certain other embodiments of the method described above and herein, the immunogen comprises at least two isolated senescent cell-associated antigens or antigenic fragments thereof, wherein (a) a first isolated senescent cell-associated antigen, or an antigenic fragment thereof that comprises at least 20 contiguous amino acids of the first senescent cell-associated antigen, and (b) a second isolated senescent cell-associated antigen or an antigenic fragment thereof that comprises at least 20 contiguous amino acids of the second senescent cell-associated antigen, are different and each independently is selected from (A) p16INK4a, (B) a senescent cell-associated antigen selected from Table 1, and (C) a senescent cell-associated antigen that is encoded by a nucleic acid sequence selected from Table 2 or Table 3. In certain particular embodiments, the at least first and the at least second isolated senescent cell-associated antigen are different and encoded by a nucleic acid sequence selected from Table 2, wherein the at least first and the at least second isolated senescent cell-associated antigens are selected from ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419 (see Table 2). In other more specific embodiments, the at least first and the at least second isolated senescent cell-associated antigens encoded by a nucleic acid sequence from Table 2 are selected from NEU1, SELO, SERP1, SERPINE1, and SNX3. In still other particular embodiments, the at least first senescent cell-associated antigen or the at least second senescent cell-associated antigen is p16INK4a.

In a more particular embodiment, the senescent cell-associated antigen is present on the cell surface of the senescent cell. In still another embodiment, when the immunogen comprises a first and the second senescent cell-associated antigen, the first and the second senescent cell-associated antigen are each present on the cell surface of the senescent cell.

In certain other embodiments, the immunogenic composition comprises a recombinant expression vector that comprises the polynucleotide of (b)(ii) operatively linked to at least one regulatory expression sequence. In a more particular embodiment, the recombinant expression vector is a viral vector. In still another specific embodiment, the viral vector is selected from an adenovirus vector, lentivirus vector, a herpes virus vector, adenovirus-associated vector, or a poxvirus vector. In another particular embodiment, the adenoviral vector is a replication-defective adenovirus. In certain specific embodiment, the replication-defective adenovirus is a recombinant human adenovirus having a serotype selected from Ad11, Ad24, Ad26, Ad34, Ad35, Ad48, Ad49, and Ad50.

In yet another embodiment of the method described above and herein, the immunogen comprises at least one polynucleotide that encodes (a) a first senescent cell-associated antigen, or an antigenic fragment thereof that comprises at least 20 contiguous amino acids of the first senescent cell-associated antigen, and (b) a second senescent cell-associated antigen or an antigenic fragment thereof that comprises at least 20 contiguous amino acids of the second senescent cell-associated antigen, wherein the first and second senescent cell-associated antigens are different and each independently is selected from (A) p16INK4a, (B) a senescent cell-associated antigen selected from Table 1, and (C) a senescent cell-associated antigen that is encoded by a nucleic acid sequence selected from Table 2 or Table 3. In certain particular embodiments, the at least first and the at least second isolated senescent cell-associated antigen are encoded by a nucleic acid sequence selected from Table 2, wherein the at least first and the at least second isolated senescent cell-associated antigens are selected from ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419 (see Table 2). In other more specific embodiments, the at least first and the at least second isolated senescent cell-associated antigens encoded by a nucleic acid sequence from Table 2 are selected independently from NEU1, SELO, SERP1, SERPINE1, and SNX3. In still other particular embodiments, the at least first senescent cell-associated antigen or the at least second senescent cell-associated antigen is p16INK4a. In still another embodiment, the immunogenic composition comprises a recombinant expression vector that comprises the at least one polynucleotide operatively linked to at least one regulatory expression sequence. In certain embodiments, the recombinant expression vector is a viral vector. In still another specific embodiment, the viral vector is selected from an adenovirus vector, lentivirus vector, a herpes virus vector, adenovirus-associated vector, or a poxvirus vector. In another particular embodiment, the adenoviral vector is a replication-defective adenovirus. In certain specific embodiment, the replication-defective adenovirus is a recombinant human adenovirus having a serotype selected from Ad11, Ad24, Ad26, Ad34, Ad35, Ad48, Ad49, and Ad50.

In yet another embodiment of the method described above and herein, the immunogen comprises at least two polynucleotides wherein a first polynucleotide encodes the first senescent cell-associated antigen, or an antigenic fragment thereof, and a second polynucleotide encodes the second senescent cell-associated antigen, or an antigenic fragment thereof. In a specific embodiment, the immunogenic composition comprises (a) a recombinant expression vector that comprising the at least two polynucleotides wherein each of the at least two polynucleotides is operatively linked to at least one regulatory expression sequence; or (b) a first recombinant expression vector that comprises the first polynucleotide operatively linked to at least one regulatory expression sequence and a second recombinant expression vector that comprises the first polynucleotide operatively linked to at least one regulatory expression sequence. In certain embodiments, the recombinant expression vector is a viral vector. In still more particular embodiments, the recombinant expression vector of (a) the first recombinant expression vector of (b) and the second recombinant expression vector of (b) are each a viral vector. In still another specific embodiment, the viral vector is selected from an adenovirus vector, lentivirus vector, a herpes virus vector, adenovirus-associated vector, or a poxvirus vector. In another particular embodiment, the adenoviral vector is a replication-defective adenovirus. In certain specific embodiment, the replication-defective adenovirus is a recombinant human adenovirus having a serotype selected from Ad11, Ad24, Ad26, Ad34, Ad35, Ad48, Ad49, and Ad50. In one particular embodiment, the first recombinant expression vector and the second recombinant expression vector are each the same or different recombinant human adenoviral vector having a serotype independently selected from Ad11, Ad24, Ad26, Ad34, Ad35, Ad48, Ad49, and Ad50.

In yet another embodiment of the method described above and herein, when the immunogen comprises a dendritic cell, the dendritic cell is modified by introducing a recombinant expression vector comprising the polynucleotide. In certain embodiments, the recombinant expression vector is a viral vector selected from an adenovirus vector, lentivirus vector, a herpes virus vector, adenovirus-associated vector, or a poxvirus vector. In another particular embodiment, the adenoviral vector is a replication-defective adenovirus. In certain specific embodiment, the replication-defective adenovirus is a recombinant human adenovirus having a serotype selected from Ad11, Ad24, Ad26, Ad34, Ad35, Ad48, Ad49, and Ad50.

In particular embodiments, with respect to the methods described above and herein, the immunogenic composition further comprises a pharmaceutically acceptable adjuvant. In other particular embodiments, with respect to the methods described above and herein, the immunogenic composition further comprises (a) a co-stimulatory polypeptide that enhances the adaptive immune response to the immunogen; (b) a polynucleotide encoding the co-stimulatory polypeptide; or (c) a recombinant expression vector that comprises the polynucleotide sequence, which is operatively linked to at least one regulatory expression sequence. In still other specific embodiments, the subject has or is at risk of developing a disease or disorder treatable by clearing senescent cells from a tissue of the subject. In still more specific embodiments, of the methods described above and herein, the disease or disorder is an age-related disease or disorder.

Also provided herein is an immunogenic composition that comprises a pharmaceutically acceptable excipient and at least one immunogenic preparation selected from: (a) an immunogenic preparation comprising a first isolated senescent cell-associated antigen, or an antigenic fragment thereof that comprises at least 20 contiguous amino acids of the first senescent cell-associated antigen, and a second isolated senescent cell-associated antigen or an antigenic fragment thereof that comprises at least 20 contiguous amino acids of the second senescent cell-associated antigen, wherein the first and second senescent cell-associated antigens are different and selected independently from p16INK4a, a senescent cell-associated antigen selected from Table 1, and a senescent cell-associated antigen that is encoded by a nucleic acid sequence selected from Table 2 or Table 3; (b) an immunogenic preparation comprising at least one polynucleotide that encodes the first senescent cell-associated antigen, or an antigenic fragment thereof, and the second senescent cell-associated antigen or an antigenic fragment thereof; (c) an immunogenic preparation comprising at least two polynucleotides wherein a first polynucleotide encodes the first senescent cell-associated antigen, or an antigenic fragment thereof, and a second polynucleotide encodes the second senescent cell-associated antigen, or an antigenic fragment thereof; (d) an immunogenic preparation comprising a senescent cell membrane preparation, a senescent cell organelle preparation, or an exosome; (e) an immunogenic preparation comprising a fusion polypeptide comprising at least two senescent cell-associated antigens, wherein each of the at least two senescent cell-associated antigens are different and selected independently from p16INK4a, a senescent cell-associated antigen selected from Table 1, and a senescent cell-associated antigen that is encoded by a nucleic acid sequence selected from Table 2 or Table 3; (f) an immunogenic preparation comprising a fusion polypeptide comprising at least two antigenic fragments wherein each of the at least two antigenic fragments comprises at least 20 contiguous amino acids of a senescent cell-associated antigen selected from p16INK4a, a senescent cell-associated antigen selected from Table 1, and a senescent cell-associated antigen that is encoded by a nucleic acid sequence selected from Table 2 or Table 3; and (g) an immunogenic preparation comprising a modified dendritic cell wherein a dendritic cell is isolated from the subject and is modified by (i) introducing a senescent cell-associated antigen, or an antigenic fragment that comprises at least 20 contiguous amino acids of the senescent cell-associated antigen, wherein the senescent cell-associated antigen is selected from (A) p16INK4a, (B) a senescent cell-associated antigen selected from Table 1, and (C) a senescent cell-associated antigen that is encoded by a nucleic acid sequence selected from Table 2 or Table 3, or (ii) introducing a polynucleotide encoding the senescent cell-associated antigen, or an antigenic fragment of (i), into the dendritic cell ex vivo to provide a modified dendritic cell, and wherein the modified dendritic cell is administered to the subject. In certain particular embodiments, the senescent cell-associated antigen that is encoded by a nucleic acid sequence selected from Table 2 is any one of ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, or ZNF419 (see Table 2). In other more specific embodiments, the senescent cell-associated antigen that is encoded by a nucleic acid sequence selected from Table 2 is any one of NEU1, SELO, SERP1, SERPINE1, or SNX3. In other specific embodiments, the senescent cell-associated antigen is p16INK4a. In other certain particular embodiments, the at least first and the at least second senescent cell-associated antigen encoded by a nucleic acid sequence selected from Table 2 are different and selected from any one of ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419 (see Table 2). In other more specific embodiments, the at least first and the at least second senescent cell-associated antigens encoded by a nucleic acid sequence selected from Table 2 is selected from any one of NEU1, SELO, SERP1, SERPINE1, and SNX3. In still other particular embodiments, the at least first senescent cell-associated antigen or the at least second senescent cell-associated antigen is p16INK4a.

In particular embodiments, with respect to the immunogenic composition described above and herein, the senescent cell-associated antigen is present on the cell surface of the senescent cell. In another particular embodiment, the first and the second senescent cell-associated antigen are each present on the cell surface of the senescent cell. In yet another specific embodiment, (i) a recombinant expression vector comprises the at least one polynucleotide of (b) operatively linked to at least one regulatory expression sequence; or (ii) a recombinant expression vector comprises the at least two polynucleotides of (c), wherein each polynucleotide is operatively linked to at least one regulatory expression sequence; or (iii) the dendritic cell is modified by introducing a recombinant expression vector comprising the polynucleotide; or (iv) a first recombinant expression vector comprises the first polynucleotide of (c) and a second recombinant expression vector comprises the second polynucleotide of (c). In particular embodiments, the recombinant expression vector of (i), (ii), and (iii), and the first and second recombination vectors of (iv) are each a viral vector. In certain embodiments, the recombinant expression vector is a viral vector selected from an adenovirus vector, lentivirus vector, a herpes virus vector, adenovirus-associated vector, or a poxvirus vector. In another particular embodiment, the adenoviral vector is a replication-defective adenovirus. In certain specific embodiment, the replication-defective adenovirus is a recombinant human adenovirus having a serotype selected from Ad11, Ad24, Ad26, Ad34, Ad35, Ad48, Ad49, and Ad50.

In certain particular embodiments described above and herein, the immunogenic composition further comprises (a) a co-stimulatory polypeptide that enhances the adaptive immune response to the immunogen; (b) a polynucleotide encoding the co-stimulatory polypeptide; or (c) a recombinant expression vector that comprises the polynucleotide sequence encoding the co-stimulatory polypeptide, which is operatively linked to at least one regulatory expression sequence. In still other embodiments, the immunogenic compositions described above and herein further comprise a pharmaceutically acceptable adjuvant.

In yet another embodiment, a recombinant antibody is provided that comprises (a) at least one immunoglobulin variable region domain that specifically binds to a senescent cell-associated antigen selected from (A) p16INK4a, (B) a senescent cell-associated antigen selected from Table 1, and (C) a senescent cell-associated antigen that is encoded by a nucleic acid sequence selected from Table 2 or Table 3; and (b) a modified human Fc region that exhibits enhanced affinity for an Fcγ receptor. In a particular embodiment, the recombinant antibody further comprises a second immunoglobulin variable region (Fv), wherein the second variable region specifically binds to the same or a different senescent cell-associated antigen selected from p16INK4a, a senescent cell-associated antigen selected from Table 1, and a senescent cell-associated antigen that is encoded by a nucleic acid sequence selected from Table 2 or Table 3. Also provided is an immunogenic composition that comprises the recombinant antibody described above and herein and a pharmaceutically acceptable carrier. In still another embodiment, a method is provided for facilitating clearance of a senescent cell from a subject, comprising administering to the subject the immunogenic composition comprising the recombinant antibody described above and herein. In certain particular embodiments, the senescent cell-associated antigen that is encoded by a nucleic acid sequence selected from Table 2 is any one of ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, or ZNF419 (see Table 2); In other more specific embodiments, the senescent cell-associated antigen that is encoded by a nucleic acid sequence selected from Table 2 is any one of NEU1, SELO, SERP1, SERPINE1, or SNX3. In still other specific embodiments, the senescent cell-associated antigen is p16INK4a.

In one embodiment, a process is provided for formulating the immunogenic composition described above and herein, comprising (a) producing the immunogenic preparation that comprises the first isolated senescent cell-associated antigen, or an antigenic fragment thereof, and the second isolated senescent cell-associated antigen or an antigenic fragment thereof, each as described above and herein, by (i) culturing a first host cell into which a recombinant expression vector comprising at least one regulatory expression sequence operatively linked to a nucleotide sequence that encodes the first senescent cell-associated antigen, or an antigenic fragment thereof in a medium and for a time sufficient to produce the first senescent cell-associated antigen; and (ii) culturing a second host cell into which a recombinant expression vector comprising at least one regulatory expression sequence operatively linked to a nucleotide sequence that encodes the second senescent cell-associated antigen, or an antigenic fragment thereof in a medium and for a time sufficient to produce the second senescent cell-associated antigen; (iii) isolating the first senescent cell-associated antigen from the first host cell culture, and isolating the second senescent cell-associated antigen from the second host cell culture; and (c) formulating the first and the second cell-associated antigens with a pharmaceutically acceptable excipient. In a particular embodiment, the medium is a serum-free medium.

Uses of the immunogenic compositions described above are also provided for evoking an immune response specific for a senescent cell in a subject, wherein the immune response comprises clearance of the senescent cell by the immune system of the subject, and for the manufacture of a medicament for evoking an immune response specific for a senescent cell in a subject, wherein the immune response comprises clearance of the senescent cell by the immune system.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

As used herein, the term "isolated" means that a material (such as a senescent cell-associated antigen or a polynucleotide encoding same) is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. An "isolated" nucleic acid could be part of a vector and/or such nucleic acid or polypeptide could be part of a composition, and still be isolated in that the vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons). Amino acids may be referred to herein according to the single letter and three letter codes, which are understood according to common textbook knowledge in the art, and therefore with which a person skilled in the art is familiar. The term "fusion polypeptide" used herein may also be used interchangeably with "fusion protein," and unless specifically indicated otherwise, the two terms are not meant to indicate molecules that have distinguishable properties or characteristics.

DETAILED DESCRIPTION

Provided herein are immunogenic compositions (e.g., vaccines) and methods for using the immunogenic compositions for inducing an immune response directed specifically against senescent cells for treatment and prophylaxis of age-related diseases and disorders, and other diseases and disorders associated or exacerbated by the presence of senescent cells. The immune response evoked by the immunogenic compositions described herein is specific for one or more senescent cell-associated antigens, particularly including one or more senescent cell-associated antigens (SCAAg) present on the cell surface of the senescent cell (SC). This specific immune response that comprises clearance (i.e., removal, elimination, destruction) of senescent cells may include a humoral or cellular immune response or both a humoral and cellular immune response. The specific immune response may also mediate antibody-dependent cell cytotoxicity (ADCC) or complement dependent cytotoxicity (CDC) or both. The one or more senescent cell-associated antigens that induce a specific immune response may be presented to a subject by administering one or more different immunogenic compositions as described in greater detail herein.

A subject in need of immunization with any one of the immunogenic compositions described herein, in certain embodiments, exhibits features of an age-related phenotype, age-related disorder, or age-sensitive trait. In certain embodiments, the age-related phenotype, age-related disorder, or age-sensitive trait may result from contact with a senescence-inducing stimulus or may result from factors that are presently considered part of the normal aging process. In other certain embodiments, the subject has been exposed to at least one senescence-inducing stimulus, which may include, for example, one or more of a chemical stimulus, an environmental stimulus, a genetic modification, a diet modification, or a combination thereof. In certain specific embodiments, the senescence-inducing stimulus comprises irradiation treatment or treatment with one or more chemotherapeutic agents. In other embodiments, the senescence-inducing stimulus is cigarette smoking or other exposure to tobacco (e.g., secondary exposure to cigarette smoke; smokeless tobacco), high fat or high sugar diet, or other environmental insult.

Immunogenic Compositions

As described in detail herein, methods are provided for evoking (i.e., inducing, stimulating, enhancing, boosting) an immune response specific for a senescent cell and that comprises clearance of the senescent cell by the immune system in a subject by administering to the subject (i.e., immunizing) one or more of the immunogenic compositions described herein. An immunogenic composition may comprise any one of the senescent cell associated antigens described herein, including but not limited to, a polypeptide or protein, or immunogenic fragment thereof; glycoprotein or immunogenic fragment thereof; a nucleic acid encoding the polypeptide, protein, or glycoprotein, or immunogenic fragment thereof; a glycolipid; a senescent cell associated carbohydrate or carbohydrate comprising molecule; and a lipid molecule. An immunogenic composition comprises one or more pharmaceutically acceptable excipients and at least one (i.e., one or more) immunogen which is a senescent cell-associated antigen, or which may be an antigenic fragment of a senescent cell-associated antigen. In a particular embodiment, two or more isolated senescent cell-associated antigens (or antigenic fragment(s) thereof) are included in an immunogenic composition, and in an even more particular embodiment, a fusion polypeptide is provided that comprises the two or more senescent cell-associated antigens (or antigenic fragment of any one or more of the two or more senescent cell-associated antigens). In another embodiment, the fusion polypeptide includes at least one or at least two senescent cell-associated antigens and a co-stimulatory polypeptide (such as by way of non-limiting example, B-7.1, ICAM-1, LFA-3, GM-CSF). In other certain embodiments, the immunogenic composition comprises a polynucleotide that encodes at least one or at least two senescent cell-associated antigens or encodes a fusion polypeptide comprising same; a recombinant expression vector comprising the polynucleotide; or an immune cell or other cell into which a senescent cell-associated antigen or a polynucleotide encoding the senescent cell-associated antigen has been introduced. Also provided herein, are immunogenic compositions that comprise a recombinant expression vector as an immunogen. In certain embodiments, the recombinant expression vector is a viral vector and comprises the polynucleotide that encodes a senescent cell associated antigen or antigenic fragment thereof. In other particular embodiments, the immunogen is a senescent cell membrane preparation, a senescent cell organelle preparation, or an exosome of a cell. Each of these immunogens and immunogenic compositions is described in greater detail herein.

For ease of discussion when describing a composition or immunogen comprising two or more senescent cell-associated antigens, for example, one of the two or more antigens may be called a first senescent cell-associated antigen and another of the two or more antigens may be called a second senescent cell-associated antigen, and another different antigen may be called a third senescent cell-associated antigen, etc. Such description may also be used in describing two or more polynucleotides that may be used as an immunogen.

As described in greater detail herein, immunogenic compositions may further comprise components that enhance an immune response to the one or more SCAAgs. For example, immunogenic compositions may further comprise a pharmaceutically acceptable adjuvant. In other embodiments, an immunogenic composition may also comprise a helper antigen or carrier protein.

Senescent Cell Associated Antigens

Cellular senescence is a stable and essentially permanent arrest of cell proliferation, which is accompanied by extensive changes in gene expression. Many types of cells, both normal cells and tumor cells, undergo senescence in response to stress. As described in the art, the phenotype of a senescence cell, such as the phenotype referred to as senescence associated secretory phenotype (SASP), is typified by secretion of numerous cytokines (e.g., inflammatory cytokines), growth factors, extracellular matrix components (ECM) and ECM-degrading enzymes, and proteases, for example. While proliferative arrest poses a formidable barrier to tumor progression (see, e.g., Campisi, *Curr. Opin. Genet. Dev.* 21:107-12 (2011); Campisi, *Trends Cell Biol.* 11:S27-31 (2001); Prieur et al., *Curr. Opin. Cell Biol.* 20:150-55 (2008)), and molecules secreted by senescent cells can stimulate tissue repair (see, e.g., Adams, Molec. *Cell* 36:2-14 (2009); Rodier et al., *J. Cell Biol.* 192:547-56 (2011)), senescent cells also secrete molecules that can cause inflammation (see, e.g., Freund et al., *Trends Mol. Med.* 16:238-46 (2010); Davalos et al., *Cancer Metastasis Rev.* 29:273-83 (2010)). Low-level, chronic inflammation is a hallmark of aging tissues, and inflammation is a major cause of, or contributor to, virtually every major age-related pathology, including cancer (Ferrucci et al., 2004, *Aging Clin. Exp. Res.* 16:240-243; Franceschi et al., 2007, *Mech. Ageing Dev.* 128:192-105; Chung et al., 2009, *Ageing Res. Rev.* 8:18-30; Davalos et al., 2010, *Cancer Metastasis Rev.* 29:273-283; Freund et al., 2010, *Trends Molec. Med.* 16:238-248). Thus, senescent cells, which increase with age and at sites of age-related pathology, might stimulate local chronic inflammation and tissue remodeling, thereby fueling both the degenerative diseases of aging as well as age-related cancer.

A senescent cell may exhibit any one or more of the following characteristics. (1) Senescence growth arrest is essentially permanent and cannot be reversed by known physiological stimuli. (2) Senescent cells increase in size, sometimes enlarging more than twofold relative to the size of nonsenescent counterparts. (3) Senescent cells express a senescence-associated β-galactosidase (SA-(β-gal), which partly reflects the increase in lysosomal mass. (4) Most senescent cells express p16INK4a, which is not commonly expressed by quiescent or terminally differentiated cells. (5) Cells that senesce with persistent DDR signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules associated with senescence, which in certain instances may be observed in the presence of persistent DDR signaling, which in certain instances may be dependent on persistent DDR signaling for their expression. (7) The nuclei of senescent cells lose structural proteins such as Lamin B1 or chromatin-associated proteins such as histones and HMGB1. See, e.g., Freund et al., *Mol. Biol. Cell* 23:2066-75 (2012); Davalos et al., *J. Cell Biol.* 201:613-29 (2013); Ivanov et al., *J. Cell Biol. DOI:* 10.1083/jcb.201212110, page 1-15; published online Jul. 1, 2013; Funayama et al., *J. Cell Biol.* 175:869-80 (2006)).

The presence of senescent cells can also be determined by detection of senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities. Without wishing to be bound by theory, the negative effects of senescent cells are believed to be the result of, at least in part, the secretion of pro-inflammatory cytokines, chemokines, growth factors, and proteases that comprise the SASP of a senescent cell (see, e.g., Coppe et al., *PLoS Biol.* 6:2853-68 (2008)). Senescent cell-associated molecules that comprise the SASP can disrupt normal tissue structure and function and stimulate malignant phenotypes in pre-malignant or non-aggressive cancer cells (see, e.g., Coppe et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005). ECM associated factors include inflammatory proteins and mediators of ECM remodeling and which are strongly induced in senescent cells (see, e.g., Kuilman et al., *Nature Reviews* 9:81-94 (2009)). Other senescent cell-associated molecules include extracellular polypeptides (proteins) described collectively as the DNA damage secretory program (DDSP) (see, e.g., Sun et al., *Nature Medicine published online* 5 Aug. 2012; doi:10.1038/nm.2890).

Senescent cell-associated antigens include molecules that are overexpressed in senescent cells compared to their quiescent or non-senescent counterparts. Certain senescent cell-associated antigens are tissue specific while others are ubiquitously overexpressed in senescent cells. In particular embodiments of the immunogenic compositions described herein, a senescent cell-associated antigen is an antigen present on the cell surface of a senescent cell (e.g., receptor proteins, channel forming proteins, proteins that facilitate diffusion or active transport of molecules and ion across the membrane, cell recognition proteins, and enzymes). These antigens may be present on the cell surface of a cell exclusively or at a greater level on senescent cells compared with non-senescent cells and are therefore useful as immunogens for evoking a specific immune response. Examples of senescent cell-associated antigens include polypeptides and proteins (including glycoproteins), lipids, glycolipids, and carbohydrate molecules that contribute to or are markers of a senescence cell.

Factors considered when selecting a senescent cell-associated antigen include, for example, expression profile, T-cell receptor threading and profiling, pre-existing tolerance, commonality between subjects and cell types as well as the potential to elicit both T-cell and B-cell immunity. Senescent cell-associated antigens can be identified by differential gene expression analysis using, for instance, gene chip profiling to characterize gene products that are either uniquely expressed or overexpressed in SC. The gene products identified from expression profiling are then matched to proteins known to be part of the surfaceome (see, e.g., Bavik et al., *Cancer Res.* January 15; 66:794-802 (2006)) to generate a subset of surface proteins specifically expressed or overexpressed on the membrane of the senescent cell. Similarly, other molecules that are specific to senescent cells can be used as antigens, such as carbohydrates, glycoproteins, lipids and gangliosides, or proteins with senescence-specific posttranslational modifications. Such molecules can be identified, for instance, by mass spectrometry analysis of fractionated lysates from senescent vs. normal cells.

In one embodiment, an immunogenic composition comprises at least 1 or at least 2, or more isolated senescent cell-associated antigens. In other embodiments an immunogenic composition comprises at least 3, 4, 5, 6, or more senescent cell-associated antigens. Exemplary senescent cell-associated antigens useful as immunogens in the immunogenic compositions described herein include any one or more of the antigens provided in Table 1 (see, e.g., International Patent Application Publication No. WO 2009/085216 (Table 1), which is incorporated herein by reference in its entirety). Other exemplary senescent cell-associated antigens useful as immunogens in the immunogenic compositions described herein include any one or more of the antigens encoded by a polynucleotide that comprises any one of the polynucleotide sequences provided in Table 2 (see also Table 2A that lists the GenBank sequences of Table 2). Non-limiting examples of SCAAgs encoded by a polynucleotide comprising a nucleotide sequence in Table 2 include ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419 (see for example Table 2). Other examples of senescent cell-associated antigens are named in Table 3 and are encoded by the polynucleotides provided in Table 3 (see also, e.g., Sun et al., *Nature Medicine published online* 5 Aug. 2012; doi: 10.1038/nm.2890.)

In a particular embodiment, an immunogenic composition comprises p16INK4a polypeptide, or an antigenic fragment thereof, for use in immunizing a subject. Most senescent cells express the tumor suppressor protein p16INK4a on the cell surface, independent of cell type and senescence inducer (see, e.g., Ohtani et al., *J. Med. Invest.* 51:146-53 (2004); Campisi et al., *Nat. Rev. Med. Cell Biol.* 8:729-40 (2007)). Expression of p16INK4a expression is typically undetectable until adulthood and the level of expression increases with age (see, e.g., Zindy et al., *Oncogene* 15:203-11 (1997)). Moreover, p16INK4a null mice develop and mature normally although they die of cancer in early middle age (see, e.g., Sharpless et al., *Nature* 413:86-91 (2001)). Without wishing to be bound by theory, p16INK4a peptides may be displayed on the surface of senescent cells in complexes with MHC (major histocompatibility) class 1 molecules.

Evoking an immune response specific for senescent cells that express a SCAAg, such as p16INK4a, wherein the immune response comprises clearance of senescent cells can provide therapeutic benefit. Results from transgenic animal model studies demonstrated that clearance of senescent cells that express p16INK4a delayed acquisition and/or progression of age related diseases (see, e.g., Baker et al., *Nature*, 479:232-36 (2011); Int'l Patent Application Publication No. WO/2012/177927). Metastasis of tumor cells was significantly inhibited in animals when senescent cells expressing p16INK4a were killed (see, e.g., Int'l Patent Application Publication No. WO 2013/090645).

Immunogenic compositions comprising a p16INK4a polypeptide, or an antigenic fragment thereof, may be prepared using p16INK4a polypeptide derived from a mammal, including but not limited to mouse, rat, or human. Polypeptide sequences for p16INK4a polypeptides from different species are available in public databases, such as GenBank. Amino acid sequences for murine p16INK4a polypeptide are available, for example, at GenBank Nos. AAK83159.1; 158352; and AAA85453.1. Amino acid sequences for human p16INK4a polypeptide are available, for example, at GenBank Nos. P42771.2; NP_000068.1; NP_001182061.1 (see also, e.g., ABC47036.1). Amino acid sequences for rat p16INK4a polypeptide are available, for example, at GenBank Nos. Q9R0Z3.1; NP_113738.1; and AAL76339.1.

An immunogen used in the immunogenic compositions described herein may comprise at least one, or at least two, or at least 3, 4, 5, 6, 7, 8 or more antigenic fragments of a senescent cell-associated antigen. Antigenic fragments may also be referred to herein as immunogenic fragments or antigenic (or immunogenic) peptides. An antigenic fragment of a senescent cell-associated antigen that may be used in the immunogenic compositions described herein comprises an immunogenic portion of a full-length senescent cell-associated antigen, Such antigenic fragments may comprise at least 5, 10, 20, 25, 30, 35, 40, 45, 50, 55, or 60 or more contiguous amino acids (or any number of contiguous amino acids between 5-60, including 5-10, 10-15, 15-20, 20-25, 25-30, 30-35, 35-40, 40-45, 45-50, 40-55, or 55-60, or more than 60 contiguous amino acids) of a senescent cell-associated polypeptide. In a more particular embodiment, an immunogen used in the immunogenic compositions described herein comprises at least 20 contiguous amino acids. An antigenic fragment of a mature or full-length senescent cell-associated antigen has one or more epitopes that induce a specific immune response, which includes production of antibodies that specifically bind to the antigenic peptide and to the immunogenic portion within the mature and full-length polypeptide from which the antigenic peptide is derived, and to a senescent cell that expresses the polypeptide.

The immunogenic compositions contemplated herein also include those with a mixture of full-length senescent cell-associated antigens (with a signal peptide sequence or without all or a portion of a signal peptide sequence) and antigenic fragments of the same or different senescent cell-associated antigens. A polypeptide from which a signal peptide sequence has been cleaved or removed may also be called a mature polypeptide. In certain embodiments, immunogenic compositions comprise immunogen(s) that comprise two or more antigenic fragments of the same senescent cell-associated antigen. In other certain embodiments, the immunogen(s) comprise at least two antigenic fragments wherein each of the at least two antigenic fragments are derived from different senescent cell-associated antigens. The senescent cell-associated antigens described herein and the antigenic fragments thereof may be produced recombinantly by using any one of a variety of molecular biology and protein expression methods and techniques routinely practiced in the art and described herein.

In other certain embodiments, immunogens for use in the methods described herein comprise fusion polypeptides comprising two or more senescent cell-associated antigens or antigenic fragments thereof. The two or more senescent cell-associated antigens or two or more antigenic fragments of the same or different senescent cell-associated antigens may be linked in tandem with or without spacer amino acids between each of the two or more antigenic moieties. The spacer (or linker) may be a single amino acid (such as for example a glycine residue) or may be two, three, four, five, six, seven, eight, nine, or ten amino acids, or may be any number of amino acids between 5 and 100 amino acids, between 5 and 50, 5 and 30, or 5 and 20 amino acids. A polypeptide linker may also include a short peptide linker that may comprise at least two amino acids that are encoded by a nucleotide sequence that is a restriction enzyme recognition site. Examples of such restriction enzyme recognition sites include, for example, BamHI, ClaI, EcoRI, HindIII, KpnI, NcoI, NheI, PmlI, PstI, SalI, and XhoI. The fusion polypeptide may be designed with or without a spacer peptide so long as the two or more antigenic moieties fold properly to maintain antigenic properties of each of the moieties that is observed when each particular antigenic moiety is not present in a fusion polypeptide. If incorporated into a fusion polypeptide, the spacer peptide separates the different antigenic moieties by a distance sufficient to aid or ensure that each properly folds into the secondary and tertiary structures necessary for the desired immunogenic activity.

Surface amino acids in flexible protein regions and which are useful as a linker include glycine (Gly), asparagine (Asn) and serine (Ser). Virtually any permutation of amino acid sequences containing Gly, Asn, and Ser would be expected to satisfy the above criteria for a peptide linker sequence. Other near-neutral amino acids, such as threonine (Thr) and alanine (Ala), may also be used in the linker sequence. Suitable spacer peptides may comprise between from 5 to 100 amino acids and in certain embodiments, comprise between from 5 to 20 amino acids in length. Examples of such linkers include, but are not limited to ($Gly_4$ Ser (SEQ ID NO:1)), (i.e., Gly-Gly-Gly-Gly-Ser)$_n$), wherein n=1-12, or n=1-8, or n=1-4; $Gly_4$ $SerGly_5$ Ser (SEQ ID NO: 2) (i.e., Gly-Gly-Gly-Gly-Ser-Gly-Gly-Gly-Gly-Ser); and ($Gly_4$ $SerGly_5$ Ser (SEQ ID NO:2))$_m$ (i.e., Gly-Gly-Gly-Gly-Ser-Gly-Gly-Gly-Gly-Gly-Ser)$_m$) wherein m=2-4.

As described herein, an antigenic fragment comprises at least one immunogenic epitope. In certain embodiments, the number of contiguous amino acid residues in an antigen fragment is sufficient to comprise a conformational epitope that may be formed by non-contiguous portions of a senescent cell associated antigen. Alternatively, a fusion polypeptide may comprise two fragments that each comprise at least 5, 10, 20, 30, 40, or 50 contiguous amino acids of a senescent cell associated antigen and together with or without a spacer moiety properly fold to form a conformational epitope.

In certain instances senescent cells may be used to screen for the presence of senescent cell associated antigens and relevant epitopes for use in preparing antigenic fragments. Such targets can be prepared using random, or selected, synthetic peptide libraries. Alternatively, synthetic peptides of approximately 10-20 amino acids in length may be prepared from an identified senescent cell associated antigen, overlapping by 5-10 residues, which are characterized using any one of a number of immunoassays available in the art. In certain instances, a T cell epitope may be identified by preparing overlapping peptides of between 5-10 contiguous amino acids (e.g., 9 amino acids) of a senescence cell associated antigen. Similarly, B cell epitopes may be identified by preparing overlapping peptides. See, for example, Sturniolo at al., *Nature Biotech.* 17: 555-61 (1999); Jameson et al., *Comput. Appl. Biosci.* 4:181-186 (1988); Nakai et al., *Trends Biochem. Sci.* 24:34-36 (1999); Hopp, *Pept. Res.* 6:183-90 (1993); Hofmann et al., *Biomed. Biochim. Acta* 46:855-66 (1987); Menendez et al., *Comput. Appl. Biosci.* 6:101-105 (1990), which describe methods for identifying antigenic epitopes.

A person skilled in the art would readily appreciate that senescent cell-associated antigens such as p16INK4a, those listed in Table 1, and those encoded by the nucleotide sequences provided in Tables 2 and 3 are exemplary sequences and that variants of each antigen may exist. These variants may have amino acid sequences that are not identical to the exemplary sequences described herein and in the art, yet the variants exhibit the same immunogenicity as the antigens comprising the exemplary sequences (i.e., the immunogenicity is not reduced in a statistically significant, clinically significant, or biologically significant manner). These variants (or species) of individual senescent cell-associated antigens may include amino acid substitutions, deletions, or additions from the exemplary amino acid sequences. A senescent cell-associated antigen species includes antigens that comprise at least 80%, 85%, 90%, 92%, 95%, 97%, 98%, or 99% amino acid sequence identity to the exemplary senescent cell-associated antigen amino acid sequences provided herein, including those in Table 1 and the amino acid sequences encoded by the nucleotide sequences provided in each of Tables 2 and 3, and those described herein for p16INK4a. Percent identity of one amino acid sequence to one or more additional sequences may be determined using any one of the alignment tools described herein and used in the art.

Often a variant will have an amino acid substituted with another amino acid that is included within the same group, such as the group of polar residues, charged residues, hydrophobic residues, and/or small residues, and the like. The effect of any amino acid substitution may be determined empirically merely by testing the resulting modified peptide, polypeptide, or fusion polypeptide for the ability to function in a biological assay, or to bind to a cognate ligand or target molecule, such as a monoclonal or polyclonal antibody.

Senescent cell-associated antigen variants also include those that have amino acid substitutions, deletions or insertions, which may be introduced during chemical synthesis or recombinant production, whichever method is used to produce the particular immunogen. Substitutions, insertions, and deletions of one or more amino acids of the amino acid sequences described herein are those that do not adversely affect or alter (i.e., decrease or reduce in a statistically or biologically significant manner) the immunogenicity of the antigen or antigenic fragment thereof in a statistically, biologically, or clinically significant manner. As described herein, retention of immunogenicity includes the capability to evoke an immune response against a senescent cell, such as production of antibodies that specifically bind to the cognate antigen present on the senescent cell.

In general, an amino acid substitution that may be included in a senescent cell-associated antigen is a conservative substitution. Conservative substitutions of amino acids are well known and may occur naturally or may be introduced when the senescent cell-associated antigen or fusion polypeptide comprising the antigen is recombinantly produced or when the polynucleotide encoding the antigen is produced. A variety of criteria understood by a person skilled in the art indicates whether an amino acid that is substituted at a particular position in an immunogenic peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the peptide or polypeptide to the sequence of a second peptide or polypeptide, respectively, using any one of the algorithms, such as Align or the BLAST algorithm, or other algorithms described herein and practiced in the art.

Amino acid substitutions, deletions, and additions may be introduced into an a senescent cell associated antigen or antigenic fragment thereof during chemical synthesis of the polynucleotide that encodes the peptide or fusion polypeptide. Alternatively, amino acid substitutions, deletions, and additions may be introduced into an immunogenic peptide or fusion polypeptide recombinantly using well-known and routinely practiced mutagenesis methods (see, e.g., Sambrook et al. *Molecular Cloning: A Laboratory Manual*, 3d ed., Cold Spring Harbor Laboratory Press, N Y 2001)). Oligonucleotide-directed site-specific (or segment specific) mutagenesis procedures may be employed to provide an altered polynucleotide that has particular codons altered according to the substitution, deletion, or insertion desired. Alternatively, random mutagenesis techniques, such as alanine scanning mutagenesis, error prone polymerase chain reaction mutagenesis, and oligonucleotide-directed mutagenesis may be used to prepare immunogenic peptide and fusion polypeptide variants (see, e.g., Sambrook et al., supra).

Assays for assessing whether a respective senescent cell associated antigen or an antigenic fragment thereof prepared for immunization folds into a conformation comparable to the antigen as expressed by a senescent cell include, for example, the ability of the protein to react with mono- or polyclonal antibodies that are specific for native or unfolded epitopes, the retention of ligand-binding functions, and the sensitivity or resistance of the mutant protein to digestion with proteases (see Sambrook et al., supra). Such variants can be identified, characterized, and/or made according to methods described herein or other methods known in the art, which are routinely practiced by persons skilled in the art.

Polynucleotides and Recombinant Expression Vectors

In certain embodiments, the immunogenic composition useful in a method for inducing an immune response specific for a senescent cell comprises at least one polynucleotide that encodes a senescent cell-associated antigens or antigenic fragment thereof as an immunogen. In certain embodiments, the at least one polynucleotide encodes at least two senescent cell-associated antigens or antigenic fragments thereof. In other embodiments, the immunogen comprises two polynucleotides, wherein each of the two polynucleotides encodes a different senescent cell-associated antigen or antigenic fragment thereof. In a more specific embodiment, a polynucleotide useful in the immunogenic compositions encodes at least or at least two or more senescent cell-associated antigens wherein the polynucleotide(s) comprises a nucleic acid sequence provided in either Table 2 or Table 3. In another embodiment, the polynucleotide of the composition comprises a nucleotide sequence that encodes a senescent cell-associated antigen provided in Table 1. In still another specific embodiment, the polynucleotide of the composition comprises a nucleotide sequence that encodes p16INK4a (including but not limited to murine, rat, non-human primate, and human p16INK4a).

A polynucleotide that is an immunogen may be administered as a "naked polynucleotide" or may be incorporated into a recombinant expression vector that is administered to the subject (see, e.g., Ulmer et al., Science 259:1745-49, 1993 and reviewed by Cohen, Science 259:1691-1692, 1993). Also provided herein are recombinant expression vectors that comprise the polynucleotide that encodes a senescent cell associated antigen or antigenic fragment thereof. To obtain efficient transcription and translation of the immunogen (i.e., the senescent cell-associated antigen or antigenic fragment thereof), the encoding polynucleotide sequences in each vector should include at least one appropriate expression control sequence (also called a regulatory expression sequence or feature) (e.g., promoter, enhancer, leader), which are described in greater detail herein, that is operatively linked to the encoding polynucleotide sequence(s). These recombinant expression vectors are thus provided for expression of the senescent cell-associated antigen or antigenic fragment thereof in any appropriate host cell that has been transformed, transduced, or transfected with a recombinant expression vector. The recombinant expression vector may also include nucleotide sequences that encode a co-stimulatory molecule, which provides transcription and translation of the senescent cell-associated antigen (or fragment thereof) and the co-stimulatory molecule in the same cell.

The recombinant expression vector may be a plasmid DNA or cosmid DNA. Plasmid DNA or cosmid DNA that contains one or more polynucleotides encoding an immunogen as described herein are readily constructed using standard techniques well known in the art. The vector genome may be typically constructed in a plasmid form that can then be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline. For analysis to confirm that the correct nucleotide sequences are incorporated in plasmids, the plasmid may be replicated in E. coli, purified, and analyzed by restriction endonuclease digestion and/or its nucleotide sequence determined by conventional methods.

In other particular embodiments, the recombinant expression vector is a viral vector. Exemplary recombinant expression viral vectors include a lentiviral vector, poxvirus vector, adenovirus vector, adenovirus-associated virus vector, or a herpes virus vector. In other embodiments, the recombinant expression vector is of prokaryotic origin, and includes recombinant bacteria and recombinant expression vectors that are expressed in bacteria.

A number of suitable, available lentiviral genome based vectors are available in the art, including those identified for human gene therapy applications (see, e.g., Pfeifer et al., Annu. Rev. Genomics Hum. Genet. 2:177-211 (2001)). Suitable lentiviral vector genomes include those based on Human Immunodeficiency Virus (HIV-1), HIV-2, feline immunodeficiency virus (FIV), equine infectious anemia virus, Simian Immunodeficiency Virus (SIV) and maedi/visna virus. A desirable characteristic of lentiviruses is that they are able to infect both dividing and non-dividing cells. Safety features of the vector genome are desirably incorporated. Safety features include self-inactivating LTR and a non-integrating genome. See, for example, U.S. Pat. No. 8,273,345 (describing lentiviral vectors for targeted delivery to a dendritic cell); U.S. Patent Application Publication No. 2010/0297168; Simmons et al., Virol. J. 3:8 (2006).

In certain embodiments, a recombinant expression vector is an adenovirus vector. The adenovirus genome is well characterized and the biology of the adenoviruses is known in the art in detail. The adenovirus is not associated with severe human pathology in immunocompetent individuals. Adenovirus particles may be used for efficiently introducing a polynucleotide into a host cell, and the virus is capable of infecting a large variety of cells.

The adenovirus has a double-stranded linear genome with inverted terminal repeats at both ends. During viral replication, the genome is packaged inside a viral capsid to form a virion. The virus enters its target cell through viral attachment followed by internalization (Hitt et al., Advances in Pharmacology 40:137-206, 1997.) Adenovirus vectors may be based on different adenoviruses that are characterized as human or non-human animal or avian serotypes. Examples of non-human animal adenoviruses include bovine, porcine, simian, murine, canine, and avian adenoviruses. Adenoviral vectors can contain regions from a single adenovirus or from two or more adenovirus serotypes.

An adenovirus may be rendered replication defective by deletion of the early-region 1 (E1) of the viral genome. Most adenoviral vectors currently used in gene therapy have a deletion in the E1 region, where genetic information of interest is introduced. Human adenoviruses have been categorized into about six different subgroups that encompass 51 distinct adenovirus serotypes. A serotype is defined on the basis of its immunological distinctiveness determined by quantitative neutralization assays using animal antisera. Simian adenoviral vectors may also be used in the methods described herein for evoking an immune response specific for a SCAAg and that comprises clearance of senescent cells. Adenoviral serotypes that may be used for constructing recombinant expression vectors include human adenoserotypes, for example, Ad1, Ad2, Ad6, Ad5, Ad11, Ad12, Ad24, Ad26, Ad34, Ad35, Ad48, Ad49, and Ad50, and simian adenoserotypes, for example, common chimpanzee adenovirus (Ch) subtypes ChAd55, ChAd73, ChAd83, ChAd146, ChAd147, and ponobo chimpanzee adenovirus (Pan) subtypes, PanAd1, PanAd2, and PanAd3.

Adenoviral vectors include recombinant vectors that are either replication-defective or replication-competent. Replication-defective adenoviral vectors typically lack the E1A gene (required for induction of adenovirus expression and DNA replication) and E1B genes (called E1) and instead contain an expression cassette consisting of a promoter and pre-mRNA processing signals that drive expression of a gene encoding a non-adenoviral polypeptide, such as an immunogen of interest. E3 genes or portions thereof may also be deleted.

Historically, the usefulness of adenovirus as a vehicle for transgene delivery has been limited by induction of neutralizing anti-adenoviral immunity following an initial administration, resulting in shorter-term and reduced levels of transgene expression. Serotype Ad5 vectors, for example, were developed (see, e.g., Chroboczek, et al., J. Virology 186:280-285 (1992)); however, neutralizing antibodies to Ad5 are highly prevalent in humans. More recently, serotype Ad5 vectors have been modified to provide more effective immunization against an antigen of interest delivered by the adenovirus. By way of example, adenoviral vectors that may be used in the methods described herein for inducing an immune response specific for a senescent cell include chimeric Ad5-based constructs in which the hexons from Ad6 is incorporated in place of the Ad5 hexon (see, e.g., Youil, et al., Human Gene Therapy 13(2): 311-320 (2002) doi: 10.1089/10430340252769824). Other Ad5/Ad6 adenoviral vectors may be used for expressing a senescent cell associated antigen for inducing an immune response against senescent cells (see, e.g., U.S. Pat. No. 8,142,794 (U.S. Patent Application Publication No. 2009/0233992).

In certain specific embodiments, the adenovirus vector used in the immunogenic compositions described herein is a replication-defective adenovirus and has a serotype that is less likely to have induced pre-existing immunity to the serotype, such as a serotype selected from Ad11, Ad24, Ad26, Ad34, Ad35, Ad48, Ad49, and Ad50. In another particular embodiment, the serotype is Ad11, AD35, or AD49. In a more particular embodiment, the serotype is AD35. In certain embodiments, two or more recombination expression vectors are used as immunogens for expression of two or more senescent cell-associated antigens or two or more two or more antigenic fragments of the same or different senescent cell-associated antigens, and each recombination vector is independently selected from an adenovirus serotype Ad11, Ad24, Ad26, Ad34, Ad35, Ad48, Ad49, and Ad50. Exemplary adenoviral vectors can be prepared according to Crucell AdVac® technology (Crucell, Leiden, The Netherlands). See, for example, U.S. Pat. Nos. 8,221,971; 8,202,723; 8,114,637; 8,052,967; 8,012,467; 7,820,440; 7,781,208; 7,749,493; 7,741,099.

A recombinant adenovirus that at least a deletion in the E1 region to accommodate insertion of genetic information related to expression of the SCAAg(s) of interest may include sequences encoding the E1B-55K gene product that increases the expression of the pIX gene present in the adenovirus and which expresses a non-functional E1B-55K gene product (see, e.g., U.S. Pat. No. 8,052,967). These adenoviruses appear more stable and/or can incorporate more exogenous DNA than the corresponding adenovirus that lacks all E1B-coding sequences. Alternatively, or in addition to, the presence of E1B-55K sequences increasing the expression of the pIX gene, the sequences preceding the pIX-coding sequence may be changed into a stronger promoter, which may be a heterologous promoter, to increase the expression of pIX, resulting in an increase of the stability of a recombinant adenovirus and/or an increase of the packaging capacity of the adenoviral particle produced.

As described herein, exogenous genetic information that encodes one or more SCAAgs of interest can be inserted into the genome where adenoviral E1 sequences have been deleted. In addition to the E1 region deletion, E3 sequences can also be deleted from such adenoviral vectors to increase the capacity for SCAA genetic information. For example, B-type adenovirus serotypes such as Ad34 and Ad35 have a different E3 region than other serotypes, which region is involved in suppressing immune response to adenoviral products.

Adenovirus capsid, in particular the penton and/or the hexon proteins, may induce an immune response to the adenoviral vector. Thus, the adenoviral vector may comprise the elements of at least one capsid protein or functional part thereof, such as fiber, penton and/or hexon proteins or a gene encoding at least one of them from a less immunogenic subtype, such as Ad35. In other certain embodiments, any one of the fiber, penton, and hexon proteins may be encoded by a gene derived from a simian (e.g., chimpanzee) adenovirus. Other deletions and various combinations of part or complete deletions of E2, E3, and E4 regions, combined with the E1 deletion, can be used, if necessary, in combination with a packaging cell comprising the genetic information lacking in the adenoviral vector when necessary for replication of the adenoviral vector. For delivery of the transgene, the adenoviral particle can be targeted specifically to target cells of interest via binding to that specific cell either through capsid-receptor binding or through other means.

Targeting of adenoviruses can be performed in many different ways to deliver the adenoviral vectors to the cells of interest using methods routinely practiced in the art. By way of example, capsid alterations (fiber, hexon and/or penton modifications, such as deletions, swaps between fibers of different serotypes, and additions of peptides and/or other binding moieties), wherein chimeric fibers are produced that recognize a receptor present on the cell of interest or wherein the binding of the penton-base is used. Other possibilities are linking targeting moieties to the capsid proteins wherein, for instance, binding peptides, known and strong binding proteins, or antibodies or parts thereof, are linked to the capsid proteins to achieve specific targeting.

In a particular embodiment, the adenovirus vector is a recombinant adenovirus of adenovirus serotype 35 (Ad35) wherein at least the Ad35 fiber knob has been replaced by the fiber knob of a serotype that binds to the Coxsackievirus and Adenovirus Receptor (CAR). The Ad35 fiber knob may be replaced with the sequence that encodes the fiber knob from serotype Ad5 or the knob, shaft and part of the tail may be replaced. The shaft and tail of the fiber may be of the carrying backbone serotype, such as Ad35, whereas the shaft domain is of the same serotype as fiber knob serotype. When the tail region is derived from the backbone serotype, the interaction of the adenovirus with the remaining part of the capsid will more likely result in production of stable vectors in the art.

In other certain embodiments, a recombinant expression vector is an adenoviral vector that is a simian adenovirus vector (see, e.g., Int'l Patent Application Publication Nos. WO 03/046124; WO 03/000851; WO 2010/085984; WO 2012/089833; U.S. Patent Application Publication Nos. 2011/0129498; 2013/0101618; U.S. Pat. No. 6,083,716). By way of non-limiting example, the adenoviral vector may be derived from a chimpanzee adenovirus, which may be a common chimpanzee adenovirus (ChAd) or a bonobo chimpanzee adenovirus (PanAd). By using a simian adenoviral vector, an adverse effect associated with the preexisting immunity in humans to common serotypes of human adenoviruses can be avoided. The adenovirus types ChAd55, ChAd73, ChAd83, ChAd146, ChAd147, PanAd1, PanAd2, and PanAd3 are characterized by a the absence of preexisting neutralizing antibody in humans directed against these adenovirus types (see, e.g., U.S. Patent Appl. Publ. No. 2011/012949, and references cited therein).

Simian adenoviral vectors may contain one or more of the fiber, hexon, and penton proteins of ChAd55, ChAd73, ChAd83, ChAd146, ChAd147, PanAd1, PanAd2, and/or PanAd3. Fiber, hexon, and penton proteins are adenovirus capsid proteins that represent the most surface exposed adenovirus epitopes. The aforementioned chimpanzee hexon, penton, and fiber protein sequences may also be used to improve other adenoviruses by replacing one or more of these major structural capsid proteins or functional fragments thereof of any adenovirus, such as any of the human adenoviruses described herein and known in the art, which provide recombinant adenoviruses with a reduced seroprevalence in humans.

As with human adenoviral vectors, simian adenoviral vectors are preferably replication defective, meaning that the adenovirus is incapable of replication because it has been engineered to comprise at least a functional deletion or a complete removal of a gene product that is essential for viral replication. For example, and as described herein, one or more genes selected from the group consisting of E1A, E1B, E2A, E2B, E3 and E4 gene can be deleted, rendered non-functional, and/or can be replaced with sequences that includes appropriate expression control sequence(s) operatively linked to the nucleotide sequence encoding one or more SCAAg(s).

In still other embodiments, the recombinant viral vector is an adenovirus-associated virus (AAV) vector. Adeno-associated virus (AAV) is a replication-deficient parvovirus that is able to infect a wide spectrum of cells without inducing any effects on cellular growth, morphology, or differentiation. AAV is non-pathogenic. The AAV genome has been sequenced and well characterized. The single-stranded DNA genome is about 4.7 kb in length and includes 145 nucleotide inverted terminal repeat (ITRs). The ITRs play a role in integration of the AAV DNA into the host cell genome. The remainder of the genome is divided into two essential regions that carry the encapsidation functions: the left-hand part of the genome, which contains the rep gene involved in viral replication and expression of the viral genes; and the right-hand part of the genome, which contains the cap gene encoding the capsid proteins. When AAV infects a host cell, the viral genome integrates into the host's chromosome resulting in latent infection of the cell. In the instances of recombinant AAV vectors having no Rep and/or Cap genes, the AAV can be non-integrating and exists transiently as an episome. AAV depends upon a helper virus (for example, adenovirus or herpesvirus) to provide genes that allow for production of AAV in the infected cell. In the case of adenovirus, genes E1A, E1B, E2A, E4 and VA provide helper functions. Upon infection with a helper virus, the AAV provirus is rescued and amplified, and both AAV and adenovirus are produced. To date, at least 11 serotypes of AAV have been identified and isolated from humans or primates.

AAV vectors are designed such that all viral genes are replaced by an expression cassette for the transgene encoding the polypeptide of interest (e.g., an SCAAg), leaving intact the essential cis elements of the genome, the inverted terminal repeats (ITRs), DNA packaging signal, and the replication origin. Replication and packaging of AAV vectors requires all AAV and Adenovirus/HSV helper functions to be provided in trans. While wild-type AAV is capable of integrating in a site-specific manner into human chromosome 19, site-specific integration of recombinant AAV does not occur to a significant extent because of the lack of Rep protein expression. Onset of transgene expression is generally delayed by 2-4 weeks.

The ability of AAV vectors to infect a broad host range, transduce both dividing and non-dividing cells in vitro and in vivo, and maintain high levels of expression of the transduced genes in the absence of a significant immune response to the transgene product in general have made AAV an attractive vector for recombinant use. AAV vector particles are thought to be non-pathogenic and are heat stable, resistant to solvents, detergents, and changes in pH and temperature. The ITRs have been shown to be the only cis elements required for replication and packaging and may contain some promoter activities. Thus, no viral genes are encoded by AAV vectors.

In another particular embodiment, the recombinant viral vector is a Herpes Simplex vector, such as a Herpes Simplex I (HSV1) or a Herpes Simplex II (HSV2) viral vector. The HSV1 genome has been sequenced and comprises 152 kb encoding at least 80 gene products, about half of which are essential for viral replication. The HSV2 genome has also been sequenced and comprises 155 kb encoding 74 gene products, corresponding closely to the HSV1 genome. The lytic pathway of HSV infection is characterized by the regulated sequential expression of three ordered classes of viral gene products: immediate early (IE or α), early (E or β), and late (L or γ) genes. Upon release of the viral DNA into the host cell nucleus, the viral genome circularizes and expression of five IE genes (infected cell protein ICP4, ICP27, ICP0, ICP22, and ICP47) is induced. V16 binds to an enhancer element present in all IE promoters and activates transcription. The IE genes are involved in transactivation of the E genes, which encode DNA polymerase and other proteins involved in altering the intracellular milieu to favor viral replication. Expression of the L genes follows which mostly encode structural proteins of the capsid, tegument, and envelope. A productive HSV infection results in death of the host cell.

The HSV genome can also be grouped according to whether they are essential or nonessential to viral replication. Essential genes are required to produce new infectious viral particles in permissive cell culture infections. Nonessential, or accessory, genes encode proteins that are not required but are important for optimum lytic replication or affect the life cycle of the virus in vivo (e.g., host range, pathogenesis, latency). In the unique short (US) region of the HSV genome, glycoprotein D is the only essential gene. Large segments of viral sequence in the US region may be replaced with a transgene of interest. The HSV genome may accommodate up to 40-50 kb of exogenous sequence.

Several factors contribute to the interest in HSV based vectors for vaccines. HSV sequences are known and well characterized; HSV elicits strong and durable immune responses by various routes of administration; HSV has a large cargo capacity (>160 kb); the viral DNA persists in the host cell nucleus as an episomal element; HSV genome carries the tk gene which can be exploited to kill infected cells with appropriate drugs (e.g., gangcyclovir). The use of vectors derived from HSV type I and type II is well known in the art and has been previously described (see, e.g., U.S. Pat. No. 6,071,692; U.S. Pat. No. 6,613,892; U.S. Pat. No. 6,838,279; WO2000/077167; WO1990/009441; U.S. Pat. No. 5,846,707; U.S. Pat. No. 5,288,641; WO2005/092374; U.S. Pat. No. 6,613,892; WO2006/004878; and US2011/0171257). Vectors based on HSV type I or type II include: replication-defective viruses; amplicon vectors; and attenuated viruses.

Attenuated, replication-competent viral vectors have mutations or deletions of non-essential genes (see, e.g., Hu and Coffin, 2003, *Int. Rev. Neurobiol.* 55:165-84; Todo, 2008, *Front. Biosci.* 13:2060-4; Varghese and Rabkin, 2002, *Cancer Gene Ther.* 9:967-78; Hunter et al., 1999, *J. Virol.* 73:6319-6326; US Patent Publication 20080089910). Non-essential HSV genes, such as thymidine kinase, ribonucleotide reductase, virion-host shut off, and ICP34.5, are involved in replication, virulence, and immune evasion and optimize viral growth in host cells. Deletion or modification of non-essential genes may yield HSV mutants with decreased pathogenicity, such as, reduced replication in normal quiescent cells but replication ability in tumor or dividing cells. ICP34.5 deleted HSV, either alone or in combination with deletion of ribonucleotide reductase, replicate selectively in malignant cells (see, e.g., Shah et al., 2003, *J. Neurooncol.* 65:203-226; Post et al., 2004, *Curr. Gene Ther.* 4:41-51). HSV has been shown to infect dendritic cells, suggesting that HSV may be used to deliver transgenes to dendritic cells for vaccination (see, e.g., Kruse t al., 2000, *J. Virol.* 74:7127-7136; Coffin et al., 1998, *Gene Ther.* 5:718-722; Mikloska et al, 2001, *J. Virol.* 75:5958-

5964). Attenuated HSV vectors for dendritic cells have been previously described (U.S. Pat. No. 6,641,817).

Replication-defective (incompetent) vectors derive from mutant HSV viruses with mutations or deletions in one or more genes essential for the lytic cycle. A transgene may be inserted in the viral genome so that it is packaged into the viral particle along with HSV DNA. Replication defective HSV are grown in complementing cell lines which provide the missing essential gene(s) in trans. Replication-defective vectors, in which one or more of the IE genes (ICP0, ICP4, ICP22, ICP27, and ICP47) are deleted in various combinations, have been constructed (see, e.g., Kaplitt et al., 1997, *J. Neurosci. Methods* 71:125-132; Krisky et al., 1998, *Gene Ther.* 5:1593-1603; Krisky et al., *Gene Ther.* 1997, 4:1120-1125; Wu et al., 1996, *J. Virol.* 70:6358-6369). Alternatively, HSV mutants with inactivated VP16 may be used to circumvent the use of complementing cell lines expression IE proteins. Inactivation of VP16 to eliminate its IE gene transactivation function in HSV vectors, combined with conditional mutations in ICP4 and ICP0 can express foreign genes without killing the host cell (see, e.g., Preston et al., 1997, *Virology* 229:228-239). In yet another example, deletion of virion host shutoff protein (VHS) from replication incompetent HSV vectors allows activation of dendritic cells and induction of antigen-specific T cell responses (see, e.g., Samady et al., 2003, *J. Virol.* 77:3768-3776).

Amplicons are plasmid-derived vectors engineered to contain both the origin of HSV DNA replication (ori) and HSV cleavage/packaging signal (pac). Upon transfection into mammalian cells with HSV helper functions, amplicons are replicated and amplified as head-to-tail linked concatamers, which are then packaged into viral particles. Several advantages of using amplicon vectors for gene delivery include: a large transgene capacity; ability to introduce multiple copies of the transgene per infected cell; ability to infect wide variety of host cells; easy construction; and limited toxicity.

There are several methods known in the art for producing amplicon particles. One prepares amplicon vectors in cells transfected with amplicon plasmid and infected with replication-defective helper HSVs. However, the use of HSV as helper virus may result in helper-contaminated vector stocks, which can induce cytotoxicity and inflammation (see, e.g., Epstein et al., 2005, *Curr. Gene Ther.* 5:445-458; Zhang et al., 2006, *J. Virol. Methods* 137:177-183; Sia et al., 2007, *J. Virol. Methods* 139:166-174). Alternatively, conditional packaging helper viruses using Cre/loxP-based site-specific recombination to remove the packaging signal may be used (Logvinoff and Epstein, 2000, *Virology* 267:102-110; Zaupa et al., 2003, *Human Gene Therapy* 14:1049-1063). Yet another option is provide a plasmid comprising the HSV genome, without the packaging signals, e.g., by using pac-deleted overlapping cosmids (see, e.g., Fraefel et al., 1996, *J. Virol.* 70:7190-7197) or a pac-deleted and ICP27-deleted BAC-HSV-1 (see, e.g., Saeki et al., 2001, *Mol. Ther.* 3:591-601).

In other certain embodiments, the immunogenic composition useful in a method for inducing an immune response specific for a senescent cell comprises a bacterial delivery system that comprises a recombinant bacterium into which a recombinant expression vector has been introduced. In a certain particular embodiment, the recombinant bacterium is a recombinant *Listeria* bacterium, which may be attenuated (see, e.g., Bower et al., *Proc. Natl. Acad. Sci. USA* 103: 5102-107 (2006); Chamekh, *Immunopharmacology and Immunotoxicology* 32:1-4 (2010); U.S. Pat. Nos. 7,695,725; 7,833,775; 7,927,606; 7,935,804; 8,287,883; 8,580,939). *Listeria* has been used to stimulate cellular immunity because of its intracellular life cycle. After the bacteria infect the host, the bacteria are taken up by phagocytes into a phagolysosomal compartment. The majority of the bacteria are subsequently degraded, and peptides of the antigen of interest are presented as MHC II-peptide complexes. The recombinant expression vector introduced into the bacteria, such as *Listeria*, comprises a nucleotide sequence that encodes at least one appropriate bacterial expression control sequence (e.g., promoter, enhancer, leader) that is operatively linked to the encoding polynucleotide sequence(s) for a senescence cell-associated antigen(s). The polynucleotide sequence encoding the senescence cell-associated antigen (SCAAg) may also comprise a signal peptide sequence (e.g., a bacterial signal peptide) fused in frame to the amino terminal end of the SCAAg. In other embodiments, the polynucleotide encodes the SCAAg fused in frame with a polypeptide that enhances expression and processing of the SCAAg. In one embodiment, the SCAAg is fused in frame with an autolysin. The autolysin polypeptide has been shown useful for efficient expression and secretion of a heterologous antigen in *Listeria* (see, e.g., U.S. Pat. No. 7,842,289).

Recombinant expression viral vectors may be incorporated into a vector particle that comprises a recombinant expression system that comprises one recombinant expression vector (also called a first recombinant expression vector) comprising a polynucleotide sequence encoding at least one senescent cell-associated antigen or antigenic fragment thereof and a second recombinant expression vector that includes a polynucleotide sequence that encodes a second senescent cell-associated antigen or antigenic fragment thereof. Alternatively the second recombinant expression vector may encode a co-stimulatory molecule.

In certain embodiments, the recombinant expression vectors or viral particles are engineered to be delivered to a target cell using methods and techniques known to and practiced by persons skilled in the art. In particular embodiments, the target cell is an immune cell that is an antigen-presenting cell, such as a dendritic cell. Such methods comprise contacting (i.e., permitting interaction) of the target cell with a vehicle that delivers the polynucleotide.

In yet another embodiment, recombinant viral vectors are recombinant viruses that are senolytic and are replication competent or conditionally replication competent. Virus replication leads to amplification, killing of the senescent cell, and introduction of the progeny virus into other senescent cells. Because of the inherent cytotoxicity and efficiency with which viruses can infect other cells, recombinant viruses may be prepared that exhibit a high enough degree of senescent cell selectivity, and hence safety, for treatment of a subject in need of removal of senescent cells to treat or prevent a disease or disorder. The viruses are constructions so that the viruses are attenuated in normal cells but retain their ability to kill senescent cells. Such engineering may include modifying the ability of viruses to bind to, or replicate in senescent cells, while others have involved the construction of replication-competent viruses encoding suicide proteins. The SCAAgs described herein may be used to target senescent cells replication competent or conditionally replication competent viruses.

The SCAAgs described herein are useful for identifying ligands, including antibodies, of the respective SCAAg, which may be used for targeting a lytic virus to senescent cells. By way of example, SCAAg as described herein may be used to prepare an antibody that specifically binds to the SCAAg. Antigen binding fragments (e.g., Fv, sFv, one or more CDRs with one or more adjacent framework regions)

of the antibody may be prepared either synthetically or recombinantly according to methods routinely practiced in the art. Mutant viral vectors may be prepared in which the viral vector comprises on its surface a viral surface protein (or portion thereof) that is fused in frame with an antigen binding fragment that specifically binds to a SCAAg, such as a senescent cell surface polypeptide, to target the viral vector to a senescent cell. In other embodiments, the viral surface protein is fused in frame with a ligand, or a senescent cell binding peptide of the ligand, of a SCAAg. Senolytic viruses include by way of non-limiting example, HSV, lentiviruses, pox viruses, adenoviruses, rhabdoviruses, measles viruses, Newcastle Disease Virus (NDV), rhabdoviruses (e.g., vesicular stomatitis virus), reovirus, and Seneca Valley viruses. See, e.g., Dalba et al., *Mol Ther.* 2007 March; 15(3):457-66. Epub 2007 Jan. 23; U.S. Pat. Nos. 5,585,096; 5,728,379; 7,501,126; 7,749,745; Doronin et al., *J. Virol.* 74:6147-55 (2000); Sarkar et al., *Cell Cycle* 2006 July; 5(14):1531-6. Epub 2006 Jul. 17; Lorence et al. (eds): Replication-Competent Viruses for Cancer Therapy. Monogr Virol. Basel, Karger, 2001, vol 22, pp 160-182 (DOI: 10.1159/000061724); Int'l Appl. Publ. No. WO 2002/053760).

Conditionally replication competent senolytic viruses also include those from which at least one regulatory element for expression of an essential viral gene is replaced with a regulatory element, such as a p16 promoter, to ensure that the virus replicates and subsequently kills only senescent cells (see, e.g., Int'l Appl. Publ. No. WO 2013/158664). A viral surface protein of such a virus may be fused in frame with an antigen binding fragment that specifically binds to a SCAAg or fused in frame with a ligand, or peptide thereof, of the SCAAg for binding specifically to a senescent cell.

In yet another embodiment, a virus such as rhabdovirus, may be engineered to target and kill senescent cells and also express an immunostimulatory molecule that promotes removal of the virus by the immune system (see, e.g., Batenchuk et al., *Blood Cancer Journal* (2013) 3, e123; doi:10.1038/bcj.2013.23; Published online 12 Jul. 2013). Without wishing to be bound by theory, the destruction of the senescent cells evokes an immune response to senescent cell associated antigens that promotes continued clearance of senescent cells.

Exosomes, Senescent Cell Membranes, Senescent Cell Lysates

In certain embodiments, the immunogenic composition for evoking an immune response specific for a senescent cell in a subject is an exosome comprising at least one senescent cell-associated antigen or antigenic fragment thereof. Exosomes are nanovesicles of endosomal origin that are secreted in the extracellular environment following fusion of late endosomal multivesicular bodies with the plasma membrane (see, e.g., Garin et al., 2001, *J. Cell Biol.* 152:165-80). Cells from various tissue types have been shown to secrete exosomes, including dendritic cells, immune cells (e.g., B-cells and T cells), tumor cells, mast cells, and senescent cells. Exosomes from different cell types exhibit discrete sets of proteins and lipid moieties that reflect their cells of origin (see, e.g., Thery et al., 1999, 147:599-610; Thery et al., 2001, *J. Immunol.* 166:7309-18). Exosomes display proteins involved in antigen presentation (MHC Class I and MHC Class II) (Iero et al., 2008, *Cell Death Differ.* 15:80-88). Their main protein markers are tetraspanins (CD63, CD9), Alix, and TSG101, and they are able to mediate immune response by activating T cells (via antigen presentation); natural killer cells (via NKG2D ligand binding); and dendritic cells (via antigen transfer) (see, e.g., Thery et al., 2009, *Nat. Rev. Immunol.* 9:581-593). Though their precise biological function and mechanism have yet to be determined and without wishing to be bound by theory, exosomes are thought to be involved in cell-cell communication, leading to immune modulation. By way of example, exosomes from dendritic cells pulsed with peptides derived from tumor antigens elicit anti-tumor immune responses in an animal model having the matching tumor (see, e.g., Wolfers et al., 2001, *Nat. Med.* 7:297-303; Zitvogel et al., 1998, *Nat. Med.* 4:594-600). Accordingly, exosomes based immunotherapy may be useful as a cell-free vaccine (see, e.g., Viaud et al., 2010, *Cancer Res.* 70:1281-5; Tan et al., 2010, *Intl. J. Nanomed.* 5:889-900).

Exosome producing cells may be any cell, preferably of mammalian origin, that produces and secretes membrane vesicles of endosomal origin by fusion of late endosomal multivesicular bodies with the plasma membrane. Endosomal producing cells include, for example, dendritic cells, B cells, tumor cells, senescent cells, T cells, and mast cells. In one embodiment, exosome-producing cells are mammalian senescent cells, mammalian T cells, and mammalian dendritic cells, typically murine (useful for preclinical studies) or human. Dendritic cell exosomes are capable of activating T cells and NK cells. In certain embodiments, exosomes may be obtained from any autologous subject-derived cells, heterologous haplotype-matched cells, or heterologous stem cells to reduce or avoid the generation of an immune response in a subject to whom the exosomes are administered. For evoking production of antibody(ies), B cells may be used as exosome producing cells because the resulting exosomes comprise accessory functions and molecules such as MHC Class II molecules that facilitate antibody production. Additionally, B cell exosomes are able to bind follicular dendritic cells, which is a feature of antibody induction. Exosomes from other cells types, such as non-antigen presenting cells, for example, senescent cells, can spread antigens or peptide-loaded MHC complexes to antigen presenting cells for more efficient presentation. Recombinant exosomes comprising recombinant MHC molecules have also been described (see, e.g., WO00/028001, incorporated herein in its entirety). In some embodiments, exosomes originating from one or more cell types may be used as an immunogen for evoking an immune response specific for a senescent cell.

One or more senescent cell-associated antigens or antigenic fragments thereof may be selected for loading of exosome producing cells. If the exosome producing cell is a senescent cell, it is naturally loaded with senescent-cell associated antigens or antigenic fragments thereof. An exosome producing senescent cell may also be modified with specific recombinant senescent cell-associated antigens or antigenic fragments thereof, co-stimulatory molecules, targeting moieties, or loaded with an exogenous antigen (i.e., a helper antigen or carrier protein) to enhance the immune response. A variety of methods known in the art may be used to load antigen presenting cells with antigens, including peptide pulsing (see, e.g., Macatonia et al., 1989, *J. Exp. Med.* 169:1255; Takahashi et al., 1993, *Int. Immunol.* 5:849), antigen pulsing (see, e.g., Inaba et al., 1990, *J. Exp. Med.* 172:631; Hsu et al., 1996, *Nat. Med.* 2:52); placing cells in contact with one or more antigenic protein complexes; placing cells in contact with cells or membranes of cells expressing antigens or antigenic peptides ("direct transfer") (see, e.g., Zou et al., *Cancer Immunol. Immunother.* 15:1); placing cells in contact with membrane vesicles containing antigens or antigenic peptides (e.g., exosomes from senescent cells) (see, e.g., U.S. Pat. No. 6,685,911); placing cells in contact with liposomes containing antigens or antigenic peptides (see, e.g., Nair et al., 1992, *J. Exp. Med.* 175:609); placing cells in contact with polynucleotides encoding antigens or antigenic peptides (optionally incorporated in vectors of plasmid, viral, or chemical type) (see, e.g., Boczkowsky et al., 1996, *J. Exp. Med.* 184:465-472; Bhardwaj et al., 1994, *J. Clin. Invest.* 94:797; Alijagie et al., 1995, *Eur. J. Immunol.* 25:3100). Methods of producing, purifying, or using exosomes for therapeutic purposes or as research tools are known in the art and have been described, for example, in U.S. Pat. No. 6,685,911; U.S. Pat. No. 7,625,573; PCT Publication Nos. WO99/03499; WO00/44389; WO00/028001; and WO97/05900, each of which is incorporated by reference herein in its entirety.

Exosomes produced by the exosome-producing cell may be collected and/or purified using techniques known in the art, such as differential centrifugation, chromatography, etc. (see, e.g., Thery et al., 1999, *Cell Biol.* 147:500-10; Lehmann et al., 2008, *Cancer Res.* 68:7864; U.S. Patent Publication No. 2004/0241176; U.S. Pat. No. 6,899,863; PCT Publication No. WO 2000/44389; each of which is incorporated herein by reference in its entirety). Methods for targeting expression of recombinant polypeptides to exosomes using exosome-specific targeting domains (e.g., C1 and/or C2 domains from lactadherin) have been described in U.S. Pat. No. 7,704,964 and Rountree et al., 2011, *Cancer Res.* 71:5235, each reference incorporated herein in its entirety. Such methods may be used to deliver chimeric senescent cell-associated antigens to exosomes if they are not naturally expressed in senescent cell exosomes. Exosome producing cells may also be modified such that exosomes include a targeting moiety on the surface. The exosomes may be targeted to a selected tissue or cell type (see, e.g., PCT Publication No. WO 2010/119256, incorporated herein in its entirety).

In certain embodiments of the present disclosure, senescent cell exosomes comprising one or more senescent-cell associated antigens may be modified to lack one or more immunosuppressive polypeptides normally found in the exosome. Such modifications may be useful for senescent cell exosomes. While cancer cells have been shown to release exosomes, cancer cell exosomes may circumvent immunosurveillance and recognition of the tumor by the immune system via inclusion of immunosuppressive polypeptides (e.g., Fas, programmed death ligand-1, programmed death ligand-2) in the cancer cell exosome (see, e.g., U.S. Patent Publication No. 2010/0092524; Iero et al., supra). Likewise, senescent cell exosomes may circumvent immunosurveillance and recognition of senescent cells by the immune system via inclusion of immunosuppressive polypeptides. Expression of immunosuppressive polypeptides may be inhibited using methods known in the art, such as siRNA, antisense, and modifications thereto (see, e.g., U.S. Patent Publication No. 2010/0092524, incorporated herein by reference in its entirety).

In certain embodiments, the immunogenicity of senescent cell exosomes may be enhanced by expressing exogenous antigens (e.g., superantigens) on the cell surface as described in U.S. Patent Publication No. 2010/0092524, incorporated herein in its entirety. Superantigens can bind directly to MHC complex without being processed. Examples of superantigens that may be incorporated into senescent cell exosomes as exogenous polypeptides include Staphylococcal enterotoxins (SEs, e.g., Staphylococcal enterotoxin A or Staphylococcal enterotoxin E); a *Streptococcus pyogenes* exotoxin (SPE), a *Staphylococcus aureus* toxic shock syndrome toxin (TSST-1); a Streptococcal mitogenic exotoxin (SME); and a Streptococcal superantigen (SSA).

In other embodiments, an immunogen used in the immunogenic compositions and methods described herein comprises a senescent cell membrane preparation. In a particular embodiment, the senescent cell preparation comprises the cell membrane (also called the plasma cell membrane or cytoplasmic cell membrane), thereby providing senescent cell associated antigens present on the cell surface of the senescent cell. Senescent cell associated antigens present on the cell membrane may include proteins and glycoproteins that are channel forming proteins, proteins that facilitate diffusion or active transport of molecules and ion across the membrane, cell recognition proteins, receptor proteins, and enzymes. In another embodiment, an organelle of a senescent cell may be an immunogen. For example, an organelle that is involved in processing, production, or transport of a cell surface molecule, for example, in certain instances, a lysozome, endoplasmic reticulum, Golgi apparatus, or an endosome, may be prepared from senescent cells. Senescent cell membranes and cell organelles may be prepared using methods known and practiced by the skilled person (see, e.g., *Current Protocols in Cell Biology*, John Wiley & Sons, 2009).

Dendritic Cell Immunogens (Vaccines)

In certain embodiments, the present disclosure provides methods of evoking an immune response specific for a senescent cell in a subject using an immunogen comprising antigen-presenting cells (APCs), e.g., dendritic cells (DCs), that include senescent cell-associated antigens, for example, by being presented on the surface of the antigen-presenting cells.

Dendritic cells play a critical role in coordinating innate and adaptive immune responses. DCs are bone-marrow derived cells characterized by dendritic morphology and high mobility that are seeded in all tissues. DCs are specialized antigen presenting cells that are capable of capturing and processing antigens, migrating from the periphery to a lymphoid organ, and presenting the antigens in a MHC-restricted manner to naive T-cells (see, e.g., Banchereau & Steinman, 1998, *Nature* 392:245-252; Steinman et al., 2003, *Ann. Rev. Immunol.* 21:685-711). Immature DCs are capable of processing and presenting antigens, which leads to immune regulation and/or suppression. Maturation (activation) of DCs is required to induce differentiation of antigen-specific T cells into effector T cells (see, e.g., Palucka et al., 2012, *Nat. Rev. Cancer* 12:265-277). Mature DCs express high levels of MHC-antigen complex and other co-stimulatory molecules, such as CD40, B7-1, B7-2, and CD1a (see, e.g., Steinman, 1991, *Ann. Rev. Immunol.* 9:271-296; Banchereau & Steinman, 1998, *Nature* 392:245-252). These molecules play key roles in stimulating T cells. Due to their properties, DC-based vaccination strategies have been developed in cancer (see, e.g., Heiser et al., 2001, *Cancer Res.* 61:338; Heiser et al., 2001, *J. Immunol.* 166:2953; Milazzo et al., 2002, *Blood* 101:977; Zu et al., 2003, *Cancer Res.* 63:2127). Likewise, DC based immunogens (vaccines) may be able to elicit $CD8^+$ T cells capable of recognizing peptide-MHC Class complexes on senescent cells and target them for destruction.

Dendritic cells may be obtained from various sources using methods known in the art. DC precursors may be purified from peripheral blood (see, e.g., Fong et al., 2003, *Annu Rev. Immunol.* 15:138). DCs may be also be differentiated from peripheral blood monocytes or $CD34^+$ hematopoietic progenitor cells ex vivo (see, e.g., Sallusto et al., 1994, *J. Exp. Med.* 179:1109; Banchereau et al., 2001, Cancer Res. 61:6451; Makensen et al., 2000, *Int. J. Cancer* 86:385). Methods for in vitro proliferation of dendritic cells from DC precursors and their use as immunogens are described in U.S. Pat. Nos. 5,851,756; 5,994,126; 6,475,483; and 8,283,163 each of which is incorporated herein by reference in its entirety. A method for isolating DCs from human peripheral blood is described in U.S. Pat. No. 5,643,786, incorporated herein by reference in its entirety. U.S. Patent Publication 2006/0063255, U.S. Patent Publication 2006/0057129, and U.S. Pat. No. 7,247,480, each of which is incorporated herein by reference in its entirety, describe methods for making dendritic cell vaccines from human embryonic stem cells.

Methods of isolating APCs, such as dendritic cells, are known in the art. Procedures such as repetitive density gradient separation, fluorescence activated cell sorting techniques, positive selection, negative selection, or a combination thereof are routinely used to obtain enriched populations of DCs. Methods for isolating DCs may be found in O'Doherty et al., 1993, *J. Exp. Med.* 178:1067-78; Young and Steinman, 1990, *J. Exp. Med.* 171:1315-32; Freudenthal et al., 1990, *Proc. Natl. Acad. Sci. USA* 57:7698-7702; Markowicz and Engleman, 1990, *J. Clin. Invest.* 85:955-961; Mehta-Damani et al, 1994, *J. Immunol.* 153:996-1003; Thomas et al., 1993, *J. Immunol.* 151:6840-6852.

Dendritic cells may be loaded with specific antigens ex vivo and then administered to a subject (see, e.g., Banchereau et al., 2005, *Nat. Rev. Immunol.* 5:296-306; Figdor et al., 2004, *Nat. Med.* 10:475-480, each of which is incorporated herein by reference in its entirety). Various methods for loading antigens to DCs have been described and are known in the art. RNA encoding a specific antigen may be pulsed into dendritic cells before administration to a subject by electroporation, cationic lipids, cationic peptides or using dendrimers (see, e.g., Boczkwoski et al. 1996, *J. Exp. Med.* 184:465; Heiser et al., 2001, *Cancer Res.* 61:338; Heiser et al., *J. Immunol.* 2001, 166:2953; U.S. Patent Publication 2006/0063255; Choi et al., 2005, *Cell Cycle* 4:669). DCs may also be loaded with protein or peptide that is purified or isolated from a target cell, chemically synthesized, or recombinantly expressed. Nucleic acid vectors encoding a specific antigen may also be used for DC loading (see, e.g., Frolkis et al., 2003, *Cancer Gene Ther.* 10:239). Exemplary vectors include plasmids, cationic lipid complexes, viral vectors, cDNA encoding antigen loaded onto dendrimers, or other small particulates that enhance uptake by phagocytic cells. U.S. Pat. No. 6,300,090 and U.S. Pat. No. 6,455,299 describe using non-replicating viral vectors comprising sequence encoding an antigen for infecting dendritic cells, resulting in antigen presentation on the DC surface.

Alternatively, DCs may be loaded with specific antigens in vivo. Antigens may be delivered directly to DCs using chimeric proteins that are comprised of a DC receptor-specific antibody fused to a selected antigen (see, e.g., Bonifaz et al., 2004, *J. Exp. Med.* 199:815-824; Bonifaz et al., 2004, *J. Exp. Med.* 196:1627-1638; Hawiger et al., 2001, *J. Exp. Med.* 194:769-780; each of which is incorporated herein by reference in its entirety). U.S. Patent Publication 2012/0070462, incorporated herein by reference in its entirety, describes targeted antigen delivery to dendritic cells using recombinant viral vectors comprising a polynucleotide encoding the antigen and a targeting molecule, which binds to a DC-specific surface marker (e.g., DC-SIGN).

In another variation on antigen loading, DCs may be fused with whole senescent cells to express a broad array of senescent cell-associated antigens. Dendritic cell fusion vaccines are known in the art and have been described in Rosenblatt et al., 2005, *Expert Opin. Biol. Ther.* 5:703-15; Rosenblatt et al., 2011, *Blood* 117:393-402; Gong et al., *Proc. Natl. Acad. Sci. USA* 97:2715-2718; Gong et al., 1997, *Nat. Med.* 3:558-561; U.S. Patent Publication 2004/0115224; U.S. Patent Publication 2005/0238627; and U.S. Patent Publication 2010/0278873, each of which is incorporated herein by reference its entirety.

Antigenic peptides useful for presentation by DCs for vaccination are peptides that stimulate a T cell mediated immune response (e.g., cytotoxic T cell response) by presentation to T cells on MHC molecules. Useful antigenic peptides and proteins for use in the present disclosure include those derived from senescent cells (e.g., senescent cell-associated antigens). Depending on the method of DC loading utilized, a senescent cell-associated antigen may be presented in a variety of forms. In some embodiments, a senescent cell-associated antigen is presented as a senescent cell lysate to DCs. In other embodiments, senescent cell-associated antigens are obtained by acid elution of peptides presented on MHC molecules of the senescent cell surface. For example, senescent cells are washed with an isotonic solution to remove media components. The cells are then treated with acid to dissociate peptides from surface MHCs, and the cells are removed from the solution containing the soluble peptides. Antigenic peptides may be obtained by chemical synthesis or produced using recombinant methods with host cells and vector expression systems. A senescent cell associated antigen may also be delivered as a polynucleotides (RNA or DNA) to a DC directly or indirectly (e.g., via a plasmid or viral vector). The antigenic peptides presented on MHC molecules are typically short peptides and may be 5, 6, 7, 8, 9, or 10 amino acids, for example.

A senescent cell associated antigen introduced into DCs may also be designed as a fusion peptide, wherein the antigen is joined to a protein or peptide sequence that enhances transport into endosomal and other intracellular compartments involved in Class II histocompatibility loading. For example, the N-terminus of such a fusion protein may comprise a suitable heterologous leader or signal sequence for the endosomal compartment and the C-terminus may comprise a transmembrane and luminal component of a member of the LAMP family for lysosomal targeting (see, e.g., U.S. Pat. No. 5,633,234; WO 02/080851; Sawada et al., 1993, *J. Biol. Chem.* 268:9014; each of which is incorporated by reference herein in its entirety). Endosomal and lysosomal sorting signals include tyrosine based signals, dileucine-based signals, acidic clusters, and transmembrane proteins labeled with ubiquitin (see, e.g., Bonifacino et al., 2003, *Annu. Rev. Biochem.* 72:395; U.S. Pat. No. 6,248,565).

Characterization of Immunogens

The immunogenicity of isolated senescent cell associated antigens, antigenic fragments, and fusion polypeptides, exosomes, cell membrane and organelle preparations, dendritic cell immunogens, and the products encoded by the polynucleotides described herein may be determined by using any one or more immunogenicity, immunochemistry, and/or cellular immune response assays, and non-human animal models routinely practiced in the art and described herein. For characterizing the immunogens described herein, use of polyclonal and/or monoclonal antibodies may be desired. The antibody may be obtained from or derived from an animal, for example, fowl (e.g., chicken) and mammals, which include but are not limited to a mouse, rat, hamster, rabbit, or other rodent, a cow, horse, sheep, goat, camel, human, or other primate. Polyclonal antisera are obtained from an animal by immunizing the animal with an immunogenic composition described herein.

Immunogenic compositions and SCAAgs may also be characterized in pre-clinical studies that evaluate the safety of the immunogenic composition to be administered to a subject. Ultimately, the safety and efficacy of immunogenic compositions will be determined by clinical studies, which are monitored by regulatory agencies.

Characterizing the immunogenic activity of an immunogen described herein may also be determined in art-accepted animal models. The capability of the immunogen to effectively induce an immune response in a subject can also be assessed in an animal model for the particular disease, disorder, or condition that is being treated or prevented by immunization. The immunogenicity of any one of the immunogens described herein may be determined by administering the immunogenic composition comprising the immunogen to a host (or subject, patient) according to immunization protocols described herein and in the art. Typically, after administering an initial dose of the immunogenic composition (also called the primary immunization) to a host, one, two or more doses of the immunogenic composition (also called boosting or booster doses) are administered.

To evaluate the immunogenicity of any one of the immunogenic compositions described herein, the immunogen may be administered to an animal by a parenteral (e.g., intravenous), intraperitoneal, intramuscular, intradermal, intraocular, or subcutaneous route. The immunogenic composition may further comprise a suitable adjuvant to enhance the immune response to the immunogen. See, e.g., Harlow et al., *Antibodies: A Laboratory Manual*, Cold Spring Harbor Laboratory (1988). Adjuvants typically used for immunization of non-human animals include but are not limited to Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, animals receive one or more booster immunizations according to a preferred schedule that may vary according to, inter alia, the immunogen, the adjuvant (if any) and/or the particular animal species. The B cell immune response may be monitored by periodically bleeding the animal, separating the sera from the collected blood, and analyzing the sera in an immunoassay, such as an ELISA or Ouchterlony diffusion assay, or the like, to determine the specific antibody titer. When an adequate antibody titer is established, the animals may be bled periodically to accumulate the polyclonal antisera.

In general, to monitor the immune response of an immunized host during pre-clinical studies in animals, sera is obtained from the animals prior to the first dose (i.e., pre-immune sera) and obtained after the final boosting dose. Sera may also be obtained after any one or more of the boosting doses between the primary dose and final boosting dose. To monitor the immune response of an immunized host during clinical studies or during post-marketing studies, sera may also be obtained from humans before the first immunization and after one or more administrations of the immunogenic compositions.

Production of senescent cell associated antigen-specific antibodies in an immunized host (including a human host) may include production of any class of immunoglobulin, including IgG, IgA, IgM, and/or IgE, and isotypes within the classes. The presence of specific IgG, IgM, IgE, and IgA may be detected in a biological sample (e.g., serum, nasal wash, lung lavage, or other tissues) obtained from an immunized host. For detection of antibodies in an immunoassay, the biological sample may be permitted to interact with or contact an antigen that is purified, isolated, partially isolated, or a fragment thereof, or to interact with or contact a senescent cell, which may be fixed (such as with ethanol or formaldehyde) or unfixed or non-denatured.

The immunogenicity of immunogens described herein may also be characterized by any number of assays and techniques practiced in the art, including immunoassays to evaluate binding and the capability of the immunogen to induce an immune response. By way of non-limiting example, immunoassays include ELISA, immunoblot, radioimmunoassay, immunohistochemistry, fluorescence activated cell sorting (FACS), Ouchterlony, and the like. Conditions for in vitro assays include temperature, buffers (including salts, cations, media), and other components that maintain the integrity of any cell used in the assay and the compound, which a person skilled in the art will be familiar and/or which can be readily determined. A person skilled in the art also readily appreciates that appropriate controls can be designed and included when performing the in vitro methods and in vivo methods described herein.

In vitro assay methods typically comprise contacting the biological sample with at least one source of the antigens described above and herein (particularly, e.g., an isolated senescence cell associated antigen or fragment thereof, a senescent cell or a lysate, membrane preparation or exosome comprising the antigen of interest) under conditions and for a time sufficient for an antibody in the sample to interact with the antigen source (i.e., mixing, combining, or in some manner permitting the biological sample and the antigen to interact). An antibody present in the biological sample that specifically binds to the antigen can be detected using any one of the exemplary detection methods described herein and in the art for detecting antibody-antigen binding. By way of non-limiting example, antibody bound to the antigen may be detected using a reagent specific for a conserved region of the antibody, such as the Fc portion of the antibody, which reagent is typically selected depending on the source of the antibody (i.e., whether the antibody is from an animal, such as a mouse, rat, goat, or sheep, etc. or whether the antibody is from a human). Such reagents typically comprise a detectable label, for example an enzyme, fluorescent label, luminescent label, or radioactive label. Additional exemplary reagents include those that detect a specific isotype or class of antibody. Many such reagents may be obtained from commercial sources.

Whether an immune response includes the capability to kill or clear senescent cells may be determined according to techniques and methods described herein and practiced in the art. An immune response that comprises selectively clearing a senescent cell or facilitating selective clearance of a senescent cell kills, removes, destroys, reduces viability, or decreases survival of a senescent cell (i.e., in some manner reduces the quantity of viable senescent cells in the animal or in the cell-based assay) in a statistically significant or biologically significant manner when compared with the immune response to kill, remove, clear, reduce viability, or decrease survival of a non-senescent cell. Such an immune response may therefore be useful for treating or preventing an age-related disease or disorder or another disease associated with or exacerbated by the presence of senescent cells. Transgenic animal models as described herein and in the art may be used to determine clearance of senescent cells (see, e.g., Baker et al., supra; *Nature,* 479:232-36 (2011); Int'l Patent Application Publication No. WO/2012/177927; Int'l Patent Application Publication No. WO 2013/090645). The transgenic animals by determining the level of a detectable label or labels that is expressed in senescent cells of the animal. Exemplary transgenic animal models contain a transgene that includes a nucleic acid that allows for controlled clearance of senescence cells (e.g., p16$^{ink4a}$ positive senescent cells). The transgene also nucleotide sequences includes a detectable label, for example, one or more of a red fluorescent protein; a green fluorescent protein; and one or more luciferases to detect clearance of senescent cells.

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta gal (SA-Bgal) (see, e.g., Dimri et al., *Proc. Natl. Acad. Sci. USA* 92: 9363-9367 (1995). The presence of the senescent cell-associated polypeptide p16 can be determined by any one of numerous immunochemistry methods practiced in the art, such as immunoblotting analysis. Expression of p16 mRNA in a cell can be measured by a variety of techniques practiced in the art including quantitative PCR. The presence and level of senescence cell associated polypeptides (e.g., polypeptides of the SASP) can be determined by using automated and high throughput assays, such as an automated Luminex array assay described in the art (see, e.g., Coppe et al., *PLoS Biol* 6: 2853-68 (2008)).

The presence of senescent cells can also be determined by detection of senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities. (see, e.g., Coppe et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005). ECM associated factors include inflammatory proteins and mediators of ECM remodeling and which are strongly induced in senescent cells (see, e.g., Kuilman et al., *Nature Reviews* 9:81-94 (2009)). Other senescent cell-associated molecules include extracellular polypeptides (proteins) described collectively as the DNA damage secretory program (DDSP) (see, e.g., Sun et al., *Nature Medicine* published online 5 Aug. 2012; doi: 10.1038/nm.2890).

Determining the effectiveness of an immune response to clear senescent cells as described herein in an animal model is typically performed using one or more statistical analyses with which a skilled person will be familiar. By way of example, statistical analyses such as two-way analysis of variance (ANOVA) may be used for determining the statistical significance of differences between animal groups treated with an agent and those that are not treated with the agent (i.e., negative control group). Statistical packages such as SPSS, MINITAB, SAS, Statistika, Graphpad, GLIM, Genstat, and BMDP are readily available and routinely used by a person skilled in the animal art.

Conditions for a particular assay including temperature, buffers (including salts, cations, media), and other components, which maintain the integrity of the antibodies within the pre-immune and immune sera and the integrity of the antigen (which may be an immunogenic peptide, dimeric peptide, or fusion polypeptide, M protein, Spa protein, or bacteria) used in the assay, are familiar to a person skilled in the art and/or which can be readily determined. A biological sample, such as serum, is contacted (mixed, combined with, or in some manner permitted to interaction) with the antigen, under conditions and for a time sufficient to permit interaction between the antigen and antibodies present in the sample. The interaction, or level of binding, of the antigen to an antibody present in an immune serum sample (or other biological sample) may be determined and compared to a level of binding of the respective antigen to antibodies present in a pre-immune sample (or an otherwise suitable negative control). An increase in the level of binding of the antigen to the immune serum sample compared with the pre-immune serum sample indicates that the immunogenic composition evoked production of specific antibodies. As noted herein, the level of binding of an immunogen to antibodies present in a sample from an immunized host is typically referred to in the art as the titer.

Adjuvants and Helper Antigens

The immunogenic compositions described herein may also comprise a suitable adjuvant. An adjuvant is intended to enhance (or improve, augment) the immune response to the immunogens described herein, including antigenic fragments and fusion polypeptides comprising the fragments (i.e., increase the level of the specific immune response in a statistically, biologically, or clinically significant manner compared with the level of the specific immune response in the absence of administering the adjuvant).

For administration in humans, a pharmaceutically acceptable adjuvant is one that has been approved or is approvable for human administration by pertinent regulatory bodies. For example, as discussed herein and known in the art, Complete Freund's adjuvant is not suitable for human administration. Desired adjuvants augment the response to the immunogen without causing conformational changes in the immunogen that might adversely affect the qualitative immune response. Suitable adjuvants include aluminum salts, such as alum (potassium aluminum sulfate), or other aluminum containing adjuvants such as aluminum hydroxide, aluminum phosphate, or aluminum sulfate. Other pharmaceutically suitable adjuvants include nontoxic lipid A-related adjuvants such as, by way of non-limiting example, nontoxic monophosphoryl lipid A (see, e.g., Persing et al., *Trends Microbiol.* 10:s32-s37 (2002)), for example, 3 De-O-acylated monophosphoryl lipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (see, e.g., Kensil et al., in *Vaccine Design: The Subunit and Adjuvant Approach* (eds. Powell and Newman, Plenum Press, N Y, 1995); U.S. Pat. No. 5,057,540). Other suitable adjuvants include oil in water emulsions, optionally in combination with immune stimulants, such as monophosphoryl lipid A (see, e.g., Stoute et al., *N. Engl. J. Med.* 336, 86-91 (1997)). Other suitable adjuvants include polymeric or monomeric amino acids such as polyglutamic acid or polylysine, liposomes, and CpG (see, e.g., Klinman, *Int. Rev. Immunol.* 25(3-4):135-54 (2006); U.S. Pat. No. 7,402,572; European Patent No. 772

619). CpG is often an adjuvant of choice when administering a polynucleotide that encodes a senescent cell associate antigen or antigenic fragment thereof (or a vector comprising the polynucleotide).

In another embodiment, the immunogenicity of an immunogen described herein may be enhanced by combining the immunogen with a helper antigen or carrier moiety. A helper antigen includes a T cell helper antigen, which is an antigen that is recognized by a T helper cell and evokes an immune response in a T helper cell. T helper cells are lymphocytes that are involved in activating and directing other immune cells such as cytotoxic T cells, B cells, and/or macrophages. Carrier moieties have been long known in the immunology art and include without limitation, keyhole limpet hemocyanin, bovine serum albumin, cationized BSA, or ovalbumin. For human use, toxoids of bacterial proteins (e.g., tetanus toxoid, diphtheria toxoid, cholera toxoid, and the like) are typically employed as carrier proteins.

In certain embodiments, the immunogen comprises at least one senescent cell associated antigen or at least one antigenic fragment thereof and a helper antigen or carrier moiety that is linked, conjugated, or attached to the antigen or antigenic fragment thereof. The helper antigen or carrier moiety may be recombinantly expressed in frame and directly linked to a senescent cell associated antigen or fragment thereof. In certain embodiments, a fusion protein comprising at least two senescent cell associated antigens or at least two antigenic fragments thereof or a combination of same may also comprise a helper antigen or carrier moiety. Alternatively, the helper antigen or carrier moiety may be chemically conjugated, linked, or attached to the senescent cell associated antigen or fragment thereof. In still another embodiment, the helper antigen or carrier moiety may be formulated together with any immunogen described herein but not covalently or non-covalently bound to the immunogen to form an immunogenic composition.

Co-Stimulatory Molecules

In another embodiment, the immunogenic compositions described herein (including those described above and immunogenic compositions comprising a recombinant antibody described below), include a co-stimulatory polypeptide. In certain embodiments, the immunogen comprises at least one senescent cell associated antigen or at least one antigenic fragment thereof and a co-stimulatory molecule that is linked, conjugated, or attached to the antigen or antigenic fragment thereof. The co-stimulatory molecule may be recombinantly expressed in frame and directly linked to a senescent cell associated antigen or fragment thereof. In certain embodiments, a fusion protein comprising at least two senescent cell associated antigen or at least two antigenic fragments thereof or a combination of same may also comprise a co-stimulatory molecule. Alternatively, the co-stimulatory molecule may be chemically conjugated, linked, or attached to the senescent cell associated antigen or fragment thereof. In still another embodiment, the co-stimulatory molecule may be formulated together with any immunogen described herein but not covalently or non-covalently bound to the immunogen to form the immunogenic composition.

Exemplary co-stimulatory molecules include, by way of example, GM-CSF, IL-2, IL-4, IL-6, IL-7, IL-15, IL-21, IL-23, TNFα, B7.1 (CD80), B7.2 (CD86), 41BB, CD40 ligand (CD40L), drug-inducible CD40 (iCD40), and the like. When an immunogenic composition comprises a polynucleotide encoding the co-stimulatory molecule, or a recombinant expression virus comprising the polynucleotide, expression of the co-stimulatory molecule is typically under the control of one or more regulatory elements selected to direct the expression of the coding sequences in a cell of choice, such as a dendritic cell.

Recombinantly engineered antigen-presenting cells such as dendritic cells, for example, may be modified by recombinant technology to express increased levels of antigen presenting machinery, adhesion and/or co-stimulatory molecules, including MHC class I/antigen complexes, MHC class II/antigen complexes, CD1, hsp70-90, CD9, CD63, CD81, CD11b, CD11c, CD40, CD54 (ICAM-1), CD63, CD80, CD86, 41BBL, OX40L, chemokine receptor CCR1-10 and CXCR1-6, mannose-rich C-type lectin receptor DEC205 and Toll-like receptors TLR4 and TLR9 or membrane-bound TGF-β. The exosomes derived from these recombinantly engineered antigen presenting cells will express these additional molecules and can transfer them to the T helper cells, T regulatory cells, or dendritic cells upon absorption.

Processes for Preparing Senescent Cell Associated Antigens, Fragments, and Polynucleotides Peptides and polypeptides may be chemically synthesized by manual techniques or by automated procedures. By way of example, solid phase polypeptide synthesis has been performed since the early 1960's. Numerous improvements to synthesis methods have been developed, and many methods have been automated and chemistries have been developed to protect the terminal ends and other reactive groups (see, e.g., Geysen et al., *J. Immun. Meth.* 102:259-274 (1987); Miranda et al., *Proc. Natl. Acad. Sci. USA* 96:1181-86 (1999); Frank et al., *Tetrahedron* 44:6031-6040 (1988); Hyrup et al., *Bioorg. Med. Chem.* 4:5-23 (1996); Perry-O'Keefe et al., *Proc. Natl. Acad. Sci. USA* 93:14670-675 (1996); Schnolzer, et al. *Int. J. Pept. Protein Res.* 40, 180-193 (1992); Hackeng et al., *Proc. Natl. Acad. Sci. USA* 94:7845-50 (1997); Creighton, T. E. Protein: Structures and Molecular Properties, pp. 55-60, W. H. Freeman and Co., New York, N.Y. (1984)). Equipment for automated synthesis of polypeptides is commercially available and may be operated according to the manufacturer's instructions. Synthesized peptides, polypeptides, and fusion polypeptides may also be obtained from any number of different custom peptide synthesizing manufacturers. If required, synthesized peptides or polypeptides may be purified using preparative reverse phase chromatography, affinity chromatography partition chromatography, gel filtration, gel electrophoresis, or ion-exchange chromatography or other methods used in the art.

Polynucleotides may also be chemically synthesized or may be constructed by recombinant methods familiar to a person skilled in the art. Polynucleotides can also be synthesized using an automatic synthesizer. The nucleotide sequence can be designed with the appropriate codons for the particular amino acid sequence desired. In general, preferred codons may be selected for the intended host in which the nucleotide sequence will be expressed. One recombinant method of preparing a polynucleotide includes assembly from overlapping oligonucleotides prepared by standard methods to provide a complete coding sequence (see, e.g., Au et al., *Biochem. Biophys. Res. Commun.* 248:200-203 (1998); Stemmer et al., *Gene* 164:49-53 (1995); Ausubel et al. (eds.), *Current Protocols in Molecular Biology*, (Greene Publ. Assoc. Inc. & John Wiley & Sons, Inc., 1993)); Sambrook et al., et al. *Molecular Cloning: A Laboratory Manual,* 3rd Ed., (Cold Spring Harbor Laboratory 2001; and elsewhere). Methods for purifying polynucleotides after either chemical synthesis or recombinant synthesis are known to persons skilled in the art (see, e.g., Ausubel et al., supra; Sambrook et al., supra).

Chemical synthesis of oligonucleotides for primers and probes has long been practiced in the art. Improved methods for synthesizing oligonucleotides and polynucleotides, which provide more rapid results, greater yields, and longer polynucleotides, have since been developed and automated (see, e.g., Gao et al., *Biopolymers* 73:579-96 (2004); Mueller et al., *Chem. Biol.* 16:337-47 (2009); Lee et al., *Nucleic Acids Res.* 38:2514-21 (2010)). Polynucleotides that encode the senescent cell-associated antigen, antigenic fragments thereof, and fusion polypeptides described herein may be synthesized commercially (see, e.g., GENSCRIPT, Piscataway, N.J.).

Polynucleotides that encode a senescent cell-associated antigen, antigenic fragment thereof, or fusion polypeptide described herein may be recombinantly expressed in a variety of different host cells. Host cells containing recombinant expression constructs may be genetically engineered (transduced, transformed, or transfected) with the vectors and/or expression constructs (for example, a cloning vector, a shuttle vector, or an expression construct). The vector or construct may be in the form of a plasmid, a viral particle, a phage, etc. The engineered host cells can be cultured in conventional nutrient media modified as appropriate for activating promoters, selecting transformants, or amplifying particular genes or encoding-nucleotide sequences. Selection and maintenance of culture conditions for particular host cells, such as temperature, pH and the like, will be readily apparent to the ordinarily skilled artisan. In general, the desired host cell is one that can be adapted to sustained propagation in culture to yield a stable cell line that can express sufficient amount of the desired peptide, polypeptide, or fusion protein. In certain embodiments, the cell line is an immortal cell line, which refers to a cell line that can be repeatedly passaged (at least ten times while remaining viable) in culture following log-phase growth. In other embodiments the host cell used to generate a cell line is a cell that is capable of unregulated growth, such as a cancer cell, or a transformed cell, or a malignant cell.

Useful bacterial expression constructs are prepared by inserting into an expression vector a structural DNA sequence encoding the desired peptide, polypeptide, or fusion protein together with suitable translation initiation and termination signals in an operative reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as the plasmid or vector is replicable and viable in the host. Thus, for example, the polynucleotides as provided herein may be included in any one of a variety of expression vector constructs as a recombinant expression construct for expressing the senescent cell-associated antigen, antigenic fragment thereof, or fusion polypeptide. Such vectors and constructs include chromosomal, nonchromosomal, and synthetic DNA sequences, e.g., bacterial plasmids; phage DNA; baculovirus; yeast plasmids; vectors derived from combinations of plasmids and phage DNA; viral DNA, such as vaccinia, adenovirus, fowl pox virus, and pseudorabies.

The appropriate DNA sequence(s) may be inserted into the vector by a variety of procedures with which the skilled person is familiar. In certain instances, the DNA sequence is inserted into an appropriate restriction endonuclease site(s) by procedures known in the art. Omission of restriction sites and the amino acid sequence encoded by the restriction site is contemplated herein and is intended to remove the possibility that a desired immunogenic epitope will be adversely altered or that an epitope will be inadvertently added that may have an undesirable immunogenicity. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)) and in Sambrook et al. (*Molecular Cloning: A Laboratory Manual*, 3rd Ed., (Cold Spring Harbor Laboratory 2001)).

The DNA sequence encoding a peptide, polypeptide, or fusion polypeptide in the expression vector is operatively linked to at least one appropriate expression control sequences (e.g., a promoter or a regulated promoter) to direct mRNA synthesis. Representative examples of such expression control sequences include LTR or SV40 promoter, *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lacI, lacZ, T3, T5, T7, gpt, lambda $P_R$, $P_L$, and trp. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a polynucleotide described herein is well within the level of ordinary skill in the art.

Design and selection of inducible, regulated promoters and/or tightly regulated promoters are known in the art and will depend on the particular host cell and expression system. The pBAD Expression System (Invitrogen Life Technologies, Carlsbad, Calif.) is an example of a tightly regulated expression system that uses the *E. coli* arabinose operon ($P_{BAD}$ or $P_{ARA}$) (see Guzman et al., *J. Bacteriology* 177:4121-30 (1995); Smith et al., *J. Biol. Chem.* 253:6931-33 (1978); Hirsh et al., *Cell* 11:545-50 (1977)), which controls the arabinose metabolic pathway. A variety of vectors employing this system are commercially available. Other examples of tightly regulated promoter-driven expression systems include PET Expression Systems (see U.S. Pat. No. 4,952,496) available from Stratagene (La Jolla, Calif.) or tet-regulated expression systems (Gossen et al., *Proc. Natl. Acad. Sci. USA* 89:5547-51 (1992); Gossen et al., *Science* 268:1766-69 (1995)). The pLP-TRE2 Acceptor Vector (BD Biosciences Clontech, Palo Alto, Calif.) is designed for use with CLONTECH's Creator™ Cloning Kits to rapidly generate a tetracycline-regulated expression construct for tightly controlled, inducible expression of a gene of interest using the site-specific Cre-lox recombination system (see, e.g., Sauer, *Methods* 14:381-92 (1998); Furth, *J. Mamm. Gland Biol. Neoplas.* 2:373 (1997)), which may also be employed for host cell immortalization (see, e.g., Cascio, *Artif. Organs* 25:529 (2001)).

Processes for producing a senescent cell-associated antigen in a host cell comprising a recombinant expression encoding the antigen may be scaled to manufacture large amounts. In another embodiment, a method of manufacture of the immunogenic compositions described herein is provided. Methods of manufacture comprise combining or mixing together the desired senescent cell-associated antigen, antigenic fragment thereof, or fusion polypeptides, polynucleotides, recombinant expression vectors, senescent cell membrane preparation, a senescent cell organelle preparation, exosome of the senescent cell, modified dendritic cell, or recombinant antibody to provide the immunogenic compositions described herein. The methods of manufacture may further comprise combining or mixing one or more physiologically suitable (or pharmaceutically suitable) excipients as described herein. The methods may further comprise combining or mixing the immunogenic composition comprising the desired immunogen with a pharmaceutically suitable adjuvant. At least one pharmaceutically suitable excipient may also be combined or mixed with the immunogenic composition comprising an adjuvant. In still further embodiments, a method of manufacture comprises chemical synthesis or recombinant production of the desired peptides, polypeptides, or fusion polypeptides. Chemical synthesis and recombinant production of the senescent cell-associated antigen, antigenic fragment thereof, and fusion polypeptides are described in detail herein. During manufacture of each immunogen, appropriate manufactures processes (such as Good Manufacturing Practices (GMP)) as required by a regulatory agency are employed. In addition, persons skilled in the art are familiar with techniques and steps to be taken for maintaining stability and integrity of the peptides or fusion polypeptides during manufacture of an immunogenic composition.

A process is provided herein for producing an immunogenic composition (or vaccine) that comprises at least one senescent cell-associated antigen. Into a first host cell a recombinant expression vector is introduced (transfected, transduced, transformed) wherein the vector comprising at least one regulatory expression sequence operatively linked to a nucleotide sequence that encodes a first senescent cell-associated antigen, or an antigenic fragment thereof. If the immunogenic composition will comprise a second senescent cell-associated antigen, a second host cell is transfected, transduced, transformed with a second recombinant expression vector comprising at least one regulatory expression sequence operatively linked to a nucleotide sequence that encodes a second senescent cell-associated antigen, or an antigenic fragment thereof. Each host cell is separately cultured in a medium for a time sufficient and under conditions appropriate for maximizing production of the antigen. Such conditions, which can readily be determined by a person skilled in the art, include maintaining the proper temperature, nutrient level, carbon dioxide level, cell density, atmospheric pressure, and removing waste in a timely manner. The respective antigens are then isolated from the host cell culture. Typically, the cells are harvested (i.e., separated) from the culture by methods practiced in the art such as centrifugation or filtration or a combination thereof. If the antigen is secreted by the host cell, the cell culture medium (also called spent medium) may be concentrated, followed by isolation of the antigen by any one of a number of isolation methods, including any number of chromatography methods and gel electrophoresis. Alternatively, if the antigen is not secreted by the host cell, the cells may be fractionated or lysed or the antigen may form inclusion bodies in the cell, which inclusion bodies are then isolated according to techniques known in the art. Once the senescent cell associated antigen is isolated, it may be formulated with one or more pharmaceutically acceptable excipients. If the immunogenic composition comprises more than one senescent cell associated antigen or fragment thereof, each antigen may be formulated separately with an excipient or the two antigens may be formulated together in the same vessel with a pharmaceutically acceptable excipient.

Passive Immunization—Recombinant Antibodies

Also provided herein are polyclonal and monoclonal antibodies that specifically bind to a senescent cell associated antigen for use in passive immunotherapeutic methods. An antibody that specifically binds to a senescent cell associated antigen (or antigenic fragment thereof, or fusion protein comprising same, or a senescent cell expressing the antigen) may belong to any immunoglobulin class, for example IgG, IgE, IgM, IgD, or IgA. The antibody may be obtained from or derived from an animal, for example, fowl (e.g., chicken) and mammals, which include but are not limited to a mouse, rat, hamster, rabbit, or other rodent, a cow, horse, sheep, goat, camel, human or other primate. The antibody may be an internalising antibody. The antibody may be a monoclonal antibody, which includes a monoclonal antibody derived from any human or non-human animal, a chimeric antibody, humanized antibody, or an antigen-binding fragment thereof.

In a particular embodiment, a recombinant antibody that specifically binds to a senescent cell-associated antigen of interest is provided. The recombinant antibody comprises at least one immunoglobulin variable region domain that specifically binds to a senescent cell-associated antigen. In certain embodiments, the recombinant antibody further comprises a modified human Fc region that exhibits enhanced affinity for an Fcγ receptor. In one embodiment the senescent cell-associated antigen is selected from Table 1 provided below. In certain other embodiments, the senescent cell-associated antigen is encoded by a nucleic acid sequence selected from Table 2 or Table 3. In another specific embodiment, the senescent cell-associated antigen is p16INK4a, for example, murine, human, or rat p16INK4a.

A recombinant antibody as described herein comprises at least one variable region domain. The at least one immunoglobulin variable region domain may comprise either the heavy chain variable region. The variable region domain may be of any size or amino acid composition and will generally comprise at least one hypervariable amino acid sequence responsible for antigen binding and which is adjacent to or in frame with one or more framework sequences. In general terms, the variable (V) region domain may be any suitable arrangement of immunoglobulin heavy ($V_H$) and/or light ($V_L$) chain variable domains. In other embodiments, the recombinant antibodies described herein comprise (1) an Fv fragment consisting of the variable regions of both the heavy and light chains, (2) recombinant single chain polypeptide molecules in which light and heavy variable regions are connected by a peptide linker (scFv proteins); or (3) minimal recognition units consisting of the amino acid residues that mimic the hypervariable region. An Fv region is defined in the immunoglobulin art as the N-terminal portion of an Fab fragment of the immunoglobulin and includes the $V_H$ (variable heavy chain) and $V_L$ (variable light chain) regions that are bound together by non-covalent interactions. Each $V_H$ comprises three complementarity determining regions (CDRs; heavy chain CDR1, CDR2, and CDR3) and each $V_L$ comprises three CDRs (light chain CDR1, CDR2, and CDR3). Thus, for example, the V region domain may be monomeric and be a $V_H$ or $V_L$ domain, which is capable of independently binding antigen with acceptable affinity. Alternatively, the V region domain may be dimeric and contain $V_H$-$V_H$, $V_H$-$V_L$, or $V_L$-$V_L$, dimers. Preferably, the V region dimer comprises at least one $V_H$ and at least one $V_L$ chain that are non-covalently associated (hereinafter referred to as $F_v$). If desired, the chains may be covalently coupled either directly, for example via a disulfide bond between the two variable domains, or through a linker, for example a peptide linker, to form a single chain Fv (scF$_v$).

An immunoglobulin variable region may be derived from a monoclonal antibody or polyclonal antibody that specifically binds to a senescent cell associated antigen. Monoclonal and polyclonal antibodies may generally be prepared by any of a variety of techniques known to persons having ordinary skill in the art. See, e.g., Harlow et al., *Antibodies: A Laboratory Manual*, Cold Spring Harbor Laboratory (1988); Peterson, *ILAR J.* 46:314-19 (2005)); Green et al., "Production of Polyclonal Antisera," in *Immunochemical Protocols* (Manson, ed.), pages 1-5 (Humana Press 1992); Harlow et al., *Antibodies: A Laboratory Manual*, Cold Spring Harbor Laboratory (1988); Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995)). Suitable animals include, for example, rabbits, sheep, goats, pigs, cattle, subhuman primates and may also include smaller mammalian species, such as mice, rats, and hamsters, or other species (see, e.g., International Patent Application Publication No. WO 91/11465 (1991) and in Losman et al., *Int. J. Cancer* 46:310, 1990). Monoclonal antibodies that specifically bind to the senescent cell associated antigen of interest and hybridomas, which are examples of immortal eukaryotic cell lines, that produce monoclonal antibodies having the desired binding specificity, may be prepared, for example, using the technique of Kohler and Milstein (*Nature*, 256: 495-97 (1976), *Eur. J. Immunol.* 6:511-19 (1975)) and improvements thereto (see, e.g., Coligan et al. (eds.), *Current Protocols in Immunology*, 1:2.5.1-2.6.7 (John Wiley & Sons 1991); U.S. Pat. Nos. 4,902,614, 4,543,439, and 4,411,993; *Monoclonal Antibodies, Hybridomas: A New Dimension in Biological Analyses*, Plenum Press, Kennett et al. (eds.) (1980); and *Antibodies: A Laboratory Manual*, Harlow and Lane (eds.), Cold Spring Harbor Laboratory Press (1988); see also, e.g., Brand et al., *Planta Med.* 70:986-92 (2004); Pasqualini et al., *Proc. Natl. Acad. Sci. USA* 101: 257-59 (2004)).

An antibody that specifically binds to the senescent cell associated antigen of interest may be derived from a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes) (see, e.g., U.S. Pat. No. 4,464,456; see also, e.g., Glasky et al., *Hybridoma* 8:377-89 (1989)); in vitro immunization of human B cells (see, e.g., Boerner et al., *J. Immunol.* 147:86-95 (1991)); fusion of spleen cells from immunized transgenic mice carrying inserted human immunoglobulin genes (see, e.g., Green et al., *Nature Genet.* 7:13 (1994); Lonberg et al., *Nature* 368:856 (1994); Taylor et al., *Int. Immun.* 6:579 (1994); U.S. Pat. No. 5,877,397; Bruggemann et al., *Curr. Opin. Biotechnol.* 8:455-58 (1997); Jakobovits et al., *Ann. N. Y. Acad. Sci.* 764:525-35 (1995)); isolation from human immunoglobulin V region phage libraries; cloning the light chain and heavy chain variable regions from a B cell that is producing an anti-cellular polypeptide antibody (WO 92/02551; U.S. Pat. No. 5,627,052; Babcook et al., *Proc. Natl. Acad. Sci. USA* 93:7843-48 (1996)); or other procedures as known in the art and based on the disclosure herein.

The Fv region may further comprise one or all of the framework regions that comprise the variable region of an immunoglobulin. If the Fv region is derived from a non-human antibody, and framework regions are included in the recombinant antibody, the antibody may be further genetically engineered to create a "humanized" antibody. Such a humanized antibody may comprise a plurality of CDRs derived from an immunoglobulin of a non-human mammalian species, at least one human variable framework region. Useful strategies for designing humanized antibodies include, by way of illustration and not limitation, identification of human variable framework regions that are most homologous to the non-human framework regions of the chimeric antibody (see, e.g., Jones et al., *Nature* 321:522-25 (1986); Riechmann et al., *Nature* 332:323-27 (1988)). Designing a humanized variable region may include determining CDR loop conformations and structural determinants of the non-human variable regions, for example, by computer modeling, and then comparing the CDR loops and determinants to known human CDR loop structures and determinants (see, e.g., Padlan et al., *FASEB* 9:133-39 (1995); Chothia et al., *Nature*, 342:377-83 (1989)). Computer modeling may also be used to compare human structural templates selected by sequence homology with the non-human variable regions (see, e.g., Bajorath et al., *Ther. Immunol.* 2:95-103 (1995); EP-0578515-A3; Davies et al., *Ann. Rev. Biochem.* 59:439-73, (1990)). If humanization of the non-human CDRs results in a decrease in binding affinity, computer modeling may aid in identifying specific amino acid residues that could be changed by site-directed or other mutagenesis techniques to partially, completely, or supra-optimally (i.e., increase to a level greater than that of the non-humanized antibody) restore affinity. Those having ordinary skill in the art are familiar with these techniques and will readily appreciate numerous variations and modifications to such design strategies.

A minimal recognition unit is an antibody fragment comprising a single complementarity-determining region (CDR). Such CDR peptides can be obtained by constructing polynucleotides that encode the CDR of an antibody of interest according to methods practiced by persons of ordinary skill in the art (see, for example, Larrick et al., *Methods: A Companion to Methods in Enzymology* 2:106, (1991); Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)). Alternatively, such CDR peptides and other antibody fragment can be synthesized using an automated peptide synthesizer.

In other embodiments, a minimal recognition unit may be identified from a peptide library. Such peptides may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833). In phage display peptide libraries, random peptide sequences are fused to a phage coat protein such that the peptides are displayed on the external surface of a filamentous phage particle.

A peptide that is a minimal recognition unit or a CDR (i.e., any one or more of three CDRs present in a heavy chain variable region and/or one or more of three CDRs present in a light chain variable region) may be identified by computer modeling techniques, which can be used for comparing and predicting a peptide sequence that will specifically bind the senescent cell-associated antigen of interest (see, e.g., Bradley et al., *Science* 309:1868 (2005); Schueler-Furman et al., *Science* 310:638 (2005)). Such computer-assisted predictive modeling techniques may also be useful for altering the binding affinity of an antibody. Amino acid substitutions may be readily accomplished using any one of a number of mutagenesis techniques described herein and used routinely in the art for making polynucleotide and polypeptide variants.

According to certain embodiments, non-human, human, or humanized heavy chain and light chain variable regions of any of the immunoglobulin molecules described herein may be constructed as scFv polypeptide fragments (single chain antibodies). See, e.g., Bird et al., *Science* 242:423-426 (1988); Huston et al., *Proc. Natl. Acad. Sci. USA* 85:5879-83 (1988)). Multi-functional scFv fusion proteins may be generated by linking a polynucleotide sequence encoding an scFv polypeptide in-frame with at least one polynucleotide sequence encoding any of a variety of known effector proteins. These methods are known in the art, and are disclosed, for example, in EP-B1-0318554, U.S. Pat. No. 5,132,405, U.S. Pat. No. 5,091,513, and U.S. Pat. No. 5,476,786. By way of example, effector proteins may include immunoglobulin constant region sequences. See, e.g., Hollenbaugh et al., *J. Immunol. Methods* 188:1-7 (1995). Other examples of effector proteins are enzymes. As a non-limiting example, such an enzyme may provide a biological activity for therapeutic purposes (see, e.g., Siemers et al., *Bioconjug. Chem.* 8:510-19 (1997)), or may provide a detectable activity, such as horseradish peroxidase-catalyzed conversion of any of a number of well-known substrates into a detectable product, for diagnostic uses.

Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246: 1275-81 (1989); Schlebusch et al., *Hybridoma* 16:47-52 (1997) and references cited therein; Rader et al., *J. Biol. Chem.* 275:13668-76 (2000); Popkov et al., *J. Mol. Biol.* 325:325-35 (2003); Andris-Widhopf et al., *J. Immunol. Methods* 242:159-31 (2000)). Antibodies isolated from non-human species or non-human immunoglobulin libraries may be genetically engineered according to methods described herein and known in the art to humanize the antibody or fragment thereof. Immunoglobulin variable region gene combinatorial libraries may be created in phage vectors that can be screened to select immunoglobulin fragments (Fab, Fv, scFv, or multimers thereof) that bind specifically to the senescent cell associated antigen of interest (see, e.g., U.S. Pat. No. 5,223,409; Huse et al., *Science* 246:1275-81 (1989); Sastry et al., *Proc. Natl. Acad. Sci. USA* 86:5728-32 (1989); Alting-Mees et al., *Strategies in Molecular Biology* 3:1-9 (1990); Kang et al., *Proc. Natl. Acad. Sci. USA* 88:4363-66 (1991); Hoogenboom et al., *J. Molec. Biol.* 227:381-388 (1992); Schlebusch et al., *Hybridoma* 16:47-52 (1997) and references cited therein; U.S. Pat. No. 6,703,015).

In certain other embodiments, antibodies are multimeric antibody fragments. Useful methodologies are described generally, for example in Hayden et al., *Curr Opin. Immunol.* 9:201-12 (1997) and Coloma et al., *Nat. Biotechnol.* 15:159-63 (1997). For example, multimeric antibody fragments may be created by phage techniques to form miniantibodies (U.S. Pat. No. 5,910,573) or diabodies (Holliger et al., *Cancer Immunol. Immunother.* 45:128-30 (1997)). Multimeric fragments may be generated that are multimers of a viral coat protein-specific Fv. Multimeric antibodies include bispecific and bifunctional antibodies comprising a first Fv specific for an antigen (e.g., E-selectin) associated with a second Fv having a different antigen specificity (see, e.g., Drakeman et al., *Expert Opin. Investig. Drugs* 6:1169-78 (1997); Koelemij et al., *J. Immunother.* 22:514-24 (1999); Marvin et al., *Acta Pharmacol. Sin.* 26:649-58 (2005); Das et al., *Methods Mol. Med.* 109:329-46 (2005)). In an exemplary embodiment, the recombinant antibody comprises at least two Fv regions (bivalent), and in other embodiments may comprise 3 or more Fv regions (i.e., multivalent). In certain embodiments, the bivalent and multivalent Fv regions each specifically bind to different senescent cell associated antigens; in other embodiments, the bivalent and multivalent regions each bind to different epitopes of the same senescent cell associated antigen. By way of non-limiting example, a bivalent recombinant antibody comprises an Fv region specific for human or mouse p16INK4a and a second Fv region that is specific for a different SCAAg (e.g., a SCAAg listed in Table 1 or a SCAAg that is encoded by a nucleotide sequence selected from Table 2 or Table 3).

Immunoglobulin framework and constant region sequences are available in the art, for example, in Kabat et al. (in *Sequences of Proteins of Immunological Interest*, 4th ed., (U.S. Dept. of Health and Human Services, U.S. Government Printing Office, 1991); see also Kabat databases available on the Internet). In a particular embodiment, the recombinant antibody comprises an Fc (constant region) derived from a human immunoglobulin. In a more specific embodiment, the Fc regions is derived from an immunoglobulin class, such as IgG, that mediates effector functions that facilitate clearance of a senescence cell from a tissue of a subject immunized with an immunogenic composition described herein, Antibodies that bind to specific cell-surface antigens on target cells (e.g., a senescent cell) can induce cytotoxicity via effector functions of antibody-dependent cellular cytotoxicity (ADCC), antibody-dependent cell-mediated phagocytosis, and complement-dependent cytotoxicity (CDC) through the Fc region of the antibody, and apoptosis of target cells directly (see, e.g., Shan et al., 2000, *Cancer Immunol. Immunother.* 48:673-683; Carter et al., 2001, *Nat. Rev. Cancer* 1:118-129; Glennie et al., 2003, *Drug Discov. Today* 8:503-510; Smith et al., 2003, *Oncogene* 22:7359-7368; Weiner and Carter, 2005, *Nat. Biotechnol.* 23:556-7). The cell mediated reaction where non-specific cytotoxic cells that express Fcγ receptors recognize bound antibody on a target cell and subsequently causes lysis of the target cell is known as antibody dependent cell mediated cytotoxicity (ADCC) (see, e.g., Raghavan et al., 1996, *Annu. Rev. Cell. Dev. Biol.* 12:181-220). Another important Fc ligand is the complement protein C1q, the binding of which mediates complement dependent cytotoxicity (see, e.g., Ward et al, 1995, *Ther. Immunol.* 2:77-94). Binding of C1q to at least two IgGs is sufficient to activate the classical complement cascade, causing osmotic lysis of target cells. Animal models and clinical trials suggest an important role for Fc receptors and ADCC in clinical efficacy of antibody therapies (see, e.g., Clynes et al., 2000, *Nat. Med.* 6:443-446; de Haij et al., 2010, *Cancer Res.* 70:3209-3217; Weng and Levy, 2003, *J. Clin. Oncol.* 21:3940-3947). In certain embodiments, antibody therapies specific for a senescent cell associated antigen may be modified to enhance ADCC activity.

For IgG antibodies, ADCC and ADCP require the engagement of the Fc region of an antibody that is bound to the surface of a target cell with Fcγ receptors (FcγRs) (see, e.g., Cohen-Solal et al., 2004, *Immunol. Lett.* 92:199-205). In humans, FcγRs comprise FcγRI (CD64); FcγRII (CD32), including FcγRIIa, FcγRIIb, and FcγRIIc isoforms; and FcγRIII (CD16), including FcγRIIIa and FcγRIIIb isoforms (see, e.g., Jefferis et al., 2002, *Immunol. Lett.* 82:57-65; Raghavan et al., 1996, *Annu. Rev. Cell Dev. Biol.* 12:181-220). FcγRs are expressed on a variety of immune cells. Binding of Fc/FcγR complex recruits these cells to sites of bound antigen, resulting in signaling and subsequent immune responses such as release of inflammation mediators, activation of B cells, endocytosis, phagocytosis, and cytoxicity. FcγRs have varying affinity for the same Fc region (FcγRI high, FcγRII and FcγRIII low). While FcγRI, FcγRIIa/c, and FcγRIII are activating receptors characterized by an intracellular immunoreceptor tyrosine-based activation motif (ITAM), FcγRIIb has an intracellular immunoreceptor tyrosine-based inhibition motif (ITIM) and is accordingly an inhibitor receptor.

IgG molecules comprise an N-linked oligosaccharide covalently linked at a conserved N297 (EU numbering system, Kabat et al., supra) residue of each of the CH2 domains of the Fc region. The oligosaccharides found in the Fc region of serum IgGs are mostly biantennary glycans of the complex type. Variations of IgG glycosylation patterns include attachment of terminal sialic acid, a third GlcNAc arm (bisecting GlcNAc), a terminal galactosylation, and α-1,6-linked core fucosylation. Oligosaccharides may contain zero (G0), one (G1) or two (G2) galactoses. The precise pattern of glycosylation depends on the structural properties of IgG subcomponents, in particular, the CH2 and CH3 domains (see, e.g., Lund et al., 2000, *Eur. J. Biochem.* 267:7246-7257). The cell lines used for recombinant monoclonal antibody synthesis may also influence oligosaccharide chain synthesis. The oligosaccharide moiety of glycoproteins is initially synthesized by the cell from lipid-linked oligosaccharides to form $Glc_3Man_9GlcNAc_2$-pyrophosphoryl-dolichol, which is transferred to the protein in the endoplasmic reticulum. The oligosaccharide portion is then sequentially processed. First, all three glucose resides are removed by glucosidases I and II to yield $Man_9GlcNAc_2$-protein. Further removal of a number of mannose residues may occur. Initially, four α1,2-linked mannoses are removed to yield a $Man_5GlcNAc_2$-protein, which is then elongated by the addition of a N-acetylglucosamine (GlcNAc) residue, producing $GlcNAcMan_5GlcNAc_2$-protein. Mannosidase II then removes the α1,3- and α1,6-linked mannoses. Then, other sugars, GlcNAc, galactose, and sialic acid, are added sequentially to yield the complex structures often found on glycoproteins.

Methods of enhancing Fc receptor binding include Fc amino acid modification and modification of Fc carbohydrate structures. For immunoglobulins, it has been demonstrated that the attachment of an N-linked oligosaccharide to Asn-297 of the CH2 domain is critical for ADCC activity. Removal of the N-linked oligosaccharide through mutation of the N-linked consensus site or by enzymatic means results in little or no ADCC activity. Removal of the core α-1,6-fucose moiety from IgG1 Fc oligosaccharides has been demonstrated to improve FcγRIII binding and ADCC activity (see, e.g., Carter, 2001, *Nat. Rev. Cancer* 1:118-129; Kanda et al., *Glycobiology*, 2006, 17:104-118; Shields et al., 2002, *J. Biol. Chem.* 277:26733-26740; Shinkawa et al., 2003, *J. Biol. Chem.*, 2003, 278:3466-3473; Niwa et al., 2004, *Cancer Res.* 64:2127-2133). The level of another glycoform, bisected N-linked carbohydrate, has also been suggested to increase ADCC (see, e.g., Umana et al, 1999, *Nat. Biotechnol.* 17:176-180; Hodoniczky et al., 2005, *Biotechnol. Prog.* 21:1644-52)

Compositions and methods for producing antibody-based therapies with modified glycosylation pattern of the Fc region are known in the art. For example, inhibition or disruption of glycoprotein processing may be used to modify Fc glycosylation to enhance ADCC (see, e.g., Rothman et al., 1989, *Mol. Immunol.* 26:1113-23). Antibodies produced from castanospermine-treated hybridomas also exhibited enhanced ADCC by NK cells (see, e.g., Kaushal and Elbein, 1995, *Methods Enzymol.* 230:316-329, incorporated herein in its entirety). U.S. Pat. No. 8,071,336, incorporated herein in its entirety, describes methods of producing antibodies comprising oligomannose-type-N-glycans with enhanced ADCC and higher binding affinity for FcγRIIIA by culturing hybridomas in the presence of kifunesine. Antibody producing cells may be genetically modified to reduce/inhibit expression of enzymes involved in glycoprotein processing. WO2009/114641, incorporated herein in its entirety, describes antibody producing cells lacking GlcNAc transferase I, yielding antibodies with enhanced ADCC. Antibodies with lower fucosylated oligosaccharide and enhanced ADCC have been produced using hybridomas expressing lower α-1,6-fucosyltransferase (see, e.g., Shinkawa et al., 2003, *J. Biol. Chem.* 278:3466-3473; European Patent Applic. Pub. No. 1176195, each of which is incorporated herein by reference in its entirety). U.S. Pat. No. 7,931,895, incorporated herein in its entirety, describes antibodies with bi-antennary glycan structures with short chains, low degree of sialylation, and non-intercalated terminal mannoses and/or terminal GlcNAcs that have enhanced ADCC activity. U.S. Patent Publication 2011/0053223, incorporated herein in its entirety, describes methods for making antibodies with Man5 glycans.

A variety of Fc sequence variants with optimized binding affinity for FcγRs and/or enhanced ADCC have been described and are known in the art. By way of example, Fc S239D/I332E double mutants have been shown to have enhanced effector function (see, e.g., Lazar et al., 2006, *Proc. Natl. Acad. Sci.* 103:4005-4010, incorporated herein in its entirety). U.S. Patent Publication 2010/0297103, incorporated herein in its entirety, describes constant region positions for cysteine substitutions for enhancing ADCC. Lazar et al. described IgG1 Fc mutations of S298A, E333A, and K334A with optimized FcγR affinity and specificity (see, e.g., Shields et al., *J. Biol. Chem.* 276:6591-6604 (2001), incorporated herein in its entirety). U.S. Patent Publication 2006/0039904, incorporated herein by reference in its entirety, describes an IgG1 Fc region high effector function amino acid residue 332E, as well as a variety of other Fc residue substitutions for enhancing ADCC. U.S. Pat. No. 8,192,737, incorporated herein in its entirety, describes IgG Fc variants at position 396 with increased ADCC activity.

Also provided herein are methods of manufacture for producing an antibody, or antigen-binding fragment thereof, that specifically binds to a senescent cell associated antigen of interest. For example a process (or method) for manufacturing an antibody may comprise determining the nucleotide sequence that encodes the antibody by using standard molecular biology techniques, including primer design, hybridization, nucleic acid isolation, cloning, and amplification, and sequencing. A polynucleotide comprising a nucleotide sequence encoding the antibody, or antigen-binding fragment thereof, may be incorporated into a recombinant expression construct (i.e., vector) according to well-known methods and principles known in the molecular biology art and described herein for preparing a recombinant expression vector.

The nucleic acid molecules encoding the antibody or antigen binding fragment, as described herein, may be propagated and expressed according to any of a variety of routinely practiced procedures for nucleic acid excision, ligation, transformation, and transfection. Thus, in certain embodiments expression of the antibody or antigen binding fragment may be preferred in a prokaryotic host cell, such as *Escherichia coli* (see, e.g., Pluckthun et al., *Methods Enzymol.* 178:497-515 (1989)). In certain other embodiments, the antibody may be expressed in a eukaryotic host cell, including animal cells (including mammalian cells); yeast (e.g., *Saccharomyces cerevisiae, Schizosaccharomyces pombe,* and *Pichia pastoris*); or plant cells. Examples of suitable animal cells include, but are not limited to, myeloma, HEK293, COS, or CHO cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the cellular polypeptide may be inserted. The regulatory elements will vary as appropriate for the particular host.

Immune Response

An immune response that results in clearance (i.e., removal, elimination, destruction) of senescent cells may include a humoral or cellular immune response or both a humoral and cellular immune response. A humoral immune response has been generally described as a response in which antibodies (i.e., immunoglobulins) specific for antigens are produced by differentiated B lymphocytes. The Fc portion of the immunoglobulin mediates certain effector functions including activation of the classical complement cascade; interaction with effector cells; and compartmentalization of immunoglobulins. Destruction of senescent cells may therefore comprise antibody dependent cell-mediated cytotoxicity (ADCC) or complement fixation and associated complement dependent cytotoxicity (CDC).

Typically, ADCC involves activation of NK cells by antibodies. An NK cell expresses CD16 which is an Fc receptor. This receptor recognizes, and binds to, the Fc portion of an antibody, such as an IgG, which has bound to the surface of a target cell. The most common Fc receptor on the surface of an NK cell is called CD16 or FcγRIII. Once the Fc receptor binds to the Fc region of IgG, the NK cell releases cytokines such as IFN-γ, and cytotoxic granules containing perforin and granzymes that enter the target cell and promote cell death by triggering apoptosis. This is similar to, but independent of, responses by cytotoxic (CTLs).

Cell mediated responses involve various types of T lymphocytes that eliminate antigens, and cells expressing the antigens, by a variety of mechanisms. For example, CD4+ helper T cells that are capable of recognizing specific antigens may release soluble mediators such as cytokines to recruit additional cells of the immune system to participate in an immune response. CD8+ cytotoxic T cells are also capable of recognizing specific antigens and may bind to and destroy or damage an antigen-bearing cell or particle. Cell mediated immune responses also include a cytotoxic T lymphocyte (CTL) response and can be important for elimination of senescent cells.

As described herein, the immune response evoked by any one of the immunogens described herein may include a specific T cell response, a specific B cell response (i.e., production of specific antibodies), or both a specific T cell immune response and B cell immune response in the immunized subject. As used herein, the immune response is said to be "specific for," "specific to," or "specifically against" a senescent cell (i.e., specific for one or more senescence cell associated antigens) when the immune response is detectable at a level greater than the level against a non-senescent cell. Also as described herein, the immune response evoked by any one of the immunogens described herein may include production of specific antibodies in the immunized subject. Interaction or binding of an antibody to a specific antigen generally involves electrostatic interactions, hydrogen bonding, Van der Waals interactions, and hydrophobic interactions. Any one of these or any combination thereof can play a role in the binding between an antibody and its antigen. As used herein, an antibody is said to be "specific for" or to "specifically bind" its cognate senescent cell associate antigen (or fragment thereof) or a senescent cell that expresses the antigen when the antibody reacts at a detectable level with the respective immunogen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. The ability of the antibody to bind to its cognate ligand may also be expressed as a dissociation constant $K_D$, and an antibody is said to specifically bind its cognate ligand if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of an antibody for a senescent cell associate antigen described herein, can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the surface plasmon resonance signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

The immunological status, including the presence, level, or extent of a specific immune response, of a subject before, during, and after active immunization with an immunogen described herein or passive immunization with a recombinant antibody described herein (or composition comprising the immunogen or antibody) may be monitored. Induction and production of cytokines and other immune modulators can be determined by methods and techniques routinely practiced in the art for determining the level of immune modulators and cytokines in a biological sample obtained from the subject before, during, and/or after treatment. An immune response, including activation and proliferation of immune cells and level of specific antibodies, in a subject may be determined by any number of well-known immunological techniques and methods with which those having ordinary skill in the art will be readily familiar. Such assays include, but need not be limited to, in vivo or in vitro determination of the presence or level of one or more cytokines (e.g., IFN-γ, IL-2, IL-4, and IL-12, and also IL-6, IL-1β, leukemia inhibitory factor, TNF-α, IL-10), lymphokines, chemokines, hormones, growth factors, and the like. Cellular activation state changes may also be determined, for example, by determining altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays may be found, for example, in Lefkovits (*Immunology Methods Manual: The Comprehensive Sourcebook of Techniques*, 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998)) and references cited therein. Immunoassays to determine the level of specific anti-senescent cell antigen antibodies in a subject are also routinely practiced in the art and described herein.

A "biological sample" may include a sample from a subject, and may be a blood sample (from which serum or plasma may be prepared), a biopsy specimen, one or more body fluids (e.g., lung lavage, ascites, mucosal washings, synovial fluid), bone marrow, lymph nodes, tissue explant, organ culture, or any other tissue or cell preparation from the subject or a biological source. A biological sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In certain embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

Animal models are also available for determining the effect of the immunogens described herein on age-sensitive traits. Such traits include for example T cell subset distribution, cataract formation, spontaneous activity, motor coordination, and cognitive capacity, physical function, body composition (e.g., sarcopenia, osteoporosis, loss of fat mass) and cardiac function. In animal models, physical function can be assessed, for example, by measuring running time, distance and work using a motorized treadmill, and grip strength using a grip meter, according to previously described protocols (e.g., Zhang et al., Animal Models of Inflammatory Pain, *Neuromethods*, Volume 49, Oct. 20, 2010, 23-40; Balkaya et al., Behavioral Testing in Mouse Models of Stroke, *Neuromethods*, Volume 47, 2010, 179-197). Lean mass, fat mass and bone mineral density can be assessed, for example, by QNMR and/or dual-energy X-ray absorptiometry measurements as previously described (e.g., Reed et al., *Physiology & Behavior*, Vol. 91, 2007, 593-600; Halldorsdottir et al., *Int. J. Body Compos. Res.*, 2009; 7(4), 147-154; Brommage et al., *AJP—Endo, Sep.* 1, 2003, Vol. 285, No. 3 E454-E459). Methods and techniques are also available for assessing many of these traits in human subjects.

Spontaneous activity of individual mice can be measured, for example, over a 48-hour period using comprehensive laboratory animal monitoring systems equipped with photocells (e.g., Columbus Instruments) as previously described (e.g., Handschin et al., J. Biol. Chem., Vol. 282, 41, 30014, Oct. 12, 2007; Pack et al., Physiol. Genomics (Sep. 19, 2006)). Motor coordination can be analyzed, for example, by performing an accelerating rotarod test. For measuring cognitive capacity, a modified Stone T-maze, which is sensitive to age-related changes in learning and memory, can be used. In animal models, illustrative age-sensitive traits and the benefit of immunization with an immunogenic composition described herein can be measured using tissues and organs of test and control mice, including fiber diameter analysis on gastrocnemius muscle, DNA damage analysis, analysis of renal and glomerulosclerosis, analysis for retinal atrophy, proteotoxic stress analysis, oxidative stress analysis, analysis of the hematopoietic system, and the like.

Methods of Treating Diseases, Disorders, and Conditions by Immunization

The immunogens, immunogenic compositions, and methods described herein are useful for treating diseases, disorders, and conditions that are treatable or preventable by clearing (i.e., removing, destroying, eliminating) senescent cells from a tissue in the subject receiving the immunization. Protocols for administering an immunogenic composition described herein may be readily established by a person skilled in the art. Typically, after administering an initial dose of an immunogenic composition comprising an immunogen (also called the primary immunization) to a subject, one, two or more doses of the immunogenic composition (also called boosting or booster doses) are administered. Administration of one or more booster immunizations may vary according to, inter alia, the immunogen, the adjuvant (if any), the co-stimulatory molecule (if any) and/or the particular animal species. As described herein, the level of an immune response (B cell, T cell, or both) after the first and each administration of an immunogen may be determined by methods described herein and in the art.

In certain embodiments, the immunogenic composition comprises a recombinant antibody(ies) that specifically bind to a SCAAg. The pharmacokinetics and clearance of the antibody can be monitored by using any one or more of the immunoassays described herein and routinely practiced in the art. The immunogenicity of the recombinant antibody can also be monitored to determine whether the recombinant antibody is evoking an undesired anti-recombinant antibody immune response.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the immunogen in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disease or disorder. Beneficial or desired clinical results from treating a subject include, but are not limited to, abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be prevented (i.e., decreasing the likelihood of occurrence or recurrence of the disease or disorder). A subject may have a genetic predisposition for developing a disease or disorder that would benefit from clearance of senescent cells or may be of a certain age wherein immunization would provide clinical benefit to delay development or reduce severity of a disease, such as an age-related disease or disorder.

A subject (i.e., patient, individual) in need of the therapeutic methods described herein is a human or non-human animal. The subject in need of medical therapies with enhanced efficacy may exhibit symptoms or sequelae of a disease described herein or may be at risk of developing the disease. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

An age-related disorder or disease or an age-sensitive trait may be associated with a senescence-inducing stimulus. The efficacy of immunization as described herein may be manifested by reducing the number of symptoms of an age-related disorder or age-sensitive trait associated with a senescence-inducing stimulus, decreasing the severity of one or more symptoms, or delaying the progression of an age-related disorder or age-sensitive trait associated with a senescence-inducing stimulus. In other particular embodiments, preventing an age-related disorder or age-sensitive trait associated with a senescence-inducing stimulus refers to preventing or delaying onset of an age-related disorder or age-sensitive trait associated with a senescence-inducing stimulus, or reoccurrence of one or more age-related disorder or age-sensitive trait associated with a senescence-inducing stimulus. The effectiveness of an immunogenic composition described herein to evoke a beneficial immune response against senescent cells can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of immunization can be analyzed using techniques known in the art, such as comparing symptoms of patients suffering from or at risk of a particular disease or disorder that have received the immunogenic composition with those of patients without such immunization or with placebo treatment.

In one embodiment, methods are provided for treating or preventing diseases or disorders related to, associated with, or caused by cellular senescence including age-related diseases and disorders. Exemplary diseases or disorders that may be treated or prevented by administering an immunogenic composition described herein include, without limitation, cognitive diseases (e.g., Alzheimer's disease and other dementias); cardiovascular disease; diabetes; motor function diseases and disorders (e.g., Parkinson's disease); cancer occurrence, cancer metastasis, cardiovascular disease, cerebrovascular disease, emphysema, osteoarthritis, peripheral vascular disease, cardiac diastolic dysfunction, benign prostatic hypertrophy, aortic aneurysm, and emphysema. Evoking an immune response that comprises clearance of senescence cells by employing the immunization methods described herein may also be useful for treating or reducing the likelihood of cancer or cancer metastasis (exemplary cancers include melanoma, prostate cancer, testicular cancer, breast cancer, brain cancer, pancreatic cancer, colon cancer, thyroid cancer, stomach cancer, lung cancer, ovarian cancer, Kaposi's sarcoma, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer; those that occur in blood, bone marrow, and lymph nodes and include generally, leukemias (myeloid and lymphocytic), lymphomas (e.g., Hodgkin lymphoma), and melanoma (including multiple myeloma). Leukemias include for example, acute lymphoblastic leukemia (ALL), acute myeloid leukemia (AML), chronic lymphocytic leukemia (CLL), chronic myelogenous leukemia (CML), and hairy cell leukemia).

The efficacy of the immunization methods may be determined and monitored by assessing one or more age-sensitive traits. Such traits include for example T cell subset distribution, cataract formation, spontaneous activity, motor coordination, and cognitive capacity, physical function, body composition (e.g., sarcopenia, osteoporosis, loss of fat mass) and cardiac function. These exemplary age-sensitive traits can be assessed using standard techniques known and available in the art. In a related embodiment, the lean mass, fat mass and bone mineral density are measured by QNMR, dual-energy X-ray absorptiometry, MRI, PET, or a combination thereof. In another related embodiment, the physical function is a measure of (1) running time, distance, and work using a motorized treadmill, (2) grip strength using a grip meter, or (3) any combination measure thereof. In another embodiment, the age-sensitive trait is a measure of a tissue or organ, wherein the measure is of fiber diameter on gastrocnemius muscle, DNA damage, renal and glomerulosclerosis, retinal atrophy, proteotoxic stress, oxidative stress, or hematopoietic system.

In certain embodiments, the immunogenic compositions described herein are administered to a subject who has a cancer or who is at risk of developing cancer. The immunogens and recombinant antibodies described herein that evoke an immune response that results in clearance of senescent cells may be used in combination with chemotherapy, radiotherapy, or both to provide clinical benefit to the subject. Therapeutic benefit includes any one or more of reducing the size of the tumor(s), inhibiting tumor progression, inhibiting tumor growth, delaying tumor colonization, and/or inhibiting, preventing, or delaying metastasis of a tumor. Enhancing the effectiveness of the chemotherapy or radiotherapy may include preventing, slowing, or decreasing development of resistance of the cancer (i.e., tumor or tumors) to the chemotherapy or radiotherapy, thereby allowing additional cycles of therapy and/or decreasing the time interval between cycles of therapy.

An age-related disease or disorder includes diabetes and can be associated with cellular senescence. Therefore, clearance of senescent cells from a subject by administering an immunogenic composition described herein may provide therapeutic benefit. Subjects suffering from type 2 diabetes can be identified using standard diagnostic methods known in the art for type 2 diabetes. Generally, diagnosis of type 2 diabetes is based on symptoms (e.g., increased thirst and frequent urination, increased hunger, weight loss, fatigue, blurred vision, slow-healing sores or frequent infections, and/or areas of darkened skin), medical history, and/or physical examination of a patient. Subjects at risk of developing type 2 diabetes include those having a family history of type 2 diabetes and those having other risk factors such as weight, fat distribution, inactivity, race, age, prediabetes, and/or gestational diabetes. Clinical benefit and improvement of a subject who has diabetes may be evaluated by stability of glucose levels. For example, an increase in the length of time between doses of insulin or a decrease in the dose of insulin required to maintain proper glucose levels in patients who receive an immunogenic composition described herein indicates improved effectiveness of the insulin. Other clinical parameters that may be monitored include level of insulin tolerance, energy expenditure, body composition, fat tissue, skeletal muscle, liver inflammation, lipotoxicity (muscle and liver lipid by imaging in vivo and muscle, liver, bone marrow, and pancreatic β-cell lipid accumulation and inflammation by histology).

Other age-related diseases or disorders that may be associated with cellular senescence are neurological diseases such as Alzheimer's disease, Parkinson's disease, mild cognitive impairment (MCI), and Motor Neuron Dysfunction (MND). Therefore, clearance of senescent cells from a subject who has or who is at risk of developing such a neurological disease may benefit by receiving an immunogenic composition described herein.

Subjects suffering from Alzheimer's disease can be identified using standard diagnostic methods known in the art for Alzheimer's disease. Generally, diagnosis of Alzheimer's disease is based on symptoms (e.g., progressive decline in memory function, gradual retreat from and frustration with normal activities, apathy, agitation or irritability, aggression, anxiety, sleep disturbance, dysphoria, aberrant motor behavior, disinhibition, social withdrawal, decreased appetite, hallucinations, dementia), medical history, neuropsychological tests, neurological and/or physical examination of a patient. Cerebrospinal fluid may also be for tested for various proteins that have been associated with Alzheimer pathology, including tau, amyloid beta peptide, and AD7C-NTP. Genetic testing is also available for early-onset familial Alzheimer disease (eFAD), an autosomal-dominant genetic disease. Clinical genetic testing is available for individuals with AD symptoms or at-risk family members of patients with early-onset disease. In the U.S., mutations for PS2, and APP may be tested in a clinical or federally approved laboratory under the Clinical Laboratory Improvement Amendments. A commercial test for PS1 mutations is also available (Elan Pharmaceuticals).

Subjects at risk of developing Alzheimer's disease include those of advanced age, those with a family history of Alzheimer's disease, those with genetic risk genes (e.g., ApoE4) or deterministic gene mutations (e.g., APP, PS1, or PS2), and those with history of head trauma or heart/vascular conditions (e.g., high blood pressure, heart disease, stroke, diabetes, high cholesterol).

Subjects suffering from MCI can be identified using standard diagnostic methods known in the art for MCI. Criteria for an MCI diagnosis typically include: an individual's report of his or her own memory problems; measurable, greater-than-normal memory impairment detected with standard memory assessment tests; normal general thinking and reasoning skills; and ability to perform normal daily activities. Generally, diagnosis of MCI is based on medical history, assessment of independent function and daily activities, assessment of mental status, neurological examination, evaluation of mood, laboratory tests including blood tests and imaging of the brain's structure of a patient. Exemplary assessments include Clinical Dementia Rating (CDR) scores (a CDR rating of about 0.5 or about 0.5 to 1.0 is often considered clinically relevant MCI) and simple memory test (paragraph recall) to establish an objective memory deficit in combination of a measure of general cognition (mini-mental state exam) to exclude a broader cognitive decline beyond memory (see, Grundman et al., Arch Neurol. 61: 59-66, 2004). In certain embodiments, subjects suffering from MCI may also suffer from Parkinson's disease or have one or more symptoms commonly associated with Parkinson's disease.

Preventing Parkinson's disease as used herein refers to preventing or delaying onset of Parkinson's disease or reoccurrence of one or more symptoms. Symptoms of Parkinson's disease are known in the art and include, but are not limited to, difficulty starting or finishing voluntary movements, jerky, stiff movements, muscle atrophy, shaking (tremors), and changes in heart rate, but normal reflexes, bradykinesia, and postural instability.

Subjects suffering from Parkinson's disease can be identified using standard diagnostic methods known in the art for Parkinson's disease. Generally, diagnosis of Parkinson's disease is based on symptoms, medical history, and neurological and/or physical examination of a patient. Subjects at risk of developing Parkinson's disease include those having a family history of Parkinson's disease and those exposed to pesticides (e.g., rotenone or paraquat), herbicides (e.g., agent orange), or heavy metals.

Subjects suffering from MND exhibit weakness, wasting, and loss of control of muscles. Some diseases affect all muscles (amyotrophic lateralsclerosis), and other diseases cause weakness and loss of function in particular muscles. Subjects develop wasting, uncontrollable twitching, spasticity (stiffness), and movements become slow and effortful. Subjects suffering from MND can be identified using standard diagnostic methods known in the art for MND. Subject are given a physical exam and neurological exam, which assesses motor and sensory skills, nerve function, hearing and speech, vision, coordination and balance, mental status, and changes in mood or behavior. To measure muscle involves the following may be performed: electromyography; laboratory tests to assess the presence of inflammation and/or infection and to measure protein creatine kinase; magnetic resonance imaging; muscle or nerve biopsies; and transcranial magnetic stimulation. Subjects at risk of developing MND include those who have genetic mutations associated with a particular MND. In adults, MNDs occur more commonly in men than in women, with symptoms appearing after age 40.

Cardiovascular disease includes high blood pressure, coronary heart disease, and heart disease, and many factors contribute to development of cardiovascular disease. These factors include aging, smoking, high cholesterol, and calcification of the cardiovascular tissue (Heart Disease and Stroke Statistics-2012 Update: A Report from the American Heart Association. Circulation (2012), 125:e5-e220 ("Heart Disease Statistics")). Subjects suffering from cardiovascular disease can be identified using standard diagnostic methods known in the art for cardiovascular disease. Generally, diagnosis of atherosclerosis and other cardiovascular disease is based on symptoms (e.g., chest pain or pressure (angina), numbness or weakness in arms or legs, difficulty speaking or slurred speech, drooping muscles in face, leg pain, high blood pressure, kidney failure and/or erectile dysfunction), medical history, and/or physical examination of a patient. Subjects at risk of developing cardiovascular disease include those having a family history of cardiovascular disease and those having other risk factors such as high blood pressure, high cholesterol, diabetes, obesity and/or smoking.

Cardiovascular disease include angina, arrhythmia, atherosclerosis, cardiomyopathy, congestive heart failure, coronary artery disease (CAD), carotid artery disease, endocarditis, heart attack (coronary thrombosis, myocardial infarction [MI]), high blood pressure/hypertension, hypercholesterolemia/hyperlipidemia, mitral valve prolapsed, peripheral artery disease (PAD) and stroke. The benefit to a subject who received an immunogenic composition described herein may be monitored using any known and established techniques, illustrative examples of which include detection or signs of narrowed, enlarged or hardened arteries during a physical exam. These include a weak or absent pulse below the narrowed area of an artery, decreased blood pressure in an affected limb, whooshing sounds (bruits) over the arteries heard using a stethoscope, signs of a pulsating bulge (aneurysm) in the abdomen or behind the knee and/or evidence of poor wound healing in an area where blood flow is restricted. Additional diagnostic tests for monitoring the effectiveness of an immunization method described herein may be performed, such as blood tests to detect cholesterol levels and blood sugar levels, Doppler ultrasound, ankle-brachial index testing, electrocardiogram (ECG), stress tests, cardiac catheterization and angiograms and/or other imaging tests.

Another age-related disease that may be treated by immunizing a subject in need with any one of the immunogenic compositions described herein is pulmonary fibrosis. Symptoms of pulmonary fibrosis are known in the art and include shortness of breath, particularly during exercise; dry, hacking cough; fast, shallow breathing; gradual unintended weight loss; tiredness; aching joints and muscles; and clubbing (widening and rounding of the tips of the fingers or toes). Subjects suffering from pulmonary fibrosis can be identified and monitored using standard diagnostic methods known in the art for pulmonary fibrosis. Generally, diagnosis of pulmonary fibrosis is based on one or more of the following exams or tests: physical exam, patient's medical history, patient's family's medical history, chest X-ray, lung function tests, blood test, bronchoalveolar lavage, lung biopsy, CT scan, and exercise testing.

Subjects at risk of developing pulmonary fibrosis include those exposed to environmental or occupational pollutants, such as asbestosis and silicosis; who smokes cigarettes; having some typical connective tissue diseases such as rheumatoid arthritis, SLE and scleroderma; having other diseases that involve connective tissue, such as sarcoidosis and Wegener's granulomatosis; having infections; taking certain medications (e.g., amiodarone, bleomycin, busufan, methotrexate, and nitrofurantoin); those subject to radiation therapy to the chest; and those whose family member has pulmonary fibrosis.

The immunization protocol used in the methods described herein will be designed dependent upon the disease or disorder to be treated, age of the subject, and on other factors with which a person skilled in the art may use to determine suitability of a subject for the immunization. For example, if a human subject is to be immunized to prevent or treat an age-related disease or disorder, an initial (i.e., primary) immunization may be administered after age 40, 45, 50, 55, 60, or older. Immunization to induce an immune response against senescent cells may also be initiated at an earlier age when the subject's health indicates initiating immunization independent of age is indicated. For example, a subject who is at risk of developing diabetes includes a subject who is overweight. By way of another example, a subject who has been diagnosed with a cancer and will receive chemotherapy, radiation, or both may benefit from the immunization methods described herein.

Pharmaceutically Suitable Immunogenic Compositions

Also provided herein are pharmaceutically suitable immunogenic compositions comprising any one or more of the immunogens described herein or a recombinant antibody described herein for evoking an immune response specific for a senescent cell. Immunogenic compositions may also be called herein immunogenic preparations, which preparations may comprise at least one immunogen and a pharmaceutically acceptable excipient. The immunogenic composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). The excipients described herein are merely exemplary and are in no way limiting. An effective amount or therapeutically effective amount refers to an amount of the immunogen or antibody administered to a subject, either as a single dose or as part of a series of doses, which is effective to produce a desired therapeutic effect.

Subjects may generally be monitored for therapeutic effectiveness using assays suitable for the condition being treated or prevented, which assays will be familiar to those having ordinary skill in the art and are described herein. The level of an immunogen or recombinant antibody that is administered to a subject may be monitored by determining the level of the immunogen or recombinant antibody, respectively, in a biological fluid, for example, in the blood, blood fraction (e.g., serum), and/or in the urine, and/or other biological sample from the subject. Any method practiced in the art to detect the immunogen or recombinant antibody may be used to measure the level of immunogen or recombinant antibody, respectively, during the course of a immunization regimen.

The dose of an immunogen or recombinant antibody described herein for evoking a specific immune response may depend upon the subject's condition, that is, stage of the disease if present, severity of symptoms caused by the disease, general health status, as well as age, gender, and weight, and other factors apparent to a person skilled in the medical art. Immunogenic compositions may be administered in a manner appropriate to the disease or disorder to be treated or prevented as determined by persons skilled in the medical arts. An appropriate dose and a suitable duration and frequency of administration will be determined by such factors as the condition of the patient, the type and severity of the patient's disease, the particular form of the active ingredient, and the method of administration. Optimal doses of an immunogen or recombinant antibody may generally be determined using experimental models and/or clinical trials. The optimal dose may depend upon the body mass, weight, or blood volume of the subject. The use of the minimum dose that is sufficient to provide an effective immune response is usually preferred. Design and execution of pre-clinical and clinical studies for an agent (including when administered for prophylactic benefit) described herein are well within the skill of a person skilled in the relevant art. For example, an amount of an immunogen or recombinant antibody may be administered at a dose between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight.

The immunogenic compositions may be administered to a subject in need thereof by any one of several routes that effectively deliver an effective amount of the immunogen or recombinant antibody. Such administrative routes include, for example, oral, topical, parenteral, enteral, rectal, intranasal, buccal, sublingual, intramuscular, transdermal, vaginal, rectal, or by intracranial injection, or any combination thereof. Such compositions may be in the form of a solid, liquid, or gas (aerosol). The administrative route is also determined by the type of immunogen or if the recombinant antibody is being administered. Immunogenic compositions comprising a senescent cell associated antigen, antigenic fragment, or fusion polypeptide may be administered intramuscularly, transdermally, intranasally, for example. Recombinant antibodies are typically administered by a parenteral route, such as intravenously.

Pharmaceutical acceptable excipients are well known in the pharmaceutical art and described, for example, in Rowe et al., *Handbook of Pharmaceutical Excipients: A Comprehensive Guide to Uses*, Properties, and Safety, 5$^{th}$ Ed., 2006, and in *Remington: The Science and Practice of Pharmacy* (Gennaro, 21$^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the immunogenic composition. In addition, antioxidants and suspending agents may also be used. In general, the type of excipient is selected based on the mode of administration, as well as the chemical composition of the active ingredient(s). Alternatively, compositions described herein may be formulated as a lyophilizate, or the immunogen or recombinant antibody may be encapsulated within liposomes using technology known in the art. Immunogenic compositions may be formulated for any appropriate manner of administration described herein and in the art.

A composition (e.g., for oral administration or delivery by injection) may be in the form of a liquid. A liquid immunogenic composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, an immunogen or recombinant antibody described herein can be used alone or in combination with appropriate additives to make tablets, powders, granules or capsules, and if desired, with diluents, buffering agents, moistening agents, preservatives, coloring agents, and flavoring agents. An immunogen or recombinant antibody included in the compositions may be formulated for oral delivery with a buffering agent, flavoring agent, e.g., in a liquid, solid or semi-solid formulation and/or with an enteric coating.

A composition comprising any one of the immunogens or recombinant antibodies described herein may be formulated for sustained or slow release. Such compositions may generally be prepared using well known technology and administered by, for example, oral, rectal or subcutaneous implantation, or by implantation at the desired target site. Sustained-release formulations may contain the immunogen or recombinant antibody dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active agent contained within a sustained release formulation depends upon the site of implantation, the rate and expected duration of release, and the nature of the condition to be treated or prevented.

For immunogenic compositions comprising a nucleic acid molecule, the nucleic acid molecule may be present within any of a variety of delivery systems known to those of ordinary skill in the art, including nucleic acid, and bacterial, viral and mammalian expression systems such as, for example, recombinant expression constructs as provided herein. Techniques for incorporating DNA into such expression systems are well known to those of ordinary skill in the art. The DNA may also be "naked," as described, for example, in Ulmer et al., *Science* 259:1745-49, 1993 and reviewed by Cohen, *Science* 259:1691-1692, 1993. The uptake of naked DNA may be increased by coating the DNA onto biodegradable beads, which are efficiently transported into the cells.

Nucleic acid molecules may be delivered into a cell according to any one of several methods described in the art (see, e.g., Akhtar et al., *Trends Cell Bio.* 2:139 (1992); *Delivery Strategies for Antisense Oligonucleotide Therapeutics*, ed Akhtar, 1995, Maurer et al., *Mol. Membr. Biol.* 16:129-40 (1999); Hofland and Huang, *Handb. Exp. Pharmacol.* 137:165-92 (1999); Lee et al., *ACS Symp. Ser.* 752:184-92 (2000); U.S. Pat. No. 6,395,713; International Patent Application Publication No. WO 94/02595); Selbo et al., *Int. J. Cancer* 87:853-59 (2000); Selbo et al., *Tumour Biol.* 23:103-12 (2002); U.S. Patent Application Publication Nos. 2001/0007666, and 2003/077829). Such delivery methods known to persons having skill in the art, include, but are not restricted to, encapsulation in liposomes, by iontophoresis, or by incorporation into other vehicles, such as biodegradable polymers; hydrogels; cyclodextrins (see, e.g., Gonzalez et al., *Bioconjug. Chem.* 10:1068-74 (1999); Wang et al., International Application Publication Nos. WO 03/47518 and WO 03/46185); poly(lactic-co-glycolic)acid (PLGA) and PLCA microspheres (also useful for delivery of peptides and polypeptides and other substances) (see, e.g., U.S. Pat. No. 6,447,796; U.S. Patent Application Publication No. 2002/130430); biodegradable nanocapsules; and bioadhesive microspheres, or by proteinaceous vectors (International Application Publication No. WO 00/53722). In another embodiment, the nucleic acid molecules for use in evoking an immune response as described herein can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives (see also, e.g., U.S. Patent Application Publication No. 2003/0077829).

Kits with unit doses of an immunogen or recombinant antibody described herein, usually in oral or injectable doses, are provided. Such kits may include a container containing the unit dose, an informational package insert describing the use and attendant benefits of the immunogen or antibody in treating pathological condition of interest, and optionally an appliance or device for delivery of the composition.

EXAMPLES

Example 1

Effect of Murine P16INK4A Polypeptide Immunization on Tumor Growth and Metastasis Most senescent cells express the tumor suppressor protein p16INK4a on the cell surface, and expression is independent of cell type and senescence inducer (see, e.g., Ohtani et al., *J. Med. Invest.* 51:146-53 (2004); Campisi et al., *Nat. Rev. Med. Cell Biol.* 8:729-40 (2007)). To characterize an immune response specific for p16INK4a, groups of mice are immunized with isolated murine p16INK4a according to procedures practiced in the art, which include an initial immunization followed by at least one booster immunization with murine p16INK4a. The presence and titer of immune sera containing anti-murine p16INK4a antibodies are monitored by periodic bleeding of the animals, preparation of sera, and performance of an immunoassay to detect specific anti-murine p16KINK4a antibodies in the murine sera. Animals that develop an anti-murine p16INK4a immune response are then exposed to chemotherapy or radiation to induce p16INK4a-positive senescent cells. The presence of senescent cells expressing p16INK4a is determined.

Animals that have an anti-murine p16INK4a immune response and control animals are then engrafted with a tumor cell line. Size of tumor(s) and metastasis are monitored in the immunized animals and compared with control animals. Additional control animal groups include p16-3MR or INK-ATTAC animals in which senescent cells are eliminated by gancyclovir and AP20187, respectively, and which may be engrafted with the tumor cell line.

Transgenic p16-3MR mice were prepared as follows. The promoter, $p16^{Ink4a}$, which is transcriptionally active in senescent cells but not in non-senescent cells (see, e.g., Wang et al., *J. Biol. Chem.* 276:48655-61 (2001); Baker et al., *Nature*, supra) was engineered into a nucleic acid construct. A fragment of the $p16^{Ink4a}$ gene promoter was introduced upstream of a nucleotide sequence encoding a trimodal reporter fusion protein. The trimodal reporter protein is termed 3MR and consists of renilla luciferase (rLUC), monomeric red fluorescent protein (mRFP) and a truncated herpes simplex virus thymidine kinase (tTK) (see, e.g., Ray et al., *Cancer Res.* 64:1323-30 (2004)). Thus, the expression of 3MR is driven by the $p16^{Ink4a}$ promoter in senescent cells only. The polypeptide sequences and the encoding polynucleotides for each of the three proteins are known in the art and are available in public databases, such as GenBank. The detectable markers, rLUC and mRFP permit detection of senescent cells by bioluminescence and fluorescence, respectively. The expression of tTK permits selective killing of senescent cells by exposure to the pro-drug ganciclovir (GCV), which is converted to a cytotoxic moiety by tTK.

Transgenic founder animals, which have a C57B16 background, were established and bred using known procedures for introducing transgenes into animals (see, e.g., Baker et al., *Nature*, 479:232-36 (2011); Int'l Patent Application Publication No. WO/2012/177927).

INK-ATTAC ($p16^{Ink4a}$ apoptosis through targeted activation of caspase) transgenic mice have an FK506-binding protein (FKBP)-caspase 8 (Casp8) fusion polypeptide under the control of the $p16^{Ink4a}$ promoter (see, e.g., Baker et al., *Nature*, supra; Int'l Patent Application Publication No. WO/2012/177927). In the presence of AP20187, a synthetic drug that induces dimerization of a membrane bound myristoylated FKBP-Casp8 fusion protein, senescent cells specifically expressing the FKBP-Casp8 fusion protein via the $p16^{ink4a}$ promoter undergo programmed cell death (apoptosis) (see, e.g., Baker, *Nature*, supra, FIG. 1 therein).

Senescent cells secret molecules that can cause inflammation (see, e.g., Freund et al., *Trends Mol. Med.* 16:238-46 (2010)), which, if chronic, will fuel various pathologies, including cancer (see, e.g., Davalos et al., *Cancer Metastasis Rev.* 29:273-83 (2010)), which is often referred to as senescence-associated secretory phenotype (SASP) as described herein. For example, IL-6 (interleukin-6) and MMP-3 (matrix metalloproteinase-3) are two prominent SASP components. Hence, in animals immunized with p16INK4a, RNA expression levels of various biomarkers associated with SASP are examined, including p16INK4a (p16), IL-6, and MMP-3. The level of expressed SASP components may also be monitored. In addition, the level of the mRFP reporter is measured.

Example 2

Effect of Human P16INK4A Polypeptide Immunization on Tumor Growth and Metastasis Murine p16INK4a and human p16INK4a share approximately 74% sequence identity. Groups of mice that are murine p16INK4a null mice and that are carrying the human p16INK4a gene are immunized with isolated human p16INK4a according to procedures practiced in the art, which include an initial immunization followed by at least one booster immunization with human p16INK4a. The human p16INK4a gene that is introduced into the animals may be under the control of the murine p16INK4a promoter. The presence and titer of immune sera containing anti-human p16INK4a antibodies are monitored by periodic bleeding of the animals, isolation of sera, and performance of an immunoassay to detect specific anti-human p16KINK4a antibodies in the sera. Animals that develop an anti-human p16INK4a immune response are then exposed to chemotherapy or radiation to induce p16INK4a-positive senescent cells. The presence of senescent cells expressing p16INK4a is determined. The presence and level of mRNA encoding SASP components is determined, and the level of expressed SASP components may also be monitored.

Animals that that have an anti-human p16INK4a immune response and control animals are then engrafted with a tumor cell line. Size of tumor(s) and metastasis are monitored in the immunized animals and compared with control animals. Additional control animal groups include p16-3MR or INK-ATTAC animals engrafted with the tumor cell line in which senescent cells are eliminated by gancyclovir and AP20187, respectively (see Example 1).

Example 3

Preparation of Antibodies that Specifically Bind to p16INK4A Polypeptide

Polyclonal antisera from mice immunized with murine p16INK4a as described in Example 1 and antisera from mice immunized with human p16INK4a are isolated. Mice are bled and the sera are separated from the blood cells. To obtain a greater volume of antisera, rabbits (such as New Zealand White) are immunized with isolated murine or human p16INK4a. The animals are bled to monitor titers before the first immunization (pre-bleed control) and after the first immunization and after each subsequent immunization. Antisera are collected. The antibodies in the sera may be purified by affinity chromatography methods according to methods and techniques routinely practiced in the art.

Example 4

Senescent Cell Associated Antigens

Polynucleotides comprising a nucleotide sequence that is important for establishing and/or maintaining senescence of a cell were identified. The GenBank accession numbers for these nucleotide sequences are provided in Table 2 (with product annotations) and in Table 2A. Polynucleotides comprising the nucleotide sequences that encode all or a portion of a senescent cell associated antigen that is important for cellular senescence (see Tables 2, 2A, and 3). The encoded polypeptides may be used as immunogens in the methods and compositions described herein. Certain polynucleotide sequences listed in Table 2A that encode a portion of a SCCAg are ESTs. The polypeptide encoded by a polynucleotide comprising these sequences was determined by genome coordinates of the EST using UCSC Human Genome annotation database version 19 (see Internet at genome.ucsc.edu/cgi-bin/hgGateway (UCSC hg v19)) to identify unique transcripts in those coordinates. The transcripts were mapped to entrez gene identifiers and symbols. The EST coordinates were determined from the all_ests table in hg19. The code to map the refseq Ids was extended by using the refGene table or the kgXref table.

Examplary SCAAgs encoded by polynucleotides comprising the nucleotide sequences provided in Table 2 include but are not limited to ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419. Senescent cells in which expression of the each of these polypeptides was suppressed decreased viability of senescent cells. Methods for evoking an immune response specific for a senescent cell in a subject, wherein the immune response comprises clearance of the senescent cell by the immune system of the subject, comprises evoking an immune response to one or more of ADAMTS7, APLP2, ATP6V0D2, BCHE, C11orf87, CD46, CYB5D2, FBXL7, GPR137B, IFI27L1, IL15RA, LAMP2, MYO10, NEU1, NHSL2, NPAS2, OR1F1, PEA15, RAB23, RARB, RNPC3, SELO, SELT, SEMA5B, SERP1, SERPINE1, SLC9A7, SNX3, TBC1D1, TBRG1, TCEANC, TFPI, TNFAIP1, TUBG2, USP18, and ZNF419. Certain polypeptides (e.g., CD46, LAMP2, NPAS2, TBRG1, TFPI, and C11orf87, and ZNF419) are represented more than once in the tables herein). Senescent cell associated antigens are also provided in Table 1.

TABLES

Senescent Cell-Associated Antigens and Polynucleotide Sequences Encoding Senescent Cell-Associated Antigens

TABLE 1

| SENESCENT CELL-ASSOCIATED ANTIGENS | |
|---|---|
| Senescent Cell-Associated Antigens | GI Reference Number |
| Mutant beta-actin (ACTB) protein | 28336 |
| Beta actin (ACTB) | 15277503 |
| drug resistance-related protein LRP | 1097308 |
| major vault protein (MVP) | 19913410 (see also GenBank Acc. No. NM_017458) |
| thyroid hormone binding protein precursor | 339647 |
| prolyl 4-hydroxylase beta subunit precursor, beta polypeptide (P4HB) | 20070125 |
| chain A, human protein disulfide isomerase (PDI) | 159162689 |
| electron-transfer-flavoprotein, beta polypeptide (ETFB) | 4503609 (see also GenBank Acc. No. NM_001985) |
| ATP synthase, H+ transporting, mitochondrial F complex, alpha subunit precursor | 4757810 |
| cathepsin B (CTSB) | 4503139 (see also GenBank Acc. No. NM_001908) |
| Un-named product 1 | 35655 |
| Un-named product 2 | 158257194 |
| Un-named product 3 | 158259937 |

TABLE 2

| GenBank No. | | Encoded Polypeptide |
|---|---|---|
| AA004279 | C6orf89 | hypothetical protein LOC221477 |
| AA012883 | RSU1 | ras suppressor protein 1 isoform 1 |
| AA020826 | CTSB | cathepsin B preproprotein |
| AA022510 | APLP2 | amyloid beta (A4) precursor-like protein 2 |
| AA029155 | | unknown |
| AA034012 | RORA | RAR-related orphan receptor A isoform b |
| AA037766 | TRNP1 | TMF regulated nuclear protein |
| AA043348 | | unknown |
| AA044835 | | unknown |
| AA044921 | GEMIN8 | gem (nuclear organelle) associated protein 8 |
| AA045247 | FREQ | frequenin homolog isoform 1 |

TABLE 2-continued

| GenBank No. | | Encoded Polypeptide |
|---|---|---|
| AA045527 | AGBL5 | ATP/GTP binding protein-like 5 isoform 1 |
| AA056548 | PARP14 | poly (ADP-ribose) polymerase family, member 14 |
| AA081349 | IVD | isovaleryl Coenzyme A dehydrogenase isoform 1 |
| AA083483 | BEST1 | bestrophin 1 isoform 1 |
| AA088857 | | unknown |
| AA088873 | | unknown |
| AA099357 | ABCA6 | ATP-binding cassette, sub-family A, member 6 |
| AA102600 | BET3L | BET3 like |
| AA115933 | TRIM35 | tripartite motif-containing 35 isoform 2 |
| AA121673 | | unknown |
| AA128261 | SHBG | sex hormone-binding globulin isoform 1 |
| AA130982 | C20orf3 | chromosome 20 open reading frame 3 |
| AA131041 | IFIT2 | interferon-induced protein with |
| AA133285 | | unknown |
| AA133962 | C16orf72 | hypothetical protein LOC29035 |
| AA133989 | IFNAR1 | interferon-alpha receptor 1 precursor |
| AA148534 | PAPPA | pregnancy-associated plasma protein A |
| AA149644 | JAM3 | junctional adhesion molecule 3 precursor |
| AA149745 | TRIM2 | tripartite motif-containing 2 isoform 1 |
| AA150242 | ARID5B | AT rich interactive domain 5B (MRF1-like) |
| AA150460 | | unknown |
| AA156605 | | unknown |
| AA156721 | ALCAM | activated leukocyte cell adhesion molecule |
| AA156723 | VAT1L | vesicle amine transport protein 1 homolog (T. |
| AA156754 | | unknown |
| AA156961 | ASCC3 | activating signal cointegrator 1 complex subunit |
| AA160474 | | unknown |
| AA169752 | YIPF5 | Yip1 domain family, member 5 |
| AA195009 | TWSG1 | twisted gastrulation precursor |
| AA196034 | | unknown |
| AA196245 | EXT2 | exostosin 2 isoform 1 |
| AA203365 | PIGV | phosphatidylinositol glycan class V |
| AA205660 | | unknown |
| AA209239 | ABHD6 | abhydrolase domain containing 6 |
| AA209487 | CMBL | carboxymethylenebutenolidase |
| AA215738 | | unknown |
| AA228366 | ITGAV | integrin alpha-V isoform 1 precursor |
| AA243427 | MDGA1 | MAM domain containing |
| AA279958 | GOPC | golgi associated PDZ and coiled-coil motif |
| AA284248 | ROR1 | receptor tyrosine kinase-like orphan receptor 1 |
| AA284829 | ZNF79 | zinc finger protein 79 |
| AA329676 | | unknown |
| AA372349 | FAM171B | KIAA1946 |
| AA393484 | PLCB1 | phosphoinositide-specific phospholipase C beta 1 |
| AA398658 | DYX1C1 | dyslexia susceptibility 1 candidate 1 isoform a |
| AA398740 | SMYD3 | SET and MYND domain containing 3 |
| AA401703 | TMEM231 | transmembrane protein 231 isoform 3 |
| AA404269 | PRICKLE1 | prickle homolog 1 |
| AA418028 | | unknown |
| AA418074 | | unknown |
| AA418816 | MRAP2 | melanocortin 2 receptor accessory protein 2 |
| AA429615 | ZNF419 | zinc finger protein 419 isoform 1 |
| AA432267 | AK3 | adenylate kinase 3 |
| AA459699 | ANKRD55 | ankyrin repeat domain 55 isoform 1 |
| AA461080 | PPARA | peroxisome proliferative activated receptor, |
| AA476916 | | unknown |
| AA481560 | | unknown |
| AA482478 | | unknown |
| AA482548 | WDR26 | WD repeat domain 26 isoform b |
| AA496034 | BAIAP2L1 | BAI1-associated protein 2-like 1 |
| AA496213 | C14orf28 | hypothetical protein LOC122525 |
| AA514384 | PHPT1 | phosphohistidine phosphatase 1 isoform 2 |
| AA514634 | VPS53 | vacuolar protein sorting 53 isoform 1 |
| AA521080 | | unknown |
| AA522514 | SEL1L3 | sel-1 suppressor of lin-12-like 3 |
| AA523543 | MFSD3 | major facilitator superfamily domain containing |
| AA523733 | CCDC132 | coiled-coil domain containing 132 isoform a |
| AA523958 | KIAA1468 | hypothetical protein LOC57614 |
| AA524669 | | unknown |
| AA526844 | MYLK | myosin light chain kinase isoform 1 |
| AA532640 | ZBTB47 | zinc finger protein 651 |
| AA532655 | LOC100286793 | |
| AA534198 | CHPF2 | chondroitin polymerizing factor 2 |
| AA535917 | | unknown |

TABLE 2-continued

| GenBank No. | | Encoded Polypeptide |
|---|---|---|
| AA543030 | ASPH | aspartate beta-hydroxylase isoform a |
| AA545764 | | HBMSF1D5-REV Human Bone Marrow Stromal Fibroblast |
| AA551075 | KCTD12 | potassium channel tetramerisation domain |
| AA554833 | MAP1B | microtubule-associated protein 1B |
| AA563621 | HSPB6 | heat shock protein, alpha-crystallin-related, |
| AA565715 | SPAG8 | sperm associated antigen 8 isoform 2 |
| AA565852 | | unknown |
| AA572675 | AFF3 | AF4/FMR2 family, member 3 isoform 2 |
| AA573452 | EDNRA | endothelin receptor type A isoform a precursor |
| AA573523 | EPB41L1 | erythrocyte membrane protein band 4.1-like 1 |
| AA576961 | PHLDA1 | pleckstrin homology-like domain, family A, |
| AA582404 | | unknown |
| AA583044 | BMP2 | bone morphogenetic protein 2 preproprotein |
| AA594609 | | unknown |
| AA599017 | DOCK1 | dedicator of cytokinesis 1 |
| AA602532 | TPP1 | tripeptidyl-peptidase I preproprotein |
| AA603472 | | unknown |
| AA609053 | ENPP5 | ectonucleotide pyrophosphatase/phosphodiesterase |
| AA628051 | STX12 | syntaxin 12 |
| AA628398 | | unknown |
| AA629286 | | unknown |
| AA631103 | | unknown |
| AA631254 | MAN1B1 | alpha 1,2-mannosidase |
| AA633992 | C11orf87 | hypothetical protein LOC399947 precursor (see also Table 3) |
| AA634220 | NFASC | neurofascin isoform 1 precursor |
| AA639752 | DNAJC3 | DnaJ (Hsp40) homolog, subfamily C, member 3 |
| AA653300 | ZKSCAN1 | zinc finger protein 36 |
| AA654142 | CERCAM | cerebral endothelial cell adhesion molecule 1 |
| AA675892 | | unknown |
| AA678047 | MMAA | RecName: Full = Putative L-type amino acid transporter 1-like protein MMAA; AltName: Full = hLAT1 3-transmembrane protein MMAA; Short = hLAT1 3TM MMAA; |
| AA678241 | SCD | stearoyl-CoA desaturase 1 |
| AA683481 | CYBASC3 | cytochrome b, ascorbate dependent 3 isoform 1 |
| AA683501 | SUMF1 | sulfatase modifying factor 1 isoform 1 |
| AA683602 | MIR548N | |
| AA699809 | MBNL1 | muscleblind-like 1 isoform a |
| AA702143 | | unknown |
| AA703280 | SERPINE2 | plasminogen activator inhibitor type 1, member 2 |
| AA706658 | | unknown |
| AA707125 | UQCC | basic FGF-repressed Zic binding protein isoform |
| AA716107 | SVEP1 | polydom |
| AA721252 | ADAM23 | ADAM metallopeptidase domain 23 preproprotein |
| AA722799 | DCBLD2 | discoidin, CUB and LCCL domain containing 2 |
| AA724665 | | unknown |
| AA732007 | ATP6V1G1 | vacuolar H+ ATPase G1 |
| AA736604 | | unknown |
| AA747309 | ZFP90 | zinc finger protein 90 |
| AA761181 | TTTY14 | |
| AA767440 | | unknown |
| AA768884 | | unknown |
| AA778684 | | unknown |
| AA805633 | DCBLD2 | discoidin, CUB and LCCL domain containing 2 |
| AA806283 | | unknown |
| AA806349 | | unknown |
| AA810263 | | unknown |
| AA810788 | | unknown |
| AA811138 | IFNAR1 | interferon-alpha receptor 1 precursor |
| AA811509 | | unknown |
| AA812232 | TXNIP | thioredoxin interacting protein |
| AA814140 | REEP5 | receptor accessory protein 5 |
| AA815089 | | unknown |
| AA827865 | C17orf39 | hypothetical protein LOC79018 |
| AA827878 | MALAT1 | |
| AA831438 | MXD4 | MAD4 |
| AA831769 | ULBP2 | UL16 binding protein 2 precursor |
| AA832474 | | unknown |
| AA833832 | | unknown |
| AA836340 | | unknown |
| AA843132 | LZTFL1 | leucine zipper transcription factor-like 1 |
| AA847654 | TCEAL3 | transcription elongation factor A (SII)-like 3 |
| AA853175 | SLC16A3 | solute carrier family 16, member 3 |

TABLE 2-continued

| GenBank No. | | Encoded Polypeptide |
|---|---|---|
| AA861784 | RUFY3 | RUN and FYVE domain containing 3 isoform 1 |
| AA872727 | FDFT1 | squalene synthase |
| AA883074 | NRBF2 | nuclear receptor binding factor 2 |
| AA886870 | ANKRD37 | ankyrin repeat domain 37 |
| AA889628 | ZNF219 | zinc finger protein 219 |
| AA889952 | COL4A3BP | alpha 3 type IV collagen binding protein isoform |
| AA890010 | SEC22B | SEC22 vesicle trafficking protein homolog B |
| AA897514 | CPD | carboxypeptidase D precursor |
| AA902480 | MDM2 | mouse double minute 2 homolog isoform MDM2 |
| AA904430 | WDR69 | WD repeat domain 69 |
| AA907927 | DTWD1 | DTW domain containing 1 |
| AA910945 | PPARA | peroxisome proliferative activated receptor, |
| AA913146 | PKP4 | plakophilin 4 isoform a |
| AA916831 | UBE2H | ubiquitin-conjugating enzyme E2H isoform 1 |
| AA917672 | ATP5L | ATP synthase, H+ transporting, mitochondrial F0 |
| AA917899 | | unknown |
| AA927870 | | unknown |
| AA928542 | | unknown |
| AA933779 | WIPI2 | WD repeat domain, phosphoinositide interacting 2 |
| AA969194 | SP110 | SP110 nuclear body protein isoform c |
| AA971753 | BBS12 | Bardet-Biedl syndrome 12 |
| AA988241 | RAB3A | RAB3A, member RAS oncogene family |
| AA988323 | VEPH1 | ventricular zone expressed PH domain homolog 1 |
| AA993518 | | unknown |
| AA995925 | NFASC | neurofascin isoform 1 precursor |
| AB000888 | SKIV2L2 | superkiller viralicidic activity 2-like 2 |
| AB002282 | EDF1 | endothelial differentiation-related factor 1 |
| AB002301 | MAST4 | microtubule associated serine/threonine kinase |
| AB002323 | DYNC1H1 | cytoplasmic dynein 1 heavy chain 1 |
| AB002347 | UBR2 | ubiquitin protein ligase E3 component n-recognin |
| AB002354 | PLEKHM1 | pleckstrin homology domain containing, family M |
| AB002365 | | unknown |
| AB002391 | HERC2P2 | |
| AB004574 | DNASE2 | deoxyribonuclease II, lysosomal precursor |
| AB005043 | SOCS1 | suppressor of cytokine signaling 1 |
| AB006756 | PCDH7 | protocadherin 7 isoform c precursor |
| AB006757 | PCDH7 | protocadherin 7 isoform c precursor |
| AB007457 | | P53TG1-C |
| AB007458 | | P53TG1-D |
| AB007875 | KIAA0415 | hypothetical protein LOC9907 |
| AB007877 | | unknown |
| AB007900 | SIPA1L1 | signal-induced proliferation-associated 1 like |
| AB007923 | | unknown |
| AB009598 | | glucuronyltransferase I |
| AB011161 | | unknown |
| AB014511 | ATP9A | ATPase, class II, type 9A |
| AB014600 | | unknown |
| AB015656 | PDE5A | phosphodiesterase 5A isoform 1 |
| AB017269 | TMEFF2 | transmembrane protein with EGF-like and two |
| AB017445 | XRCC4 | X-ray repair cross complementing protein 4 |
| AB017498 | | Lipoprotein Receptor Related Protein 5 |
| AB018283 | | unknown |
| AB018322 | TMCC1 | transmembrane and coiled-coil domain family 1 |
| AB018580 | AKR1C3 | aldo-keto reductase family 1, member C3 |
| AB019691 | AKAP9 | A-kinase anchor protein 9 isoform 3 |
| AB020335 | | unknown |
| AB020635 | AHCYL2 | S-adenosylhomocysteine hydrolase-like 2 isoform |
| AB020645 | GLS | glutaminase precursor |
| AB020657 | IVNS1ABP | influenza virus NS1A binding protein |
| AB020663 | DMXL2 | Dmx-like 2 |
| AB020712 | SEC31A | SEC31 homolog A isoform 1 |
| AB020717 | SYNJ1 | synaptojanin 1 isoform b |
| AB022663 | RNF14 | ring finger protein 14 isoform 1 |
| AB022918 | | alpha2,3-sialyltransferase ST3Gal VI |
| AB023147 | C22orf9 | hypothetical protein LOC23313 isoform a |
| AB023179 | | unknown |
| AB024518 | IL33 | interleukin 33 precursor |
| AB024703 | RNF11 | ring finger protein 11 |
| AB029040 | DOPEY1 | dopey family member 1 |
| AB029290 | MACF1 | microfilament and actin filament cross-linker |
| AB030655 | EFEMP2 | EGF-containing fibulin-like extracellular matrix |
| AB030710 | | unknown |
| AB032261 | SCD | stearoyl-CoA desaturase 1 |
| AB032987 | | unknown |
| AB032996 | FAM40B | hypothetical protein LOC57464 isoform a |
| AB033007 | ERGIC1 | endoplasmic reticulum-golgi intermediate |

TABLE 2-continued

| GenBank No. | | Encoded Polypeptide |
|---|---|---|
| AB033010 | PNKD | myofibrillogenesis regulator 1 isoform 1 |
| AB033055 | | unknown |
| AB033080 | PIGB | phosphatidylinositol glycan, class B |
| AB033832 | PDGFD | platelet derived growth factor D isoform 2 |
| AB034747 | LITAF | lipopolysaccharide-induced TNF-alpha factor |
| AB036063 | p53R2 | ribonucleotide reductase |
| AB037738 | KCTD16 | potassium channel tetramerisation domain |
| AB037791 | KIAA1370 | hypothetical protein LOC56204 |
| AB037813 | | unknown |
| AB037823 | | unknown |
| AB037853 | KIAA1432 | connexin 43-interacting protein 150 isoform a |
| AB037925 | NFKBIZ | nuclear factor of kappa light polypeptide gene |
| AB039327 | CASK | calcium/calmodulin-dependent serine protein |
| AB039947 | XB51 | X11L-binding protein 51 |
| AB046692 | hAO | aldeyde oxidase |
| AB046809 | | unknown |
| AB046842 | PPP4R4 | HEAT-like repeat-containing protein isoform 1 |
| AB046844 | GPR107 | G protein-coupled receptor 107 isoform 1 |
| AB047360 | SNX 3A | sorting nexin 3A |
| AB049654 | MRPL36 | mitochondrial ribosomal protein L36 precursor |
| AB051486 | EXOC4 | SEC8 protein isoform a |
| AB053318 | NBEAL1 | neurobeachin-like 1 isoform 3 |
| AB053319 | NBEAL1 | neurobeachin-like 1 isoform 3 |
| AB056106 | ABI3BP | ABI gene family, member 3 (NESH) binding protein |
| AC004770 | | unknown |
| AC004997 | | unknown |
| AC005339 | | unknown |
| AC007182 | | unknown |
| AD000092 | | unknown |
| AF001602 | PON2 | paraoxonase 2 isoform 2 |
| AF003934 | GDF15 | growth differentiation factor 15 |
| AF005774 | CFLAR | CASP8 and FADD-like apoptosis regulator isoform |
| AF006516 | ABI1 | abl-interactor 1 isoform a |
| AF007162 | CRYAB | crystallin, alpha B |
| AF009616 | CFLAR | CASP8 and FADD-like apoptosis regulator isoform |
| AF010314 | ENC1 | ectodermal-neural cortex (with BTB-like domain) |
| AF010446 | | MHC class I related protein 1 isoform B (MR1B) |
| AF011466 | LPAR2 | lysophosphatidic acid receptor 2 |
| AF014403 | SKIV2L2 | superkiller viralicidic activity 2-like 2 |
| AF015186 | SFRS2 | splicing factor, arginine/serine-rich 2 |
| AF017987 | SFRP1 | secreted frizzled-related protein 1 precursor |
| AF019214 | HBP1 | HMG-box transcription factor 1 |
| AF021834 | TFPI | tissue factor pathway inhibitor isoform a |
| AF026071 | TNFRSF25 | tumor necrosis factor receptor superfamily, |
| AF029674 | CREB3 | cAMP responsive element binding protein 3 |
| AF029750 | | tapasin (NGS-17) |
| AF031469 | MR1 | major histocompatibility complex, class |
| AF033026 | PAPSS1 | 3'-phosphoadenosine 5'-phosphosulfate synthase |
| AF039217 | INVS | inversin isoform b |
| AF039690 | SDCCAG8 | serologically defined colon cancer antigen 8 |
| AF040704 | TUSC4 | tumor suppressor candidate 4 |
| AF041459 | CFLAR | CASP8 and FADD-like apoptosis regulator isoform |
| AF043732 | PDE5A | phosphodiesterase 5A isoform 1 |
| AF043977 | CLCA2 | chloride channel accessory 2 precursor |
| AF045451 | NAB1 | NGFI-A binding protein 1 |
| AF047020 | AMACR | alpha-methylacyl-CoA racemase isoform 1 |
| AF047338 | SLC12A4 | solute carrier family 12, member 4 isoform a |
| AF052059 | SEL1L | sel-1 suppressor of lin-12-like precursor |
| AF052094 | EPAS1 | endothelial PAS domain protein 1 |
| AF052151 | FAM89B | family with sequence similarity 89, member B |
| AF053453 | TSPAN6 | transmembrane 4 superfamily member 6 |
| AF056322 | SP100 | nuclear antigen Sp100 isoform 1 |
| AF060922 | BNIP3L | BCL2/adenovirus E1B 19 kD-interacting protein |
| AF061731 | ACIN1 | apoptotic chromatin condensation inducer 1 |
| AF061735 | ATP5H | ATP synthase, H+ transporting, mitochondrial F0 |
| AF062483 | SNX3 | sorting nexin 3 isoform a |
| AF063591 | CD200 | CD200 antigen isoform b |
| AF064243 | ITSN1 | intersectin 1 isoform ITSN-1 |
| AF064484 | | natural resistance-associated macrophage protein 2 non-IRE form (NRAMP2) |
| AF064771 | DGKA | diacylglycerol kinase, alpha 80 kDa |
| AF065214 | PLA2G4C | phospholipase A2, group IVC isoform 1 precursor |

TABLE 2-continued

| GenBank No. | | Encoded Polypeptide |
|---|---|---|
| AF065385 | P2RX6 | purinergic receptor P2X6 isoform 1 |
| AF065854 | | unknown |
| AF067286 | TAPBP | tapasin isoform 1 precursor |
| AF070524 | CNIH3 | cornichon homolog 3 |
| AF070569 | C17orf91 | hypothetical protein LOC84981 |
| AF070571 | | unknown |
| AF070596 | DNAH3 | dynein, axonemal, heavy chain 3 |
| AF072098 | TPT1 | tumor protein, translationally-controlled 1 |
| AF073890 | CTSZ | cathepsin Z preproprotein |
| AF078844 | DDX42 | DEAD box polypeptide 42 protein |
| AF082283 | BCL10 | B-cell CLL/lymphoma 10 |
| AF083068 | PARP3 | poly (ADP-ribose) polymerase family, member 3 |
| AF086256 | | unknown |
| AF086333 | MOSPD1 | motile sperm domain containing 1 |
| AF087847 | | GABA-A receptor-associated protein like 1 (GABARAPL1) |
| AF090891 | TAX1BP1 | Tax1 (human T-cell leukemia virus type I) |
| AF092128 | ITM2B | integral membrane protein 2B |
| AF092137 | MIR548N | |
| AF094754 | GLRB | glycine receptor, beta isoform A precursor |
| AF095727 | MPZL1 | myelin protein zero-like 1 isoform a |
| AF095771 | BBS9 | parathyroid hormone-responsive B1 isoform 2 |
| AF096296 | | thymic stroma chemokine-1 precursor |
| AF096304 | TM7SF2 | transmembrane 7 superfamily member 2 |
| AF097493 | GLS | glutaminase precursor |
| AF098951 | ABCG2 | ATP-binding cassette, sub-family G, member 2 |
| AF101051 | | senescence-associated epithelial membrane protein (SEMP1) |
| AF105974 | HBA1 | alpha 1 globin |
| AF106069 | | deubiquitinating enzyme (UNPH4) |
| AF109681 | | integrin alpha-11 subunit precursor (ITGA11) |
| AF112216 | CMPK1 | UMP-CMP kinase 1 isoform a |
| AF113211 | | unknown |
| AF114488 | | intersectin short isoform (ITSN) |
| AF115512 | DNAJB9 | DnaJ (Hsp40) homolog, subfamily B, member 9 |
| AF116574 | | astrotactin2 (ASTN2) |
| AF116616 | SCD | stearoyl-CoA desaturase 1 |
| AF116827 | COG6 | RecName: Full = Conserved oligomeric Golgi complex subunit 6; Short = COG complex subunit 6; AltName: Full = Component of oligomeric Golgi complex 6; |
| AF118274 | SLC45A1 | DNB5 |
| AF118887 | VAV3 | vav 3 guanine nucleotide exchange factor isoform |
| AF119835 | KITLG | KIT ligand isoform b precursor |
| AF119863 | MEG3 | *Homo sapiens* MEG3 mRNA, partial sequence, imprinted gene. |
| AF121856 | SNX6 | sorting nexin 6 isoform b |
| AF123758 | CLN8 | ceroid-lipofuscinosis, neuronal 8 |
| AF123759 | CLN8 | ceroid-lipofuscinosis, neuronal 8 |
| AF126782 | DHRS7 | dehydrogenase/reductase (SDR family) member 7 |
| AF127481 | AKAP13 | A-kinase anchor protein 13 isoform 1 |
| AF130089 | C14orf45 | hypothetical protein LOC80127 |
| AF130090 | NRIP1 | nuclear receptor interacting protein 1 |
| AF130104 | | unknown |
| AF131743 | LOC100302652 | hypothetical protein LOC100302652 |
| AF131747 | ENDOD1 | endonuclease domain containing 1 precursor |
| AF131801 | ATL1 | atlastin GTPase 1 isoform b |
| AF132203 | SCD | stearoyl-CoA desaturase 1 |
| AF133207 | HSPB8 | heat shock 22 kDa protein 8 |
| AF133425 | TSPAN1 | tetraspan 1 |
| AF134149 | KCNK6 | potassium channel, subfamily K, member 6 |
| AF134715 | TNFSF13B | tumor necrosis factor superfamily, member 13b |
| AF135266 | NUPR1 | p8 protein isoform a |
| AF135593 | VPS41 | vacuolar protein sorting 41 isoform 1 |
| AF139131 | CNTD1 | cyclin N-terminal domain containing 1 |
| AF144488 | SPATA7 | spermatogenesis-associated protein 7 isoform a |
| AF151074 | 2-Mar | membrane-associated ring finger (C3HC4) 2 |
| AF151810 | STARD10 | START domain containing 10 |
| AF151861 | | CGI-103 protein |
| AF153415 | C9orf5 | hypothetical protein LOC23731 |
| AF153820 | | inwardly-rectifying potassium channel Kir2.1 (KCNJ2) |
| AF155158 | MCM7 | minichromosome maintenance complex component 7 |
| AF157324 | RER1 | RER1 retention in endoplasmic reticulum 1 |
| AF158185 | POLH | DNA-directed DNA polymerase eta |
| AF158555 | GLS | glutaminase precursor |

TABLE 2-continued

| GenBank No. | Encoded Polypeptide | |
|---|---|---|
| AF159570 | RGS5 | regulator of G-protein signalling 5 |
| AF161526 | TMBIM4 | transmembrane BAX inhibitor motif containing 4 |
| AF162769 | GLRX | glutaredoxin (thioltransferase) |
| AF164794 | SERINC1 | serine incorporator 1 |
| AF165187 | AGTRAP | angiotensin II receptor-associated protein |
| AF165520 | | phorbolin I protein (PBI) |
| AF169312 | ANGPTL4 | angiopoietin-like 4 protein isoform a precursor |
| AF169676 | FLRT2 | fibronectin leucine rich transmembrane protein 2 |
| AF172398 | F11R | F11 receptor precursor |
| AF176518 | FBXL2 | F-box and leucine-rich repeat protein 2 |
| AF178532 | | aspartyl protease (BACE2) |
| AF179281 | IDS | iduronate-2-sulfatase isoform a precursor |
| AF180519 | GABARAPL3 | Homo sapiens GABA-A receptor-associated protein mRNA, complete cds. |
| AF182273 | CYP3A4 | cytochrome P450, family 3, subfamily A, |
| AF182414 | TMBIM4 | transmembrane BAX inhibitor motif containing 4 |
| AF183417 | MAP1LC3B | microtubule-associated proteins 1A/1B light |
| AF183419 | AK3 | adenylate kinase 3 |
| AF186773 | DYRK3 | dual-specificity tyrosine-(Y)-phosphorylation |
| AF188298 | DAB2 | disabled homolog 2 |
| AF197952 | PRDX5 | peroxiredoxin 5 isoform a precursor |
| AF201370 | MDM2 | mouse double minute 2 homolog isoform MDM2 |
| AF205218 | IVNS1ABP | influenza virus NS1A binding protein |
| AF212995 | CUL4B | cullin 4B isoform 1 |
| AF216292 | HSPA5 | heat shock 70 kDa protein 5 |
| AF216962 | CNNM2 | cyclin M2 isoform 1 |
| AF217974 | ADAMTSL4 | thrombospondin repeat containing 1 isoform 1 |
| AF217990 | HERPUD1 | homocysteine-inducible, endoplasmic reticulum |
| AF218365 | | Ets transcription factor TEL2E (TEL2) |
| AF220026 | TRIM5 | tripartite motif protein TRIM5 isoform alpha |
| AF225981 | | calcium transport ATPase ATP2C1 (ATP2C1) |
| AF228422 | C15orf48 | normal mucosa of esophagus specific 1 |
| AF229179 | | Collectrin |
| AF230398 | TRIM23 | ADP-ribosylation factor domain protein 1 isoform |
| AF230411 | PML | promyelocytic leukemia protein isoform 2 |
| AF230904 | SH3KBP1 | SH3-domain kinase binding protein 1 isoform a |
| AF230924 | CUTA | cutA divalent cation tolerance homolog isoform |
| AF232772 | HAS3 | hyaluronan synthase 3 isoform b |
| AF232905 | C1QTNF1 | C1q and tumor necrosis factor related protein 1 |
| AF237813 | ABAT | 4-aminobutyrate aminotransferase precursor |
| AF239756 | MPZL1 | myelin protein zero-like 1 isoform a |
| AF240468 | COPA | coatomer protein complex, subunit alpha isoform |
| AF246144 | CCNDBP1 | cyclin D-type binding-protein 1 isoform 1 |
| AF247168 | C1orf63 | hypothetical protein LOC57035 |
| AF248966 | | unknown |
| AF250226 | ADCY6 | adenylate cyclase 6 isoform b |
| AF251025 | ZFYVE1 | zinc finger, FYVE domain containing 1 isoform 1 |
| AF251054 | NDRG3 | N-myc downstream regulated gene 3 isoform a |
| AF257659 | CALU | calumenin isoform b precursor |
| AF263293 | SH3GLB1 | SH3-containing protein SH3GLB1 |
| AF267855 | ERGIC1 | endoplasmic reticulum-golgi intermediate |
| AF267856 | | unknown |
| AF274948 | C20orf24 | Homo sapiens putative Rab5-interacting protein mRNA, complete cds. |
| AF276658 | MAP1LC3A | microtubule-associated protein 1 light chain 3 |
| AF278532 | | beta-netrin |
| AF280094 | SP110 | SP110 nuclear body protein isoform c |
| AF285119 | PHPT1 | phosphohistidine phosphatase 1 isoform 2 |
| AF288208 | B3GNT2 | UDP-GlcNAc:betaGal |
| AF288391 | FAM129A | niban protein isoform 2 |
| AF295039 | CABYR | calcium-binding tyrosine |
| AF302786 | GNPTG | N-acetylglucosamine-1-phosphotransferase, gamma |
| AF303378 | TBRG1 | transforming growth factor beta regulator 1 |
| AF313413 | C5orf62 | putative small membrane protein NID67 |
| AF315325 | | cytochrome P450 variant 3A7 (CYP3A7) |
| AF316824 | CENPP | centromere protein P |
| AF316873 | PINK1 | PTEN induced putative kinase 1 precursor |
| AF325213 | TSPAN10 | tetraspanin 10 |
| AF327923 | TMEM120A | transmembrane protein 120A |
| AF329088 | C4orf49 | ovary-specific acidic protein |
| AF330205 | SCOC | short coiled-coil protein isoform 4 |
| AF348078 | SUCNR1 | succinate receptor 1 |
| AF353618 | RSPH3 | radial spoke 3 homolog |
| AF353992 | TM2D3 | TM2 domain containing 3 isoform a |
| AF355465 | ZMAT3 | p53 target zinc finger protein isoform 1 |

TABLE 2-continued

| GenBank No. | | Encoded Polypeptide |
|---|---|---|
| AF356193 | | caspase recruitment domain protein 6 |
| AF380356 | XG | XG glycoprotein isoform 2 precursor |
| AF478446 | NR1H4 | nuclear receptor subfamily 1, group H, member 4 |
| AF493931 | RGS7 | regulator of G-protein signaling 7 |
| AF495383 | ADAM9 | *Homo sapiens* disintegrin/metalloproteinase domain 9 short protein precursor (ADAM9) mRNA, complete cds; alternatively spliced. |
| AF513360 | | Enverin |
| AF542051 (AFFX-HUMISGF3A)/ M97935__3 | SH3KBP1 | SH3-domain kinase binding protein 1 isoform a |
| AFFX-HUMISGF3A/ M97935__5 | | |
| AFFX-HUMISGF3A/ M97935__MA | | |
| AFFX-HUMISGF3A/ M97935__MB | | |
| AI003763 | LMF1 | lipase maturation factor 1 |
| AI022882 | PAM | peptidylglycine alpha-amidating monooxygenase |
| AI023433 | GALNT5 | N-acetylgalactosaminyltransferase 5 |
| AI023774 | LETM2 | leucine zipper-EF-hand containing transmembrane |
| AI038737 | | unknown |
| AI040029 | B4GALT7 | xylosylprotein beta 1,4-galactosyltransferase 7 |
| AI040305 | CDH11 | cadherin 11, type 2 preproprotein |
| AI040324 | | unknown |
| AI041217 | | unknown |
| AI051046 | | unknown |
| AI051127 | | unknown |
| AI052003 | VPS13B | vacuolar protein sorting 13B isoform 5 |
| AI052103 | C6orf170 | hypothetical protein LOC221322 |
| AI052536 | SNX1 | sorting nexin 1 isoform a |
| AI056692 | | unknown |
| AI074333 | RALGPS1 | Ral GEF with PH domain and SH3 binding motif 1 |
| AI077660 | | unknown |
| AI079540 | YIF1B | Yip1 interacting factor homolog B isoform 7 |
| AI081779 | SGSM3 | small G protein signaling modulator 3 |
| AI091079 | | unknown |
| AI092511 | DPP4 | dipeptidylpeptidase IV |
| AI092770 | | unknown |
| AI092931 | SERF2 | small EDRK-rich factor 2 |
| AI096389 | MAST4 | microtubule associated serine/threonine kinase |
| AI096706 | | unknown |
| AI097463 | GALNTL1 | UDP-N-acetyl-alpha-D-galactosamine:polypeptide |
| AI110886 | PAPPA | pregnancy-associated plasma protein A |
| AI122754 | STS | steryl-sulfatase precursor |
| AI123348 | | unknown |
| AI125204 | TMEM217 | transmembrane protein 217 isoform 1 |
| AI125670 | | unknown |
| AI129626 | DCLK1 | doublecortin-like kinase 1 |
| AI129628 | | unknown |
| AI133137 | C20orf108 | hypothetical protein LOC116151 |
| AI139993 | LOC651250 | *Homo sapiens* cDNA FLJ33831 fis, clone CTONG2003937. |
| AI147621 | C10orf32 | hypothetical protein LOC119032 |
| AI150000 | LAMP2 | lysosomal-associated membrane protein 2 isoform |
| AI150117 | TOPORS | topoisomerase I binding, arginine/serine-rich |
| AI160126 | LOC728855 | *Homo sapiens* mRNA, chromosome 1 specific transcript KIAA0493. |
| AI160339 | | unknown |
| AI160540 | KLHDC8B | kelch domain containing 8B |
| AI167292 | SYTL4 | synaptotagmin-like 4 |
| AI183997 | RGS5 | regulator of G-protein signalling 5 |
| AI187364 | | unknown |
| AI188104 | | unknown |
| AI188161 | FLRT2 | fibronectin leucine rich transmembrane protein 2 |
| AI188389 | TMEM9B | TMEM9 domain family, member B precursor |
| AI190413 | | unknown |
| AI200538 | | unknown |
| AI200555 | | unknown |
| AI202327 | CPEB2 | cytoplasmic polyadenylation element binding |

TABLE 2-continued

| GenBank No. | | Encoded Polypeptide |
|---|---|---|
| AI202969 | OSBPL3 | oxysterol-binding protein-like protein 3 isoform |
| AI215102 | RAB11A | Ras-related protein Rab-11A |
| AI218542 | | unknown |
| AI222435 | | unknown |
| AI223870 | DNAJC21 | DnaJ homology subfamily A member 5 isoform 1 |
| AI224105 | PLCB4 | phospholipase C beta 4 isoform a |
| AI243677 | ARSK | arylsulfatase K precursor |
| AI247763 | GALNT5 | N-acetylgalactosaminyltransferase 5 |
| AI248598 | LAMP1 | lysosomal-associated membrane protein 1 |
| AI254547 | PDLIM4 | PDZ and LIM domain 4 isoform 1 |
| AI261321 | FAM82A1 | family with sequence similarity 82, member A1 |
| AI262560 | CNPY3 | trinucleotide repeat containing 5 precursor |
| AI264121 | PLXDC2 | plexin domain containing 2 precursor |
| AI268315 | GFPT1 | glucosamine-fructose-6-phosphate |
| AI270356 | | unknown |
| AI275162 | DLGAP1 | discs large homolog-associated protein 1 isoform |
| AI276880 | ETNK1 | ethanolamine kinase 1 isoform A |
| AI278445 | | unknown |
| AI279062 | SLC22A15 | solute carrier family 22, member 15 |
| AI290475 | RAB23 | Ras-related protein Rab-23 |
| AI291123 | MEG3 | *Homo sapiens* MEG3 mRNA, partial sequence, imprinted gene. |
| AI291989 | GBA2 | bile acid beta-glucosidase |
| AI307750 | C5orf41 | luman-recruiting factor |
| AI307760 | MRPS22 | mitochondrial ribosomal protein S22 |
| AI307802 | ANKRD29 | ankyrin repeat domain 29 |
| AI312083 | | unknown |
| AI313324 | | unknown |
| AI332407 | SFRP1 | secreted frizzled-related protein 1 precursor |
| AI333326 | 11-Sep | septin 11 |
| AI334015 | ABCB5 | ATP-binding cassette, sub-family B, member 5 |
| AI337304 | GOPC | golgi associated PDZ and coiled-coil motif |
| AI341146 | E2F7 | E2F transcription factor 7 |
| AI341234 | | unknown |
| AI341246 | TRAP1 | TNF receptor-associated protein 1 precursor |
| AI341602 | C4orf48 | hypothetical protein LOC401115 |
| AI342246 | | unknown |
| AI346026 | PLEKHA1 | pleckstrin homology domain containing, family A |
| AI348009 | | unknown |
| AI348094 | | unknown |
| AI354864 | GPC1 | glypican 1 precursor |
| AI356412 | LYN | Yamaguchi sarcoma viral (v-yes-1) oncogene |
| AI359676 | | unknown |
| AI361227 | NFE2L1 | nuclear factor erythroid 2-like 1 |
| AI363270 | TRIM38 | tripartite motif-containing 38 |
| AI369073 | LOC283788 | *Homo sapiens* cDNA FLJ31053 fis, clone HSYRA2000640, highly similar to Homo sapiens FRG1 mRNA. |
| AI373299 | | unknown |
| AI374756 | LOC400927 | *Homo sapiens* cDNA FLJ34950 fis, clone NT2RP7017284, highly similar to Casein kinase I isoform epsilon (EC 2.7.11.1). |
| AI376997 | C5orf44 | hypothetical protein LOC80006 isoform 2 |
| AI378035 | | unknown |
| AI378788 | DCBLD2 | discoidin, CUB and LCCL domain containing 2 |
| AI379338 | ASAH1 | N-acylsphingosine amidohydrolase 1 isoform b |
| AI380156 | | unknown |
| AI382026 | MUC12 | SubName: Full = MUC12 protein; Flags: Fragment; |
| AI391633 | | unknown |
| AI393091 | KIAA1632 | hypothetical protein LOC57724 |
| AI393706 | | unknown |
| AI393725 | | unknown |
| AI418538 | FLJ44606 | |
| AI418892 | TM9SF4 | transmembrane 9 superfamily protein member 4 |
| AI420817 | | unknown |
| AI421559 | RALGDS | ral guanine nucleotide dissociation stimulator |
| AI422414 | | unknown |
| AI431643 | RRAS2 | related RAS viral (r-ras) oncogene homolog 2 |
| AI433463 | MME | membrane metallo-endopeptidase |
| AI435399 | | unknown |
| AI435514 | | unknown |
| AI439556 | TXNIP | thioredoxin interacting protein |
| AI446414 | KITLG | KIT ligand isoform b precursor |
| AI446756 | MALAT1 | |
| AI453452 | ZNF654 | zinc finger protein 654 |
| AI457817 | JAG1 | jagged 1 precursor |

TABLE 2-continued

| GenBank No. | | Encoded Polypeptide |
|---|---|---|
| AI458439 | | unknown |
| AI459140 | | unknown |
| AI460037 | NAPEPLD | N-acyl phosphatidylethanolamine phospholipase D |
| AI469425 | | unknown |
| AI472310 | KCNRG | potassium channel regulator isoform 2 |
| AI472339 | TMED4 | transmembrane emp24 protein transport domain |
| AI473891 | | unknown |
| AI474054 | DRAM2 | transmembrane protein 77 |
| AI475544 | MALAT1 | |
| AI478147 | ATP10D | ATPase, class V, type 10D |
| AI479082 | GAS6 | growth arrest-specific 6 isoform 1 precursor |
| AI479419 | | unknown |
| AI493587 | ZFP106 | zinc finger protein 106 homolog |
| AI498144 | C20orf194 | hypothetical protein LOC25943 |
| AI498395 | | unknown |
| AI522053 | | unknown |
| AI523391 | | unknown |
| AI525212 | APLP2 | amyloid beta (A4) precursor-like protein 2 |
| AI537887 | STOM | stomatin isoform a |
| AI559300 | SPATA18 | spermatogenesis associated 18 homolog |
| AI569974 | | unknown |
| AI571796 | SEC14L2 | SEC14-like 2 isoform 1 |
| AI582773 | | unknown |
| AI613010 | | unknown |
| AI623211 | LOC645166 | *Homo sapiens* cDNA, FLJ18771. |
| AI625741 | UBE2W | ubiquitin-conjugating enzyme E2W (putative) |
| AI631210 | | unknown |
| AI632212 | RNPC3 | RNA-binding region (RNP1, RRM) containing 3 |
| AI632728 | | unknown |
| AI633503 | GALNT5 | N-acetylgalactosaminyltransferase 5 |
| AI633523 | GNPTAB | N-acetylglucosamine-1-phosphate transferase |
| AI634046 | CFLAR | CASP8 and FADD-like apoptosis regulator isoform |
| AI634580 | SYNPO2 | synaptopodin 2 isoform c |
| AI636233 | TMEM8A | transmembrane protein 8 (five membrane-spanning |
| AI638405 | MEG3 | *Homo sapiens* MEG3 mRNA, partial sequence, imprinted gene. |
| AI638420 | CLIC4 | chloride intracellular channel 4 |
| AI638768 | | unknown |
| AI638771 | | unknown |
| AI650285 | | unknown |
| AI650819 | CUL4B | cullin 4B isoform 1 |
| AI651603 | | unknown |
| AI651786 | | unknown |
| AI652452 | | unknown |
| AI652681 | | unknown |
| AI653037 | CSTF3 | cleavage stimulation factor subunit 3 isoform 1 |
| AI653117 | | unknown |
| AI653327 | | unknown |
| AI654636 | | unknown |
| AI655057 | RIT1 | Ras-like without CAAX 1 |
| AI655524 | PAQR8 | progestin and adipoQ receptor family member |
| AI655763 | NHLRC3 | NHL repeat containing 3 isoform a |
| AI656232 | OTUB2 | OTU domain, ubiquitin aldehyde binding 2 |
| AI656481 | | unknown |
| AI658662 | SYNPO2 | synaptopodin 2 isoform c |
| AI659225 | CASK | calcium/calmodulin-dependent serine protein |
| AI659456 | USP9X | ubiquitin specific protease 9, X-linked isoform |
| AI659800 | C13orf31 | hypothetical protein LOC144811 |
| AI668610 | | unknown |
| AI668625 | | unknown |
| AI669498 | ZBTB4 | zinc finger and BTB domain containing 4 |
| AI670852 | PTPRB | protein tyrosine phosphatase, receptor type, B |
| AI671049 | CCNE1 | cyclin E1 isoform 1 |
| AI671186 | | unknown |
| AI672159 | | unknown |
| AI672432 | DUSP28 | dual specificity phosphatase 28 |
| AI674647 | SPPL2A | signal peptide peptidase-like 2A |
| AI675453 | PLXNA3 | plexin A3 precursor |
| AI675682 | SLC2A12 | solute carrier family 2 (facilitated glucose |
| AI676022 | ACCS | 1-aminocyclopropane-1-carboxylate synthase |
| AI677701 | RBM24 | RNA binding motif protein 24 isoform 1 |
| AI683805 | | unknown |
| AI689225 | | unknown |
| AI690274 | PYROXD2 | pyridine nucleotide-disulphide oxidoreductase |
| AI693193 | | unknown |

TABLE 2-continued

| GenBank No. | Encoded Polypeptide | |
|---|---|---|
| AI693862 | | unknown |
| AI694303 | APBB2 | amyloid beta A4 precursor protein-binding, |
| AI700633 | SERINC5 | developmentally regulated protein TPO1 |
| AI701428 | GLRB | glycine receptor, beta isoform A precursor |
| AI703142 | ZNF814 | zinc finger protein 814 |
| AI703496 | | unknown |
| AI718223 | PRDX5 | peroxiredoxin 5 isoform a precursor |
| AI719655 | | unknown |
| AI732587 | | unknown |
| AI733041 | CTTNBP2NL | CTTNBP2 N-terminal like |
| AI733474 | GPR155 | G protein-coupled receptor 155 isoform 9 |
| AI735261 | DRAM2 | transmembrane protein 77 |
| AI738556 | TNFRSF10D | tumor necrosis factor receptor superfamily, |
| AI738896 | TNFAIP3 | tumor necrosis factor, alpha-induced protein 3 |
| AI740460 | | unknown |
| AI740589 | C22orf23 | hypothetical protein LOC84645 |
| AI741056 | SELPLG | selectin P ligand |
| AI741110 | ARSD | arylsulfatase D isoform a precursor |
| AI742029 | | unknown |
| AI742434 | | unknown |
| AI743115 | NDUFA11 | NADH dehydrogenase (ubiquinone) 1 alpha |
| AI743534 | ARHGAP24 | Rho GTPase activating protein 24 isoform 1 |
| AI743744 | | unknown |
| AI743792 | ST6GAL1 | ST6 beta-galactosamide |
| AI743979 | | unknown |
| AI744658 | TSPAN16 | transmembrane 4 superfamily member 16 |
| AI753143 | | unknown |
| AI753792 | RRAS2 | related RAS viral (r-ras) oncogene homolog 2 |
| AI754693 | | unknown |
| AI760252 | HAPLN1 | hyaluronan and proteoglycan link protein 1 |
| AI761250 | | unknown |
| AI761561 | HK2 | hexokinase 2 |
| AI761947 | ARHGAP24 | Rho GTPase activating protein 24 isoform 1 |
| AI762782 | IDUA | alpha-L-iduronidase precursor |
| AI765327 | | unknown |
| AI768122 | EIF4G3 | eukaryotic translation initiation factor 4 |
| AI783924 | PLSCR3 | phospholipid scramblase 3 |
| AI793200 | TRIM45 | tripartite motif-containing 45 isoform 1 |
| AI793340 | | unknown |
| AI795908 | PHLDA1 | pleckstrin homology-like domain, family A, |
| AI795923 | RHBDD1 | rhomboid domain containing 1 |
| AI796536 | | unknown |
| AI797353 | KIAA1324L | hypothetical protein LOC222223 isoform 1 |
| AI797678 | | unknown |
| AI797684 | RCN3 | reticulocalbin 3, EF-hand calcium binding domain |
| AI801013 | HCCS | holocytochrome c synthase |
| AI803010 | | unknown |
| AI803088 | ADAMTSL1 | ADAMTS-like 1 isoform 4 precursor |
| AI803181 | TMEM47 | transmembrane protein 47 |
| AI805050 | RAB6B | RAB6B, member RAS oncogene family |
| AI805301 | | unknown |
| AI806169 | | unknown |
| AI806583 | LYPLAL1 | lysophospholipase-like 1 |
| AI806674 | HS2ST1 | heparan sulfate 2-O-sulfotransferase 1 isoform |
| AI806905 | | unknown |
| AI806927 | | unknown |
| AI807023 | RAB8B | RAB8B, member RAS oncogene family |
| AI807532 | EPHX4 | abhydrolase domain containing 7 |
| AI807917 | CCDC149 | coiled-coil domain containing 149 isoform 2 |
| AI809404 | | unknown |
| AI810266 | | unknown |
| AI810572 | PGPEP1 | pyroglutamyl-peptidase I |
| AI810669 | | unknown |
| AI810767 | | unknown |
| AI811298 | OSR2 | odd-skipped related 2 isoform a |
| AI814116 | LOC100130691 | |
| AI814274 | SBSN | suprabasin isoform 2 precursor |
| AI814587 | KIAA1715 | Lunapark |
| AI816071 | FAM174A | family with sequence similarity 174, member A |
| AI816243 | STX12 | syntaxin 12 |
| AI817448 | LOC100130522 | *Homo sapiens* cDNA FLJ31742 fis, clone NT2RI2007214. |
| AI819386 | | unknown |
| AI821404 | PAPSS2 | 3'-phosphoadenosine 5'-phosphosulfate synthase 2 |
| AI821935 | FBXL7 | F-box and leucine-rich repeat protein 7 |
| AI823600 | | unknown |

TABLE 2-continued

| GenBank No. | | Encoded Polypeptide |
|---|---|---|
| AI823980 | RBKS | ribokinase |
| AI824013 | | unknown |
| AI825800 | PDIA3 | protein disulfide-isomerase A3 precursor |
| AI825987 | | unknown |
| AI828035 | GLS | glutaminase precursor |
| AI829920 | UBE2H | ubiquitin-conjugating enzyme E2H isoform 1 |
| AI830201 | | unknown |
| AI832193 | GNB1L | guanine nucleotide binding protein |
| AI859242 | | unknown |
| AI860341 | DLEC1 | deleted in lung and esophageal cancer 1 isoform |
| AI860764 | XPO1 | exportin 1 |
| AI860874 | WDR63 | WD repeat domain 63 |
| AI861942 | LDLR | low density lipoprotein receptor precursor |
| AI862120 | MAMDC2 | MAM domain containing 2 precursor |
| AI862255 | ATP6V0E1 | ATPase, H+ transporting, lysosomal 9 kDa, V0 |
| AI862559 | ANGPTL6 | angiopoietin-like 6 precursor |
| AI867198 | SLC5A3 | solute carrier family 5 (inositol transporters), |
| AI868167 | EFHA2 | EF-hand domain family, member A2 |
| AI869717 | SLC38A10 | solute carrier family 38, member 10 isoform a |
| AI870615 | PDK2 | pyruvate dehydrogenase kinase 2 precursor |
| AI870617 | | unknown |
| AI879064 | | unknown |
| AI884858 | TUSC3 | tumor suppressor candidate 3 isoform a |
| AI885170 | C9orf16 | hypothetical protein LOC79095 |
| AI885178 | MAPRE3 | microtubule-associated protein, RP/EB family, |
| AI886656 | AQP11 | aquaporin 11 |
| AI888786 | ZNF449 | zinc finger protein 449 |
| AI889160 | CABLES1 | Cdk5 and Abl enzyme substrate 1 isoform 2 |
| AI889584 | BOD1L | biorientation of chromosomes in cell division |
| AI890529 | POLH | DNA-directed DNA polymerase eta |
| AI890761 | | unknown |
| AI911687 | CLN5 | ceroid-lipofuscinosis, neuronal 5 |
| AI911972 | | unknown |
| AI912583 | GLIPR1 | GLI pathogenesis-related 1 precursor |
| AI912976 | RNU5E | *Homo sapiens* RNA, U5E small nuclear (RNU5E), non-coding RNA. |
| AI913533 | LOC283267 | *Homo sapiens* cDNA FLJ30003 fis, clone 3NB691000113. |
| AI913749 | PLEKHH2 | pleckstrin homology domain containing, family H |
| AI915827 | | unknown |
| AI916555 | COPZ2 | coatomer protein complex, subunit zeta 2 |
| AI921238 | CDC14B | CDC14 homolog B isoform 3 |
| AI921586 | ALDOA | fructose-bisphosphate aldolase A |
| AI922855 | CPE | carboxypeptidase E preproprotein |
| AI922968 | MAST4 | microtubule associated serine/threonine kinase |
| AI923675 | SLFN5 | schlafen family member 5 |
| AI924150 | GLT25D1 | glycosyltransferase 25 domain containing 1 |
| AI924426 | ELL2 | elongation factor, RNA polymerase II, 2 |
| AI927770 | SEL1L | sel-1 suppressor of lin-12-like precursor |
| AI928387 | | unknown |
| AI929792 | | unknown |
| AI932310 | C14orf4 | chromosome 14 open reading frame 4 |
| AI933861 | C11orf17 | chromosome 11 open reading frame 17 |
| AI934569 | ASAH1 | N-acylsphingosine amidohydrolase 1 isoform b |
| AI935115 | TMEM188 | transmembrane protein 188 |
| AI935162 | | unknown |
| AI935415 | TAX1BP1 | Tax1 (human T-cell leukemia virus type I) |
| AI935917 | PRKAA1 | protein kinase, AMP-activated, alpha 1 catalytic |
| AI936560 | ARHGAP20 | Rho GTPase activating protein 20 |
| AI936769 | | unknown |
| AI939544 | | unknown |
| AI950273 | MEG3 | *Homo sapiens* MEG3 mRNA, partial sequence, imprinted gene. |
| AI951454 | SPR | sepiapterin reductase |
| AI952357 | MDM2 | mouse double minute 2 homolog isoform MDM2 |
| AI955001 | | unknown |
| AI955713 | | unknown |
| AI961401 | KLHL24 | DRE1 protein |
| AI962377 | PPFIBP1 | PTPRF interacting protein binding protein 1 |
| AI970061 | GPR155 | G protein-coupled receptor 155 isoform 9 |
| AI970289 | MEG3 | *Homo sapiens* MEG3 mRNA, partial sequence, imprinted gene. |
| AI970972 | | unknown |
| AI971519 | DTWD1 | DTW domain containing 1 |
| AI982754 | CLU | clusterin isoform 2 |
| AI983904 | | unknown |
| AI984136 | NENF | neuron derived neurotrophic factor precursor |

TABLE 2-continued

| GenBank No. | | Encoded Polypeptide |
|---|---|---|
| AI989567 | ST3GAL6 | alpha2,3-sialyltransferase VI |
| AI989799 | | unknown |
| AI991033 | HSPG2 | heparan sulfate proteoglycan 2 precursor |
| AI992095 | ZNF771 | zinc finger protein 771 |
| AI992283 | TRAF4 | TNF receptor-associated factor 4 |
| AJ131212 | RNASE7 | ribonuclease, RNase A family, 7 precursor |
| AJ227860 | COTL1 | coactosin-like 1 |
| AJ243951 | | deafness locus associated putative guanine nucleotide exchange factor (DelGEF gene, splice variant DelGEF 2) |
| AJ245600 | DEPDC7 | novel 58.3 KDA protein isoform 1 |
| AJ251830 | PERP | PERP, TP53 apoptosis effector |
| AJ252246 | GRIK2 | glutamate receptor, ionotropic, kainate 2 |
| AJ276395 | FN1 | fibronectin 1 isoform 1 preproprotein |
| AJ276888 | MDM2 | mouse double minute 2 homolog isoform MDM2 |
| AJ301610 | GRIK2 | glutamate receptor, ionotropic, kainate 2 |
| AJ406928 | | keratin associated protein 1.5 (KRTAP1.5 gene) |
| AJ406929 | | keratin associated protein 2.1b (KRTAP2.1B gene) |
| AJ406932 | | keratin associated protein 3.2 (KRTAP3.2 gene) |
| AJ422148 | LRRC25 | leucine rich repeat containing 25 precursor |
| AJ457063 | | high tyrosine glycine keratin associated protein 7.1(partial) (KRTAP7.1 gene) |
| AK000162 | ACSS2 | acyl-CoA synthetase short-chain family member 2 |
| AK000168 | KIAA1919 | sodium-dependent glucose transporter 1 |
| AK000345 | DHRS2 | dehydrogenase/reductase member 2 isoform 2 |
| AK000684 | TMEM135 | transmembrane protein 135 |
| AK000778 | NR3C2 | nuclear receptor subfamily 3, group C, member 2 |
| AK000826 | RAB7A | RAB7, member RAS oncogene family |
| AK000938 | ZNF691 | zinc finger protein 691 |
| AK001007 | | unknown |
| AK001029 | UBQLN2 | ubiquilin 2 |
| AK001619 | PDE4DIP | phosphodiesterase 4D interacting protein isoform |
| AK001684 | ATP2C1 | calcium-transporting ATPase 2C1 isoform 1c |
| AK001821 | | unknown |
| AK001913 | LOC100302652 | hypothetical protein LOC100302652 |
| AK002054 | COBLL1 | COBL-like 1 |
| AK002207 | SPG20 | spartin |
| AK021433 | YIPF3 | natural killer cell-specific antigen KLIP1 |
| AK021539 | DSEL | dermatan sulfate epimerase-like |
| AK021586 | AGRN | agrin precursor |
| AK021925 | SLC41A3 | solute carrier family 41, member 3 isoform 1 |
| AK022198 | | unknown |
| AK022459 | PIGB | phosphatidylinositol glycan, class B |
| AK022566 | B4GALT7 | xylosylprotein beta 1,4-galactosyltransferase 7 |
| AK022644 | DBNDD1 | dysbindin (dystrobrevin binding protein 1) |
| AK022817 | NAPB | N-ethylmaleimide-sensitive factor attachment |
| AK022871 | TOLLIP | toll interacting protein |
| AK022883 | TMEM30A | transmembrane protein 30A isoform 1 |
| AK022885 | C9orf16 | hypothetical protein LOC79095 |
| AK023113 | RNF213 | ring finger protein 213 |
| AK023116 | SP140L | SP140 nuclear body protein-like |
| AK023166 | | unknown |
| AK023230 | TTC23 | tetratricopeptide repeat domain 23 |
| AK023297 | MOV10 | Mov10, Moloney leukemia virus 10, homolog |
| AK023343 | | unknown |
| AK023348 | GRN | granulin precursor |
| AK023679 | DISP1 | dispatched A |
| AK023743 | | unknown |
| AK023778 | WDTC1 | WD and tetratricopeptide repeats 1 |
| AK023817 | KIAA1632 | hypothetical protein LOC57724 |
| AK024029 | MOAP1 | modulator of apoptosis 1 |
| AK024050 | UBE2W | ubiquitin-conjugating enzyme E2W (putative) |
| AK024064 | | |
| AK024256 | CACHD1 | cache domain containing 1 |
| AK024446 | ABCC10 | ATP-binding cassette, sub-family C, member 10 |
| AK024712 | CHSY3 | chondroitin sulfate synthase 3 |
| AK024724 | LYPLA2 | lysophospholipase II |
| AK024845 | RAB4B | ras-related GTP-binding protein 4b |
| AK024846 | | unknown |
| AK024896 | SLC5A3 | solute carrier family 5 (inositol transporters), |
| AK024898 | | unknown |
| AK025063 | FAM84A | family with sequence similarity 84, member A |
| AK025253 | | unknown |
| AK025301 | USP53 | ubiquitin specific protease 53 |
| AK025432 | KIAA0564 | hypothetical protein LOC23078 isoform a |
| AK025464 | TPRG1L | tumor protein p63 regulated 1-like |

TABLE 2-continued

| GenBank No. | | Encoded Polypeptide |
|---|---|---|
| AK025608 | C22orf9 | hypothetical protein LOC23313 isoform a |
| AK025872 | | unknown |
| AK026026 | | unknown |
| AK026106 | TLL2 | tolloid-like 2 precursor |
| AK026195 | | unknown |
| AK026392 | | unknown |
| AK026498 | CYP2U1 | cytochrome P450, family 2, subfamily U, |
| AK026577 | ALDOA | fructose-bisphosphate aldolase A |
| AK026697 | CDS1 | CDP-diacylglycerol synthase 1 |
| AK026720 | | unknown |
| AK026747 | PION | pigeon homolog |
| AK026784 | | unknown |
| AK026808 | HERC4 | hect domain and RLD 4 isoform a |
| AK026921 | | unknown |
| AK026966 | | unknown |
| AK027151 | LAMA4 | laminin, alpha 4 isoform 2 precursor |
| AK027199 | | unknown |
| AK027246 | SC5DL | sterol-C5-desaturase |
| AK054668 | SLFN5 | schlafen family member 5 |
| AK075503 | P4HB | prolyl 4-hydroxylase, beta subunit precursor |
| AK075558 | C1orf187 | chromosome 1 open reading frame 187 precursor |
| AK090412 | | unknown |
| AK090434 | | unknown |
| AK091691 | | unknown |
| AK091716 | LOC728190 | Homo sapiens cDNA FLJ34397 fis, clone HCHON2001110. |
| AK091986 | | unknown |
| AK092855 | AP1G2 | adaptor-related protein complex 1, gamma 2 |
| AK095719 | FLJ42709 | Homo sapiens cDNA FLJ38400 fis, clone FEBRA2008159. |
| AK096921 | | unknown |
| AK097618 | C19orf51 | hypothetical protein LOC352909 |
| AK097652 | | unknown |
| AK097997 | LZTS2 | leucine zipper, putative tumor suppressor 2 |
| AK098058 | MAPK12 | mitogen-activated protein kinase 12 |
| AK098125 | | unknown |
| AK098337 | | unknown |
| AK098354 | PACS2 | phosphofurin acidic cluster sorting protein 2 |
| AK098414 | SNRK | SNF related kinase |
| AK098812 | PVR | poliovirus receptor isoform alpha |
| AL008583 | | unknown |
| AL021366 | | unknown |
| AL022165 | | unknown |
| AL031177 | | unknown |
| AL031178 | | unknown |
| AL031295 | | unknown |
| AL031429 | | unknown |
| AL031651 | | unknown |
| AL031667 | | unknown |
| AL034418 | | unknown |
| AL034550 | | unknown |
| AL035413 | | unknown |
| AL035541 | | unknown |
| AL037339 | PTK2 | PTK2 protein tyrosine kinase 2 isoform b |
| AL038787 | | unknown |
| AL039447 | UBAP1 | ubiquitin associated protein 1 |
| AL039706 | IFI27L1 | interferon, alpha-inducible protein 27-like 1 |
| AL039811 | | unknown |
| AL039831 | RAVER2 | ribonucleoprotein, PTB-binding 2 |
| AL040222 | | unknown |
| AL040341 | TTC14 | tetratricopeptide repeat domain 14 isoform a |
| AL041747 | | unknown |
| AL042483 | SPATA18 | spermatogenesis associated 18 homolog |
| AL044019 | SNX29 | sorting nexin 29 |
| AL044056 | MRVI1 | JAW1-related protein isoform b |
| AL044126 | | unknown |
| AL044170 | NBR1 | neighbor of BRCA1 gene 1 |
| AL044570 | | unknown |
| AL045717 | ERO1LB | endoplasmic reticulum oxidoreductin 1-Lbeta |
| AL046017 | FAM46C | hypothetical protein LOC54855 |
| AL046979 | TNS1 | tensin |
| AL048423 | | unknown |
| AL049226 | FAM63B | hypothetical protein LOC54629 isoform b |
| AL049369 | RCAN1 | calcipressin 1 isoform b |
| AL049548 | | unknown |
| AL049646 | | unknown |
| AL049699 | | unknown |

TABLE 2-continued

| GenBank No. | | Encoded Polypeptide |
|---|---|---|
| AL049709 | | unknown |
| AL049923 | OSBPL8 | oxysterol-binding protein-like protein 8 isoform |
| AL049933 | GNAI1 | guanine nucleotide binding protein (G protein), |
| AL049942 | | unknown |
| AL050022 | TCTN3 | tectonic 3 isoform a precursor |
| AL050069 | DOK5 | docking protein 5 |
| AL050154 | | unknown |
| AL050217 | | unknown |
| AL050332 | | unknown |
| AL050374 | | unknown |
| AL050388 | SOD2 | manganese superoxide dismutase isoform A |
| AL078596 | | unknown |
| AL080081 | | unknown |
| AL080214 | IFFO1 | intermediate filament family orphan isoform 4 |
| AL080220 | | unknown |
| AL096732 | | unknown |
| AL096740 | UBE3B | ubiquitin protein ligase E3B |
| AL109824 | | unknown |
| AL110115 | | unknown |
| AL110191 | | unknown |
| AL110209 | PLA2G15 | lysophospholipase 3 (lysosomal phospholipase A2) |
| AL117354 | | unknown |
| AL117381 | | unknown |
| AL117468 | | unknown |
| AL117598 | | unknown |
| AL118520 | | unknown |
| AL118571 | REEP3 | receptor accessory protein 3 |
| AL118843 | LOC100286793 | |
| AL119957 | DNAJC3 | DnaJ (Hsp40) homolog, subfamily C, member 3 |
| AL120021 | KLHL24 | DRE1 protein |
| AL120354 | ZNF654 | zinc finger protein 654 |
| AL121829 | | unknown |
| AL121883 | | unknown |
| AL132665 | BNIP3L | BCL2/adenovirus E1B 19 kD-interacting protein |
| AL133001 | SULF2 | sulfatase 2 isoform b precursor |
| AL133084 | ERCC6 | excision repair cross-complementing rodent |
| AL133580 | SCOC | short coiled-coil protein isoform 4 |
| AL134420 | | unknown |
| AL134489 | RPP38 | ribonuclease P/MRP 38 subunit |
| AL134724 | LOC151162 | *Homo sapiens* clone 24711 mRNA sequence. |
| AL135342 | ZNF561 | zinc finger protein 561 |
| AL136561 | SGIP1 | SH3-domain GRB2-like (endophilin) interacting |
| AL136597 | KLHL7 | kelch-like 7 isoform 2 |
| AL136629 | TSPYL1 | TSPY-like 1 |
| AL136653 | RASSF4 | Ras association domain family 4 |
| AL136658 | C14orf1 | ergosterol biosynthetic protein 28 |
| AL136680 | GBP3 | guanylate binding protein 3 |
| AL136693 | CYBRD1 | cytochrome b reductase 1 isoform 1 |
| AL136733 | UBAP1 | ubiquitin associated protein 1 |
| AL136797 | AHI1 | Abelson helper integration site 1 isoform a |
| AL136807 | SERP1 | stress-associated endoplasmic reticulum protein |
| AL136829 | | unknown |
| AL136835 | | unknown |
| AL136944 | | unknown |
| AL137370 | LMBRD2 | LMBR1 domain containing 2 |
| AL137432 | SUSD1 | sushi domain containing 1 precursor |
| AL138104 | KIAA1432 | connexin 43-interacting protein 150 isoform a |
| AL138349 | PRUNE2 | prune homolog 2 |
| AL139228 | | unknown |
| AL157430 | | unknown |
| AL157437 | | unknown |
| AL157473 | KIAA1217 | sickle tail isoform 1 |
| AL157485 | | unknown |
| AL161958 | THY1 | Thy-1 cell surface antigen preproprotein |
| AL161999 | CYFIP2 | cytoplasmic FMR1 interacting protein 2 |
| AL162047 | NCOA4 | nuclear receptor coactivator 4 isoform 1 |
| AL162060 | | unknown |
| AL353132 | | unknown |
| AL354872 | | unknown |
| AL355532 | | unknown |
| AL355685 | | unknown |
| AL355815 | | unknown |
| AL357536 | C20orf30 | hypothetical protein LOC29058 isoform 1 |
| AL359052 | ITGBL1 | integrin, beta-like 1 (with EGF-like repeat |
| AL359601 | ELMOD1 | ELMO/CED-12 domain containing 1 isoform 1 |
| AL359605 | | unknown |

TABLE 2-continued

| GenBank No. | | Encoded Polypeptide |
|---|---|---|
| AL359622 | ANKRD34A | ankyrin repeat domain 34 |
| AL365347 | | unknown |
| AL365404 | GPR108 | G protein-coupled receptor 108 isoform 2 |
| AL389942 | MIR146A | unknown |
| AL389956 | FBXO32 | F-box only protein 32 isoform 1 |
| AL390186 | | unknown |
| AL390216 | STOX2 | storkhead box 2 |
| AL391688 | | unknown |
| AL512687 | NOMO1 | nodal modulator 1 precursor |
| AL512694 | NADSYN1 | NAD synthetase 1 |
| AL512737 | SLC22A23 | solute carrier family 22, member 23 isoform b |
| AL512766 | FAM54B | hypothetical protein LOC56181 isoform a |
| AL513583 | GM2A | GM2 ganglioside activator precursor |
| AL515318 | SH3BGRL | SH3 domain binding glutamic acid-rich protein |
| AL515916 | LMF1 | lipase maturation factor 1 |
| AL520200 | ABHD14B | abhydrolase domain containing 14B |
| AL520774 | MDH2 | mitochondrial malate dehydrogenase precursor |
| AL520900 | TMEM219 | transmembrane protein 219 |
| AL522395 | SHISA4 | shisa homolog 4 precursor |
| AL522667 | C5orf32 | hypothetical protein LOC84418 |
| AL523076 | MAP1B | microtubule-associated protein 1B |
| AL523860 | | unknown |
| AL524093 | | unknown |
| AL529434 | | unknown |
| AL530264 | CEP68 | centrosomal protein 68 kDa |
| AL533234 | | unknown |
| AL535113 | PLCB4 | phospholipase C beta 4 isoform a |
| AL536553 | | unknown |
| AL537457 | NEFL | neurofilament, light polypeptide 68 kDa |
| AL540260 | PIK3IP1 | HGFL protein isoform 1 |
| AL547782 | DHRSX | dehydrogenase/reductase (SDR family) X-linked |
| AL551046 | HSPB6 | heat shock protein, alpha-crystallin-related, |
| AL552450 | SYNPO2 | synaptopodin 2 isoform c |
| AL553774 | KIAA1462 | hypothetical protein LOC57608 |
| AL555086 | JAK1 | janus kinase 1 |
| AL560266 | FCRLA | Fc receptor-like and mucin-like 1 |
| AL561930 | PI4K2A | phosphatidylinositol 4-kinase type 2 alpha |
| AL562686 | EXOC2 | Sec5 protein |
| AL564683 | CEBPB | CCAAT/enhancer binding protein beta |
| AL565238 | C5orf41 | luman-recruiting factor |
| AL565449 | TPT1 | tumor protein, translationally-controlled 1 |
| AL565741 | C5orf30 | hypothetical protein LOC90355 |
| AL565767 | CIRBP | cold inducible RNA binding protein |
| AL566172 | ATP6V0D1 | ATPase, H+ transporting, lysosomal, V0 subunit |
| AL566528 | NEFL | neurofilament, light polypeptide 68 kDa |
| AL567779 | MCFD2 | multiple coagulation factor deficiency 2 |
| AL569506 | FLJ43663 | *Homo sapiens* cDNA FLJ43663 fis, clone SYNOV4005989. |
| AL569575 | ANTXR1 | anthrax toxin receptor 1 isoform 1 precursor |
| AL569601 | DKK3 | dickkopf homolog 3 precursor |
| AL570661 | CD46 | CD46 antigen, complement regulatory protein |
| AL571375 | SCD5 | stearoyl-CoA desaturase 5 isoform a |
| AL572206 | C18orf32 | hypothetical protein LOC497661 |
| AL573201 | ENDOD1 | endonuclease domain containing 1 precursor |
| AL573637 | UXS1 | UDP-glucuronate decarboxylase 1 |
| AL573722 | TMEM150A | transmembrane protein 150A isoform 1 |
| AL574319 | PDK2 | pyruvate dehydrogenase kinase 2 precursor |
| AL583909 | KIAA1539 | hypothetical protein LOC80256 |
| AL589603 | SYNPO2 | synaptopodin 2 isoform c |
| AL832227 | | unknown |
| AL833204 | ABI3BP | ABI gene family, member 3 (NESH) binding protein |
| AL833762 | | unknown |
| AU118882 | EDNRA | endothelin receptor type A isoform a precursor |
| AU121431 | FAM63B | hypothetical protein LOC54629 isoform b |
| AU134977 | NEAT1 | Human MEN1 region clone epsilon/beta mRNA, 3' fragment. |
| AU135154 | ADAM10 | ADAM metallopeptidase domain 10 precursor |
| AU138166 | STS | steryl-sulfatase precursor |
| AU143929 | FANK1 | fibronectin type III and ankyrin repeat domains |
| AU144083 | ARSD | arylsulfatase D isoform a precursor |
| AU144243 | PIGB | phosphatidylinositol glycan, class B |
| AU144247 | CLIP4 | CAP-GLY domain containing linker protein family, |
| AU145361 | CBLB | Cas-Br-M (murine) ecotropic retroviral |
| AU145941 | CDC14B | CDC14 homolog B isoform 3 |
| AU146771 | SNX18 | sorting nexin 18 isoform c |

TABLE 2-continued

| GenBank No. | | Encoded Polypeptide |
|---|---|---|
| AU150078 | | unknown |
| AU150319 | TAPBPL | TAP binding protein-like precursor |
| AU151560 | | unknown |
| AU152410 | C15orf17 | hypothetical protein LOC57184 |
| AU153366 | IKBKB | inhibitor of nuclear factor kappa B kinase beta |
| AU153583 | | unknown |
| AU154125 | SEC22B | SEC22 vesicle trafficking protein homolog B |
| AU154469 | SLC11A2 | solute carrier family 11 (proton-coupled |
| AU155376 | | unknown |
| AU156421 | | unknown |
| AU156721 | PAPPA | pregnancy-associated plasma protein A |
| AU157541 | OBFC2A | oligonucleotide/oligosaccharide-binding fold |
| AU157716 | | unknown |
| AU160004 | IGF2BP3 | insulin-like growth factor 2 mRNA binding |
| AU160685 | GPR180 | G protein-coupled receptor 180 precursor |
| AV648367 | TMEM66 | transmembrane protein 66 precursor |
| AV661099 | NF1 | neurofibromin isoform 1 |
| AV661152 | UGP2 | UDP-glucose pyrophosphorylase 2 isoform a |
| AV681975 | | unknown |
| AV682252 | GLIPR1 | GLI pathogenesis-related 1 precursor |
| AV682567 | KTELC1 | KTEL (Lys-Tyr-Glu-Leu) containing 1 precursor |
| AV691323 | UGT1A7 | UDP glycosyltransferase 1 family, polypeptide A7 |
| AV692127 | GALNT1 | polypeptide N-acetylgalactosaminyltransferase 1 |
| AV693216 | PLXNB1 | plexin B1 precursor |
| AV694039 | LOC90110 | Homo sapiens mRNA; cDNA DKFZp564O2364 (from clone DKFZp564O2364). |
| AV696976 | LYNX1 | Ly-6 neurotoxin-like protein 1 isoform a |
| AV697515 | RDH10 | retinol dehydrogenase 10 |
| AV700174 | C14orf182 | hypothetical protein LOC283551 |
| AV700323 | | unknown |
| AV700415 | | unknown |
| AV700514 | CLN5 | ceroid-lipofuscinosis, neuronal 5 |
| AV700626 | | unknown |
| AV701177 | ARRDC4 | arrestin domain containing 4 |
| AV701283 | | unknown |
| AV701750 | | unknown |
| AV702575 | | unknown |
| AV703259 | IDS | iduronate-2-sulfatase isoform a precursor |
| AV703555 | | unknown |
| AV704551 | COMMD6 | COMM domain containing 6 isoform a |
| AV704962 | SC4MOL | sterol-C4-methyl oxidase-like isoform 1 |
| AV705559 | LPIN1 | lipin 1 |
| AV707142 | | unknown |
| AV708945 | CATSPER2 | sperm-associated cation channel 2 isoform 2 |
| AV712413 | | unknown |
| AV712912 | TMEM167B | transmembrane protein 167B precursor |
| AV713913 | | unknown |
| AV714268 | PLA2G12A | phospholipase A2, group XIIA precursor |
| AV714462 | | unknown |
| AV717561 | ATP6V0E1 | ATPase, H+ transporting, lysosomal 9 kDa, V0 |
| AV722628 | | unknown |
| AV722990 | PCDHB15 | protocadherin beta 15 precursor |
| AV723308 | NTNG1 | netrin G1 isoform 1 |
| AV724329 | PGM2L1 | phosphoglucomutase 2-like 1 |
| AV725328 | PRNP | prion protein preproprotein |
| AV725364 | IQCK | IQ motif containing K |
| AV728606 | PDCD4 | programmed cell death 4 isoform 2 |
| AV734793 | ZDBF2 | zinc finger, DBF-type containing 2 |
| AV734843 | | unknown |
| AV741657 | LUZP1 | leucine zipper protein 1 |
| AV751731 | TOM1L2 | target of myb1-like 2 isoform 3 |
| AV756141 | CSF2RB | colony stimulating factor 2 receptor, beta |
| AV756532 | MTCH2 | mitochondrial carrier 2 |
| AV757675 | OPTN | optineurin |
| AV758342 | LOC100131801 | |
| AV760596 | MED31 | mediator of RNA polymerase II transcription, |
| AV762892 | SNHG9 | Homo sapiens mRNA; cDNA DKFZp686N06141 (from clone DKFZp686N06141). |
| AW000928 | NPAS2 | neuronal PAS domain protein 2 |
| AW001777 | | unknown |
| AW001847 | APLP2 | amyloid beta (A4) precursor-like protein 2 |
| AW003508 | C3orf23 | hypothetical protein LOC285343 isoform 1 |
| AW003889 | | unknown |
| AW004076 | | unknown |
| AW005237 | | unknown |

TABLE 2-continued

| GenBank No. | | Encoded Polypeptide |
|---|---|---|
| AW005535 | RAP2B | RAP2B, member of RAS oncogene family precursor |
| AW005545 | | unknown |
| AW006123 | FBXO32 | F-box only protein 32 isoform 1 |
| AW006185 | | unknown |
| AW006345 | SSR1 | signal sequence receptor, alpha precursor |
| AW006750 | KLHL24 | DRE1 protein |
| AW007289 | ADAMTS7 | ADAM metallopeptidase with thrombospondin type 1 |
| AW008051 | AGRN | agrin precursor |
| AW008976 | SNX25 | sorting nexin 25 |
| AW009436 | FDPS | farnesyl diphosphate synthase isoform a |
| AW009747 | SYNPO2 | synaptopodin 2 isoform c |
| AW015537 | ZNF469 | zinc finger protein 469 |
| AW021673 | | unknown |
| AW024350 | | unknown |
| AW026241 | | unknown |
| AW028100 | MTMR7 | myotubularin related protein 7 |
| AW029619 | CKAP4 | cytoskeleton-associated protein 4 |
| AW043602 | | unknown |
| AW043859 | | unknown |
| AW050627 | ADAP1 | centaurin, alpha 1 |
| AW051365 | SLC35E1 | solute carrier family 35, member E1 |
| AW052044 | HSPA5 | heat shock 70 kDa protein 5 |
| AW052084 | | unknown |
| AW052179 | COL4A5 | type IV collagen alpha 5 isoform 2 precursor |
| AW058459 | TMEM171 | transmembrane protein 171 isoform 2 |
| AW071793 | MXD1 | MAX dimerization protein 1 |
| AW080618 | | unknown |
| AW080999 | NR3C2 | nuclear receptor subfamily 3, group C, member 2 |
| AW086021 | | unknown |
| AW089415 | SFRP4 | secreted frizzled-related protein 4 precursor |
| AW090182 | TMEM79 | transmembrane protein 79 |
| AW090529 | MOXD1 | monooxygenase, DBH-like 1 isoform 2 |
| AW102637 | NFASC | neurofascin isoform 1 precursor |
| AW105337 | | unknown |
| AW118878 | SVIL | supervillin isoform 2 |
| AW129145 | POLI | DNA polymerase iota |
| AW130600 | | unknown |
| AW131553 | | unknown |
| AW134492 | | unknown |
| AW135176 | CCDC146 | coiled-coil domain containing 146 |
| AW136198 | | unknown |
| AW138767 | ELOVL7 | elongation of very long chain fatty acids-like |
| AW139131 | DLG1 | discs, large homolog 1 isoform 1 |
| AW139393 | | unknown |
| AW139538 | | unknown |
| AW149492 | GOSR2 | golgi SNAP receptor complex member 2 isoform B |
| AW150720 | RDH10 | retinol dehydrogenase 10 |
| AW150953 | DHCR7 | 7-dehydrocholesterol reductase |
| AW151360 | | unknown |
| AW157619 | CES2 | carboxylesterase 2 isoform 2 |
| AW166562 | | unknown |
| AW167727 | | unknown |
| AW167793 | GNS | glucosamine (N-acetyl)-6-sulfatase precursor |
| AW168154 | ZBTB1 | zinc finger and BTB domain containing 1 isoform |
| AW168942 | | unknown |
| AW169973 | METTL8 | methyltransferase like 8 |
| AW170015 | PLCXD2 | phosphatidylinositol-specific phospholipase C, X |
| AW172311 | | unknown |
| AW173623 | SERINC3 | tumor differentially expressed protein 1 |
| AW182938 | MCART6 | mitochondrial carrier triple repeat 6 |
| AW183074 | SDHC | succinate dehydrogenase complex, subunit C |
| AW188464 | USP53 | ubiquitin specific protease 53 |
| AW189467 | | unknown |
| AW190479 | | unknown |
| AW190565 | LOXL4 | lysyl oxidase-like 4 precursor |
| AW193531 | CDK6 | cyclin-dependent kinase 6 |
| AW194730 | STK17A | serine/threonine kinase 17a |
| AW194947 | ENPP4 | ectonucleotide pyrophosphatase/phosphodiesterase |
| AW195071 | | unknown |
| AW195928 | SMURF2 | SMAD specific E3 ubiquitin protein ligase 2 |
| AW204088 | | unknown |
| AW205616 | | unknown |
| AW205686 | | unknown |

TABLE 2-continued

| GenBank No. | | Encoded Polypeptide |
|---|---|---|
| AW206037 | | unknown |
| AW206234 | FLJ42709 | Homo sapiens cDNA FLJ38400 fis, clone FEBRA2008159. |
| AW206414 | | unknown |
| AW206419 | | unknown |
| AW235061 | SLC1A1 | solute carrier family 1, member 1 |
| AW236958 | ASAP1 | development and differentiation enhancing factor |
| AW237258 | APH1B | presenilin stabilization factor-like isoform 1 |
| AW241549 | | unknown |
| AW241832 | ATXN10 | ataxin 10 |
| AW242315 | PTGER3 | Homo sapiens PTGER3 mRNA for prostaglandin E receotor EP3 subtype 3 isoform, partial cds, clone: FLJ80357SAAF. |
| AW242973 | RAB4B | ras-related GTP-binding protein 4b |
| AW245401 | | unknown |
| AW264036 | BCL6 | B-cell lymphoma 6 protein isoform 1 |
| AW264082 | FAM110B | hypothetical protein LOC90362 |
| AW268365 | ERO1L | ERO1-like precursor |
| AW268719 | | unknown |
| AW269686 | RAP2B | RAP2B, member of RAS oncogene family precursor |
| AW270037 | | unknown |
| AW270170 | | unknown |
| AW271409 | DCBLD1 | discoidin, CUB and LCCL domain containing 1 |
| AW272255 | | unknown |
| AW273796 | | unknown |
| AW274503 | | unknown |
| AW274856 | SAP18 | Sin3A-associated protein, 18 kDa |
| AW275049 | | unknown |
| AW276078 | LOC387763 | hypothetical protein LOC387763 |
| AW290940 | | unknown |
| AW291402 | | unknown |
| AW291696 | TBRG1 | transforming growth factor beta regulator 1 |
| AW293849 | | unknown |
| AW294630 | | unknown |
| AW294729 | GRIA3 | glutamate receptor, ionotrophic, AMPA 3 isoform |
| AW294765 | FBXO22 | F-box only protein 22 isoform a |
| AW296788 | MAP1A | microtubule-associated protein 1A |
| AW299226 | CD36 | CD36 antigen |
| AW299245 | CEP290 | centrosomal protein 290 kDa |
| AW299452 | | unknown |
| AW300004 | | unknown |
| AW300140 | ZNF599 | zinc finger protein 599 |
| AW300953 | | unknown |
| AW300959 | MMAA | RecName: Full = Putative L-type amino acid transporter 1-like protein MMAA; AltName: Full = hLAT1 3-transmembrane protein MMAA; Short = hLAT1 3TM MMAA; |
| AW301861 | MAT2A | methionine adenosyltransferase II, alpha |
| AW303865 | PYGB | brain glycogen phosphorylase |
| AW304174 | SPATA1 | spermatogenesis associated 1 |
| AW338089 | MED31 | mediator of RNA polymerase II transcription, |
| AW339310 | DTNA | dystrobrevin alpha isoform 2 |
| AW340588 | | unknown |
| AW341649 | | unknown |
| AW364693 | CCDC30 | coiled-coil domain containing 30 |
| AW392551 | | unknown |
| AW411259 | | unknown |
| AW418882 | UST | uronyl-2-sulfotransferase |
| AW439843 | LOC285550 | hypothetical protein LOC285550 |
| AW449728 | GPR155 | G protein-coupled receptor 155 isoform 9 |
| AW449754 | LYNX1 | Ly-6 neurotoxin-like protein 1 isoform a |
| AW450035 | NAV2 | neuron navigator 2 isoform 1 |
| AW452022 | ODF2L | outer dense fiber of sperm tails 2-like isoform |
| AW452620 | LYSMD4 | LysM, putative peptidoglycan-binding, domain |
| AW452656 | | unknown |
| AW452681 | | unknown |
| AW468201 | B3GNTL1 | UDP-GlcNAc:betaGal |
| AW469351 | CLVS1 | |
| AW469523 | DGAT2 | diacylglycerol O-acyltransferase 2 |
| AW469790 | | unknown |
| AW471181 | | unknown |
| AW511227 | MIB2 | mindbomb homolog 2 |
| AW511319 | | unknown |
| AW511595 | | unknown |
| AW513227 | ZNF285A | zinc finger protein 285 |

TABLE 2-continued

| GenBank No. | | Encoded Polypeptide |
|---|---|---|
| AW513612 | CPXM2 | carboxypeptidase X (M14 family), member 2 |
| AW514038 | | unknown |
| AW514401 | SEPW1 | selenoprotein W, 1 |
| AW515704 | SCYL1 | SCY1-like 1 isoform A |
| AW516297 | | unknown |
| AW517464 | ORAI3 | ORAI calcium release-activated calcium modulator |
| AW517686 | ATP2B4 | plasma membrane calcium ATPase 4 isoform 4a |
| AW518714 | | unknown |
| AW571715 | DDX49 | DEAD (Asp-Glu-Ala-Asp) box polypeptide 49 |
| AW575245 | FCRLA | Fc receptor-like and mucin-like 1 |
| AW575493 | GRAMD3 | GRAM domain containing 3 isoform 2 |
| AW575737 | | unknown |
| AW576457 | | unknown |
| AW591809 | | unknown |
| AW593996 | 3-Mar | membrane-associated ring finger (C3HC4) 3 |
| AW611550 | | unknown |
| AW612657 | LYPLAL1 | lysophospholipase-like 1 |
| AW628045 | CXorf23 | hypothetical protein LOC256643 |
| AW628835 | | unknown |
| AW629527 | TPRG1 | tumor protein p63 regulated 1 |
| AW665086 | | unknown |
| AW665155 | POLH | DNA-directed DNA polymerase eta |
| AW665748 | | unknown |
| AW665758 | | Unknown |
| AW665892 | | Unknown |
| AW771007 | ZNF862 | SubName: Full = Putative uncharacterized protein ENSP00000353120; |
| AW771190 | | unknown |
| AW771590 | RHOQ | ras-like protein TC10 precursor |
| AW779916 | | Unknown |
| AW850158 | ADAM19 | ADAM metallopeptidase domain 19 preproprotein |
| AW954107 | MAN2B2 | mannosidase, alpha, class 2B, member 2 |
| AW955612 | FBN1 | fibrillin 1 precursor |
| AW958475 | RPS27L | ribosomal protein S27-like |
| AW960707 | | Unknown |
| AW962850 | SLFN5 | schlafen family member 5 |
| AW963328 | | Unknown |
| AW970888 | | Unknown |
| AW975183 | | Unknown |
| AW978375 | OSBPL8 | oxysterol-binding protein-like protein 8 isoform |
| AW979182 | | Unknown |
| AW979271 | PDE4D | phosphodiesterase 4D isoform 2 |
| AY007239 | MOXD1 | monooxygenase, DBH-like 1 isoform 2 |
| AY008268 | | GTP-binding protein SAR1 (SAR1) |
| AY008372 | | oxysterol binding protein-related protein 3 (ORP3) |
| AY009128 | ISCU | iron-sulfur cluster assembly enzyme isoform |
| AY014180 | SMURF2 | SMAD specific E3 ubiquitin protein ligase 2 |
| AY028632 | CAT | catalase |
| AY079172 | ATP6V0D2 | ATPase, H+ transporting, lysosomal 38 kDa, V0 |
| AY090780 | | Unknown |
| AY099509 | C3orf34 | hypothetical protein LOC84984 |
| AY134855 | | smooth muscle myosin heavy chain 11 isoform SM1-like protein |
| AY185496 | SERPINA9 | serine (or cysteine) proteinase inhibitor, clade |
| BC000019 | CDH6 | cadherin 6, type 2 preproprotein |
| BC000027 | TMED3 | transmembrane emp24 domain containing 3 |
| BC000102 | COL4A3BP | alpha 3 type IV collagen binding protein isoform |
| BC000182 | ANXA4 | annexin IV |
| BC000196 | CCNG1 | cyclin G1 |
| BC000232 | | receptor accessory protein 5 |
| BC000296 | OSBPL2 | oxysterol-binding protein-like protein 2 isoform |
| BC000314 | RTN1 | reticulon 1 isoform A |
| BC000324 | | Granulin |
| BC000351 | PCYT2 | phosphate cytidylyltransferase 2, ethanolamine |
| BC000353 | MYOD1 | myogenic differentiation 1 |
| BC000373 | APLP2 | amyloid beta (A4) precursor-like protein 2 |
| BC000419 | TXNRD2 | thioredoxin reductase 2 precursor |
| BC000474 | TP53I3 | tumor protein p53 inducible protein 3 |
| BC000580 | P4HTM | hypoxia-inducible factor prolyl 4-hydroxylase |
| BC000596 | RPL23AP7 | *Homo sapiens* ribosomal protein L23a pseudogene 7, mRNA (cDNA clone IMAGE: 3346366). |
| BC000638 | | ORM1-like 3 |
| BC000686 | EPDR1 | ependymin related protein 1 precursor |

TABLE 2-continued

| GenBank No. | | Encoded Polypeptide |
|---|---|---|
| BC000687 | TRAM1 | translocation associated membrane protein 1 |
| BC000704 | TSPAN3 | transmembrane 4 superfamily member 8 isoform 1 |
| BC000737 | RGS4 | regulator of G-protein signaling 4 isoform 1 |
| BC000836 | YPEL5 | yippee-like 5 |
| BC000856 | | Unknown |
| BC000899 | BET1 | blocked early in transport 1 |
| BC000905 | RAB1A | RAB1A, member RAS oncogene family isoform 1 |
| BC000961 | | degenerative spermatocyte homolog 1, lipid desaturase (Drosophila) |
| BC001001 | VPS8 | vacuolar protein sorting 8 homolog isoform b |
| BC001099 | SELO | selenoprotein O |
| BC001207 | MAGED4 | melanoma antigen family D, 4 |
| BC001255 | NCBP2 | nuclear cap binding protein subunit 2, 20 kDa |
| BC001281 | TNFRSF10B | tumor necrosis factor receptor superfamily, |
| BC001364 | SEC22B | SEC22 vesicle trafficking protein homolog B |
| BC001387 | PLA2G16 | HRAS-like suppressor 3 |
| BC001467 | ADI1 | acireductone dioxygenase 1 |
| BC001595 | NT5C2 | 5'-nucleotidase, cytosolic II |
| BC001689 | SLC25A20 | carnitine/acylcarnitine translocase |
| BC001727 | ANKRD10 | ankyrin repeat domain 10 |
| BC001745 | D4S234E | brain neuron cytoplasmic protein 1 |
| BC001805 | | Unknown |
| BC001867 | ATPIF1 | ATPase inhibitory factor 1 isoform 2 precursor |
| BC001875 | MFI2 | Homo sapiens, clone IMAGE: 4858804, mRNA. |
| BC002480 | SRD5A3 | steroid 5 alpha-reductase 3 |
| BC002510 | RAB6B | RAB6B, member RAS oncogene family |
| BC002571 | ABHD14A | abhydrolase domain containing 14A |
| BC002637 | TRIB2 | tribbles homolog 2 |
| BC002660 | TMOD1 | tropomodulin 1 |
| BC002704 | STAT1 | signal transducer and activator of transcription |
| BC002709 | | Unknown |
| BC002713 | MXD4 | MAD4 |
| BC002752 | | Unknown |
| BC002794 | TNFRSF14 | tumor necrosis factor receptor superfamily, |
| BC002842 | HIST1H2BD | histone cluster 1, H2bd |
| BC003064 | DAB2 | disabled homolog 2 |
| BC003096 | PDLIM4 | PDZ and LIM domain 4 isoform 1 |
| BC003128 | ZDHHC9 | zinc finger, DHHC domain containing 9 |
| BC003143 | | dual specificity phosphatase 6 |
| BC003164 | MBOAT7 | membrane bound O-acyltransferase domain |
| BC003170 | UBAP2L | ubiquitin associated protein 2-like isoform a |
| BC003177 | CALCOCO1 | coiled-coil transcriptional coactivator isoform |
| BC003358 | RPL10 | ribosomal protein L10 |
| BC003503 | | RNA binding motif protein 4B |
| BC003561 | AP1S1 | adaptor-related protein complex 1, sigma 1 |
| BC003564 | ATP6V1G1 | vacuolar H+ ATPase G1 |
| BC003602 | H2AFJ | Homo sapiens cDNA FLJ10903 fis, clone OVARC1000006, highly similar to HISTONE H2A.1. |
| BC003610 | | milk fat globule-EGF factor 8 protein |
| BC003614 | DAPK1 | death-associated protein kinase 1 |
| BC003637 | DDIT3 | DNA-damage-inducible transcript 3 |
| BC003658 | SAR1A | SAR1a gene homolog 1 |
| BC003660 | DPH5 | diphthine synthase isoform b |
| BC003667 | RPS27L | ribosomal protein S27-like |
| BC003686 | SNAP23 | synaptosomal-associated protein 23 isoform |
| BC004108 | | immunoglobulin superfamily, member 8 |
| BC004130 | CALCOCO2 | calcium binding and coiled-coil domain 2 |
| BC004153 | GPR62 | G protein-coupled receptor 62 |
| BC004162 | PPARA | peroxisome proliferative activated receptor, |
| BC004180 | | keratin associated protein 4-12 |
| BC004191 | | dynactin 5 (p25) |
| BC004241 | LAMA4 | laminin, alpha 4 isoform 2 precursor |
| BC004269 | FAM167B | hypothetical protein LOC84734 |
| BC004276 | TMEM8A | transmembrane protein 8 (five membrane-spanning |
| BC004283 | AHNAK2 | AHNAK nucleoprotein 2 |
| BC004331 | HSDL2 | hydroxysteroid dehydrogenase like 2 |
| BC004371 | APLP2 | amyloid beta (A4) precursor-like protein 2 |
| BC004395 | APOL2 | apolipoprotein L2 |
| BC004443 | ATP6V1E1 | vacuolar H+ ATPase E1 isoform a |
| BC004446 | C20orf24 | Homo sapiens putative Rab5-interacting protein mRNA, complete cds. |
| BC004535 | ZDHHC16 | Abl-philin 2 isoform 1 |
| BC004566 | MRPS21 | mitochondrial ribosomal protein S21 |
| BC004818 | | Unknown |
| BC004911 | BSCL2 | seipin isoform 1 |

TABLE 2-continued

| GenBank No. | | Encoded Polypeptide |
|---|---|---|
| BC004936 | SCD5 | stearoyl-CoA desaturase 5 isoform a |
| BC004942 | PGPEP1 | pyroglutamyl-peptidase I |
| BC004948 | LRRC41 | MUF1 protein |
| BC005009 | | yippee-like 3 (*Drosophila*) |
| BC005047 | DUSP6 | dual specificity phosphatase 6 isoform a |
| BC005050 | NICN1 | nicolin 1 |
| BC005056 | DNAJC30 | DnaJ (Hsp40) homolog subfamily C member 30 |
| BC005073 | CYHR1 | cysteine/histidine-rich 1 isoform 1 |
| BC005078 | | coiled-coil domain containing 93 |
| BC005127 | PLIN2 | adipose differentiation-related protein |
| BC005147 | FKBP1A | FK506 binding protein 1A, 12 kDa |
| BC005193 | UFM1 | ubiquitin-fold modifier 1 precursor |
| BC005247 | C10orf110 | *Homo sapiens* uncharacterized hypothalamus protein HT009 mRNA, complete cds. |
| BC005259 | XRCC4 | X-ray repair cross complementing protein 4 |
| BC005334 | CETN2 | caltractin |
| BC005374 | ERP44 | thioredoxin domain containing 4 (endoplasmic |
| BC005807 | SCD | stearoyl-CoA desaturase 1 |
| BC005810 | CLEC11A | stem cell growth factor precursor |
| BC005876 | ATP6V0B | ATPase, H+ transporting, lysosomal 21 kDa, V0 |
| BC005884 | | Unknown |
| BC005896 | HYAL3 | hyaluronoglucosaminidase 3 precursor |
| BC005903 | POLR2L | DNA directed RNA polymerase II polypeptide L |
| BC005924 | PSG3 | pregnancy specific beta-1-glycoprotein 3 |
| BC005931 | | hemoglobin, alpha 1 |
| BC005980 | UBE2D1 | ubiquitin-conjugating enzyme E2D 1 |
| BC006088 | SERINC3 | tumor differentially expressed protein 1 |
| BC006110 | C7orf70 | hypothetical protein LOC84792 |
| BC006163 | | dynactin 1 (p150, glued homolog, *Drosophila*) |
| BC006164 | | Unknown |
| BC006211 | SDF4 | stromal cell derived factor 4 isoform 2 |
| BC006249 | GUK1 | guanylate kinase 1 isoform b |
| BC006270 | | Unknown |
| BC006279 | ZNF627 | zinc finger protein 627 |
| BC006362 | PPAPDC3 | phosphatidic acid phosphatase type 2 domain |
| BC006373 | SRD5A1 | steroid-5-alpha-reductase 1 |
| BC006374 | ROR1 | receptor tyrosine kinase-like orphan receptor 1 |
| BC006405 | TXNDC17 | thioredoxin-like 5 |
| BC006422 | PFKL | RecName: Full = 6-phosphofructokinase, liver type; EC = 2.7.1.11; AltName: Full = Phosphofructokinase 1; AltName: Full = Phosphohexokinase; AltName: Full = Phosphofructo-1-kinase isozyme B; Short = PFK-B; |
| BC008034 | CUEDC1 | CUE domain-containing 1 |
| BC008300 | PCNXL2 | pecanex-like 2 |
| BC008410 | PMS1 | postmeiotic segregation 1 isoform a |
| BC008745 | CRTAP | cartilage associated protein precursor |
| BC008992 | | docking protein 5 |
| BC009735 | | Unknown |
| BC010024 | HKR1 | GLI-Kruppel family member HKR1 |
| BC010942 | ACAT1 | acetyl-Coenzyme A acetyltransferase 1 precursor |
| BC011002 | | Unknown |
| BC012344 | ZNF333 | zinc finger protein 333 |
| BC012846 | IDH1 | isocitrate dehydrogenase 1 (NADP+), soluble |
| BC013633 | | Unknown |
| BC014207 | ELMO2 | engulfment and cell motility 2 |
| BC014579 | AKR1C1 | aldo-keto reductase family 1, member C1 |
| BC014974 | YIF1B | Yip1 interacting factor homolog B isoform 7 |
| BC015232 | | transmembrane protein 136 |
| BC015390 | | hypothetical protein LOC644242 |
| BC015429 | | Unknown |
| BC015449 | | Unknown |
| BC016291 | | Unknown |
| BC016828 | ASAH1 | N-acylsphingosine amidohydrolase 1 isoform b |
| BC017771 | CCDC90B | coiled-coil domain containing 90B precursor |
| BC017927 | ERAP2 | endoplasmic reticulum aminopeptidase 2 |
| BC018336 | HSD11B1L | short-chain dehydrogenase/reductase 10 isoform |
| BC018681 | NDST2 | heparan glucosaminyl |
| BC018756 | MOXD1 | monooxygenase, DBH-like 1 isoform 2 |
| BC019064 | FAM40B | hypothetical protein LOC57464 isoform a |
| BC020925 | SLC38A10 | solute carrier family 38, member 10 isoform a |
| BC021286 | C1orf187 | chromosome 1 open reading frame 187 precursor |
| BC021680 | C5orf46 | hypothetical protein LOC389336 precursor |
| BC021861 | LOC554202 | *Homo sapiens* cDNA FLJ42400 fis, clone ASTRO2003581. |
| BC022066 | ARMCX5 | armadillo repeat containing, X-linked 5 |

TABLE 2-continued

| GenBank No. | | Encoded Polypeptide |
|---|---|---|
| BC022487 | GCLC | glutamate-cysteine ligase, catalytic subunit |
| BC022967 | DCAF5 | WD repeat domain 22 |
| BC025250 | METTL8 | methyltransferase like 8 |
| BC028703 | LASS3 | LAG1 longevity assurance homolog 3 |
| BC029051 | ARSB | arylsulfatase B isoform 1 precursor |
| BC029442 | | Unknown |
| BC029828 | B4GALNT1 | beta-1,4-N-acetyl-galactosaminyl transferase 1 |
| BC030005 | MCTP1 | multiple C2 domains, transmembrane 1 isoform L |
| BC030130 | WFS1 | wolframin |
| BC031620 | SNX19 | sorting nexin 19 |
| BC031811 | | Unknown |
| BC032004 | GRIA3 | glutamate receptor, ionotrophic, AMPA 3 isoform |
| BC032406 | WDR78 | WD repeat domain 78 isoform 1 |
| BC033311 | HAS1 | hyaluronan synthase 1 |
| BC033513 | TEX261 | testis expressed sequence 261 |
| BC033663 | LAMA3 | laminin alpha 3 subunit isoform 1 |
| BC034236 | | hypothetical protein MGC39821 |
| BC034248 | NBR2 | Homo sapiens cDNA, FLJ17910. |
| BC034275 | ASPHD1 | aspartate beta-hydroxylase domain containing 1 |
| BC035749 | C13orf31 | hypothetical protein LOC144811 |
| BC036225 | | coiled-coil domain containing 147 |
| BC036405 | KIAA1908 | Homo sapiens mRNA for KIAA1908 protein, partial cds. |
| BC036453 | PHYHIPL | phytanoyl-CoA 2-hydroxylase interacting |
| BC037317 | KIAA1107 | hypothetical protein LOC23285 |
| BC037359 | ZNF846 | zinc finger protein 846 |
| BC039509 | | hypothetical protein LOC340109 |
| BC040924 | SYT16 | synaptotagmin XIV-like |
| BC040952 | PIK3C2A | phosphoinositide-3-kinase, class 2 alpha |
| BC040965 | RORA | RAR-related orphan receptor A isoform b |
| BC041127 | ALCAM | activated leukocyte cell adhesion molecule |
| BC041355 | C3orf52 | TPA-induced transmembrane protein |
| BC041482 | | Unknown |
| BC041664 | BEST1 | bestrophin 1 isoform 1 |
| BC042510 | CEL | carboxyl ester lipase precursor |
| BC042953 | | Unknown |
| BC043411 | | Unknown |
| BE042976 | PIK3IP1 | HGFL protein isoform 1 |
| BE043477 | ATP6V0E1 | ATPase, H+ transporting, lysosomal 9 kDa, V0 |
| BE044272 | DYNLL1 | dynein light chain 1 |
| BE044480 | CYB5D2 | cytochrome b5 domain containing 2 |
| BE045549 | MIB2 | mindbomb homolog 2 |
| BE046443 | CYLD | ubiquitin carboxyl-terminal hydrolase CYLD |
| BE048525 | | Unknown |
| BE048919 | | Unknown |
| BE092211 | CHID1 | chitinase domain containing 1 isoform b |
| BE138888 | | Unknown |
| BE147896 | VPS53 | vacuolar protein sorting 53 isoform 1 |
| BE217875 | | Unknown |
| BE219277 | HDAC11 | histone deacetylase 11 isoform 1 |
| BE220330 | C7orf46 | hypothetical protein LOC340277 isoform 1 |
| BE221817 | | Unknown |
| BE222746 | DUSP22 | dual specificity phosphatase 22 |
| BE251303 | | Unknown |
| BE262551 | APC2 | adenomatosis polyposis coli 2 |
| BE271644 | CDH23 | cadherin-like 23 isoform 1 precursor |
| BE301252 | FLJ23867 | SubName: Full = cDNA FLJ23867 fis, clone LNG09729; |
| BE302191 | STK38L | serine/threonine kinase 38 like |
| BE326919 | SAT1 | Synthetic construct DNA, clone: pF1KB8373, Homo sapiens SAT1 gene for spermidine/spermine N1-acetyltransferase 1, without stop codon, in Flexi system. |
| BE328850 | TLCD1 | TLC domain containing 1 isoform 2 |
| BE348597 | C3orf58 | hypothetical protein LOC205428 isoform a |
| BE348679 | NHSL2 | NHS-like 2 |
| BE349022 | SUMF2 | sulfatase modifying factor 2 isoform b |
| BE349147 | CPD | carboxypeptidase D precursor |
| BE379006 | CD59 | CD59 antigen preproprotein |
| BE408081 | C1orf122 | hypothetical protein LOC127687 isoform 1 |
| BE439489 | XPR1 | xenotropic and polytropic retrovirus receptor |
| BE465475 | KLHL29 | RecName: Full = Kelch-like protein 29; AltName: Full = Kelch repeat and BTB domain-containing protein 9; |
| BE466675 | IBSP | integrin-binding sialoprotein precursor |
| BE466825 | ZNF565 | zinc finger protein 565 |

TABLE 2-continued

| GenBank No. | | Encoded Polypeptide |
|---|---|---|
| BE501385 | C12orf60 | hypothetical protein LOC144608 |
| BE501464 | TRIM4 | tripartite motif protein TRIM4 isoform alpha |
| BE501976 | | Unknown |
| BE502785 | ALCAM | activated leukocyte cell adhesion molecule |
| BE502982 | YPEL2 | yippee-like 2 |
| BE503425 | LOX | lysyl oxidase preproprotein |
| BE504180 | STK10 | serine/threonine kinase 10 |
| BE541641 | SLC38A10 | solute carrier family 38, member 10 isoform a |
| BE547542 | DCBLD1 | discoidin, CUB and LCCL domain containing 1 |
| BE549656 | RCN1 | reticulocalbin 1 precursor |
| BE549937 | FGF14 | fibroblast growth factor 14 isoform 1B |
| BE550486 | SLC2A3 | SubName: Full = Solute carrier family 2 (Facilitated glucose transporter), member 3, isoform CRA_a; SubName: Full = cDNA, FLJ92716, Homo sapiens solute carrier family 2 (facilitated glucosetransporter), member 3 (SLC2A3), mRNA; |
| BE551877 | FBXW7 | F-box and WD repeat domain containing 7 isoform |
| BE565675 | FAM45A | hypothetical protein LOC404636 |
| BE568660 | CHURC1 | churchill domain containing 1 |
| BE615277 | PVR | poliovirus receptor isoform alpha |
| BE622627 | PIK3R3 | phosphoinositide-3-kinase, regulatory subunit 3 |
| BE644809 | PCDH7 | protocadherin 7 isoform c precursor |
| BE644818 | SPPL2B | signal peptide peptidase-like 2B isoform 3 |
| BE645771 | GFPT1 | glucosamine-fructose-6-phosphate |
| BE646146 | LOC729678 | Homo sapiens cDNA FLJ37851 fis, clone BRSSN2014294. |
| BE646573 | NFKBIZ | nuclear factor of kappa light polypeptide gene |
| BE669858 | SAMD9L | sterile alpha motif domain containing 9-like |
| BE671156 | | Unknown |
| BE671224 | STK11 | serine/threonine protein kinase 11 |
| BE672313 | FAM110B | hypothetical protein LOC90362 |
| BE672499 | MIR548F5 | |
| BE672676 | | Unknown |
| BE673226 | | Unknown |
| BE673587 | SLC14A1 | solute carrier family 14 (urea transporter), |
| BE674089 | LHFP | lipoma HMGIC fusion partner precursor |
| BE674460 | MAN1A1 | mannosidase, alpha, class 1A, member 1 |
| BE674466 | | Unknown |
| BE675337 | | Unknown |
| BE675516 | NEAT1 | Human MEN1 region clone epsilon/beta mRNA, 3' fragment. |
| BE677131 | ANKRD6 | ankyrin repeat domain 6 |
| BE740761 | | Unknown |
| BE741920 | NDUFA11 | NADH dehydrogenase (ubiquinone) 1 alpha |
| BE744389 | RNASEK | ribonuclease kappa |
| BE787063 | | Unknown |
| BE813017 | SHC3 | src homology 2 domain-containing transforming |
| BE856341 | LAYN | layilin |
| BE857601 | MAP1LC3A | microtubule-associated protein 1 light chain 3 |
| BE869583 | PRDX6 | peroxiredoxin 6 |
| BE875567 | AGTRAP | angiotensin II receptor-associated protein |
| BE877420 | | Unknown |
| BE877796 | MIR548G | |
| BE877955 | | Unknown |
| BE880245 | GNS | glucosamine (N-acetyl)-6-sulfatase precursor |
| BE880828 | MCFD2 | multiple coagulation factor deficiency 2 |
| BE882538 | TBC1D1 | TBC1 (tre-2/USP6, BUB2, cdc16) domain family, |
| BE883841 | | Unknown |
| BE886225 | SAMD9L | sterile alpha motif domain containing 9-like |
| BE888744 | IFIT2 | interferon-induced protein with |
| BE889628 | ERAP2 | endoplasmic reticulum aminopeptidase 2 |
| BE890745 | ARL1 | ADP-ribosylation factor-like 1 |
| BE892293 | | Unknown |
| BE892574 | LACTB | lactamase, beta isoform a |
| BE893893 | MAP1LC3B | microtubule-associated proteins 1A/1B light |
| BE895437 | TK2 | thymidine kinase 2, mitochondrial |
| BE897886 | RHOQ | ras-like protein TC10 precursor |
| BE904551 | CASC4 | cancer susceptibility candidate 4 isoform a |
| BE906233 | C1orf183 | hypothetical protein LOC55924 isoform a |
| BE930512 | MDM2 | mouse double minute 2 homolog isoform MDM2 |
| BE958291 | MTAP | 5'-methylthioadenosine phosphorylase |
| BE961916 | FBXO18 | F-box only protein, helicase, 18 isoform 1 |
| BE962027 | | Unknown |
| BE962299 | C7orf42 | hypothetical protein LOC55069 |

TABLE 2-continued

| GenBank No. | | Encoded Polypeptide |
|---|---|---|
| BE962354 | TCTN3 | tectonic 3 isoform a precursor |
| BE962615 | | Unknown |
| BE963444 | LYRM1 | LYR motif containing 1 |
| BE965311 | METRN | meteorin, glial cell differentiation regulator |
| BE966604 | SAMD9L | sterile alpha motif domain containing 9-like |
| BE966768 | MXRA7 | transmembrane anchor protein 1 isoform 2 |
| BE967275 | | Unknown |
| BE967311 | | Unknown |
| BE967331 | ALG2 | alpha-1,3-mannosyltransferase ALG2 |
| BE967532 | | Unknown |
| BE971383 | SAT1 | Synthetic construct DNA, clone: pF1KB8373, Homo sapiens SAT1 gene for spermidine/spermine N1-acetyltransferase 1, without stop codon, in Flexi system. |
| BF000155 | TRAF4 | TNF receptor-associated factor 4 |
| BF001267 | DOCK7 | dedicator of cytokinesis 7 |
| BF002195 | | Unknown |
| BF002844 | COBLL1 | COBL-like 1 |
| BF003134 | CLCA2 | chloride channel accessory 2 precursor |
| BF030331 | LRRC8A | leucine rich repeat containing 8 family, member |
| BF033242 | CES2 | carboxylesterase 2 isoform 2 |
| BF035563 | KIAA1324L | hypothetical protein LOC222223 isoform 1 |
| BF055311 | | Unknown |
| BF055343 | GALNTL2 | UDP-N-acetyl-alpha-D-galactosamine:polypeptide |
| BF055474 | PHF11 | PHD finger protein 11 isoform b |
| BF056746 | PAX8 | paired box 8 isoform PAX8A |
| BF061003 | KCNC4 | Shaw-related voltage-gated potassium channel |
| BF061543 | | Unknown |
| BF062384 | SLC39A11 | solute carrier family 39, member 11 isoform 1 |
| BF062886 | VRK3 | vaccinia related kinase 3 isoform 1 |
| BF063896 | | Unknown |
| BF107618 | PAPPA | pregnancy-associated plasma protein A |
| BF108666 | LOC375190 | hypothetical protein LOC375190 |
| BF108695 | LOC285550 | hypothetical protein LOC285550 |
| BF109303 | | Unknown |
| BF109660 | OXR1 | oxidation resistance 1 isoform 1 |
| BF109854 | ST7L | suppression of tumorigenicity 7-like isoform 1 |
| BF111214 | ADAMTSL1 | ADAMTS-like 1 isoform 4 precursor |
| BF111326 | KCNJ2 | potassium inwardly-rectifying channel J2 |
| BF111651 | PPAPDC1B | phosphatidic acid phosphatase type 2 domain |
| BF112171 | | Unknown |
| BF114745 | | Unknown |
| BF116042 | | Unknown |
| BF125756 | GABARAPL1 | GABA(A) receptor-associated protein like 1 |
| BF130943 | PPAPDC1A | phosphatidic acid phosphatase type 2 domain |
| BF195608 | | Unknown |
| BF196943 | USP53 | ubiquitin specific protease 53 |
| BF197222 | PHF10 | PHD finger protein 10 isoform a |
| BF203664 | | Unknown |
| BF215644 | | Unknown |
| BF218115 | HIPK2 | homeodomain interacting protein kinase 2 isoform |
| BF218804 | ATP13A3 | ATPase type 13A3 |
| BF218922 | VCAN | versican isoform 1 precursor |
| BF221525 | ROR1 | receptor tyrosine kinase-like orphan receptor 1 |
| BF221547 | PDE5A | phosphodiesterase 5A isoform 1 |
| BF222826 | | Unknown |
| BF222867 | | Unknown |
| BF240286 | TOB1 | transducer of ERBB2, 1 |
| BF242905 | ALCAM | activated leukocyte cell adhesion molecule |
| BF244081 | C4orf3 | hypothetical protein LOC401152 |
| BF244402 | FBXO32 | F-box only protein 32 isoform 1 |
| BF246115 | MT1F | metallothionein 1F |
| BF304759 | LRP1 | low density lipoprotein-related protein 1 |
| BF308548 | TUSC2 | tumor suppressor candidate 2 |
| BF337528 | ORMDL3 | ORM1-like 3 |
| BF340123 | RFK | riboflavin kinase |
| BF340635 | ATP6V1G2 | ATPase, H+ transporting, lysosomal, V1 subunit |
| BF342661 | MAP2 | microtubule-associated protein 2 isoform 1 |
| BF343672 | DCPS | mRNA decapping enzyme |
| BF344265 | PBXIP1 | pre-B-cell leukemia homeobox interacting protein |
| BF346014 | IDS | iduronate-2-sulfatase isoform a precursor |
| BF382281 | BLOC1S2 | biogenesis of lysosome-related organelles |

TABLE 2-continued

| GenBank No. | | Encoded Polypeptide |
|---|---|---|
| BF382393 | NAPEPLD | N-acyl phosphatidylethanolamine phospholipase D |
| BF431309 | LOC100130987 | Homo sapiens cDNA FLJ38836 fis, clone MESAN2002519, weakly similar to Mus musculus cell cycle checkpoint control protein Mrad9 gene. |
| BF431973 | ZNF397 | zinc finger protein 397 isoform 2 |
| BF432276 | | Unknown |
| BF432376 | GALNTL2 | UDP-N-acetyl-alpha-D-galactosamine:polypeptide |
| BF432478 | PINK1 | PTEN induced putative kinase 1 precursor |
| BF432956 | SCN2A | sodium channel, voltage-gated, type II, alpha |
| BF433005 | HGSNAT | heparan-alpha-glucosaminide N-acetyltransferase |
| BF433180 | | Unknown |
| BF433475 | ERCC6 | excision repair cross-complementing rodent |
| BF435617 | | Unknown |
| BF435852 | ACOX1 | acyl-Coenzyme A oxidase 1 isoform b |
| BF437602 | ZNF561 | zinc finger protein 561 |
| BF438014 | | Unknown |
| BF438386 | | Unknown |
| BF439451 | CEBPZ | CCAAT/enhancer binding protein zeta |
| BF439488 | EDEM3 | ER degradation enhancer, mannosidase alpha-like |
| BF445273 | SLC3A1 | solute carrier family 3, member 1 |
| BF446673 | HMCN1 | hemicentin 1 precursor |
| BF448048 | SETD3 | SET domain containing 3 isoform a |
| BF476080 | | Unknown |
| BF507342 | PPM1K | protein phosphatase 1K (PP2C domain containing) |
| BF508244 | AKR1C2 | aldo-keto reductase family 1, member C2 |
| BF508344 | | Unknown |
| BF510490 | WDR26 | WD repeat domain 26 isoform b |
| BF510581 | BTBD11 | BTB (POZ) domain containing 11 isoform a |
| BF510588 | TSHZ3 | zinc finger protein 537 |
| BF511231 | | Unknown |
| BF512162 | C3orf55 | hypothetical protein LOC152078 isoform 1 |
| BF512190 | | Unknown |
| BF515031 | KIFC2 | kinesin family member C2 |
| BF570193 | MGAT4B | alpha-1,3-mannosyl-glycoprotein |
| BF570412 | ABHD12 | abhydrolase domain containing 12 isoform a |
| BF575213 | SOD2 | manganese superoxide dismutase isoform A |
| BF575514 | NAMPT | nicotinamide phosphoribosyltransferase |
| BF589322 | RSPO3 | R-spondin 3 precursor |
| BF590274 | TBCK | TBC domain-containing protein kinase-like |
| BF593252 | ADSSL1 | adenylosuccinate synthase like 1 isoform 2 |
| BF593917 | | Unknown |
| BF663461 | SLC38A10 | solute carrier family 38, member 10 isoform a |
| BF666293 | KDSR | 3-ketodihydrosphingosine reductase precursor |
| BF670447 | RHOQ | ras-like protein TC10 precursor |
| BF672306 | | Unknown |
| BF676462 | SHC4 | rai-like protein |
| BF676980 | GCLC | glutamate-cysteine ligase, catalytic subunit |
| BF680588 | STEAP2 | six transmembrane epithelial antigen of the |
| BF691045 | | Unknown |
| BF692332 | SELT | selenoprotein T precursor |
| BF696757 | | Unknown |
| BF699855 | GALNT7 | polypeptide N-acetylgalactosaminyltransferase 7 |
| BF718769 | PPP1R7 | protein phosphatase 1, regulatory subunit 7 |
| BF723626 | MKLN1 | muskelin 1, intracellular mediator containing |
| BF724137 | C7orf58 | hypothetical protein LOC79974 isoform 1 |
| BF724210 | | Unknown |
| BF724944 | MCART1 | Homo sapiens cDNA FLJ34088 fis, clone FCBBF3005698. |
| BF726934 | CPXM2 | carboxypeptidase X (M14 family), member 2 |
| BF732712 | GPRASP2 | G protein-coupled receptor associated sorting |
| BF792631 | CDC14B | CDC14 homolog B isoform 3 |
| BF797381 | CAMK2D | calcium/calmodulin-dependent protein kinase II |
| BF939176 | MYOZ2 | myozenin 2 |
| BF939292 | STX4 | syntaxin 4 |
| BF939365 | CALU | calumenin isoform b precursor |
| BF939833 | DLEU2 | |
| BF939919 | MAPKAP1 | mitogen-activated protein kinase associated |
| BF940211 | CCDC148 | coiled-coil domain containing 148 |
| BF940276 | RFNG | radical fringe |
| BF956762 | MEG3 | Homo sapiens MEG3 mRNA, partial sequence, imprinted gene. |
| BF966015 | ZNF18 | zinc finger protein 18 |
| BF968134 | MXRA7 | transmembrane anchor protein 1 isoform 2 |

TABLE 2-continued

| GenBank No. | Encoded Polypeptide | |
|---|---|---|
| BF968960 | TM2D1 | beta-amyloid binding protein precursor |
| BF969982 | KCNC4 | Shaw-related voltage-gated potassium channel |
| BF970829 | OSBPL8 | oxysterol-binding protein-like protein 8 isoform |
| BF973568 | | Unknown |
| BF974389 | FAM89B | family with sequence similarity 89, member B |
| BF977145 | | Unknown |
| BF978611 | MPZL1 | myelin protein zero-like 1 isoform a |
| BF978689 | RHOQ | ras-like protein TC10 precursor |
| BF982174 | SDPR | serum deprivation response protein |
| BF982927 | SLC5A3 | solute carrier family 5 (inositol transporters), |
| BF983379 | CD59 | CD59 antigen preproprotein |
| BF983948 | SRPRB | signal recognition particle receptor, beta |
| BF984227 | SYNPO2 | synaptopodin 2 isoform c |
| BG027926 | | Unknown |
| BG030576 | BTBD8 | BTB (POZ) domain containing 8 |
| BG031974 | IGF2R | insulin-like growth factor 2 receptor precursor |
| BG054844 | RND3 | ras homolog gene family, member E precursor |
| BG107203 | RABGAP1L | RAB GTPase activating protein 1-like isoform A |
| BG107676 | | Unknown |
| BG111808 | | Unknown |
| BG112359 | | Unknown |
| BG122789 | ARHGAP22 | Rho GTPase activating protein 2 |
| BG149557 | RORA | RAR-related orphan receptor A isoform b |
| BG163267 | HSP90AB1 | SubName: Full = Heat shock protein 90 kDa alpha (Cytosolic), class B member 1, isoform CRA_a; SubName: Full = cDNA, FLJ92550, *Homo sapiens* heat shock 90 kDa protein 1, beta (HSPCB), mRNA; |
| BG163756 | | Unknown |
| BG164365 | MAP1B | microtubule-associated protein 1B |
| BG167841 | MOBKL2C | MOB1, Mps One Binder kinase activator-like 2C |
| BG169689 | SLC41A2 | solute carrier family 41, member 2 |
| BG170130 | C6orf89 | hypothetical protein LOC221477 |
| BG177759 | WDR26 | WD repeat domain 26 isoform b |
| BG200452 | BANK1 | B-cell scaffold protein with ankyrin repeats 1 |
| BG230614 | CD47 | CD47 antigen isoform 1 precursor |
| BG231932 | TPP1 | tripeptidyl-peptidase I preproprotein |
| BG236006 | | Unknown |
| BG250310 | ZFP36L1 | butyrate response factor 1 |
| BG250585 | | Unknown |
| BG251175 | DLG1 | discs, large homolog 1 isoform 1 |
| BG252490 | DNAJB4 | DnaJ (Hsp40) homolog, subfamily B, member 4 |
| BG252899 | | Unknown |
| BG260394 | SNCA | alpha-synuclein isoform NACP140 |
| BG260623 | ZNF319 | zinc finger protein 319 |
| BG284890 | | Unknown |
| BG285881 | PRICKLE2 | prickle-like 2 |
| BG289443 | | Unknown |
| BG290577 | SPAG9 | sperm associated antigen 9 isoform 1 |
| BG291039 | | Unknown |
| BG292040 | | Unknown |
| BG292389 | ERAP2 | endoplasmic reticulum aminopeptidase 2 |
| BG292405 | | |
| BG326045 | BHLHE40 | basic helix-loop-helix family, member e40 |
| BG326897 | EXD3 | exonuclease 3'-5' domain containing 3 |
| BG327863 | TTTY14 | |
| BG339064 | | Unknown |
| BG340967 | TRAPPC1 | trafficking protein particle complex 1 |
| BG341906 | ARF3 | ADP-ribosylation factor 3 |
| BG354573 | PSG8 | pregnancy specific beta-1-glycoprotein 8 isoform |
| BG386566 | H2AFJ | *Homo sapiens* cDNA FLJ10903 fis, clone OVARC1000006, highly similar to HISTONE H2A.1. |
| BG427393 | APLP2 | amyloid beta (A4) precursor-like protein 2 |
| BG432350 | C20orf108 | hypothetical protein LOC116151 |
| BG434272 | PAPPA | pregnancy-associated plasma protein A |
| BG469257 | MMP24 | matrix metalloproteinase 24 preproprotein |
| BG475299 | CTTN | cortactin isoform a |
| BG501219 | TMEM167A | transmembrane protein 167A precursor |
| BG534245 | | Unknown |
| BG537190 | FTL | ferritin, light polypeptide |
| BG537255 | | Unknown |
| BG538564 | | Unknown |
| BG620958 | | Unknown |
| BG913589 | DNAJC3 | DnaJ (Hsp40) homolog, subfamily C, member 3 |
| BI438189 | | Purified pancreatic islet |
| BM128432 | IGFBP5 | insulin-like growth factor binding protein 5 |

TABLE 2-continued

| GenBank No. | | Encoded Polypeptide |
|---|---|---|
| BM677498 | MGC23284 | *Homo sapiens* hypothetical protein MGC23284, mRNA (cDNA clone IMAGE: 4637796), partial cds. |
| BM992214 | | Unknown |
| BQ007522 | | Unknown |
| BQ183759 | | Unknown |
| BQ187042 | | Unknown |
| BQ876971 | CRTAP | cartilage associated protein precursor |
| BU069195 | C2orf74 | hypothetical protein LOC339804 isoform 1 |
| BU074567 | C14orf37 | hypothetical protein LOC145407 precursor |
| BU078629 | ZFYVE16 | zinc finger, FYVE domain containing 16 |
| BU430052 | FGD2 | FYVE, RhoGEF and PH domain containing 2 |
| CA431092 | | Unknown |
| D10537 | | major structural protein of myelin |
| D13287 | MTX1 | metaxin 1 isoform 1 |
| D17391 | COL4A4 | alpha 4 type IV collagen precursor |
| D21089 | XPC | xeroderma pigmentosum, complementation group C |
| D29810 | DCBLD2 | discoidin, CUB and LCCL domain containing 2 |
| D31421 | SGMS2 | sphingomyelin synthase 2 |
| D38299 | PTGER3 | *Homo sapiens* PTGER3 mRNA for prostaglandin E receotor EP3 subtype 3 isoform, partial cds, clone: FLJ80357SAAF. |
| D43967 | RUNX1 | runt-related transcription factor 1 isoform |
| D45864 | PRKG1 | protein kinase, cGMP-dependent, type I isoform |
| D50579 | CES2 | carboxylesterase 2 isoform 2 |
| D50683 | TGFBR2 | transforming growth factor, beta receptor II |
| D63807 | | Unknown |
| D79994 | KANK1 | KN motif and ankyrin repeat domains 1 isoform a |
| D80010 | LPIN1 | lipin 1 |
| D83485 | PDIA3 | protein disulfide-isomerase A3 precursor |
| D84105 | CD46 | CD46 antigen, complement regulatory protein |
| D86586 | CLEC11A | stem cell growth factor precursor |
| D86985 | KIAA0232 | hypothetical protein LOC9778 |
| D87292 | | Rhodanese |
| H04482 | OSTM1 | osteopetrosis associated transmembrane protein 1 |
| H05023 | RGS7BP | regulator of G-protein signaling 7 binding |
| H05025 | C5orf53 | IgA-inducing protein precursor |
| H07095 | | Unknown |
| H10659 | MMAA | RecName: Full = Putative L-type amino acid transporter 1-like protein MMAA; AltName: Full = hLAT1 3-transmembrane protein MMAA; Short = hLAT1 3TM MMAA; |
| H10766 | GTF2F2 | general transcription factor IIF, polypeptide 2, |
| H11075 | HEATR7A | HEAT repeat containing 7A isoform 1 |
| H14241 | SLC48A1 | heme-responsive gene 1 |
| H23979 | CD200 | CD200 antigen isoform b |
| H24398 | C11orf87 | hypothetical protein LOC399947 precursor (see also AA633992 herein and Table 3) |
| H25097 | USP53 | ubiquitin specific protease 53 |
| H27948 | C17orf103 | transcript expressed during hematopoiesis 2 |
| H72927 | TMEM179B | transmembrane protein 179B |
| H84390 | | Unknown |
| H89790 | MEG3 | *Homo sapiens* MEG3 mRNA, partial sequence, imprinted gene. |
| H93077 | | Unknown |
| H97567 | | Unknown |
| H98105 | | Unknown |
| H98994 | PLEKHA8 | pleckstrin homology domain containing, family A |
| J03202 | LAMC1 | laminin, gamma 1 precursor |
| J03225 | TFPI | tissue factor pathway inhibitor isoform a |
| J04183 | LAMP2 | lysosomal-associated membrane protein 2 isoform |
| J04755 | | ferritin H processed pseudogene |
| K02920 | GBA | glucocerebrosidase precursor |
| L06633 | CYTIP | cytohesin 1 interacting protein |
| L08835 | | Unknown |
| L11315 | DDR1 | discoidin domain receptor family, member 1 |
| L11669 | MFSD10 | major facilitator superfamily domain containing |
| L12002 | ITGA4 | integrin alpha 4 precursor |
| L12711 | TKT | transketolase isoform 1 |
| L13720 | GAS6 | growth arrest-specific 6 isoform 1 precursor |
| L13852 | UBA7 | ubiquitin-like modifier activating enzyme 7 |
| L14611 | RORA | RAR-related orphan receptor A isoform b |
| L16895 | | lysyl oxidase (LOX) |

TABLE 2-continued

| GenBank No. | Encoded Polypeptide | |
|---|---|---|
| L20817 | DDR1 | discoidin domain receptor family, member 1 |
| L27489 | PTGER3 | *Homo sapiens* PTGER3 mRNA for prostaglandin E receotor EP3 subtype 3 isoform, partial cds, clone: FLJ80357SAAF. |
| L38019 | ITPR1 | inositol 1,4,5-triphosphate receptor, type 1 |
| L38969 | THBS3 | thrombospondin 3 precursor |
| L41690 | TRADD | TNFRSF1A-associated via death domain |
| L42374 | PPP2R5B | beta isoform of regulatory subunit B56, protein |
| M10943 | | metallothionein-If |
| M11734 | CSF2 | colony stimulating factor 2 precursor |
| M14016 | UROD | uroporphyrinogen decarboxylase |
| M15329 | IL1A | interleukin 1, alpha proprotein |
| M15330 | | interleukin 1-beta (IL1B) |
| M22921 | B4GALT1 | UDP-Gal:betaGlcNAc beta 1,4- |
| M25915 | CLU | clusterin isoform 2 |
| M27968 | FGF2 | fibroblast growth factor 2 |
| M28880 | ANK1 | ankyrin 1 isoform 9 |
| M31125 | PSG6 | pregnancy specific beta-1-glycoprotein 6 isoform |
| M32221 | PSAP | prosaposin isoform a preproprotein |
| M33376 | | pseudo-chlordecone reductase |
| M33653 | COL13A1 | alpha 1 type XIII collagen isoform 1 |
| M34421 | PSG9 | pregnancy specific beta-1-glycoprotein 9 |
| M34715 | | pregnancy-specific beta-1-glycoprotein |
| M55580 | SAT1 | Synthetic construct DNA, clone: pF1KB8373, *Homo sapiens* SAT1 gene for spermidine/spermine N1-acetyltransferase 1, without stop codon, in Flexi system. |
| M55983 | DNASE1 | deoxyribonuclease I precursor |
| M59916 | SMPD1 | sphingomyelin phosphodiesterase 1, acid |
| M59917 | | acid sphingomyelinase (ASM) |
| M65062 | IGFBP5 | insulin-like growth factor binding protein 5 |
| M68874 | PLA2G4A | cytosolic phospholipase A2, group IVA |
| M76453 | CSF1 | colony stimulating factor 1 isoform c precursor |
| M76477 | GM2A | GM2 ganglioside activator precursor |
| M79321 | LYN | Yamaguchi sarcoma viral (v-yes-1) oncogene |
| M79462 | PML | promyelocytic leukemia protein isoform 2 |
| M81635 | STOM | stomatin isoform a |
| M81768 | SLC9A1 | solute carrier family 9, isoform A1 |
| M83248 | SPP1 | secreted phosphoprotein 1 isoform a |
| M87507 | | interleukin-1 beta convertase |
| M95548 | SLC3A1 | solute carrier family 3, member 1 |
| M98399 | CD36 | CD36 antigen |
| M98478 | TGM2 | transglutaminase 2 isoform a |
| M98528 | | Unknown |
| N20923 | | neuron-specific protein; protein phosphatase inhibitor |
| N20927 | RAP2B | RAP2B, member of RAS oncogene family precursor |
| N21202 | | Unknown |
| N21643 | | Unknown |
| N22918 | PPM1M | protein phosphatase 1M isoform a |
| N30152 | | Unknown |
| N30169 | PSG5 | pregnancy specific beta-1-glycoprotein 5 |
| N30209 | CLVS1 | |
| N30649 | SQSTM1 | sequestosome 1 isoform 2 |
| N33403 | MYO10 | myosin X |
| N34514 | | Unknown |
| N35896 | PPFIBP1 | PTPRF interacting protein binding protein 1 |
| N36085 | | Unknown |
| N36759 | C6orf225 | hypothetical protein LOC619208 |
| N36762 | | Unknown |
| N39536 | NOMO3 | nodal modulator 3 precursor |
| N45228 | GABBR1 | gamma-aminobutyric acid (GABA) B receptor 1 |
| N45309 | PCYOX1 | prenylcysteine oxidase 1 precursor |
| N48315 | PPARA | peroxisome proliferative activated receptor, |
| N49852 | NALCN | voltage gated channel like 1 |
| N51370 | | Unknown |
| N51413 | | Unknown |
| N51708 | | Unknown |
| N51836 | | Unknown |
| N52532 | SECISBP2L | SECIS binding protein 2-like |
| N52767 | GTF2F2 | general transcription factor IIF, polypeptide 2, |
| N58363 | | Unknown |
| N63706 | | Unknown |
| N63748 | ZBTB4 | zinc finger and BTB domain containing 4 |
| N66571 | | Unknown |
| N66633 | LHFPL2 | lipoma HMGIC fusion partner-like 2 |

TABLE 2-continued

| GenBank No. | | Encoded Polypeptide |
|---|---|---|
| N71074 | SEC22A | SEC22 vesicle trafficking protein homolog A |
| N71923 | | Unknown |
| N79662 | GSTA4 | glutathione S-transferase alpha 4 |
| N90755 | CAP2 | adenylyl cyclase-associated protein 2 |
| N92494 | ARL6IP5 | ADP-ribosylation-like factor 6 interacting |
| N95414 | ITGA2 | integrin alpha 2 precursor |
| N95437 | LMCD1 | LIM and cysteine-rich domains 1 |
| NM_000034 | ALDOA | fructose-bisphosphate aldolase A |
| NM_000043 | FAS | tumor necrosis factor receptor superfamily, |
| NM_000046 | ARSB | arylsulfatase B isoform 1 precursor |
| NM_000049 | ASPA | aspartoacylase |
| NM_000055 | BCHE | butyrylcholinesterase precursor |
| NM_000060 | BTD | biotinidase precursor |
| NM_000062 | SERPING1 | serpin peptidase inhibitor, clade G, member 1 |
| NM_000064 | C3 | complement component 3 precursor |
| NM_000072 | CD36 | CD36 antigen |
| NM_000077 | CDKN2A | cyclin-dependent kinase inhibitor 2A isoform 3 |
| NM_000081 | LYST | lysosomal trafficking regulator |
| NM_000099 | CST3 | cystatin C precursor |
| NM_000100 | CSTB | cystatin B |
| NM_000107 | DDB2 | damage-specific DNA binding protein 2 |
| NM_000120 | EPHX1 | epoxide hydrolase 1 |
| NM_000123 | ERCC5 | XPG-complementing protein |
| NM_000124 | ERCC6 | excision repair cross-complementing rodent |
| NM_000132 | F8 | coagulation factor VIII isoform a precursor |
| NM_000137 | FAH | fumarylacetoacetase |
| NM_000147 | FUCA1 | fucosidase, alpha-L-1, tissue precursor |
| NM_000156 | GAMT | guanidinoacetate N-methyltransferase isoform a |
| NM_000161 | GCH1 | GTP cyclohydrolase 1 isoform 1 |
| NM_000163 | GHR | growth hormone receptor precursor |
| NM_000169 | GLA | alpha-galactosidase A precursor |
| NM_000175 | GPI | glucose phosphate isomerase |
| NM_000177 | GSN | gelsolin isoform c |
| NM_000183 | HADHB | mitochondrial trifunctional protein, beta |
| NM_000191 | HMGCL | 3-hydroxy-3-methylglutaryl CoA lyase isoform 1 |
| NM_000202 | IDS | iduronate-2-sulfatase isoform a precursor |
| NM_000203 | IDUA | alpha-L-iduronidase precursor |
| NM_000227 | LAMA3 | laminin alpha 3 subunit isoform 1 |
| NM_000235 | LIPA | lipase A precursor |
| NM_000247 | MICA | RecName: Full = MHC class I polypeptide-related sequence A; Short = MIC-A; Flags: Precursor; |
| NM_000281 | PCBD1 | pterin-4 alpha-carbinolamine |
| NM_000291 | PGK1 | phosphoglycerate kinase 1 |
| NM_000297 | PKD2 | polycystin 2 |
| NM_000305 | PON2 | paraoxonase 2 isoform 2 |
| NM_000311 | PRNP | prion protein preproprotein |
| NM_000376 | VDR | vitamin D (1,25-dihydroxyvitamin D3) receptor |
| NM_000381 | MID1 | midline 1 |
| NM_000389 | CDKN1A | cyclin-dependent kinase inhibitor 1A |
| NM_000391 | TPP1 | tripeptidyl-peptidase I preproprotein |
| NM_000396 | CTSK | cathepsin K preproprotein |
| NM_000401 | EXT2 | exostosin 2 isoform 1 |
| NM_000404 | GLB1 | galactosidase, beta 1 isoform b |
| NM_000407 | GP1BB | glycoprotein Ib, beta polypeptide precursor |
| NM_000413 | HSD17B1 | hydroxysteroid (17-beta) dehydrogenase 1 |
| NM_000428 | LTBP2 | latent transforming growth factor beta binding |
| NM_000449 | RFX5 | regulatory factor X, 5 |
| NM_000459 | TEK | TEK tyrosine kinase, endothelial precursor |
| NM_000476 | AK1 | adenylate kinase 1 |
| NM_000480 | AMPD3 | adenosine monophosphate deaminase 3 isoform 1A |
| NM_000484 | APP | amyloid beta A4 protein isoform a precursor |
| NM_000487 | ARSA | arylsulfatase A isoform b |
| NM_000501 | ELN | elastin isoform a precursor |
| NM_000512 | GALNS | galactosamine (N-acetyl)-6-sulfate sulfatase |
| NM_000521 | HEXB | hexosaminidase B preproprotein |
| NM_000527 | LDLR | low density lipoprotein receptor precursor |
| NM_000558 | HBA1 | alpha 1 globin |
| NM_000576 | IL1B | interleukin 1, beta proprotein |
| NM_000581 | GPX1 | glutathione peroxidase 1 isoform 1 |
| NM_000584 | IL8 | interleukin 8 precursor |
| NM_000585 | IL15 | interleukin 15 preproprotein |
| NM_000593 | TAP1 | transporter 1, ATP-binding cassette, sub-family |
| NM_000596 | IGFBP1 | insulin-like growth factor binding protein 1 |
| NM_000599 | IGFBP5 | insulin-like growth factor binding protein 5 |
| NM_000600 | IL6 | interleukin 6 precursor |
| NM_000602 | SERPINE1 | plasminogen activator inhibitor-1 isoform 1 |

TABLE 2-continued

| GenBank No. | | Encoded Polypeptide |
|---|---|---|
| NM_000611 | CD59 | CD59 antigen preproprotein |
| NM_000617 | SLC11A2 | solute carrier family 11 (proton-coupled |
| NM_000638 | VTN | vitronectin precursor |
| NM_000640 | IL13RA2 | interleukin 13 receptor, alpha 2 precursor |
| NM_000662 | NAT1 | N-acetyltransferase 1 isoform b |
| NM_000679 | ADRA1B | alpha-1B-adrenergic receptor |
| NM_000711 (replaced by NM_199173.4) | | bone gamma-carboxyglutamate (gla) protein (BGLAP) |
| NM_000714 | TSPO | translocator protein isoform PBR |
| NM_000717 | CA4 | carbonic anhydrase IV precursor |
| NM_000722 | CACNA2D1 | calcium channel, voltage-dependent, alpha |
| NM_000757 | CSF1 | colony stimulating factor 1 isoform c precursor |
| NM_000765 | CYP3A7 | cytochrome P450, family 3, subfamily A, |
| NM_000786 | CYP51A1 | cytochrome P450, family 51, subfamily A, |
| NM_000801 | FKBP1A | FK506 binding protein 1A, 12 kDa |
| NM_000804 | FOLR3 | folate receptor 3 precursor |
| NM_000817 | GAD1 | glutamate decarboxylase 1 isoform GAD67 |
| NM_000820 | GAS6 | growth arrest-specific 6 isoform 1 precursor |
| NM_000824 | GLRB | glycine receptor, beta isoform A precursor |
| NM_000852 | GSTP1 | glutathione transferase |
| NM_000876 | IGF2R | insulin-like growth factor 2 receptor precursor |
| NM_000885 | ITGA4 | integrin alpha 4 precursor |
| NM_000899 | KITLG | KIT ligand isoform b precursor |
| NM_000901 | NR3C2 | nuclear receptor subfamily 3, group C, member 2 |
| NM_000916 | OXTR | oxytocin receptor |
| NM_000919 | PAM | peptidylglycine alpha-amidating monooxygenase |
| NM_000930 | PLAT | plasminogen activator, tissue isoform 1 |
| NM_000933 | PLCB4 | phospholipase C beta 4 isoform a |
| NM_000942 | PPIB | peptidylprolyl isomerase B precursor |
| NM_000965 | RARB | retinoic acid receptor, beta isoform 1 |
| NM_001001548 | CD36 | CD36 antigen |
| NM_001001669 | FLJ41603 | hypothetical protein LOC389337 |
| NM_001001713 | SH3BGR | SH3-binding domain and glutamic acid-rich |
| NM_001017974 | P4HA2 | prolyl 4-hydroxylase, alpha II subunit isoform 2 |
| NM_001030050 | KLK3 | prostate specific antigen isoform 5 |
| NM_001031702 | SEMA5B | semaphorin 5B isoform 1 |
| NM_001032409 | OAS1 | 2',5'-oligoadenylate synthetase 1 isoform 3 |
| NM_001033053 | NLRP1 | NLR family, pyrin domain containing 1 isoform 1 |
| NM_001047 | SRD5A1 | steroid-5-alpha-reductase 1 |
| NM_001055 | SULT1A1 | sulfotransferase family, cytosolic, 1A, |
| NM_001083 | PDE5A | phosphodiesterase 5A isoform 1 |
| NM_001108 (replaced by NM_138448.3) | | acylphosphatase 2, muscle type (ACYP2), |
| NM_001110 | ADAM10 | ADAM metallopeptidase domain 10 precursor |
| NM_001124 | ADM | adrenomedullin precursor |
| NM_001146 | ANGPT1 | angiopoietin 1 precursor |
| NM_001151 | SLC25A4 | adenine nucleotide translocator 1 |
| NM_001153 | ANXA4 | annexin IV |
| NM_001154 | ANXA5 | annexin 5 |
| NM_001159 | AOX1 | aldehyde oxidase 1 |
| NM_001174 | | unknown |
| NM_001183 | ATP6AP1 | ATPase, H+ transporting, lysosomal accessory |
| NM_001196 | BID | BH3 interacting domain death agonist isoform 2 |
| NM_001200 | BMP2 | bone morphogenetic protein 2 preproprotein |
| NM_001216 | CA9 | carbonic anhydrase IX precursor |
| NM_001251 | CD68 | CD68 antigen isoform B |
| NM_001252 | CD70 | tumor necrosis factor ligand superfamily, member |
| NM_001257 | CDH13 | cadherin 13 preproprotein |
| NM_001259 | CDK6 | cyclin-dependent kinase 6 |
| NM_001268 | RCBTB2 | regulator of chromosome condensation and BTB |
| NM_001283 | AP1S1 | adaptor-related protein complex 1, sigma 1 |
| NM_001304 | CPD | carboxypeptidase D precursor |
| NM_001330 | CTF1 | cardiotrophin 1 isoform 1 |
| NM_001343 | DAB2 | disabled homolog 2 |
| NM_001344 | DAD1 | defender against cell death 1 |
| NM_001345 | DGKA | diacylglycerol kinase, alpha 80 kDa |
| NM_001346 | DGKG | diacylglycerol kinase gamma isoform 1 |
| NM_001353 | AKR1C1 | aldo-keto reductase family 1, member C1 |
| NM_001355 | DDT | D-dopachrome tautomerase |
| NM_001360 | DHCR7 | 7-dehydrocholesterol reductase |
| NM_001386 | DPYSL2 | dihydropyrimidinase-like 2 |
| NM_001397 | ECE1 | endothelin converting enzyme 1 isoform 4 |
| NM_001442 | FABP4 | fatty acid binding protein 4, adipocyte |
| NM_001448 | GPC4 | glypican 4 precursor |

TABLE 2-continued

| GenBank No. | | Encoded Polypeptide |
|---|---|---|
| NM_001458 | FLNC | gamma filamin isoform a |
| NM_001478 | B4GALNT1 | beta-1,4-N-acetyl-galactosaminyl transferase 1 |
| NM_001498 | GCLC | glutamate-cysteine ligase, catalytic subunit |
| NM_001511 | CXCL1 | chemokine (C—X—C motif) ligand 1 |
| NM_001518 | GTF2I | general transcription factor IIi isoform 1 |
| NM_001531 | MR1 | major histocompatibility complex, class |
| NM_001540 | HSPB1 | heat shock protein beta-1 |
| NM_001547 | IFIT2 | interferon-induced protein with |
| NM_001548 | IFIT1 | interferon-induced protein with |
| NM_001549 | IFIT3 | interferon-induced protein with |
| NM_001552 | IGFBP4 | insulin-like growth factor binding protein 4 |
| NM_001553 | IGFBP7 | insulin-like growth factor binding protein 7 |
| NM_001565 | CXCL10 | small inducible cytokine B10 precursor |
| NM_001611 | ACP5 | acid phosphatase 5, tartrate resistant |
| NM_001628 | AKR1B1 | aldo-keto reductase family 1, member B1 |
| NM_001642 | APLP2 | amyloid beta (A4) precursor-like protein 2 |
| NM_001647 | APOD | apolipoprotein D precursor |
| NM_001660 | ARF4 | ADP-ribosylation factor 4 |
| NM_001684 | ATP2B4 | plasma membrane calcium ATPase 4 isoform 4a |
| NM_001724 | BPGM | bisphosphoglycerate mutase |
| NM_001752 | CAT | catalase |
| NM_001780 | CD63 | CD63 antigen isoform A |
| NM_001792 | CDH2 | cadherin 2, type 1 preproprotein |
| NM_001797 | CDH11 | cadherin 11, type 2 preproprotein |
| NM_001807 | CEL | carboxyl ester lipase precursor |
| NM_001823 | CKB | brain creatine kinase |
| NM_001846 | COL4A2 | alpha 2 type IV collagen preproprotein |
| NM_001860 | SLC31A2 | solute carrier family 31 (copper transporters), |
| NM_001873 | CPE | carboxypeptidase E preproprotein |
| NM_001893 | CSNK1D | casein kinase 1, delta isoform 2 |
| NM_001908 | CTSB | cathepsin B preproprotein |
| NM_001909 | CTSD | cathepsin D preproprotein |
| NM_001913 | CUX1 | cut-like homeobox 1 isoform b |
| NM_001914 | CYB5A | cytochrome b-5 isoform 2 |
| NM_001920 | DCN | decorin isoform a preproprotein |
| NM_001924 | GADD45A | growth arrest and DNA-damage-inducible, alpha |
| NM_001954 | DDR1 | discoidin domain receptor family, member 1 |
| NM_001957 | EDNRA | endothelin receptor type A isoform a precursor |
| NM_001967 | EIF4A2 | eukaryotic translation initiation factor 4A2 |
| NM_001985 | ETFB | electron-transfer-flavoprotein, beta polypeptide |
| NM_001999 | FBN2 | fibrillin 2 precursor |
| NM_002004 | | farnesyl diphosphate synthase (FDPS) |
| NM_002006 | FGF2 | fibroblast growth factor 2 |
| NM_002016 | FLG | filaggrin |
| NM_002032 | FTH1 | ferritin, heavy polypeptide 1 |
| NM_002056 | GFPT1 | glucosamine-fructose-6-phosphate |
| NM_002064 | GLRX | glutaredoxin (thioltransferase) |
| NM_002081 | GPC1 | glypican 1 precursor |
| NM_002087 | GRN | granulin precursor |
| NM_002133 | HMOX1 | heme oxygenase (decyclizing) 1 |
| NM_002162 | ICAM3 | intercellular adhesion molecule 3 precursor |
| NM_002184 | IL6ST | interleukin 6 signal transducer isoform 1 |
| NM_002189 | IL15RA | interleukin 15 receptor, alpha isoform 2 |
| NM_002197 | ACO1 | aconitase 1 |
| NM_002198 | IRF1 | interferon regulatory factor 1 |
| NM_002203 | ITGA2 | integrin alpha 2 precursor |
| NM_002204 | ITGA3 | integrin alpha 3 isoform a precursor |
| NM_002205 | ITGA5 | integrin alpha 5 precursor |
| NM_002213 | ITGB5 | integrin, beta 5 precursor |
| NM_002227 | JAK1 | janus kinase 1 |
| NM_002231 | CD82 | CD82 antigen isoform 1 |
| NM_002254 | KIF3C | kinesin family member 3C |
| NM_002275 | KRT15 | keratin 15 |
| NM_002290 | LAMA4 | laminin, alpha 4 isoform 2 precursor |
| NM_002291 | LAMB1 | laminin, beta 1 precursor |
| NM_002294 | LAMP2 | lysosomal-associated membrane protein 2 isoform |
| NM_002309 | LIF | leukemia inhibitory factor (cholinergic |
| NM_002317 | LOX | lysyl oxidase preproprotein |
| NM_002332 | LRP1 | low density lipoprotein-related protein 1 |
| NM_002337 | LRPAP1 | low density lipoprotein receptor-related protein |
| NM_002350 | LYN | Yamaguchi sarcoma viral (v-yes-1) oncogene |
| NM_002357 | MXD1 | MAX dimerization protein 1 |
| NM_002372 | MAN2A1 | mannosidase, alpha, class 2A, member 1 |
| NM_002389 | CD46 | CD46 antigen, complement regulatory protein |
| NM_002392 | MDM2 | mouse double minute 2 homolog isoform MDM2 |
| NM_002395 | ME1 | SubName: Full = Cadherin; Flags: Fragment; |

TABLE 2-continued

| GenBank No. | | Encoded Polypeptide |
|---|---|---|
| NM_002406 | MGAT1 | mannosyl (alpha-1,3-)-glycoprotein |
| NM_002407 | SCGB2A1 | secretoglobin, family 2A, member 1 precursor |
| NM_002408 | MGAT2 | mannosyl (alpha-1,6-)-glycoprotein |
| NM_002425 | MMP10 | matrix metalloproteinase 10 preproprotein |
| NM_002426 | MMP12 | matrix metalloproteinase 12 preproprotein |
| NM_002448 | MSX1 | msh homeobox 1 |
| NM_002450 | | metallothionein 1L (gene/pseudogene) (MT1L) |
| NM_002463 | MX2 | myxovirus resistance protein 2 |
| NM_002477 | MYL5 | myosin regulatory light chain 5 |
| NM_002513 | NME3 | nucleoside diphosphate kinase 3 |
| NM_002517 | NPAS1 | neuronal PAS domain protein 1 |
| NM_002518 | NPAS2 | neuronal PAS domain protein 2 |
| NM_002527 | NTF3 | neurotrophin 3 isoform 1 preproprotein |
| NM_002555 | SLC22A18 | tumor suppressing subtransferable candidate 5 |
| NM_002560 | P2RX4 | purinergic receptor P2X4 |
| NM_002575 | SERPINB2 | serine (or cysteine) proteinase inhibitor, clade |
| NM_002581 | PAPPA | pregnancy-associated plasma protein A |
| NM_002589 | PCDH7 | protocadherin 7 isoform c precursor |
| NM_002626 | PFKL | RecName: Full = 6-phosphofructokinase, liver type; EC = 2.7.1.11; AltName: Full = Phosphofructokinase 1; AltName: Full = Phosphohexokinase; AltName: Full = Phosphofructo-1-kinase isozyme B; Short = PFK-B; |
| NM_002631 | PGD | phosphogluconate dehydrogenase |
| NM_002647 | PIK3C3 | catalytic phosphatidylinositol 3-kinase 3 |
| NM_002675 | PML | promyelocytic leukemia protein isoform 2 |
| NM_002676 | PMM1 | phosphomannomutase 1 |
| NM_002778 | PSAP | prosaposin isoform a preproprotein |
| NM_002780 | PSG4 | pregnancy specific beta-1-glycoprotein 4 isoform |
| NM_002781 | PSG5 | pregnancy specific beta-1-glycoprotein 5 |
| NM_002782 | PSG6 | pregnancy specific beta-1-glycoprotein 6 isoform |
| NM_002783 | PSG7 | pregnancy specific beta-1-glycoprotein 7 |
| NM_002784 | PSG9 | pregnancy specific beta-1-glycoprotein 9 |
| NM_002830 | PTPN4 | protein tyrosine phosphatase, non-receptor type |
| NM_002845 | PTPRM | protein tyrosine phosphatase, receptor type, M |
| NM_002848 | PTPRO | receptor-type protein tyrosine phosphatase O |
| NM_002849 | PTPRR | protein tyrosine phosphatase, receptor type, R |
| NM_002870 | RAB13 | RAB13, member RAS oncogene family |
| NM_002886 | RAP2B | RAP2B, member of RAS oncogene family precursor |
| NM_002923 | RGS2 | regulator of G-protein signaling 2 |
| NM_002924 | RGS7 | regulator of G-protein signaling 7 |
| NM_002963 | S100A7 | S100 calcium binding protein A7 |
| NM_002970 | SAT1 | Synthetic construct DNA, clone: pF1KB8373, Homo sapiens SAT1 gene for spermidine/spermine N1-acetyltransferase 1, without stop codon, in Flexi system. |
| NM_002975 | CLEC11A | stem cell growth factor precursor |
| NM_002977 | SCN9A | sodium channel, voltage-gated, type IX, alpha |
| NM_002979 | SCP2 | sterol carrier protein 2 isoform 1 proprotein |
| NM_002985 | CCL5 | small inducible cytokine A5 precursor |
| NM_003009 | SEPW1 | selenoprotein W, 1 |
| NM_003012 | SFRP1 | secreted frizzled-related protein 1 precursor |
| NM_003014 | SFRP4 | secreted frizzled-related protein 4 precursor |
| NM_003022 | SH3BGRL | SH3 domain binding glutamic acid-rich protein |
| NM_003038 | SLC1A4 | solute carrier family 1, member 4 isoform 1 |
| NM_003059 | SLC22A4 | solute carrier family 22 member 4 |
| NM_003060 | SLC22A5 | solute carrier family 22 member 5 |
| NM_003134 | SRP14 | signal recognition particle 14 kDa (homologous |
| NM_003144 | SSR1 | signal sequence receptor, alpha precursor |
| NM_003151 | STAT4 | signal transducer and activator of transcription |
| NM_003165 | STXBP1 | syntaxin binding protein 1 isoform a |
| NM_003172 | SURF1 | surfeit 1 |
| NM_003174 | SVIL | supervillin isoform 2 |
| NM_003236 | TGFA | transforming growth factor, alpha isoform 1 |
| NM_003238 | TGFB2 | transforming growth factor, beta 2 isoform 1 |
| NM_003242 | TGFBR2 | transforming growth factor, beta receptor II |
| NM_003244 | TGIF1 | TG-interacting factor isoform c |
| NM_003246 | THBS1 | thrombospondin 1 precursor |
| NM_003254 | TIMP1 | tissue inhibitor of metalloproteinase 1 |
| NM_003265 | TLR3 | toll-like receptor 3 precursor |
| NM_003272 | GPR137B | G protein-coupled receptor 137B |
| NM_003275 | TMOD1 | tropomodulin 1 |
| NM_003289 | TPM2 | tropomyosin 2 (beta) isoform 2 |
| NM_003326 | TNFSF4 | tumor necrosis factor (ligand) superfamily, |
| NM_003330 | TXNRD1 | thioredoxin reductase 1 isoform 3 |

TABLE 2-continued

| GenBank No. | | Encoded Polypeptide |
|---|---|---|
| NM_003344 | UBE2H | ubiquitin-conjugating enzyme E2H isoform 1 |
| NM_003433 | ZNF132 | zinc finger protein 132 |
| NM_003451 | ZNF177 | zinc finger protein 177 |
| NM_003469 | SCG2 | secretogranin II precursor |
| NM_003475 | RASSF7 | Ras association (RalGDS/AF-6) domain family |
| NM_003492 | TMEM187 | transmembrane protein 187 |
| NM_003494 | DYSF | dysferlin isoform 12 |
| NM_003516 | HIST2H2AA3 | histone cluster 2, H2aa3 |
| NM_003517 | HIST2H2AC | histone cluster 2, H2ac |
| NM_003528 | HIST2H2BE | histone cluster 2, H2be |
| NM_003543 | HIST1H4H | histone cluster 1, H4h |
| NM_003548 | HIST2H4A | histone cluster 2, H4a |
| NM_003588 | CUL4B | cullin 4B isoform 1 |
| NM_003595 | TPST2 | tyrosylprotein sulfotransferase 2 |
| NM_003596 | TPST1 | tyrosylprotein sulfotransferase 1 |
| NM_003619 | PRSS12 | neurotrypsin precursor |
| NM_003620 | PPM1D | protein phosphatase 1D |
| NM_003622 | PPFIBP1 | PTPRF interacting protein binding protein 1 |
| NM_003633 | ENC1 | ectodermal-neural cortex (with BTB-like domain) |
| NM_003635 | NDST2 | heparan glucosaminyl |
| NM_003641 | IFITM1 | interferon induced transmembrane protein 1 |
| NM_003670 | BHLHE40 | basic helix-loop-helix family, member e40 |
| NM_003676 | DEGS1 | degenerative spermatocyte homolog 1, lipid |
| NM_003688 | CASK | calcium/calmodulin-dependent serine protein |
| NM_003725 | HSD17B6 | hydroxysteroid (17-beta) dehydrogenase 6 |
| NM_003730 | RNASET2 | ribonuclease T2 precursor |
| NM_003733 | OASL | 2'-5'-oligoadenylate synthetase-like isoform a |
| NM_003744 | NUMB | numb homolog isoform 1 |
| NM_003746 | DYNLL1 | dynein light chain 1 |
| NM_003748 | ALDH4A1 | aldehyde dehydrogenase 4A1 isoform a precursor |
| NM_003768 | PEA15 | phosphoprotein enriched in astrocytes 15 |
| NM_003784 | SERPINB7 | serine (or cysteine) proteinase inhibitor, clade |
| NM_003789 | TRADD | TNFRSF1A-associated via death domain |
| NM_003790 | TNFRSF25 | tumor necrosis factor receptor superfamily, |
| NM_003793 | CTSF | cathepsin F precursor |
| NM_003811 | TNFSF9 | tumor necrosis factor (ligand) superfamily, |
| NM_003812 | ADAM23 | ADAM metallopeptidase domain 23 preproprotein |
| NM_003813 | ADAM21 | ADAM metallopeptidase domain 21 preproprotein |
| NM_003825 | SNAP23 | synaptosomal-associated protein 23 isoform |
| NM_003851 | CREG1 | cellular repressor of E1A-stimulated genes |
| NM_003878 | GGH | gamma-glutamyl hydrolase precursor |
| NM_003879 | CFLAR | CASP8 and FADD-like apoptosis regulator isoform |
| NM_003896 | ST3GAL5 | ST3 beta-galactoside alpha-2,3-sialyltransferase |
| NM_003900 | SQSTM1 | sequestosome 1 isoform 2 |
| NM_003928 | | Unknown |
| NM_003945 | ATP6V0E1 | ATPase, H+ transporting, lysosomal 9 kDa, V0 |
| NM_003992 | CLK3 | CDC-like kinase 3 isoform a |
| NM_004010 | DMD | dystrophin Dp427p1 isoform |
| NM_004030 | | Unknown |
| NM_004045 | ATOX1 | antioxidant protein 1 |
| NM_004048 | B2M | beta-2-microglobulin precursor |
| NM_004059 | CCBL1 | kynurenine aminotransferase I isoform a |
| NM_004073 | PLK3 | polo-like kinase 3 |
| NM_004110 | FDXR | ferredoxin reductase isoform 2 precursor |
| NM_004138 | KRT33A | keratin 33A |
| NM_004148 | NINJ1 | ninjurin 1 |
| NM_004161 | RAB1A | RAB1A, member RAS oncogene family isoform 1 |
| NM_004163 | RAB27B | RAB27B, member RAS oncogene family |
| NM_004165 | RRAD | Ras-related associated with diabetes |
| NM_004170 | SLC1A1 | solute carrier family 1, member 1 |
| NM_004221 | IL32 | interleukin 32 isoform A |
| NM_004233 | CD83 | CD83 antigen isoform b |
| NM_004265 | FADS2 | fatty acid desaturase 2 |
| NM_004290 | RNF14 | ring finger protein 14 isoform 1 |
| NM_004318 | ASPH | aspartate beta-hydroxylase isoform a |
| NM_004327 | BCR | *Homo sapiens* breakpoint cluster region, mRNA (cDNA clone IMAGE: 4500154). |
| NM_004339 | PTTG1IP | pituitary tumor-transforming gene 1 |
| NM_004343 | CALR | calreticulin precursor |
| NM_004346 | CASP3 | caspase 3 preproprotein |
| NM_004356 | CD81 | CD81 antigen |
| NM_004357 | CD151 | CD151 antigen |
| NM_004381 | ATF6B | activating transcription factor 6 beta isoform |
| NM_004388 | CTBS | chitobiase, di-N-acetyl-precursor |

TABLE 2-continued

| GenBank No. | | Encoded Polypeptide |
|---|---|---|
| NM_004403 | DFNA5 | deafness, autosomal dominant 5 protein isoform |
| NM_004411 | DYNC1I1 | dynein, cytoplasmic 1, intermediate chain 1 |
| NM_004414 | RCAN1 | calcipressin 1 isoform b |
| NM_004490 | GRB14 | growth factor receptor-bound protein 14 |
| NM_004508 | IDI1 | isopentenyl-diphosphate delta isomerase |
| NM_004509 | SP110 | SP110 nuclear body protein isoform c |
| NM_004542 | NDUFA3 | NADH dehydrogenase (ubiquinone) 1 alpha |
| NM_004545 | NDUFB1 | NADH dehydrogenase (ubiquinone) 1 beta |
| NM_004546 | NDUFB2 | NADH dehydrogenase (ubiquinone) 1 beta |
| NM_004556 | NFKBIE | nuclear factor of kappa light polypeptide gene |
| NM_004591 | CCL20 | chemokine (C-C motif) ligand 20 isoform 1 |
| NM_004614 | TK2 | thymidine kinase 2, mitochondrial |
| NM_004642 | CDK2AP1 | CDK2-associated protein 1 |
| NM_004649 | C21orf33 | es1 protein isoform Ia precursor |
| NM_004657 | SDPR | serum deprivation response protein |
| NM_004668 | MGAM | maltase-glucoamylase |
| NM_004688 | NMI | N-myc and STAT interactor |
| NM_004696 | SLC16A4 | solute carrier family 16, member 4 |
| NM_004710 | SYNGR2 | synaptogyrin 2 |
| NM_004734 | DCLK1 | doublecortin-like kinase 1 |
| NM_004748 | CCPG1 | cell cycle progression 1 isoform 2 |
| NM_004751 | GCNT3 | glucosaminyl (N-acetyl) transferase 3, mucin |
| NM_004753 | DHRS3 | dehydrogenase/reductase (SDR family) member 3 |
| NM_004791 | ITGBL1 | integrin, beta-like 1 (with EGF-like repeat |
| NM_004815 | ARHGAP29 | PTPL1-associated RhoGAP 1 |
| NM_004862 | LITAF | lipopolysaccharide-induced TNF-alpha factor |
| NM_004899 | BRE | brain and reproductive organ-expressed (TNFRSF1A |
| NM_004905 | PRDX6 | peroxiredoxin 6 |
| NM_004932 | CDH6 | cadherin 6, type 2 preproprotein |
| NM_004934 | CDH18 | cadherin 18, type 2 preproprotein |
| NM_004938 | DAPK1 | death-associated protein kinase 1 |
| NM_005010 | NRCAM | neuronal cell adhesion molecule isoform A |
| NM_005019 | PDE1A | phosphodiesterase 1A isoform 1 |
| NM_005020 | PDE1C | phosphodiesterase 1C |
| NM_005044 | PRKX | protein kinase, X-linked |
| NM_005065 | SEL1L | sel-1 suppressor of lin-12-like precursor |
| NM_005098 | MSC | musculin |
| NM_005101 | ISG15 | ISG15 ubiquitin-like modifier precursor |
| NM_005103 | FEZ1 | zygin 1 isoform 1 |
| NM_005113 | GOLGA5 | Golgi autoantigen, golgin subfamily a, 5 |
| NM_005123 | NR1H4 | nuclear receptor subfamily 1, group H, member 4 |
| NM_005125 | CCS | copper chaperone for superoxide dismutase |
| NM_005167 | PPM1J | protein phosphatase 1J (PP2C domain containing) |
| NM_005168 | RND3 | ras homolog gene family, member E precursor |
| NM_005195 | CEBPD | CCAAT/enhancer binding protein delta |
| NM_005200 (replaced by NM_003119.2) | | paraplegia 7 (pure and complicated autosomal recessive) (SPG7) |
| NM_005204 | MAP3K8 | mitogen-activated protein kinase kinase kinase |
| NM_005213 | CSTA | cystatin A |
| NM_005245 | FAT1 | FAT tumor suppressor 1 precursor |
| NM_005319 | HIST1H1C | histone cluster 1, H1c |
| NM_005326 | HAGH | hydroxyacylglutathione hydrolase isoform 2 |
| NM_005340 | HINT1 | *Homo sapiens* cDNA: FLJ22904 fis, clone KAT05632. |
| NM_005345 | HSPA1A | heat shock 70 kDa protein 1A |
| NM_005346 | HSPA1B | heat shock 70 kDa protein 1B |
| NM_005354 | JUND | jun D proto-oncogene |
| NM_005393 | PLXNB3 | plexin B3 isoform 2 |
| NM_005419 | STAT2 | signal transducer and activator of transcription |
| NM_005505 | SCARB1 | scavenger receptor class B, member 1 isoform 2 |
| NM_005506 | SCARB2 | scavenger receptor class B, member 2 |
| NM_005512 | LRRC32 | leucine rich repeat containing 32 precursor |
| NM_005525 | HSD11B1 | 11-beta-hydroxysteroid dehydrogenase 1 |
| NM_005528 | DNAJC4 | DnaJ (Hsp40) homolog, subfamily C, member 4 |
| NM_005532 | IFI27 | interferon, alpha-inducible protein 27 isoform |
| NM_005533 | IFI35 | interferon-induced protein 35 |
| NM_005541 | INPP5D | SH2 containing inositol phosphatase isoform a |
| NM_005547 | IVL | involucrin |
| NM_005557 | KRT16 | keratin 16 |
| NM_005561 | LAMP1 | lysosomal-associated membrane protein 1 |
| NM_005567 | LGALS3BP | galectin 3 binding protein |
| NM_005569 | LIMK2 | LIM domain kinase 2 isoform 2a |
| NM_005575 | LNPEP | leucyl/cystinyl aminopeptidase isoform 1 |
| NM_005584 | MAB21L1 | mab-21-like protein 1 |

TABLE 2-continued

| GenBank No. | | Encoded Polypeptide |
|---|---|---|
| NM_005625 | SDCBP | syntenin isoform 3 |
| NM_005642 | TAF7 | TATA box-binding protein-associated factor 2F |
| NM_005645 | TAF13 | TBP-associated factor 13 |
| NM_005665 | EVI5 | ecotropic viral integration site 5 |
| NM_005667 | RNF103 | ring finger protein 103 |
| NM_005713 | COL4A3BP | alpha 3 type IV collagen binding protein isoform |
| NM_005715 | UST | uronyl-2-sulfotransferase |
| NM_005720 | ARPC1B | actin related protein 2/3 complex subunit 1B |
| NM_005724 | TSPAN3 | transmembrane 4 superfamily member 8 isoform 1 |
| NM_005745 | BCAP31 | B-cell receptor-associated protein 31 isoform a |
| NM_005755 | EBI3 | Epstein-Barr virus induced 3 precursor |
| NM_005756 | GPR64 | G protein-coupled receptor 64 isoform 1 |
| NM_005765 | ATP6AP2 | ATPase, H+ transporting, lysosomal accessory |
| NM_005780 | LHFP | lipoma HMGIC fusion partner precursor |
| NM_005794 | DHRS2 | dehydrogenase/reductase member 2 isoform 2 |
| NM_005817 | PLIN3 | mannose 6 phosphate receptor binding protein 1 |
| NM_005824 | LRRC17 | leucine rich repeat containing 17 isoform 2 |
| NM_005875 | EIF1B | translation factor sui1 homolog |
| NM_005896 | IDH1 | isocitrate dehydrogenase 1 (NADP+), soluble |
| NM_005899 | NBR1 | neighbor of BRCA1 gene 1 |
| NM_005907 | MAN1A1 | mannosidase, alpha, class 1A, member 1 |
| NM_005908 | MANBA | mannosidase, beta A, lysosomal precursor |
| NM_005926 | MFAP1 | microfibrillar-associated protein 1 |
| NM_005935 | AFF1 | myeloid/lymphoid or mixed-lineage leukemia |
| NM_005950 | MT1G | metallothionein 1G |
| NM_005951 | MT1H | metallothionein 1H |
| NM_005952 | MT1X | metallothionein 1X |
| NM_005965 | | Unknown |
| NM_005979 | S100A13 | S100 calcium binding protein A13 |
| NM_006002 | UCHL3 | ubiquitin carboxyl-terminal esterase L3 |
| NM_006005 | WFS1 | wolframin |
| NM_006010 | MANF | mesencephalic astrocyte-derived neurotrophic |
| NM_006019 | TCIRG1 | T-cell, immune regulator 1 isoform a |
| NM_006024 | TAX1BP1 | Tax1 (human T-cell leukemia virus type I) |
| NM_006033 | LIPG | endothelial lipase precursor |
| NM_006038 | SPATA2 | spermatogenesis associated 2 |
| NM_006058 | TNIP1 | TNFAIP3 interacting protein 1 |
| NM_006096 | NDRG1 | N-myc downstream regulated 1 |
| NM_006102 (replaced by NM_016134.3) | | carboxypeptidase Q (CPQ) |
| NM_006106 | YAP1 | Yes-associated protein 1, 65 kDa isoform 1 |
| NM_006113 | VAV3 | vav 3 guanine nucleotide exchange factor isoform |
| NM_006134 | TMEM50B | transmembrane protein 50B |
| NM_006141 | DYNC1LI2 | dynein, cytoplasmic, light intermediate |
| NM_006145 | DNAJB1 | DnaJ (Hsp40) homolog, subfamily B, member 1 |
| NM_006200 | PCSK5 | proprotein convertase subtilisin/kexin type 5 |
| NM_006223 | PIN4 | protein (peptidyl-prolyl cis/trans isomerase) |
| NM_006227 | PLTP | phospholipid transfer protein isoform a |
| NM_006244 | PPP2R5B | beta isoform of regulatory subunit B56, protein |
| NM_006255 | PRKCH | protein kinase C, eta |
| NM_006256 | PKN2 | protein kinase N2 |
| NM_006258 | PRKG1 | protein kinase, cGMP-dependent, type I isoform |
| NM_006260 | DNAJC3 | DnaJ (Hsp40) homolog, subfamily C, member 3 |
| NM_006285 | TESK1 | testis-specific protein kinase 1 |
| NM_006290 | TNFAIP3 | tumor necrosis factor, alpha-induced protein 3 |
| NM_006307 | SRPX | sushi-repeat-containing protein, X-linked |
| NM_006315 | PCGF3 | ring finger protein 3 |
| NM_006332 | IFI30 | interferon, gamma-inducible protein 30 |
| NM_006349 | ZNHIT1 | zinc finger, HIT domain containing 1 |
| NM_006369 | LRRC41 | MUF1 protein |
| NM_006384 | CIB1 | calcium and integrin binding 1 |
| NM_006404 | PROCR | endothelial protein C receptor precursor |
| NM_006406 | PRDX4 | peroxiredoxin 4 |
| NM_006407 | ARL6IP5 | ADP-ribosylation-like factor 6 interacting |
| NM_006416 | SLC35A1 | solute carrier family 35 (CMP-sialic acid |
| NM_006423 | RABAC1 | Rab acceptor 1 |
| NM_006426 | DPYSL4 | dihydropyrimidinase-like 4 |
| NM_006462 | RBCK1 | RanBP-type and C3HC4-type zinc finger containing |
| NM_006472 | TXNIP | thioredoxin interacting protein |
| NM_006493 | CLN5 | ceroid-lipofuscinosis, neuronal 5 |
| NM_006505 | PVR | poliovirus receptor isoform alpha |
| NM_006517 | SLC16A2 | solute carrier family 16, member 2 |
| NM_006520 | DYNLT3 | dynein, light chain, Tctex-type 3 |
| NM_006526 | ZNF217 | zinc finger protein 217 |
| NM_006536 | CLCA2 | chloride channel accessory 2 precursor |

TABLE 2-continued

| GenBank No. | | Encoded Polypeptide |
|---|---|---|
| NM_006542 | SPHAR | S-phase response (cyclin-related) |
| NM_006547 | IGF2BP3 | insulin-like growth factor 2 mRNA binding |
| NM_006577 | B3GNT2 | UDP-GlcNAc:betaGal |
| NM_006608 | PHTF1 | putative homeodomain transcription factor 1 |
| NM_006634 | VAMP5 | vesicle-associated membrane protein 5 |
| NM_006642 | SDCCAG8 | serologically defined colon cancer antigen 8 |
| NM_006670 | TPBG | trophoblast glycoprotein precursor |
| NM_006675 | TSPAN9 | tetraspanin 9 |
| NM_006676 | USP20 | ubiquitin specific protease 20 |
| NM_006682 | FGL2 | fibrinogen-like 2 precursor |
| NM_006698 | BLCAP | bladder cancer associated protein |
| NM_006702 | PNPLA6 | neuropathy target esterase isoform b |
| NM_006720 | ABLIM1 | actin-binding LIM protein 1 isoform c |
| NM_006727 | CDH10 | cadherin 10, type 2 preproprotein |
| NM_006730 | DNASE1L1 | deoxyribonuclease I-like 1 precursor |
| NM_006755 | TALDO1 | transaldolase 1 |
| NM_006759 | UGP2 | UDP-glucose pyrophosphorylase 2 isoform a |
| NM_006763 | BTG2 | B-cell translocation gene 2 |
| NM_006767 | LZTR1 | leucine-zipper-like transcription regulator 1 |
| NM_006803 | AP3M2 | adaptor-related protein complex 3, mu 2 subunit |
| NM_006810 | PDIA5 | protein disulfide isomerase A5 precursor |
| NM_006822 | RAB40B | RAB40B, member RAS oncogene family |
| NM_006823 | PKIA | cAMP-dependent protein kinase inhibitor alpha |
| NM_006829 | C10orf116 | adipose specific 2 |
| NM_006830 | UQCR | ubiquinol-cytochrome c reductase, 6.4 kDa |
| NM_006851 | GLIPR1 | GLI pathogenesis-related 1 precursor |
| NM_006876 | B3GNT1 | UDP-GlcNAc:betaGal |
| NM_006905 | PSG1 | pregnancy specific beta-1-glycoprotein 1 |
| NM_006918 | SC5DL | sterol-C5-desaturase |
| NM_007034 | DNAJB4 | DnaJ (Hsp40) homolog, subfamily B, member 4 |
| NM_007036 | ESM1 | endothelial cell-specific molecule 1 isoform a |
| NM_007048 | BTN3A1 | butyrophilin, subfamily 3, member A1 isoform d |
| NM_007076 | FICD | Huntingtin interacting protein E |
| NM_007167 | ZMYM6 | zinc finger protein 258 |
| NM_007168 | ABCA8 | ATP-binding cassette, sub-family A member 8 |
| NM_007173 | PRSS23 | protease, serine, 23 precursor |
| NM_007213 | PRAF2 | PRAT domain family, member 2 |
| NM_007260 | LYPLA2 | lysophospholipase II |
| NM_007271 | STK38 | serine/threonine kinase 38 |
| NM_007274 | ACOT7 | acyl-CoA thioesterase 7 isoform hBACHd |
| NM_007278 | GABARAP | GABA(A) receptor-associated protein |
| NM_007287 | MME | membrane metallo-endopeptidase |
| NM_007315 | STAT1 | signal transducer and activator of transcription |
| NM_007325 | GRIA3 | glutamate receptor, ionotrophic, AMPA 3 isoform |
| NM_007341 | SH3BGR | SH3-binding domain and glutamic acid-rich |
| NM_007350 | PHLDA1 | pleckstrin homology-like domain, family A, |
| NM_012067 | AKR7A3 | aldo-keto reductase family 7, member A3 |
| NM_012081 | ELL2 | elongation factor, RNA polymerase II, 2 |
| NM_012090 | MACF1 | microfilament and actin filament cross-linker |
| NM_012093 | AK5 | adenylate kinase 5 isoform 1 |
| NM_012105 | BACE2 | beta-site APP-cleaving enzyme 2 isoform A |
| NM_012155 | EML2 | echinoderm microtubule associated protein like |
| NM_012168 | FBXO2 | F-box only protein 2 |
| NM_012193 | FZD4 | frizzled 4 precursor |
| NM_012200 | B3GAT3 | beta-1,3-glucuronyltransferase 3 |
| NM_012201 | GLG1 | golgi apparatus protein 1 isoform 1 |
| NM_012213 | MLYCD | malonyl-CoA decarboxylase precursor |
| NM_012215 | MGEA5 | meningioma expressed antigen 5 (hyaluronidase) |
| NM_012228 | MSRB2 | methionine sulfoxide reductase B2 precursor |
| NM_012243 | SLC35A3 | solute carrier family 35 member 3A |
| NM_012249 | RHOQ | ras-like protein TC10 precursor |
| NM_012250 | RRAS2 | related RAS viral (r-ras) oncogene homolog 2 |
| NM_012252 | TFEC | transcription factor EC isoform a |
| NM_012268 | PLD3 | phospholipase D3 |
| NM_012281 | KCND2 | potassium voltage-gated channel, Shal-related |
| NM_012328 | DNAJB9 | DnaJ (Hsp40) homolog, subfamily B, member 9 |
| NM_012329 | MMD | monocyte to macrophage |
| NM_012342 | BAMBI | BMP and activin membrane-bound inhibitor |
| NM_012360 | OR1F1 | olfactory receptor, family 1, subfamily F, |
| NM_012396 | PHLDA3 | pleckstrin homology-like domain, family A, |
| NM_012413 | QPCT | glutaminyl-peptide cyclotransferase precursor |
| NM_012419 | RGS17 | regulator of G-protein signalling 17 |
| NM_012429 | SEC14L2 | SEC14-like 2 isoform 1 |
| NM_012430 | SEC22A | SEC22 vesicle trafficking protein homolog A |
| NM_012431 | SEMA3E | semaphorin 3E precursor |
| NM_012434 | SLC17A5 | sialin |

TABLE 2-continued

| GenBank No. | | Encoded Polypeptide |
|---|---|---|
| NM_012449 | STEAP1 | six transmembrane epithelial antigen of the |
| NM_013229 | APAF1 | apoptotic peptidase activating factor 1 isoform |
| NM_013231 | FLRT2 | fibronectin leucine rich transmembrane protein 2 |
| NM_013281 | FLRT3 | fibronectin leucine rich transmembrane protein 3 |
| NM_013312 | HOOK2 | hook homolog 2 isoform 1 |
| NM_013314 | BLNK | B-cell linker isoform 1 |
| NM_013325 | ATG4B | APG4 autophagy 4 homolog B isoform a |
| NM_013335 | GMPPA | GDP-mannose pyrophosphorylase A |
| NM_013343 | | Unknown |
| NM_013352 | DSE | dermatan sulfate epimerase precursor |
| NM_013379 | DPP7 | dipeptidyl peptidase 7 preproprotein |
| NM_013381 | TRHDE | thyrotropin-releasing hormone degrading enzyme |
| NM_013390 | TMEM2 | transmembrane protein 2 isoform a |
| NM_013399 | C16orf5 | cell death inducing protein |
| NM_013943 | CLIC4 | chloride intracellular channel 4 |
| NM_013959 | NRG1 | neuregulin 1 isoform ndf43b |
| NM_013960 | NRG1 | neuregulin 1 isoform ndf43b |
| NM_014015 | DEXI | dexamethasone-induced protein |
| NM_014028 | OSTM1 | osteopetrosis associated transmembrane protein 1 |
| NM_014045 | LRP10 | *Homo sapiens* LRP10 mRNA for low density lipoprotein receptor-related protein 10, complete cds. |
| NM_014068 | PSORS1C1 | SEEK1 protein |
| NM_014145 | C20orf30 | hypothetical protein LOC29058 isoform 1 |
| NM_014158 (replaced by NM_152692.4) | | C1GALT1-specific chaperone 1 (C1GALT1C1) |
| NM_014182 | ORMDL2 | ORMDL2 |
| NM_014244 | ADAMTS2 | ADAM metallopeptidase with thrombospondin type 1 |
| NM_014266 | HCST | hematopoietic cell signal transducer isoform 2 |
| NM_014268 | MAPRE2 | microtubule-associated protein, RP/EB family, |
| NM_014278 | HSPA4L | heat shock 70 kDa protein 4-like |
| NM_014294 | TRAM1 | translocation associated membrane protein 1 |
| NM_014297 | ETHE1 | ETHE1 protein precursor |
| NM_014298 | QPRT | quinolinate phosphoribosyltransferase |
| NM_014314 | DDX58 | DEAD/H (Asp-Glu-Ala-Asp/His) box polypeptide |
| NM_014350 | TNFAIP8 | tumor necrosis factor, alpha-induced protein 8 |
| NM_014391 | ANKRD1 | cardiac ankyrin repeat protein |
| NM_014392 | D4S234E | brain neuron cytoplasmic protein 1 |
| NM_014396 | VPS41 | vacuolar protein sorting 41 isoform 1 |
| NM_014399 | TSPAN13 | tetraspan NET-6 |
| NM_014454 | SESN1 | sestrin 1 |
| NM_014548 | TMOD2 | neuronal tropomodulin isoform a |
| NM_014556 | | Unknown |
| NM_014563 | TRAPPC2 | trafficking protein particle complex 2 isoform |
| NM_014584 | ERO1L | ERO1-like precursor |
| NM_014646 | LPIN2 | lipin 2 |
| NM_014650 | ZNF432 | zinc finger protein 432 |
| NM_014652 | IPO13 | importin 13 |
| NM_014668 | GREB1 | growth regulation by estrogen in breast cancer 1 |
| NM_014713 | LAPTM4A | lysosomal protein transmembrane 4 alpha |
| NM_014723 | SNPH | syntaphilin |
| NM_014730 | MLEC | malectin precursor |
| NM_014734 | KIAA0247 | hypothetical protein LOC9766 precursor |
| NM_014751 | MTSS1 | metastasis suppressor 1 |
| NM_014774 | KIAA0494 | hypothetical protein LOC9813 |
| NM_014799 | HEPH | hephaestin isoform c |
| NM_014804 | KIAA0753 | hypothetical protein LOC9851 |
| NM_014840 | NUAK1 | AMPK-related protein kinase 5 |
| NM_014844 | TECPR2 | tectonin beta-propeller repeat containing 2 |
| NM_014845 | FIG4 | Sac domain-containing inositol phosphatase 3 |
| NM_014888 | FAM3C | family with sequence similarity 3, member C |
| NM_014890 | FILIP1L | filamin A interacting protein 1-like isoform 1 |
| NM_014900 | COBLL1 | COBL-like 1 |
| NM_014905 | GLS | glutaminase precursor |
| NM_014934 | DZIP1 | DAZ interacting protein 1 isoform 2 |
| NM_014936 | ENPP4 | ectonucleotide pyrophosphatase/phosphodiesterase |
| NM_014942 | ANKRD6 | ankyrin repeat domain 6 |
| NM_014943 | ZHX2 | zinc fingers and homeoboxes 2 |
| NM_014945 | ABLIM3 | actin binding LIM protein family, member 3 |
| NM_014950 | ZBTB1 | zinc finger and BTB domain containing 1 isoform |
| NM_014951 | ZNF365 | zinc finger protein 365 isoform C |
| NM_015000 | STK38L | serine/threonine kinase 38 like |

TABLE 2-continued

| GenBank No. | | Encoded Polypeptide |
|---|---|---|
| NM_015271 | TRIM2 | tripartite motif-containing 2 isoform 1 |
| NM_015364 | LY96 | MD-2 protein precursor |
| NM_015392 | NPDC1 | neural proliferation, differentiation and |
| NM_015415 | BRP44 | brain protein 44 |
| NM_015516 | TSKU | tsukushin precursor |
| NM_015556 | SIPA1L1 | signal-induced proliferation-associated 1 like |
| NM_015654 | NAT9 | N-acetyltransferase 9 |
| NM_015705 | SGSM3 | small G protein signaling modulator 3 |
| NM_015865 | SLC14A1 | solute carrier family 14 (urea transporter), |
| NM_015878 | AZIN1 | ornithine decarboxylase antizyme inhibitor |
| NM_015917 | GSTK1 | glutathione S-transferase kappa 1 isoform a |
| NM_015919 | ZNF226 | zinc finger protein 226 isoform b |
| NM_015920 | RPS27L | ribosomal protein S27-like |
| NM_015967 | PTPN22 | protein tyrosine phosphatase, non-receptor type |
| NM_015976 | SNX7 | sorting nexin 7 isoform a |
| NM_015987 | HEBP1 | heme binding protein 1 |
| NM_015996 | | |
| NM_016040 | TMED5 | transmembrane emp24 protein transport domain |
| NM_016061 | YPEL5 | yippee-like 5 |
| NM_016109 | | |
| NM_016127 | TMEM66 | transmembrane protein 66 precursor |
| NM_016134 | PGCP | plasma glutamate carboxypeptidase precursor |
| NM_016142 | HSD17B12 | hydroxysteroid (17-beta) dehydrogenase 12 |
| NM_016151 | TAOK2 | TAO kinase 2 isoform 1 |
| NM_016152 | RARB | retinoic acid receptor, beta isoform 1 |
| NM_016154 | RAB4B | ras-related GTP-binding protein 4b |
| NM_016162 | ING4 | inhibitor of growth family, member 4 isoform 1 |
| NM_016219 | MAN1B1 | alpha 1,2-mannosidase |
| NM_016226 | VPS29 | vacuolar protein sorting 29 isoform 2 |
| NM_016227 | C1orf9 | chromosome 1 open reading frame 9 protein |
| NM_016235 | GPRC5B | G protein-coupled receptor, family C, group 5, |
| NM_016243 | CYB5R1 | cytochrome b5 reductase 1 |
| NM_016255 | FAM8A1 | family with sequence similarity 8, member A1 |
| NM_016275 | SELT | selenoprotein T precursor |
| NM_016303 | WBP5 | WW domain binding protein 5 |
| NM_016311 | ATPIF1 | ATPase inhibitory factor 1 isoform 2 precursor |
| NM_016352 | CPA4 | carboxypeptidase A4 preproprotein |
| NM_016399 | TRIAP1 | p53-inducible cell-survival factor |
| NM_016422 | RNF141 | ring finger protein 141 |
| NM_016423 | ZNF219 | zinc finger protein 219 |
| NM_016429 | COPZ2 | coatomer protein complex, subunit zeta 2 |
| NM_016437 | TUBG2 | tubulin, gamma 2 |
| NM_016530 | RAB8B | RAB8B, member RAS oncogene family |
| NM_016547 | SDF4 | stromal cell derived factor 4 isoform 2 |
| NM_016557 | CCRL1 | chemokine (C-C motif) receptor-like 1 |
| NM_016577 | RAB6B | RAB6B, member RAS oncogene family |
| NM_016582 | SLC15A3 | solute carrier family 15, member 3 |
| NM_016588 | NRN1 | neuritin precursor |
| NM_016599 | MYOZ2 | myozenin 2 |
| NM_016608 | ARMCX1 | armadillo repeat containing, X-linked 1 |
| NM_016621 | PHF21A | BRAF35/HDAC2 complex isoform b |
| NM_016651 | DACT1 | dapper 1 isoform 1 |
| NM_016656 | RRAGB | Ras-related GTP binding B long isoform |
| NM_016657 | KDELR3 | KDEL receptor 3 isoform a |
| NM_016830 | VAMP1 | vesicle-associated membrane protein 1 isoform 1 |
| NM_016938 | EFEMP2 | EGF-containing fibulin-like extracellular matrix |
| NM_017414 | USP18 | ubiquitin specific protease 18 |
| NM_017415 | KLHL3 | kelch-like 3 |
| NM_017423 | GALNT7 | polypeptide N-acetylgalactosaminyltransferase 7 |
| NM_017445 | | unknown |
| NM_017458 | MVP | major vault protein |
| NM_017514 | PLXNA3 | plexin A3 precursor |
| NM_017554 | PARP14 | poly (ADP-ribose) polymerase family, member 14 |
| NM_017567 | NAGK | N-Acetylglucosamine kinase |
| NM_017627 (replaced by NM_031407.6) | | HECT, UBA and WWE domain containing 1, E3 ubiquitin protein ligase (HUWE1) |
| NM_017649 | CNNM2 | cyclin M2 isoform 1 |
| NM_017655 | GIPC2 | PDZ domain protein GIPC2 |
| NM_017661 | ZNF280D | suppressor of hairy wing homolog 4 isoform 1 |
| NM_017679 | BCAS3 | breast carcinoma amplified sequence 3 isoform 1 |
| NM_017680 | ASPN | asporin precursor |
| NM_017684 | VPS13C | vacuolar protein sorting 13C protein isoform 2A |
| NM_017692 | APTX | aprataxin isoform a |
| NM_017706 | WDR55 | WD repeat domain 55 |
| NM_017712 | PGPEP1 | pyroglutamyl-peptidase I |

TABLE 2-continued

| GenBank No. | | Encoded Polypeptide |
|---|---|---|
| NM_017733 | PIGG | phosphatidylinositol glycan anchor biosynthesis, |
| NM_017739 | POMGNT1 | SubName: Full = Protein O-linked mannose beta1,2-N-acetylglucosaminyltransferase; |
| NM_017742 | ZCCHC2 | zinc finger, CCHC domain containing 2 |
| NM_017750 | RETSAT | all-trans-13,14-dihydroretinol saturase |
| NM_017784 | OSBPL10 | oxysterol-binding protein-like protein 10 |
| NM_017814 | TMEM161A | transmembrane protein 161A precursor |
| NM_017836 | SLC41A3 | solute carrier family 41, member 3 isoform 1 |
| NM_017837 | PIGV | phosphatidylinositol glycan class V |
| NM_017856 | GEMIN8 | gem (nuclear organelle) associated protein 8 |
| NM_017870 | TMEM132A | transmembrane protein 132A isoform a |
| NM_017901 | TPCN1 | two pore segment channel 1 isoform 1 |
| NM_017935 | BANK1 | B-cell scaffold protein with ankyrin repeats 1 |
| NM_017938 | FAM70A | hypothetical protein LOC55026 isoform 1 |
| NM_017947 | MOCOS | molybdenum cofactor sulfurase |
| NM_017983 | WIPI1 | WD repeat domain, phosphoinositide interacting |
| NM_017992 (replaced by NM_025191.3) | | ER degradation enhancer, mannosidase alpha-like 3 (EDEM3) |
| NM_018042 | SLFN12 | schlafen family member 12 |
| NM_018046 | AGGF1 | angiogenic factor VG5Q |
| NM_018075 | ANO10 | transmembrane protein 16K |
| NM_018113 | LMBR1L | lipocalin-interacting membrane receptor |
| NM_018129 | PNPO | pyridoxine 5′-phosphate oxidase |
| NM_018153 | ANTXR1 | anthrax toxin receptor 1 isoform 1 precursor |
| NM_018161 | NADSYN1 | NAD synthetase 1 |
| NM_018191 | RCBTB1 | regulator of chromosome condensation (RCC1) and |
| NM_018217 | EDEM2 | ER degradation enhancer, mannosidase alpha-like |
| NM_018229 | MUDENG | Mu-2 related death-inducing protein |
| NM_018267 | | |
| NM_018291 | FGGY | FGGY carbohydrate kinase domain containing |
| NM_018293 | ZNF654 | zinc finger protein 654 |
| NM_018295 | TMEM140 | transmembrane protein 140 |
| NM_018334 | LRRN3 | leucine rich repeat neuronal 3 precursor |
| NM_018357 | LARP6 | La ribonucleoprotein domain family, member 6 |
| NM_018368 | LMBRD1 | liver regeneration p-53 related protein |
| NM_018370 | DRAM1 | DNA-damage regulated autophagy modulator 1 |
| NM_018371 | CSGALNACT1 | chondroitin sulfate |
| NM_018381 | C19orf66 | hypothetical protein LOC55337 |
| NM_018418 | SPATA7 | spermatogenesis-associated protein 7 isoform a |
| NM_018447 | TMEM111 | transmembrane protein 111 |
| NM_018490 | LGR4 | leucine-rich repeat-containing G protein-coupled |
| NM_018494 | LRDD | leucine rich repeat and death domain containing |
| NM_018530 | GSDMB | gasdermin B isoform 1 |
| NM_018584 | CAMK2N1 | calcium/calmodulin-dependent protein kinase II |
| NM_018638 | ETNK1 | ethanolamine kinase 1 isoform A |
| NM_018639 | WSB2 | WD SOCS-box protein 2 |
| NM_018648 | NOP10 | nucleolar protein family A, member 3 |
| NM_018656 | SLC35E3 | solute carrier family 35, member E2 |
| NM_018835 | RC3H2 | ring finger and CCCH-type zinc finger domains 2 |
| NM_018840 | C20orf24 | *Homo sapiens* putative Rab5-interacting protein mRNA, complete cds. |
| NM_018973 | DPM3 | dolichyl-phosphate mannosyltransferase |
| NM_018999 | FAM190B | granule cell antiserum positive 14 |
| NM_019059 | TOMM7 | translocase of outer mitochondrial membrane 7 |
| NM_019099 | C1orf183 | hypothetical protein LOC55924 isoform 2 |
| NM_019114 | EPB41L4B | erythrocyte membrane protein band 4.1 like 4B |
| NM_019555 | ARHGEF3 | Rho guanine nucleotide exchange factor 3 isoform |
| NM_019556 | MOSPD1 | motile sperm domain containing 1 |
| NM_019885 | CYP26B1 | cytochrome P450, family 26, subfamily b, |
| NM_020127 | TUFT1 | tuftelin 1 isoform 1 |
| NM_020139 | BDH2 | 3-hydroxybutyrate dehydrogenase, type 2 |
| NM_020154 | C15orf24 | chromosome 15 open reading frame 24 precursor |
| NM_020166 | MCCC1 | methylcrotonoyl-Coenzyme A carboxylase 1 (alpha) |
| NM_020182 | PMEPA1 | transmembrane prostate androgen-induced protein |
| NM_020199 | C5orf15 | keratinocytes associated transmembrane protein 2 |
| NM_020215 | | Unknown |
| NM_020224 | | Unknown |
| NM_020234 | DTWD1 | DTW domain containing 1 |
| NM_020299 | AKR1B10 | aldo-keto reductase family 1, member B10 |
| NM_020347 | LZTFL1 | leucine zipper transcription factor-like 1 |
| NM_020353 | PLSCR4 | phospholipid scramblase 4 isoform a |

TABLE 2-continued

| GenBank No. | | Encoded Polypeptide |
|---|---|---|
| NM_020372 | SLC22A17 | solute carrier family 22, member 17 isoform b |
| NM_020375 | C12orf5 | TP53-induced glycolysis and apoptosis regulator |
| NM_020379 | MAN1C1 | mannosidase, alpha, class 1C, member 1 |
| NM_020399 | GOPC | golgi associated PDZ and coiled-coil motif |
| NM_020448 | NIPAL3 | NIPA-like domain containing 3 |
| NM_020524 | PBXIP1 | pre-B-cell leukemia homeobox interacting protein |
| NM_020639 | RIPK4 | ankyrin repeat domain 3 |
| NM_020644 | TMEM9B | TMEM9 domain family, member B precursor |
| NM_020650 | RCN3 | reticulocalbin 3, EF-hand calcium binding domain |
| NM_020663 | RHOJ | ras homolog gene family, member J precursor |
| NM_020689 | SLC24A3 | solute carrier family 24 |
| NM_020755 | SERINC1 | serine incorporator 1 |
| NM_020760 | HECW2 | HECT, C2 and WW domain containing E3 ubiquitin |
| NM_020815 | PCDH10 | protocadherin 10 isoform 1 precursor |
| NM_020841 | OSBPL8 | oxysterol-binding protein-like protein 8 isoform |
| NM_021007 | SCN2A | sodium channel, voltage-gated, type II, alpha |
| NM_021013 | KRT34 | keratin 34 |
| NM_021016 | PSG3 | pregnancy specific beta-1-glycoprotein 3 |
| NM_021035 | ZNFX1 | zinc finger, NFX1-type containing 1 |
| NM_021070 | LTBP3 | latent transforming growth factor beta binding |
| NM_021101 | CLDN1 | claudin 1 |
| NM_021106 | RGS3 | regulator of G-protein signalling 3 isoform 6 |
| NM_021127 | PMAIP1 | phorbol-12-myristate-13-acetate-induced protein |
| NM_021136 | RTN1 | reticulon 1 isoform A |
| NM_021137 | TNFAIP1 | tumor necrosis factor, alpha-induced protein 1 |
| NM_021151 | CROT | peroxisomal carnitine O-octanoyltransferase |
| NM_021173 | POLD4 | DNA-directed DNA polymerase delta 4 |
| NM_021199 | SQRDL | sulfide dehydrogenase like precursor |
| NM_021203 | SRPRB | signal recognition particle receptor, beta |
| NM_021219 | JAM2 | junctional adhesion molecule 2 precursor |
| NM_021229 | NTN4 | netrin 4 precursor |
| NM_021244 | RRAGD | Ras-related GTP binding D |
| NM_021249 | SNX6 | sorting nexin 6 isoform b |
| NM_021616 | TRIM34 | tripartite motif protein 34 isoform 2 |
| NM_021622 | PLEKHA1 | pleckstrin homology domain containing, family A |
| NM_021626 | SCPEP1 | serine carboxypeptidase 1 precursor |
| NM_021637 | TMEM35 | transmembrane protein 35 |
| NM_021643 | TRIB2 | tribbles homolog 2 |
| NM_021727 | FADS3 | fatty acid desaturase 3 |
| NM_021731 | C19orf28 | hypothetical protein LOC126321 isoform a |
| NM_021783 | EDA2R | X-linked ectodysplasin receptor |
| NM_021825 | CCDC90B | coiled-coil domain containing 90B precursor |
| NM_021827 | CCDC81 | coiled-coil domain containing 81 isoform 1 |
| NM_021980 | OPTN | optineurin |
| NM_021994 | ZNF277 | zinc finger protein (C2H2 type) 277 |
| NM_021999 | ITM2B | integral membrane protein 2B |
| NM_022001 | | unknown |
| NM_022060 | ABHD4 | abhydrolase domain containing 4 |
| NM_022083 (replaced by NM_052966.3) | | sequence similarity 129, member A (FAM129A) |
| NM_022087 | GALNT11 | N-acetylgalactosaminyltransferase 11 |
| NM_022117 | TSPYL2 | TSPY-like 2 |
| NM_022121 | PERP | PERP, TP53 apoptosis effector |
| NM_022128 | RBKS | ribokinase |
| NM_022129 | PBLD | MAWD binding protein isoform a |
| NM_022135 | POPDC2 | popeye protein 2 |
| NM_022147 | RTP4 | 28 kD interferon responsive protein |
| NM_022152 | TMBIM1 | transmembrane BAX inhibitor motif containing 1 |
| NM_022168 | IFIH1 | interferon induced with helicase C domain 1 |
| NM_022171 | TCTA | T-cell leukemia translocation altered |
| NM_022338 | C11orf24 | hypothetical protein LOC53838 precursor |
| NM_022350 | ERAP2 | endoplasmic reticulum aminopeptidase 2 |
| NM_022368 | PJA1 | praja 1 isoform c |
| NM_022450 | RHBDF1 | rhomboid family 1 |
| NM_022464 | SIL1 | SIL1 protein precursor |
| NM_022470 | ZMAT3 | p53 target zinc finger protein isoform 1 |
| NM_022473 | ZFP106 | zinc finger protein 106 homolog |
| NM_022477 | NDRG3 | N-myc downstream regulated gene 3 isoform a |
| NM_022736 | MFSD1 | major facilitator superfamily domain containing |
| NM_022742 | CCDC136 | coiled-coil domain containing 136 |
| NM_022743 | SMYD3 | SET and MYND domain containing 3 |
| NM_022748 | TNS3 | tensin 3 |
| NM_022750 | PARP12 | poly ADP-ribose polymerase 12 |

TABLE 2-continued

| GenBank No. | | Encoded Polypeptide |
|---|---|---|
| NM_022765 | MICAL1 | microtubule associated monoxygenase, calponin |
| NM_022772 | EPS8L2 | epidermal growth factor receptor pathway |
| NM_022783 | DEPDC6 | DEP domain containing 6 |
| NM_022837 | | unknown |
| NM_022902 | SLC30A5 | solute carrier family 30 (zinc transporter), |
| NM_023034 | WHSC1L1 | WHSC1L1 protein isoform long |
| NM_023037 | FRY | furry homolog |
| NM_023039 | ANKRA2 | ankyrin repeat, family A (RFXANK-like), 2 |
| NM_023073 | C5orf42 | hypothetical protein LOC65250 |
| NM_023112 | OTUB2 | OTU domain, ubiquitin aldehyde binding 2 |
| NM_023915 | GPR87 | G protein-coupled receptor 87 |
| NM_023928 | AACS | acetoacetyl-CoA synthetase |
| NM_024006 | VKORC1 | vitamin K epoxide reductase complex, subunit 1 |
| NM_024028 | PCYOX1L | prenylcysteine oxidase 1 like precursor |
| NM_024042 | METRN | meteorin, glial cell differentiation regulator |
| NM_024047 | NUDT9 | nudix-type motif 9 isoform a |
| NM_024056 | TMEM106C | transmembrane protein 106C isoform a |
| NM_024064 (replaced by NM_006255.3) | | protein kinase C, eta (PRKCH) |
| NM_024097 | C1orf50 | hypothetical protein LOC79078 |
| NM_024105 | ALG12 | alpha-1,6-mannosyltransferase ALG12 |
| NM_024112 | C9orf16 | hypothetical protein LOC79095 |
| NM_024292 | UBL5 | ubiquitin-like 5 |
| NM_024315 | C7orf23 | chromosome 7 open reading frame 23 |
| NM_024324 | CRELD2 | cysteine-rich with EGF-like domains 2 isoform a |
| NM_024341 | ZNF557 | zinc finger protein 557 isoform a |
| NM_024430 | PSTPIP2 | proline-serine-threonine phosphatase interacting |
| NM_024500 | | unknown |
| NM_024512 | LRRC2 | leucine rich repeat containing 2 |
| NM_024523 | GCC1 | Golgi coiled-coil protein 1 |
| NM_024532 | SPAG16 | sperm associated antigen 16 isoform 1 |
| NM_024536 | CHPF | chondroitin polymerizing factor |
| NM_024539 | RNF128 | ring finger protein 128 isoform 1 |
| NM_024549 | TCTN1 | tectonic family member 1 isoform 3 |
| NM_024564 | | Unknown |
| NM_024574 | C4orf31 | hypothetical protein LOC79625 precursor |
| NM_024577 | SH3TC2 | SH3 domain and tetratricopeptide repeats 2 |
| NM_024599 | RHBDF2 | rhomboid, veinlet-like 6 isoform 2 |
| NM_024602 | HECTD3 | HECT domain containing 3 |
| NM_024617 | ZCCHC6 | zinc finger, CCHC domain containing 6 |
| NM_024620 | ZNF329 | zinc finger protein 329 |
| NM_024649 | BBS1 | Bardet-Biedl syndrome 1 |
| NM_024691 | ZNF419 | zinc finger protein 419 isoform 1 |
| NM_024728 | C7orf10 | dermal papilla derived protein 13 |
| NM_024763 | WDR78 | WD repeat domain 78 isoform 1 |
| NM_024766 | C2orf34 | hypothetical protein LOC79823 |
| NM_024770 | METTL8 | methyltransferase like 8 |
| NM_024801 | | Unknown |
| NM_024806 | C11orf63 | hypothetical protein LOC79864 isoform 1 |
| NM_024819 | DCAKD | dephospho-CoA kinase domain containing |
| NM_024825 | PODNL1 | podocan-like 1 isoform 2 |
| NM_024837 | ATP8B4 | ATPase class I type 8B member 4 |
| NM_024841 | PRR5L | protor-2 isoform a |
| NM_024843 | CYBRD1 | cytochrome b reductase 1 isoform 1 |
| NM_024887 | DHDDS | dehydrodolichyl diphosphate synthase isoform a |
| NM_024913 | C7orf58 | hypothetical protein LOC79974 isoform 1 |
| NM_024924 | | Unknown |
| NM_024935 | | Unknown |
| NM_025000 | DCAF17 | DDB1 and CUL4 associated factor 17 isoform 1 |
| NM_025024 | | Unknown |
| NM_025076 | UXS1 | UDP-glucuronate decarboxylase 1 |
| NM_025133 | FBXO11 | F-box only protein 11 isoform 1 |
| NM_025139 | ARMC9 | armadillo repeat containing 9 |
| NM_025140 | CCDC92 | coiled-coil domain containing 92 |
| NM_025149 | ACSF2 | acyl-CoA synthetase family member 2 precursor |
| NM_025165 | ELL3 | elongation factor RNA polymerase II-like 3 |
| NM_025182 | KIAA1539 | hypothetical protein LOC80256 |
| NM_025202 | EFHD1 | EF-hand domain family, member D1 |
| NM_025208 | PDGFD | platelet derived growth factor D isoform 2 |
| NM_025217 | ULBP2 | UL16 binding protein 2 precursor |
| NM_025226 | | Unknown |
| NM_030641 | APOL6 | apolipoprotein L6 |
| NM_030778 (replaced by NM_014376.2) | | cytoplasmic FMR1 interacting protein 2 (CYFIP2) |
| NM_030790 | ITFG1 | integrin alpha FG-GAP repeat containing 1 |

TABLE 2-continued

| GenBank No. | | Encoded Polypeptide |
|---|---|---|
| NM_030799 | YIPF5 | Yip1 domain family, member 5 |
| NM_030801 | MAGED4B | melanoma antigen family D, 4B isoform 1 |
| NM_030802 | FAM117A | family with sequence similarity 117, member A |
| NM_030810 | TXNDC5 | thioredoxin domain containing 5 isoform 3 |
| NM_030882 | APOL2 | apolipoprotein L2 |
| NM_030911 | CDADC1 | cytidine and dCMP deaminase domain containing 1 |
| NM_030952 | NUAK2 | NUAK family, SNF1-like kinase, 2 |
| NM_030963 | RNF146 | ring finger protein 146 |
| NM_030967 | KRTAP1-1 | keratin associated protein 1-1 |
| NM_030975 | KRTAP9-9 | keratin associated protein 9-9 |
| NM_030977 | | unknown |
| NM_031244 | SIRT5 | sirtuin 5 isoform 2 |
| NM_031246 | PSG2 | pregnancy specific beta-1-glycoprotein 2 |
| NM_031285 (replaced by NM_006675.4) | | tetraspanin 9 (TSPAN9), transcript variant 1 |
| NM_031286 | SH3BGRL3 | SH3 domain binding glutamic acid-rich protein |
| NM_031301 | APH1B | presenilin stabilization factor-like isoform 1 |
| NM_031305 | ARHGAP24 | Rho GTPase activating protein 24 isoform 1 |
| NM_031458 | PARP9 | poly (ADP-ribose) polymerase family, member 9 |
| NM_031961 | KRTAP9-2 | keratin associated protein 9.2 |
| NM_032211 | LOXL4 | lysyl oxidase-like 4 precursor |
| NM_032412 | C5orf32 | hypothetical protein LOC84418 |
| NM_032591 | SLC9A7 | solute carrier family 9, member 7 |
| NM_032623 | C4orf49 | ovary-specific acidic protein |
| NM_032784 | RSPO3 | R-spondin 3 precursor |
| NM_032789 | PARP10 | poly (ADP-ribose) polymerase family, member 10 |
| NM_032812 | PLXDC2 | plexin domain containing 2 precursor |
| NM_032866 | CGNL1 | cingulin-like 1 |
| NM_033255 | EPSTI1 | epithelial stromal interaction 1 isoform 1 |
| NM_033405 | PRIC285 | PPAR-alpha interacting complex protein 285 |
| NM_033407 | DOCK7 | dedicator of cytokinesis 7 |
| NM_037370 | CCNDBP1 | cyclin D-type binding-protein 1 isoform 1 |
| NM_052822 | | unknown |
| NM_052839 | PANX2 | pannexin 2 isoform 2 |
| NM_052866 | ADAMTSL1 | ADAMTS-like 1 isoform 4 precursor |
| NM_052885 | SLC2A13 | solute carrier family 2 (facilitated glucose |
| NM_052889 | CARD16 | caspase-1 dominant-negative inhibitor pseudo-ICE |
| NM_052941 | GBP4 | guanylate binding protein 4 |
| NM_052958 | C8orf34 | hypothetical protein LOC116328 |
| NM_053056 | CCND1 | cyclin D1 |
| NM_078474 | TM2D3 | TM2 domain containing 3 isoform a |
| NM_078483 | SLC36A1 | solute carrier family 36 member 1 |
| NM_078487 | CDKN2B | cyclin-dependent kinase inhibitor 2B isoform 2 |
| NM_080657 | RSAD2 | radical S-adenosyl methionine domain containing |
| NM_080669 | SLC46A1 | proton-coupled folate transporter |
| NM_133477 | SYNPO2 | synaptopodin 2 isoform c |
| NM_138924 | GAMT | guanidinoacetate N-methyltransferase isoform a |
| NM_139266 | STAT1 | signal transducer and activator of transcription |
| NM_144657 | HDX | highly divergent homeobox |
| NM_144717 | IL20RB | interleukin 20 receptor beta precursor |
| NM_144724 | MARVELD2 | MARVEL domain containing 2 isoform 1 |
| NM_144974 | CCDC122 | coiled-coil domain containing 122 |
| NM_144975 | SLFN5 | schlafen family member 5 |
| NM_145058 | RILPL2 | Rab interacting lysosomal protein-like 2 |
| NM_145259 | ACVR1C | activin A receptor, type IC isoform 2 |
| NM_145301 | FAM18B2 | hypothetical protein LOC201158 isoform 2 |
| NM_145316 | TMEM217 | transmembrane protein 217 isoform 1 |
| NM_145731 | SYNGR1 | synaptogyrin 1 isoform 1a |
| NM_152282 | ACPL2 | acid phosphatase-like 2 precursor |
| NM_152532 | | Unknown |
| NM_152565 | ATP6V0D2 | ATPase, H+ transporting, lysosomal 38 kDa, V0 |
| NM_152597 | FSIP1 | fibrous sheath interacting protein 1 |
| NM_152634 | TCEANC | TFIIS central domain-containing protein 1 |
| NM_152701 | ABCA13 | ATP binding cassette, sub-family A (ABC1), |
| NM_152703 | SAMD9L | sterile alpha motif domain containing 9-like |
| NM_152748 | KIAA1324L | hypothetical protein LOC222223 isoform 1 |
| NM_152757 | C20orf200 | hypothetical protein LOC253868 |
| NM_152791 | ZNF555 | zinc finger protein 555 |
| NM_152910 | DGKH | diacylglycerol kinase, eta isoform 2 |
| NM_153218 | C13orf31 | hypothetical protein LOC144811 |
| NM_153487 | MDGA1 | MAM domain containing |
| NM_170753 | PGBD3 | hypothetical protein LOC267004 |
| NM_171846 | LACTB | lactamase, beta isoform a |
| NM_172037 | RDH10 | retinol dehydrogenase 10 |

TABLE 2-continued

| GenBank No. | | Encoded Polypeptide |
|---|---|---|
| NM_173217 | ST6GAL1 | ST6 beta-galactosamide |
| NM_173354 | SIK1 | salt-inducible kinase 1 |
| NM_173617 | | Unknown |
| NM_176821 | NLRP10 | NLR family, pyrin domain containing 10 |
| NM_177424 | STX12 | syntaxin 12 |
| NM_177974 | CASC4 | cancer susceptibility candidate 4 isoform a |
| NM_178550 | C1orf110 | hypothetical protein LOC339512 |
| NM_178821 | WDR69 | WD repeat domain 69 |
| NM_181597 | UPP1 | uridine phosphorylase 1 |
| NM_181782 | NCOA7 | nuclear receptor coactivator 7 isoform 2 |
| NM_182752 | TPRG1L | tumor protein p63 regulated 1-like |
| NM_183079 | PRNP | prion protein preproprotein |
| NM_198183 | UBE2L6 | ubiquitin-conjugating enzyme E2L 6 isoform 2 |
| NM_198576 | AGRN | agrin precursor |
| NM_199139 | XAF1 | XIAP associated factor 1 isoform 1 |
| NM_206833 | CTXN1 | cortexin 1 |
| NM_207380 | C15orf52 | hypothetical protein LOC388115 |
| NM_213589 | RAPH1 | Ras association and pleckstrin homology domains |
| NR_001568 | BCYRN1 | Homo sapiens brain cytoplasmic RNA 1 (non-protein coding) (BCYRN1), non-coding RNA. |
| R14890 | HECW2 | HECT, C2 and WW domain containing E3 ubiquitin |
| R22891 | | Unknown |
| R24779 | | Unknown |
| R32065 | PSG3 | pregnancy specific beta-1-glycoprotein 3 |
| R34841 | SOD2 | manganese superoxide dismutase isoform A |
| R38084 | GIT2 | G protein-coupled receptor kinase interacting |
| R44930 | | Unknown |
| R49343 | SEC14L2 | SEC14-like 2 isoform 1 |
| R52665 | | Unknown |
| R62907 | DAB2 | disabled homolog 2 |
| R78604 | IPP | intracisternal A particle-promoted polypeptide |
| R79120 | DAB2 | disabled homolog 2 |
| R98767 | CAMK2D | calcium/calmodulin-dependent protein kinase II |
| S57296 | ERBB2 | erbB-2 isoform b |
| S68290 | AKR1C1 | aldo-keto reductase family 1, member C1 |
| S69189 | ACOX1 | acyl-Coenzyme A oxidase 1 isoform b |
| S69738 | CCL2 | small inducible cytokine A2 precursor |
| S70123 | LDLR | low density lipoprotein receptor precursor |
| S81491 | | Stat2 type (partial) |
| S81545 | EDNRA | endothelin receptor type A isoform a precursor |
| S81916 | PGK1 | phosphoglycerate kinase 1 |
| T03492 | | Unknown |
| T17299 | CACNA2D2 | calcium channel, voltage-dependent, alpha |
| T30183 | BCR | Homo sapiens breakpoint cluster region, mRNA (cDNA clone IMAGE: 4500154). |
| T50399 | HBA2 | alpha 2 globin |
| T63497 | | Unknown |
| T70087 | EPAS1 | endothelial PAS domain protein 1 |
| T78402 | | Unknown |
| T84558 | NIPAL3 | NIPA-like domain containing 3 |
| T94585 | ACOT13 | acyl-CoA thioesterase 13 isoform 2 |
| U04897 | RORA | RAR-related orphan receptor A isoform b |
| U05598 | | dihydrodiol dehydrogenase |
| U10473 | B4GALT1 | UDP-Gal:betaGlcNAc beta 1,4- |
| U11058 | KCNMA1 | large conductance calcium-activated potassium |
| U13698 | CASP1 | caspase 1 isoform alpha precursor |
| U13699 | CASP1 | caspase 1 isoform alpha precursor |
| U13700 | CASP1 | caspase 1 isoform alpha precursor |
| U16307 | GLIPR1 | GLI pathogenesis-related 1 precursor |
| U17714 | | putative tumor suppressor ST13 |
| U19599 | BAX | Homo sapiens bax epsilon mRNA, complete cds. |
| U24267 | | pyrroline-5-carboxylate dehydrogenase (P5CDh) |
| U25147 | SLC25A1 | solute carrier family 25 (mitochondrial carrier; |
| U27143 | HINT1 | Homo sapiens cDNA: FLJ22904 fis, clone KAT05632. |
| U36190 | CRIP2 | cysteine-rich protein 2 |
| U36501 | SP100 | nuclear antigen Sp100 isoform 1 |
| U37283 | MFAP5 | microfibrillar associated protein 5 precursor |
| U37546 | BIRC3 | baculoviral IAP repeat-containing protein 3 |
| U38321 | MMP19 | matrix metalloproteinase 19 isoform rasi-1 |
| U40053 | | lanosterol 14-alpha demethylase (CYP51P2) pseudogene |
| U40372 | | 3',5' cyclic nucleotide phosphodiesterase (HSPDE1C3A) |
| U42349 | TUSC3 | tumor suppressor candidate 3 isoform a |

TABLE 2-continued

| GenBank No. | | Encoded Polypeptide |
|---|---|---|
| U43559 | RDH5 | retinol dehydrogenase 5 (11-cis and 9-cis) |
| U47674 | ASAH1 | N-acylsphingosine amidohydrolase 1 isoform b |
| U48437 | APLP1 | amyloid precursor-like protein 1 isoform 2 |
| U48705 | | receptor tyrosine kinase DDR |
| U49188 | SERINC3 | tumor differentially expressed protein 1 |
| U49396 | | ionotropic ATP receptor P2X5b |
| U50529 | | BRCA2 region |
| U55936 | SNAP23 | synaptosomal-associated protein 23 isoform |
| U58111 | VEGFC | vascular endothelial growth factor C |
| U61276 | JAG1 | jagged 1 precursor |
| U62325 | APBB2 | amyloid beta A4 precursor protein-binding, |
| U62858 | IL13RA1 | interleukin 13 receptor, alpha 1 precursor |
| U67280 | CALU | calumenin isoform b precursor |
| U72937 | ATRX | transcriptional regulator ATRX isoform 1 |
| U73936 | JAG1 | jagged 1 precursor |
| U76833 | FAP | fibroblast activation protein, alpha subunit |
| U77706 | LAMA4 | laminin, alpha 4 isoform 2 precursor |
| U77914 | JAG1 | jagged 1 precursor |
| U77917 | PTPRR | protein tyrosine phosphatase, receptor type, R |
| U79277 | | Unknown |
| U79297 | | Unknown |
| U82671 | | Unknown |
| U83508 | ANGPT1 | angiopoietin 1 precursor |
| U84138 | RAD51L1 | RAD51-like 1 isoform 3 |
| U84246 | NEU1 | neuraminidase precursor |
| U85995 | BBS9 | parathyroid hormone-responsive B1 isoform 2 |
| U89281 | HSD17B6 | hydroxysteroid (17-beta) dehydrogenase 6 |
| U89330 | MAP2 | microtubule-associated protein 2 isoform 1 |
| U89386 | PAFAH2 | platelet-activating factor acetylhydrolase 2 |
| U90552 | BTN3A1 | butyrophilin, subfamily 3, member A1 isoform d |
| U92268 | MAPK11 | mitogen-activated protein kinase 11 |
| U92816 | | c33.6 unnamed HERV-H protein |
| U94831 | | multispanning membrane protein |
| V00489 | | alpha-globin |
| W01715 | NAPEPLD | N-acyl phosphatidylethanolamine phospholipase D |
| W03103 | ASAP1 | development and differentiation enhancing factor |
| W15435 | NIPAL3 | NIPA-like domain containing 3 |
| W46388 | | Unknown |
| W46994 | STAU2 | staufen homolog 2 isoform e |
| W61007 | NFAT5 | nuclear factor of activated T-cells 5 isoform a |
| W65310 | | Unknown |
| W67995 | FXC1 | mitochondrial import inner membrane translocase |
| W72466 | | Unknown |
| W72564 | LOC100134259 | *Homo sapiens* cDNA FLJ35178 fis, clone PLACE6014043. |
| W73272 | PDE8A | phosphodiesterase 8A isoform 1 |
| W73431 | FN1 | fibronectin 1 isoform 1 preproprotein |
| W73788 | TTC14 | tetratricopeptide repeat domain 14 isoform a |
| W74476 | | Unknown |
| W74640 | | Unknown |
| W81648 | CSGALNACT2 | chondroitin sulfate |
| W87466 | | Unknown |
| W91876 | | Unknown |
| W92744 | ZNF84 | zinc finger protein 84 |
| W93554 | SH3PXD2A | SH3 multiple domains 1 |
| W93695 | CLN8 | ceroid-lipofuscinosis, neuronal 8 |
| X06989 | APP | amyloid beta A4 protein isoform a precursor |
| X15132 | SOD2 | manganese superoxide dismutase isoform A |
| X15306 | | heavy neurofilament subunit (NF-H) |
| X16354 | | transmembrane carcinoembryonic antigen BGPa (formerly TM1-CEA) |
| X16447 | CD59 | CD59 antigen preproprotein |
| X56841 | HLA-E | major histocompatibility complex, class I, E |
| X61094 | GM2A | GM2 ganglioside activator precursor |
| X63338 | | HB2B gene for high sulfur keratin |
| X64116 | | PVR gene for poliovirus receptor (exon 1) |
| X65232 | ZNF79 | zinc finger protein 79 |
| X68742 | ITGA1 | integrin, alpha 1 precursor |
| X74039 | PLAUR | plasminogen activator, urokinase receptor |
| X76775 | | HLA-DMA |
| X79683 | | beta2 laminin |
| X83858 | PTGER3 | *Homo sapiens* PTGER3 mRNA for prostaglandin E receotor EP3 subtype 3 isoform, partial cds, clone: FLJ80357SAAF. |
| X90579 | CYP3A5 | cytochrome P450, family 3, subfamily A, |
| XM_042066 (replaced by | | mitogen-activated protein kinase kinase kinase 1, E3 ubiquitin protein ligase (MAP3K1) |

TABLE 2-continued

| GenBank No. | | Encoded Polypeptide |
|---|---|---|
| NM_005921.1) | | |
| XM_290629 | | AHNAK nucleoprotein 2 (AHNAK2) |
| (replaced by | | |
| NM_138420.2) | | |
| XM_371461 | | Unknown |
| XM_379298 | | Unknown |
| XM_927270 | | Unknown |
| XM_927532 | | Unknown |
| XM_930405 | | Unknown |
| XM_934030 | | Unknown |
| XM_936467 | | Unknown |
| XM_937514 | | Unknown |
| XM_940706 | | Unknown |
| XM_943119 | | transcription elongation factor A (SII), 1 |
| (replaced by | | |
| NM_201437.1) | | (TCEA1) |
| XM_943477 | | Unknown |
| Y09846 | | shc pseudogene, p66 isoform |
| Z21533 | HHEX | hematopoietically expressed homeobox |
| Z38765 | | Unknown |
| Z97053 | | Unknown |

TABLE 2A

POLYNUCLEOTIDES ENCODING SENESCENT CELL-ASSOCIATED ANTIGENS

| | | | | | | | |
|---|---|---|---|---|---|---|---|
| AA004279 | AA205660 | AA545764 | AA736604 | AA988241 | AB030710 | AF029750 | AF098951 |
| AA012883 | AA209239 | AA551075 | AA747309 | AA988323 | AB032261 | AF031469 | AF101051 |
| AA020826 | AA209487 | AA554833 | AA761181 | AA993518 | AB032987 | AF033026 | AF105974 |
| AA022510 | AA215738 | AA563621 | AA767440 | AA995925 | AB032996 | AF039217 | AF106069 |
| AA029155 | AA228366 | AA565715 | AA768884 | AB000888 | AB033007 | AF039690 | AF109681 |
| AA034012 | AA243427 | AA565852 | AA778684 | AB002282 | AB033010 | AF040704 | AF112216 |
| AA037766 | AA279958 | AA572675 | AA805633 | AB002301 | AB033055 | AF041459 | AF113211 |
| AA043348 | AA284248 | AA573452 | AA806283 | AB002323 | AB033080 | AF043732 | AF114488 |
| AA044835 | AA284829 | AA573523 | AA806349 | AB002347 | AB033832 | AF043977 | AF115512 |
| AA044921 | AA329676 | AA576961 | AA810263 | AB002354 | AB034747 | AF045451 | AF116574 |
| AA045247 | AA372349 | AA582404 | AA810788 | AB002365 | AB036063 | AF047020 | AF116616 |
| AA045527 | AA393484 | AA583044 | AA811138 | AB002391 | AB037738 | AF047338 | AF116827 |
| AA056548 | AA398658 | AA594609 | AA811509 | AB004574 | AB037791 | AF052059 | AF118274 |
| AA081349 | AA398740 | AA599017 | AA812232 | AB005043 | AB037813 | AF052094 | AF118887 |
| AA083483 | AA401703 | AA602532 | AA814140 | AB006756 | AB037823 | AF052151 | AF119835 |
| AA088857 | AA404269 | AA603472 | AA815089 | AB006757 | AB037853 | AF053453 | AF119863 |
| AA088873 | AA418028 | AA609053 | AA827865 | AB007457 | AB037925 | AF056322 | AF121856 |
| AA099357 | AA418074 | AA628051 | AA827878 | AB007458 | AB039327 | AF060922 | AF123758 |
| AA102600 | AA418816 | AA628398 | AA831438 | AB007875 | AB039947 | AF061731 | AF123759 |
| AA115933 | AA429615 | AA629286 | AA831769 | AB007877 | AB046692 | AF061735 | AF126782 |
| AA121673 | AA432267 | AA631103 | AA832474 | AB007900 | AB046809 | AF062483 | AF127481 |
| AA128261 | AA459699 | AA631254 | AA833832 | AB007923 | AB046842 | AF063591 | AF130089 |
| AA130982 | AA461080 | AA633992 | AA836340 | AB009598 | AB046844 | AF064243 | AF130090 |
| AA131041 | AA476916 | AA634220 | AA843132 | AB011161 | AB047360 | AF064484 | AF130104 |
| AA133285 | AA481560 | AA639752 | AA847654 | AB014511 | AB049654 | AF064771 | AF131743 |
| AA133962 | AA482478 | AA653300 | AA853175 | AB014600 | AB051486 | AF065214 | AF131747 |
| AA133789 | AA482548 | AA654142 | AA861784 | AB015656 | AB053318 | AF065385 | AF131801 |
| AA148534 | AA496034 | AA675892 | AA872727 | AB017269 | AB053319 | AF065854 | AF132203 |
| AA149644 | AA496213 | AA678047 | AA883074 | AB017445 | AB056106 | AF067286 | AF133207 |
| AA149745 | AA514384 | AA678241 | AA886870 | AB017498 | AC004770 | AF070524 | AF133425 |
| AA150242 | AA514634 | AA683481 | AA889628 | AB018283 | AC004997 | AF070569 | AF134149 |
| AA150460 | AA521080 | AA683501 | AA889952 | AB018322 | AC005339 | AF070571 | AF134715 |
| AA156605 | AA522514 | AA683602 | AA890010 | AB018580 | AC007182 | AF070596 | AF135266 |
| AA156721 | AA523543 | AA699809 | AA897514 | AB019691 | AD000092 | AF072098 | AF135593 |
| AA156723 | AA523733 | AA702143 | AA902480 | AB020335 | AF001602 | AF073890 | AF139131 |
| AA156754 | AA523958 | AA703280 | AA904430 | AB020635 | AF003934 | AF078844 | AF144488 |
| AA156961 | AA524669 | AA706658 | AA907927 | AB020645 | AF005774 | AF082283 | AF151074 |
| AA160474 | AA526844 | AA707125 | AA910945 | AB020657 | AF006516 | AF083068 | AF151810 |
| AA169752 | AA532640 | AA716107 | AA913146 | AB020663 | AF007162 | AF086256 | AF151861 |
| AA195009 | AA532655 | AA721252 | AA916831 | AB020712 | AF009616 | AF086333 | AF153415 |
| AA196034 | AA534198 | AA722799 | AA916712 | AB020717 | AF010314 | AF087847 | AF153820 |
| AA196245 | AA535917 | AA724665 | AA917899 | AB022663 | AF010446 | AF090891 | AF155158 |
| AA203365 | AA543030 | AA732007 | AA927870 | AB022918 | AF011466 | AF092128 | AF157324 |
| AA928542 | AB024703 | AF019214 | AF095771 | AB023147 | AF014403 | AF092137 | AF158185 |
| AA933779 | AB029040 | AF021834 | AF096296 | AB023179 | AF015186 | AF094754 | AF158555 |
| AA969194 | AB029290 | AF026071 | AF096304 | AB024518 | AF017987 | AF095727 | AF159570 |
| AA971753 | AB030655 | AF029674 | AF097493 | AF161526 | AF274948 | AI051046 | AI248598 |

TABLE 2A-continued

POLYNUCLEOTIDES ENCODING SENESCENT CELL-ASSOCIATED ANTIGENS

| | | | |
|---|---|---|---|
| AF162769 | AF276658 | AI051127 | AI254547 |
| AF164794 | AF278532 | AI052003 | AI261321 |
| AF165187 | AF280094 | AI052103 | AI262560 |
| AF165520 | AF285119 | AI052536 | AI264121 |
| AF169312 | AF288208 | AI056692 | AI268315 |
| AF169676 | AF288391 | AI074333 | AI270356 |
| AF172398 | AF295039 | AI077660 | AI275162 |
| AF176518 | AF302786 | AI079540 | AI276880 |
| AF178532 | AF303378 | AI081779 | AI278445 |
| AF179281 | AF313413 | AI091079 | AI279062 |
| AF180519 | AF315325 | AI092511 | AI290475 |
| AF182273 | AF316824 | AI092770 | AI291123 |
| AF182414 | AF316873 | AI092931 | AI291989 |
| AF183417 | AF325213 | AI096389 | AI307750 |
| AF183419 | AF327923 | AI096706 | AI307760 |
| AF186773 | AF329088 | AI097463 | AI307802 |
| AF188298 | AF330205 | AI110886 | AI312083 |
| AF197952 | AF348078 | AI122754 | AI313324 |
| AF201370 | AF353618 | AI123348 | AI332407 |
| AF205218 | AF353992 | AI125204 | AI333326 |
| AF212995 | AF355465 | AI125670 | AI334015 |
| AF216292 | AF356193 | AI129626 | AI337304 |
| AF216962 | AF380356 | AI129628 | AI341146 |
| AF217974 | AF478446 | AI133137 | AI341234 |
| AF217990 | AF493931 | AI139993 | AI341246 |
| AF218365 | AF495383 | AI147621 | AI341602 |
| AF220026 | AF513360 | AI150000 | AI342246 |
| AF225981 | AF542051 | AI150117 | AI346026 |
| AF228422 | AFFX- | AI160126 | AI348009 |
| AF229179 | HUMISGF3A/M | AI160339 | AI348094 |
| AF230398 | 97935_3 | AI160540 | AI354864 |
| AF230411 | AFFX- | AI167292 | AI356412 |
| AF230904 | HUMISGF3A/M | AI183997 | AI359676 |
| AF230924 | 97935_5 | AI187364 | AI361227 |
| AF232772 | AFFX- | AI188104 | AI363270 |
| AF232905 | HUMISGF3A/M | AI188161 | AI369073 |
| AF237813 | 97935_MA | AI188389 | AI373299 |
| AF239756 | AFFX- | AI190413 | AI374756 |
| AF240468 | HUMISGF3A/M | AI200538 | AI376997 |
| AF246144 | 97935_MB | AI200555 | AI378035 |
| AF247168 | AI003763 | AI202327 | AI378788 |
| AF248966 | AI022882 | AI202969 | AI379338 |
| AF250226 | AI023433 | AI215102 | AI380156 |
| AF251025 | AI023774 | AI218542 | AI382026 |
| AF251054 | AI038737 | AI222435 | AI391633 |
| AF257659 | AI040029 | AI223870 | AI393091 |
| AF263293 | AI040305 | AI224105 | AI393706 |
| AF267855 | AI040324 | AI243677 | AI393725 |
| AF267856 | AI041217 | AI247763 | AI418538 |
| AI418892 | AI638771 | AI738896 | AI810767 |
| AI420817 | AI650285 | AI740460 | AI811298 |
| AI421559 | AI650819 | AI740589 | AI814116 |
| AI422414 | AI651603 | AI741056 | AI814274 |
| AI431643 | AI651786 | AI741110 | AI814587 |
| AI433463 | AI652452 | AI742029 | AI816071 |
| AI435399 | AI652681 | AI742434 | AI816243 |
| AI435514 | AI653037 | AI743115 | AI817448 |
| AI439556 | AI653117 | AI743534 | AI819386 |
| AI446414 | AI653327 | AI743744 | AI821404 |
| AI446756 | AI654636 | AI743792 | AI821935 |
| AI453452 | AI655057 | AI743979 | AI823600 |
| AI457817 | AI655524 | AI744658 | AI823980 |
| AI458439 | AI655763 | AI753143 | AI824013 |
| AI459140 | AI656232 | AI753792 | AI825800 |
| AI460037 | AI656481 | AI754693 | AI825987 |
| AI469425 | AI658662 | AI760252 | AI828035 |
| AI472310 | AI659225 | AI761250 | AI829920 |
| AI472339 | AI659456 | AI761561 | AI830201 |
| AI473891 | AI659800 | AI761947 | AI832193 |
| AI474054 | AI668610 | AI762782 | AI859242 |
| AI475544 | AI668625 | AI765327 | AI860341 |
| AI478147 | AI669498 | AI768122 | AI860764 |
| AI479082 | AI670852 | AI783924 | AI860874 |
| AI479419 | AI671049 | AI793200 | AI861942 |
| AI493587 | AI671186 | AI793340 | AI862120 |
| AI498144 | AI672159 | AI795908 | AI862255 |
| AI498395 | AI672432 | AI795923 | AI862559 |
| AI522053 | AI674647 | AI796536 | AI867198 |
| AI523391 | AI675453 | AI797353 | AI868167 |
| AI525212 | AI675682 | AI797678 | AI869717 |
| AI537887 | AI676022 | AI797684 | AI870615 |
| AI559300 | AI677701 | AI801013 | AI870617 |
| AI569974 | AI683805 | AI803010 | AI879064 |
| AI571796 | AI689225 | AI803088 | AI884858 |
| AI582773 | AI690274 | AI803181 | AI885170 |
| AI613010 | AI693193 | AI805050 | AI885178 |
| AI623211 | AI693862 | AI805301 | AI886656 |
| AI625741 | AI694303 | AI806169 | AI888786 |
| AI631210 | AI700633 | AI806583 | AI889160 |
| AI632212 | AI701428 | AI806674 | AI889584 |
| AI632728 | AI703142 | AI806905 | AI890529 |
| AI633503 | AI703496 | AI806927 | AI890761 |
| AI633523 | AI718223 | AI807023 | AI911687 |
| AI634046 | AI719655 | AI807532 | AI911972 |
| AI634580 | AI732587 | AI807917 | AI912583 |
| AI636233 | AI733041 | AI809404 | AI912976 |
| AI638405 | AI733474 | AI810266 | AI913533 |
| AI638420 | AI735261 | AI810572 | AI913749 |
| AI638768 | AI738556 | AI810669 | AI915827 |
| AI916555 | AJ406929 | AK024846 | AL031178 |
| AI921238 | AJ406932 | AK024896 | AL031295 |
| AI921586 | AJ422148 | AK024898 | AL031429 |
| AI922855 | AJ457063 | AK025063 | AL031651 |
| AI922968 | AK000162 | AK025253 | AL031667 |
| AI923675 | AK000168 | AK025301 | AL034418 |
| AI924150 | AK000345 | AK025432 | AL034550 |
| AI924426 | AK000684 | AK025464 | AL035413 |
| AI927770 | AK000778 | AK025608 | AL035541 |
| AI928387 | AK000826 | AK025872 | AL037339 |
| AI929792 | AK000938 | AK026026 | AL038787 |
| AI932310 | AK001007 | AK026106 | AL039447 |
| AI933861 | AK001029 | AK026195 | AL039706 |
| AI934569 | AK001619 | AK026392 | AL039811 |
| AI935115 | AK001684 | AK026498 | AL039831 |
| AI935162 | AK001821 | AK026577 | AL040222 |
| AI935415 | AK001913 | AK026697 | AL040341 |
| AI935917 | AK002054 | AK026720 | AL041747 |
| AI936560 | AK002207 | AK026747 | AL042483 |
| AI936769 | AK021433 | AK026784 | AL044019 |
| AI939544 | AK021539 | AK026808 | AL044056 |
| AI950273 | AK021586 | AK026921 | AL044126 |
| AI951454 | AK021925 | AK026966 | AL044170 |
| AI952357 | AK022198 | AK027151 | AL044570 |
| AI955001 | AK022459 | AK027199 | AL045717 |
| AI955713 | AK022566 | AK027246 | AL046017 |
| AI961401 | AK022644 | AK054668 | AL046979 |
| AI962377 | AK022817 | AK075503 | AL048423 |
| AI970061 | AK022871 | AK075558 | AL049226 |
| AI970289 | AK022883 | AK090412 | AL049369 |
| AI970972 | AK022885 | AK090434 | AL049548 |
| AI971519 | AK023113 | AK091691 | AL049646 |
| AI982754 | AK023116 | AK091716 | AL049699 |
| AI983904 | AK023166 | AK091986 | AL049709 |
| AI984136 | AK023230 | AK092855 | AL049923 |
| AI989567 | AK023297 | AK095719 | AL049933 |
| AI989799 | AK023343 | AK096921 | AL049942 |
| AI991033 | AK023348 | AK097618 | AL050022 |
| AI992095 | AK023679 | AK097652 | AL050069 |
| AI992283 | AK023743 | AK097997 | AL050154 |
| AJ131212 | AK023778 | AK098058 | AL050217 |
| AJ227860 | AK023817 | AK098125 | AL050332 |
| AJ243951 | AK024029 | AK098337 | AL050374 |
| AJ245600 | AK024050 | AK098354 | AL050388 |
| AJ251830 | AK024064 | AK098414 | AL078596 |
| AJ252246 | AK024256 | AK098812 | AL080081 |
| AJ276395 | AK024446 | AL008583 | AL080214 |
| AJ276888 | AK024712 | AL021366 | AL080220 |
| AJ301610 | AK024724 | AL022165 | AL096732 |
| AJ406928 | AK024845 | AL031177 | AL096740 |
| AL109824 | AL353132 | AL565741 | AV681975 |
| AL110115 | AL354872 | AL565767 | AV682252 |
| AL110191 | AL355532 | AL566172 | AV682567 |
| AL110209 | AL355685 | AL566528 | AV691323 |
| AL117354 | AL355815 | AL567779 | AV692127 |

TABLE 2A-continued

POLYNUCLEOTIDES ENCODING SENESCENT CELL-ASSOCIATED ANTIGENS

| | | | |
|---|---|---|---|
| AL117381 | AL357536 | AL569506 | AV693216 |
| AL117468 | AL359052 | AL569575 | AV694039 |
| AL117598 | AL359601 | AL569601 | AV696976 |
| AL118520 | AL359605 | AL570661 | AV697515 |
| AL118571 | AL359622 | AL571375 | AV700174 |
| AL118843 | AL365347 | AL572206 | AV700323 |
| AL119957 | AL365404 | AL573201 | AV700415 |
| AL120021 | AL389942 | AL573637 | AV700514 |
| AL120354 | AL389956 | AL573722 | AV700626 |
| AL121829 | AL390186 | AL574319 | AV701177 |
| AL121883 | AL390216 | AL583909 | AV701283 |
| AL132665 | AL391688 | AL589603 | AV701750 |
| AL133001 | AL512687 | AL832227 | AV702575 |
| AL133084 | AL512694 | AL833204 | AV703259 |
| AL133580 | AL512737 | AL833762 | AV703555 |
| AL134420 | AL512766 | AU118882 | AV704551 |
| AL134489 | AL513583 | AU121431 | AV704962 |
| AL134724 | AL515318 | AU134977 | AV705559 |
| AL135342 | AL515916 | AU135154 | AV707142 |
| AL136561 | AL520200 | AU138166 | AV708945 |
| AL136597 | AL520774 | AU143929 | AV712413 |
| AL136629 | AL520900 | AU144083 | AV712912 |
| AL136653 | AL522395 | AU144243 | AV713913 |
| AL136658 | AL522667 | AU144247 | AV714268 |
| AL136680 | AL523076 | AU145361 | AV714462 |
| AL136693 | AL523860 | AU145941 | AV717561 |
| AL136733 | AL524093 | AU146771 | AV722628 |
| AL136797 | AL529434 | AU150078 | AV722990 |
| AL136807 | AL530264 | AU150319 | AV723308 |
| AL136829 | AL533234 | AU151560 | AV724329 |
| AL136835 | AL535113 | AU152410 | AV725328 |
| AL136944 | AL536553 | AU153366 | AV725364 |
| AL137370 | AL537457 | AU153583 | AV728606 |
| AL137432 | AL540260 | AU154125 | AV734793 |
| AL138104 | AL547782 | AU154469 | AV734843 |
| AL138349 | AL551046 | AU155376 | AV741657 |
| AL139228 | AL552450 | AU156421 | AV751731 |
| AL157430 | AL553774 | AU156721 | AV756141 |
| AL157437 | AL555086 | AU157541 | AV756532 |
| AL157473 | AL560266 | AU157716 | AV757675 |
| AL157485 | AL561930 | AU160004 | AV758342 |
| AL161958 | AL562686 | AU160685 | AV760596 |
| AL161999 | AL564683 | AV648367 | AV762892 |
| AL162047 | AL565238 | AV661099 | AW000928 |
| AL162060 | AL565449 | AV661152 | AW001777 |
| AW001847 | AW149492 | AW274503 | AW515704 |
| AW003508 | AW150720 | AW274856 | AW516267 |
| AW003889 | AW150953 | AW275049 | AW517464 |
| AW004076 | AW151360 | AW276078 | AW517686 |
| AW005237 | AW157619 | AW290940 | AW518714 |
| AW005535 | AW166562 | AW291402 | AW571715 |
| AW005545 | AW167727 | AW291696 | AW575245 |
| AW006123 | AW167793 | AW293849 | AW575493 |
| AW006185 | AW168154 | AW294630 | AW575737 |
| AW006345 | AW168942 | AW294729 | AW576156 |
| AW006750 | AW169973 | AW294765 | AW591809 |
| AW007289 | AW170015 | AW296788 | AW593996 |
| AW008051 | AW172311 | AW299226 | AW611550 |
| AW008976 | AW173623 | AW299245 | AW612657 |
| AW009436 | AW182938 | AW299452 | AW628045 |
| AW009747 | AW183074 | AW300004 | AW628835 |
| AW015537 | AW188464 | AW300140 | AW629527 |
| AW021673 | AW189467 | AW300953 | AW665086 |
| AW024350 | AW190479 | AW300959 | AW665155 |
| AW026241 | AW190565 | AW301861 | AW665748 |
| AW028100 | AW193531 | AW303865 | AW665758 |
| AW029619 | AW194730 | AW304174 | AW665892 |
| AW043602 | AW194947 | AW338089 | AW771007 |
| AW043859 | AW195071 | AW339310 | AW771190 |
| AW050627 | AW195928 | AW340588 | AW771590 |
| AW051365 | AW204088 | AW341649 | AW779916 |
| AW052044 | AW205616 | AW364693 | AW850158 |
| AW052084 | AW205686 | AW392551 | AW954107 |
| AW052179 | AW206037 | AW411259 | AW955612 |
| AW058459 | AW206234 | AW418882 | AW958475 |
| AW071793 | AW206414 | AW439843 | AW960707 |
| AW080618 | AW206419 | AW449728 | AW962850 |
| AW080999 | AW235061 | AW449754 | AW963328 |
| AW086021 | AW236958 | AW450035 | AW970888 |
| AW089415 | AW237258 | AW452022 | AW975183 |
| AW090182 | AW241549 | AW452620 | AW978375 |
| AW090529 | AW241832 | AW452656 | AW979182 |
| AW102637 | AW242315 | AW452681 | AW979271 |
| AW105337 | AW242973 | AW468201 | AY007239 |
| AW118878 | AW245401 | AW469351 | AY008268 |
| AW129145 | AW264036 | AW469523 | AY008372 |
| AW130600 | AW264082 | AW469790 | AY009128 |
| AW131553 | AW268365 | AW471181 | AY014180 |
| AW134492 | AW268719 | AW511227 | AY028632 |
| AW135176 | AW269686 | AW511319 | AY079172 |
| AW136198 | AW270037 | AW511595 | AY090780 |
| AW138767 | AW270170 | AW513227 | AY099509 |
| AW139131 | AW271409 | AW513612 | AY134855 |
| AW139393 | AW272255 | AW514038 | AY185496 |
| AW139538 | AW273796 | AW514401 | BC000019 |
| BC000027 | BC002842 | BC005193 | BC018336 |
| BC000102 | BC003064 | BC005247 | BC018681 |
| BC000182 | BC003096 | BC005259 | BC018756 |
| BC000196 | BC003128 | BC005334 | BC019064 |
| BC000232 | BC003143 | BC005374 | BC020925 |
| BC000296 | BC003164 | BC005807 | BC021286 |
| BC000314 | BC003170 | BC005810 | BC021680 |
| BC000324 | BC003177 | BC005876 | BC021861 |
| BC000351 | BC003358 | BC005884 | BC022066 |
| BC000353 | BC003503 | BC005896 | BC022487 |
| BC000373 | BC003561 | BC005903 | BC022967 |
| BC000419 | BC003564 | BC005924 | BC025250 |
| BC000474 | BC003602 | BC005931 | BC028703 |
| BC000580 | BC003610 | BC005980 | BC029051 |
| BC000596 | BC003614 | BC006088 | BC029442 |
| BC000638 | BC003637 | BC006110 | BC029828 |
| BC000686 | BC003658 | BC006163 | BC030005 |
| BC000687 | BC003660 | BC006164 | BC030130 |
| BC000704 | BC003667 | BC006211 | BC031620 |
| BC000737 | BC003686 | BC006249 | BC031811 |
| BC000836 | BC004108 | BC006270 | BC032004 |
| BC000856 | BC004130 | BC006279 | BC032406 |
| BC000899 | BC004153 | BC006362 | BC033311 |
| BC000905 | BC004162 | BC006373 | BC033513 |
| BC000961 | BC004180 | BC006374 | BC033663 |
| BC001001 | BC004191 | BC006405 | BC034236 |
| BC001099 | BC004241 | BC006422 | BC034248 |
| BC001207 | BC004269 | BC008034 | BC034275 |
| BC001255 | BC004276 | BC008300 | BC035749 |
| BC001281 | BC004283 | BC008410 | BC036225 |
| BC001364 | BC004331 | BC008745 | BC036405 |
| BC001387 | BC004371 | BC008992 | BC036453 |
| BC001467 | BC004395 | BC009735 | BC037317 |
| BC001595 | BC004443 | BC010024 | BC037359 |
| BC001689 | BC004446 | BC010942 | BC039509 |
| BC001727 | BC004535 | BC011002 | BC040924 |
| BC001745 | BC004566 | BC012344 | BC040952 |
| BC001805 | BC004818 | BC012846 | BC040965 |
| BC001867 | BC004911 | BC013633 | BC041127 |
| BC001875 | BC004936 | BC014207 | BC041355 |
| BC002480 | BC004942 | BC014579 | BC041482 |
| BC002510 | BC004948 | BC014974 | BC041664 |
| BC002571 | BC005009 | BC015232 | BC042510 |
| BC002637 | BC005047 | BC015390 | BC042953 |
| BC002660 | BC005050 | BC015429 | BC043411 |
| BC002704 | BC005056 | BC015449 | BE042976 |
| BC002709 | BC005073 | BC016291 | BE043477 |
| BC002713 | BC005078 | BC016828 | BE044272 |
| BC002752 | BC005127 | BC017771 | BE044480 |
| BC002794 | BC005147 | BC017927 | BE045549 |
| BE046443 | BE669858 | BE966604 | BF240286 |
| BE048525 | BE671156 | BE966768 | BF242905 |
| BE048919 | BE671224 | BE967275 | BF244081 |
| BE092211 | BE672313 | BE967311 | BF244402 |
| BE138888 | BE672499 | BE967331 | BF246115 |
| BE147896 | BE672676 | BE967532 | BF304759 |
| BE217875 | BE673226 | BE971383 | BF308548 |
| BE219277 | BE673587 | BF000155 | BF337528 |
| BE220330 | BE674089 | BF001267 | BF340123 |

TABLE 2A-continued

POLYNUCLEOTIDES ENCODING SENESCENT CELL-ASSOCIATED ANTIGENS

| | | | |
|---|---|---|---|
| BE221817 | BE674460 | BF002195 | BF340635 |
| BE222746 | BE674466 | BF002844 | BF342661 |
| BE251303 | BE675337 | BF003134 | BF343672 |
| BE262551 | BE675516 | BF030331 | BF344265 |
| BE271644 | BE677131 | BF033242 | BF346014 |
| BE301252 | BE740761 | BF035563 | BF382281 |
| BE302191 | BE741920 | BF055311 | BF382393 |
| BE326919 | BE744389 | BF055343 | BF431309 |
| BE328850 | BE787063 | BF055474 | BF431973 |
| BE348597 | BE813017 | BF056746 | BF432276 |
| BE348679 | BE856341 | BF061003 | BF432376 |
| BE349022 | BE857601 | BF061543 | BF432478 |
| BE349147 | BE869583 | BF062384 | BF432956 |
| BE379006 | BE875567 | BF062886 | BF433005 |
| BE408081 | BE877420 | BF063896 | BF433180 |
| BE439489 | BE877796 | BF107618 | BF433475 |
| BE465475 | BE877955 | BF108666 | BF435617 |
| BE466675 | BE880245 | BF108695 | BF435852 |
| BE466825 | BE880828 | BF109303 | BF437602 |
| BE501385 | BE882538 | BF109660 | BF438014 |
| BE501464 | BE883841 | BF109854 | BF438386 |
| BE501976 | BE886225 | BF111214 | BF439451 |
| BE502785 | BE888744 | BF111326 | BF439488 |
| BE502982 | BE889628 | BF111651 | BF445273 |
| BE503425 | BE890745 | BF112171 | BF446673 |
| BE504180 | BE892293 | BF114745 | BF448048 |
| BE541641 | BE892574 | BF116042 | BF476080 |
| BE547542 | BE893893 | BF125756 | BF507342 |
| BE549656 | BE895437 | BF130943 | BF508244 |
| BE549937 | BE897886 | BF195608 | BF508344 |
| BE550486 | BE904551 | BF196943 | BF510490 |
| BE551877 | BE906233 | BF197222 | BF510581 |
| BE565675 | BE930512 | BF203664 | BF510588 |
| BE568660 | BE958291 | BF215644 | BF511231 |
| BE615277 | BE961916 | BF218115 | BF512162 |
| BE622627 | BE962027 | BF218804 | BF512190 |
| BE644809 | BE962299 | BF218922 | BF515031 |
| BE644818 | BE962354 | BF221525 | BF570193 |
| BE645771 | BE962615 | BF221547 | BF570412 |
| BE646146 | BE963444 | BF222826 | BF575213 |
| BE646573 | BE965311 | BF222867 | BF575514 |
| BF589322 | BG054844 | BG538564 | H93077 |
| BF590274 | BG107203 | BG620958 | H97567 |
| BF593252 | BG107676 | BG913589 | H98105 |
| BF593917 | BG111808 | BI438189 | H98994 |
| BF663461 | BG112359 | BM128432 | J03202 |
| BF666293 | BG122789 | BM677498 | J03225 |
| BF670447 | BG149557 | BM992214 | J04183 |
| BF672306 | BG163267 | BQ007522 | J04755 |
| BF676462 | BG163756 | BQ183759 | K02920 |
| BF676980 | BG164365 | BQ187042 | L06633 |
| BF680588 | BG167841 | BQ876971 | L08835 |
| BF691045 | BG169689 | BU069195 | L11315 |
| BF692332 | BG170130 | BU074567 | L11669 |
| BF696757 | BG177759 | BU078629 | L12002 |
| BF699855 | BG200452 | BU430052 | L12711 |
| BF718769 | BG230614 | CA431092 | L13720 |
| BF723626 | BG231932 | D10537 | L13852 |
| BF724137 | BG236006 | D13287 | L14611 |
| BF724210 | BG250310 | D17391 | L16895 |
| BF724944 | BG250585 | D21089 | L20817 |
| BF726934 | BG251175 | D29810 | L27489 |
| BF732712 | BG252490 | D31421 | L38019 |
| BF792631 | BG252899 | D38299 | L38969 |
| BF797381 | BG260394 | D43967 | L41690 |
| BF939176 | BG260623 | D45864 | L42374 |
| BF939292 | BG284890 | D50579 | M10943 |
| BF939365 | BG285881 | D50683 | M11734 |
| BF939833 | BG289443 | D63807 | M14016 |
| BF939919 | BG290577 | D79994 | M15329 |
| BF940211 | BG291039 | D80010 | M15330 |
| BF940276 | BG292040 | D83485 | M22921 |
| BF956762 | BG292389 | D84105 | M25915 |
| BF966015 | BG292405 | D86586 | M27968 |
| BF968134 | BG326045 | D86985 | M28880 |
| BF968960 | BG326897 | D87292 | M31125 |
| BF969982 | BG327863 | H04482 | M32221 |
| BF970829 | BG339064 | H05023 | M33376 |
| BF973568 | BG340967 | H05025 | M33653 |
| BF974389 | BG341906 | H07095 | M34421 |
| BF977145 | BG354573 | H10659 | M34715 |
| BF978611 | BG386566 | H10766 | M55580 |
| BF978689 | BG427393 | H11075 | M55983 |
| BF982174 | BG432350 | H14241 | M59916 |
| BF982927 | BG434272 | H23979 | M59917 |
| BF983379 | BG469257 | H24398 | M65062 |
| BF983948 | BG475299 | H25097 | M68874 |
| BF984227 | BG501219 | H27948 | M76453 |
| BG027926 | BG534245 | H72927 | M76477 |
| BG030576 | BG537190 | H84390 | M79321 |
| BG031974 | BG537255 | H89790 | M79462 |
| M81635 | NM_000055 | NM_000501 | NM_001033053 |
| M81768 | NM_000060 | NM_000512 | NM_001047 |
| M83248 | NM_000062 | NM_000521 | NM_001055 |
| M87507 | NM_000064 | NM_000527 | NM_001083 |
| M95548 | NM_000072 | NM_000558 | NM_001108 |
| M98399 | NM_000077 | NM_000576 | NM_001110 |
| M98478 | NM_000081 | NM_000581 | NM_001124 |
| M98528 | NM_000099 | NM_000584 | NM_001146 |
| N20923 | NM_000100 | NM_000585 | NM_001151 |
| N20927 | NM_000107 | NM_000593 | NM_001153 |
| N21202 | NM_000120 | NM_000596 | NM_001154 |
| N21643 | NM_000123 | NM_000599 | NM_001159 |
| N22918 | NM_000124 | NM_000600 | NM_001174 |
| N30152 | NM_000132 | NM_000602 | NM_001183 |
| N30169 | NM_000137 | NM_000611 | NM_001196 |
| N30209 | NM_000147 | NM_000617 | NM_001200 |
| N30649 | NM_000156 | NM_000638 | NM_001216 |
| N33403 | NM_000161 | NM_000640 | NM_001251 |
| N34514 | NM_000163 | NM_000662 | NM_001252 |
| N35896 | NM_000169 | NM_000679 | NM_001257 |
| N36085 | NM_000175 | NM_000711 | NM_001259 |
| N36759 | NM_000177 | NM_000714 | NM_001268 |
| N36762 | NM_000183 | NM_000717 | NM_001283 |
| N39536 | NM_000191 | NM_000722 | NM_001304 |
| N45228 | NM_000202 | NM_000757 | NM_001330 |
| N45309 | NM_000203 | NM_000765 | NM_001343 |
| N48315 | NM_000227 | NM_000786 | NM_001344 |
| N49852 | NM_000235 | NM_000801 | NM_001345 |
| N51370 | NM_000247 | NM_000804 | NM_001346 |
| N51413 | NM_000281 | NM_000817 | NM_001353 |
| N51708 | NM_000291 | NM_000820 | NM_001355 |
| N51836 | NM_000297 | NM_000824 | NM_001360 |
| N52532 | NM_000305 | NM_000852 | NM_001386 |
| N52767 | NM_000311 | NM_000876 | NM_001397 |
| N58363 | NM_000376 | NM_000885 | NM_001442 |
| N63706 | NM_000381 | NM_000899 | NM_001448 |
| N63748 | NM_000389 | NM_000901 | NM_001458 |
| N66571 | NM_000391 | NM_000916 | NM_001478 |
| N66633 | NM_000396 | NM_000919 | NM_001498 |
| N71074 | NM_000401 | NM_000930 | NM_001511 |
| N71923 | NM_000404 | NM_000933 | NM_001518 |
| N79662 | NM_000407 | NM_000942 | NM_001531 |
| N90755 | NM_000413 | NM_000965 | NM_001540 |
| N92494 | NM_000428 | NM_001001548 | NM_001547 |
| N95414 | NM_000449 | NM_001001669 | NM_001548 |
| N95437 | NM_000459 | NM_001001713 | NM_001549 |
| NM_000034 | NM_000476 | NM_001017974 | NM_001552 |
| NM_000043 | NM_000480 | NM_001030050 | NM_001553 |
| NM_000046 | NM_000484 | NM_001031702 | NM_001565 |
| NM_000049 | NM_000487 | NM_001032409 | NM_001611 |
| NM_001628 | NM_002291 | NM_002970 | NM_003641 |
| NM_001642 | NM_002294 | NM_002975 | NM_003670 |
| NM_001647 | NM_002309 | NM_002977 | NM_003676 |
| NM_001660 | NM_002317 | NM_002979 | NM_003688 |
| NM_001684 | NM_002332 | NM_002985 | NM_003725 |
| NM_001724 | NM_002337 | NM_003009 | NM_003730 |
| NM_001752 | NM_002350 | NM_003012 | NM_003733 |
| NM_001780 | NM_002357 | NM_003014 | NM_003744 |
| NM_001792 | NM_002372 | NM_003022 | NM_003746 |
| NM_001797 | NM_002389 | NM_003038 | NM_003748 |
| NM_001807 | NM_002392 | NM_003059 | NM_003768 |
| NM_001823 | NM_002395 | NM_003060 | NM_003784 |
| NM_001846 | NM_002406 | NM_003134 | NM_003789 |

TABLE 2A-continued

POLYNUCLEOTIDES ENCODING SENESCENT CELL-ASSOCIATED ANTIGENS

| | | | |
|---|---|---|---|
| NM_001860 | NM_002407 | NM_003144 | NM_003790 |
| NM_001873 | NM_002408 | NM_003151 | NM_003793 |
| NM_001893 | NM_002425 | NM_003165 | NM_003811 |
| | NM_002426 | NM_003172 | NM_003812 |
| NM_001909 | NM_002448 | NM_003174 | NM_003813 |
| NM_001913 | NM_002450 | NM_003236 | NM_003825 |
| NM_001914 | NM_002463 | NM_003238 | NM_003851 |
| NM_001920 | NM_002477 | NM_003242 | NM_003878 |
| NM_001924 | NM_002513 | NM_003244 | NM_003879 |
| NM_001954 | NM_002517 | NM_003246 | NM_003896 |
| NM_001957 | NM_002518 | NM_003254 | NM_003900 |
| NM_001967 | NM_002527 | NM_003265 | NM_003928 |
| | NM_002555 | NM_003272 | NM_003945 |
| NM_001999 | NM_002560 | NM_003275 | NM_003992 |
| NM_002004 | NM_002575 | NM_003289 | NM_004010 |
| NM_002006 | NM_002581 | NM_003326 | NM_004030 |
| NM_002016 | NM_002589 | NM_003330 | NM_004045 |
| NM_002032 | NM_002626 | NM_003344 | NM_004048 |
| NM_002056 | NM_002631 | NM_003433 | NM_004059 |
| NM_002064 | NM_002647 | NM_003451 | NM_004073 |
| NM_002081 | NM_002675 | NM_003469 | NM_004110 |
| NM_002087 | NM_002676 | NM_003475 | NM_004138 |
| NM_002133 | NM_002778 | NM_003492 | NM_004148 |
| NM_002162 | NM_002780 | NM_003494 | NM_004161 |
| NM_002184 | NM_002781 | NM_003516 | NM_004163 |
| NM_002189 | NM_002782 | NM_003517 | NM_004165 |
| NM_002197 | NM_002783 | NM_003528 | NM_004170 |
| NM_002198 | NM_002784 | NM_003543 | NM_004221 |
| NM_002203 | NM_002830 | NM_003548 | NM_004233 |
| NM_002204 | NM_002845 | NM_003588 | NM_004265 |
| NM_002205 | NM_002848 | NM_003595 | NM_004290 |
| NM_002213 | NM_002849 | NM_003596 | NM_004318 |
| NM_002227 | NM_002870 | NM_003619 | NM_004327 |
| NM_002231 | NM_002886 | NM_003620 | NM_004339 |
| NM_002254 | NM_002923 | NM_003622 | NM_004343 |
| NM_002275 | NM_002924 | NM_003633 | NM_004346 |
| NM_002290 | NM_002963 | NM_003635 | NM_004356 |
| NM_004357 | NM_005213 | NM_005951 | NM_006547 |
| NM_004381 | NM_005245 | NM_005952 | NM_006577 |
| NM_004388 | NM_005319 | NM_005965 | NM_006608 |
| NM_004403 | NM_005326 | NM_005979 | NM_006634 |
| NM_004411 | NM_005340 | NM_006002 | NM_006642 |
| NM_004414 | NM_005345 | NM_006005 | NM_006670 |
| NM_004490 | NM_005346 | NM_006010 | NM_006675 |
| NM_004508 | NM_005354 | NM_006019 | NM_006676 |
| NM_004509 | NM_005393 | NM_006024 | NM_006682 |
| NM_004542 | NM_005419 | NM_006033 | NM_006698 |
| NM_004545 | NM_005505 | NM_006038 | NM_006702 |
| NM_004546 | NM_005506 | NM_006058 | NM_006720 |
| NM_004556 | NM_005512 | NM_006096 | NM_006727 |
| NM_004591 | NM_005525 | NM_006102 | NM_006730 |
| NM_004614 | NM_005528 | NM_006106 | NM_006755 |
| NM_004642 | NM_005532 | NM_006113 | NM_006759 |
| NM_004649 | NM_005533 | NM_006134 | NM_006763 |
| NM_004657 | NM_005541 | NM_006141 | NM_006767 |
| NM_004668 | NM_005547 | NM_006145 | NM_006803 |
| NM_004688 | NM_005557 | NM_006200 | NM_006810 |
| NM_004696 | NM_005561 | NM_006223 | NM_006822 |
| NM_004710 | NM_005567 | NM_006227 | NM_006823 |
| NM_004734 | NM_005569 | NM_006244 | NM_006829 |
| NM_004748 | NM_005575 | NM_006255 | NM_006830 |
| NM_004751 | NM_005584 | NM_006256 | NM_006851 |
| NM_004753 | NM_005625 | NM_006258 | NM_006876 |
| NM_004791 | NM_005642 | NM_006260 | NM_006905 |
| NM_004815 | NM_005645 | NM_006285 | NM_006918 |
| NM_004862 | NM_005665 | NM_006290 | NM_007034 |
| NM_004899 | NM_005667 | NM_006307 | NM_007036 |
| NM_004905 | NM_005713 | NM_006315 | NM_007048 |
| NM_004932 | NM_005715 | NM_006332 | NM_007076 |
| NM_004934 | NM_005720 | NM_006349 | NM_007167 |
| NM_004938 | NM_005724 | NM_006369 | NM_007168 |
| NM_005010 | NM_005745 | NM_006384 | NM_007173 |
| NM_005019 | NM_005755 | NM_006404 | NM_007213 |
| NM_005020 | NM_005756 | NM_006406 | NM_007260 |
| NM_005044 | NM_005765 | NM_006407 | NM_007271 |
| NM_005065 | NM_005780 | NM_006416 | NM_007274 |
| NM_005098 | NM_005794 | NM_006423 | NM_007278 |
| NM_005101 | NM_005817 | NM_006426 | NM_007287 |
| NM_005103 | NM_005824 | NM_006462 | NM_007315 |
| NM_005113 | NM_005875 | NM_006472 | NM_007325 |
| NM_005123 | NM_005896 | NM_006493 | NM_007341 |
| NM_005125 | NM_005899 | NM_006505 | NM_007350 |
| NM_005167 | NM_005907 | NM_006517 | NM_012067 |
| NM_005168 | NM_005908 | NM_006520 | NM_012081 |
| NM_005195 | NM_005926 | NM_006526 | NM_012090 |
| NM_005200 | NM_005935 | NM_006536 | NM_012093 |
| NM_005204 | NM_005950 | NM_006542 | NM_012105 |
| NM_012155 | NM_014266 | NM_015654 | NM_017414 |
| NM_012168 | NM_014268 | NM_015705 | NM_017415 |
| NM_012193 | NM_014278 | NM_015865 | NM_017423 |
| NM_012200 | NM_014294 | NM_015878 | NM_017445 |
| NM_012201 | NM_014297 | NM_015917 | |
| NM_012213 | NM_014298 | NM_015919 | NM_017514 |
| NM_012215 | NM_014314 | NM_015920 | NM_017554 |
| NM_012228 | NM_014350 | NM_015967 | NM_017567 |
| NM_012243 | NM_014391 | NM_015976 | NM_017627 |
| NM_012249 | NM_014392 | NM_015987 | NM_017649 |
| NM_012250 | NM_014396 | NM_015996 | NM_017655 |
| NM_012252 | NM_014399 | NM_016040 | NM_017661 |
| NM_012268 | NM_014454 | NM_016061 | NM_017679 |
| NM_012281 | NM_014548 | NM_016109 | NM_017680 |
| NM_012328 | NM_014556 | NM_016127 | NM_017684 |
| NM_012329 | NM_014563 | NM_016134 | NM_017692 |
| NM_012342 | NM_014584 | NM_016142 | NM_017706 |
| NM_012360 | NM_014646 | NM_016151 | NM_017712 |
| NM_012396 | NM_014650 | NM_016152 | NM_017733 |
| NM_012413 | NM_014652 | NM_016154 | NM_017739 |
| NM_012419 | NM_014668 | NM_016162 | NM_017742 |
| NM_012429 | NM_014713 | NM_016219 | NM_017750 |
| NM_012430 | NM_014723 | NM_016226 | NM_017784 |
| NM_012431 | NM_014730 | NM_016227 | NM_017814 |
| NM_012434 | NM_014734 | NM_016235 | NM_017836 |
| NM_012449 | NM_014751 | NM_016243 | NM_017837 |
| NM_013229 | NM_014774 | NM_016255 | NM_017856 |
| NM_013231 | NM_014799 | NM_016275 | NM_017870 |
| NM_013281 | NM_014804 | NM_016303 | NM_017901 |
| NM_013312 | NM_014840 | NM_016311 | NM_017935 |
| NM_013314 | NM_014844 | NM_016352 | NM_017938 |
| NM_013325 | NM_014845 | NM_016399 | NM_017947 |
| NM_013335 | NM_014888 | NM_016422 | NM_017983 |
| NM_013343 | NM_014890 | NM_016423 | NM_017992 |
| NM_013352 | NM_014900 | NM_016429 | NM_018042 |
| NM_013379 | NM_014905 | NM_016437 | NM_018046 |
| NM_013381 | NM_014934 | NM_016530 | NM_018075 |
| NM_013390 | NM_014936 | NM_016547 | NM_018113 |
| NM_013399 | NM_014942 | NM_016557 | NM_018129 |
| NM_013943 | NM_014943 | NM_016577 | NM_018153 |
| NM_013959 | NM_014945 | NM_016582 | NM_018161 |
| NM_013960 | NM_014950 | NM_016588 | NM_018191 |
| NM_014015 | NM_014951 | NM_016599 | NM_018217 |
| NM_014028 | NM_015000 | NM_016608 | NM_018229 |
| NM_014045 | NM_015271 | NM_016621 | NM_018267 |
| NM_014068 | NM_015364 | NM_016651 | NM_018291 |
| NM_014145 | NM_015392 | NM_016656 | NM_018293 |
| NM_014158 | NM_015415 | NM_016657 | NM_018295 |
| NM_014182 | NM_015516 | NM_016830 | NM_018334 |
| NM_014244 | NM_015556 | NM_016938 | NM_018357 |
| NM_018368 | NM_020841 | NM_022470 | NM_024728 |
| NM_018370 | NM_021007 | NM_022473 | NM_024763 |
| NM_018371 | NM_021013 | NM_022477 | NM_024766 |
| NM_018381 | NM_021016 | NM_022736 | NM_024770 |
| NM_018418 | NM_021035 | NM_022742 | NM_024801 |
| NM_018447 | NM_021070 | NM_022743 | NM_024806 |
| NM_018490 | NM_021101 | NM_022748 | NM_024819 |
| NM_018494 | NM_021106 | NM_022750 | NM_024825 |
| NM_018530 | NM_021127 | NM_022765 | NM_024837 |
| NM_018584 | NM_021136 | NM_022772 | NM_024841 |
| NM_018638 | NM_021137 | NM_022783 | NM_024843 |
| NM_018639 | NM_021151 | NM_022837 | NM_024887 |
| NM_018648 | NM_021173 | NM_022902 | NM_024913 |
| NM_018656 | NM_021199 | NM_023034 | NM_024924 |
| NM_018835 | NM_021203 | NM_023037 | NM_024935 |
| NM_018840 | NM_021219 | NM_023039 | NM_025000 |
| NM_018973 | NM_021229 | NM_023073 | NM_025024 |

TABLE 2A-continued

POLYNUCLEOTIDES ENCODING SENESCENT CELL-ASSOCIATED ANTIGENS

| | | | | | | | |
|---|---|---|---|---|---|---|---|
| NM_018999 | NM_021244 | NM_023112 | NM_025076 | NM_052885 | NM_183079 | U27143 | W67995 |
| NM_019059 | NM_021249 | NM_023915 | NM_025133 | NM_052889 | NM_198183 | U36190 | W72466 |
| NM_019099 | NM_021616 | NM_023928 | NM_025139 | NM_052941 | NM_198576 | U36501 | W72564 |
| NM_019114 | NM_021622 | NM_024006 | NM_025140 | NM_052958 | NM_199139 | U37283 | W73272 |
| NM_019555 | NM_021626 | NM_024028 | NM_025149 | NM_053056 | NM_206833 | U37546 | W73431 |
| NM_019556 | NM_021637 | NM_024042 | NM_025165 | NM_078474 | NM_207380 | U38321 | W73788 |
| NM_019885 | NM_021643 | NM_024047 | NM_025182 | NM_078483 | NM_213589 | U40053 | W74476 |
| NM_020127 | NM_021727 | NM_024056 | NM_025202 | NM_078487 | NR_001568 | U40372 | W74640 |
| NM_020130 | NM_021731 | NM_024064 | NM_025208 | NM_080657 | R14890 | U42349 | W81648 |
| NM_020154 | NM_021783 | NM_024097 | NM_025217 | NM_080669 | R22891 | U43559 | W87466 |
| NM_020166 | NM_021825 | NM_024105 | NM_025226 | NM_133477 | R24779 | U47674 | W91876 |
| NM_020182 | NM_021827 | NM_024112 | NM_030641 | NM_138924 | R32065 | U48437 | W92744 |
| NM_020199 | NM_021980 | NM_024292 | NM_030778 | NM_139266 | R34841 | U48705 | W93554 |
| NM_020215 | NM_021994 | NM_024315 | NM_030790 | NM_144657 | R38084 | U49188 | W93695 |
| NM_020224 | NM_021999 | NM_024324 | NM_030799 | NM_144717 | R44930 | U49396 | X06989 |
| NM_020234 | NM_022001 | NM_024341 | NM_030801 | NM_144724 | R49343 | U50529 | X15132 |
| NM_020299 | NM_022060 | NM_024430 | NM_030802 | NM_144974 | R52665 | U55936 | X15306 |
| NM_020347 | NM_022083 | NM_024500 | NM_030810 | NM_144975 | R62907 | U58111 | X16354 |
| NM_020353 | NM_022087 | NM_024512 | NM_030882 | NM_145058 | R78604 | U61276 | XI 6447 |
| NM_020372 | NM_022117 | NM_024523 | NM_030911 | NM_145259 | R79120 | U62325 | X56841 |
| NM_020375 | NM_022121 | NM_024532 | NM_030952 | NM_145301 | R98767 | U62858 | X61094 |
| NM_020377 | NM_022128 | NM_024536 | NM_030963 | NM_145316 | S57296 | U67280 | X63338 |
| NM_020399 | NM_022129 | NM_024539 | NM_030967 | NM_145731 | S68290 | U72937 | X64116 |
| NM_020448 | NM_022135 | NM_024549 | NM_030975 | NM_152282 | S69189 | U73936 | X65232 |
| NM_020524 | NM_022147 | NM_024564 | NM_030977 | NM_152532 | S69738 | U76833 | X68742 |
| NM_020639 | NM_022152 | NM_024574 | NM_031244 | NM_152565 | S70123 | U77706 | X74039 |
| NM_020644 | NM_022168 | NM_024577 | NM_031246 | NM_152597 | S81491 | U77914 | X76775 |
| NM_020650 | NM_022171 | NM_024599 | NM_031285 | NM_152634 | S81545 | U77917 | X79683 |
| NM_020663 | NM_022338 | NM_024602 | NM_031286 | NM_152701 | S81916 | U79277 | X83858 |
| NM_020689 | NM_022350 | NM_024617 | NM_031301 | NM_152703 | T03492 | U79297 | X90579 |
| NM_020755 | NM_022368 | NM_024620 | NM_031305 | NM_152748 | T17299 | U82671 | XM_042066 |
| NM_020760 | NM_022450 | NM_024649 | NM_031458 | NM_152757 | T30183 | U83508 | XM_290629 |
| NM_020815 | NM_022464 | NM_024691 | NM_031961 | NM_152791 | T50399 | U84138 | XM_371461 |
| NM_032211 | NM_153487 | T78402 | U89281 | NM_152910 | T63497 | U84246 | XM_379298 |
| NM_032412 | NM_170753 | T84558 | U89330 | NM_153218 | T70087 | U85995 | XM_927270 |
| NM_032591 | NM_171846 | T94585 | U89386 | XM_927532 | | | |
| NM_032623 | NM_172037 | U04897 | U90552 | XM_930405 | | | |
| NM_032784 | NM_173217 | U05598 | U92268 | XM_934030 | | | |
| NM_032789 | NM_173354 | U10473 | U92816 | XM_936467 | | | |
| NM_032812 | NM_173617 | U11058 | U94831 | XM_937514 | | | |
| NM_032866 | NM_176821 | U13698 | V00489 | XM_940706 | | | |
| NM_033255 | NM_177424 | U13699 | W01715 | XM_943119 | | | |
| NM_033405 | NM_177974 | U13700 | W03103 | XM_943477 | | | |
| NM_033407 | NM_178550 | U16307 | W15435 | Y09846 | | | |
| NM_037370 | NM_178821 | U17714 | W46388 | Z21533 | | | |
| NM_052822 | NM_181597 | U19599 | W46994 | Z38765 | | | |
| NM_052839 | NM_181782 | U24267 | W61007 | Z97053 | | | |
| NM_052866 | NM_182752 | U25147 | W65310 | | | | |

TABLE 3

POLYNUCLEOTIDES ENCODING SENESCENT CELL-ASSOCIATED ANTIGENS

| GENE SYMBOL | GENE PRODUCT DESCRIPTION | GENBANK # | PUBMED # | LOGFC |
|---|---|---|---|---|
| CLCA2 | CLCA family member 2, chloride channel regulator | BF003134 | 10362588, 10437792 | 4.79 |
| CLCA2 | CLCA family member 2, chloride channel regulator | NM_006536 | 10362588, 10437792 | 4.51 |
| IL33 | interleukin 33 | AB024518 | 10566975, 12477932 | 4.24 |
| CLCA2 | CLCA family member 2, chloride channel regulator | AF043977 | 10362588, 10437792 | 4.22 |
| CLCA2 | CLCA family member 2, chloride channel regulator | NM_006536 | 10362588, 10437792 | 3.87 |
| RP4-692D3.1 | hypothetical protein LOC728621 | AW364693 | 16710767 | 3.75 |
| SYNPO2 | synaptopodin2 | AI634580 | 8593614, 11076863, | 3.74 |
| GLS | glutaminase | AF097493 | 3531404, 6682827, 6 | 3.53 |
| AB13BP | ABI gene family, member 3 (NESH) binding protein | NM_024801 | 11501947, 12477932 | 3.52 |
| BCHE | butyrylcholinesterase | NM_000055 | 1769657, 1769658, 2 | 3.51 |
| LOC727770 | similar to ankyrin repeat domain 20 family, member A1 | AI359676 | | 3.51 |
| OSAP | ovary-specific acidic protein | AF329088 | 12477932 | 3.44 |
| PLAT | plasminogen activator, tissue | NM_000930 | 1301152, 1310033, 1 | 3.42 |
| IL1A | interleukin 1, alpha | M15329 | 1548758, 1584804, 1 | 3.42 |
| IFIT2 | interferon-induced protein with tetratricopeptide repeats 2 | AA131041 | 1377167, 245816, 3 | 3.39 |
| CDH10 | cadherin 10, type 2 (T2-cadherin) | NM_006727 | 2059658, 10386616 | 3.37 |
| IL1B | interleukin 1, beta | NM_000576 | 1548758, 1753956, 1 | 3.33 |
| SPATA18 | spermatogenesis associated 18 homolog (rat) | AI559300 | 12477932, 14702039 | 3.31 |
| | | AI422414 | | 3.29 |
| IL1B | interleukin 1, beta | M15330 | 1548758, 173956, 1 | 3.29 |

TABLE 3-continued

POLYNUCLEOTIDES ENCODING SENESCENT CELL-ASSOCIATED ANTIGENS

| GENE SYMBOL | GENE PRODUCT DESCRIPTION | GENBANK # | PUBMED # | LOGFC |
|---|---|---|---|---|
| PAPPA | pregnancy-associated plasma protein A, poppalysin 1 | AI110886 | 1721035, 2422961, 2 | 3.25 |
| GLS | glutaminase | NM_014905 | 3531404, 6682827, 6 | 3.23 |
| ABI38P | ABI gene family, member 3 (NESH) binding protein | AB056106 | 11501947, 12477932 | 3.2 |
| SYNPO2 | synaptopodin 2 | AW009747 | 8593614, 11076863, | 3.16 |
| PAPPA | pregnancy-associated plasma protein A, pappalysin 1 | BF107618 | 1721035, 2422961, 2 | 3.14 |
| C11orf87 | chromosome 11 open reading frame 87 | AA633992 | 12477932 | 3.12 |
| PAPPA | pregnancy-associated plasma protein A, pappalysin 1 | BF107618 | 1721035, 2422961, 2 | 3.11 |
| SLC16A4 | solute carrier family 16, member 4 (monocarboxylic acid transporter 5) | NM_004696 | 8125298, 9373149, 9 | 3.1 |
| SCN2A | sodium channel, voltage-gated, type II, alpha subunit | BF432956 | 1317301, 1325650, 1 | 3.09 |
| RNF128 | ring finger protein 128 | NM_024539 | 12477932, 12705856 | 3.07 |
| AKR1C3 | adlo-keto reductace family 1, member C3 (3-alpha hydroxysteroid dehydrogenase, type II) | AB018580 | 762489, 7650035, 7 | 3.03 |
| IL13RA2 | interleukin 13 receptor, alpha 2 | NM_000640 | 8663118, 9083087, 9 | 2.99 |
| GDF15 | growth differentiation factor 15 | AF003934 | 8125298, 9326641, 9 | 2.93 |
| SULF2 | sulfatase 2 | AL133001 | 10574462, 11549316 | 2.92 |
| KRT34 | keratin 34 | NM_021013 | 2431943, 7686952, 9 | 2.89 |
| FBX032 | F-box protein 32 | BF244402 | 11679633, 11717410 | 2.89 |
| | | AA594609 | | 2.88 |
| | | BC043411 | | 2.88 |
| ESM1 | endothelial cell-specific molecule 1 | NM_007036 | 8702785, 11025405 | 2.85 |
| PAPPA | pregnancy-associated plasma protein A, pappalysin 1 | AA148534 | 1721035, 2422961, 2 | 2.81 |
| MEG3 | maternally expressed 3 (non-protein coding) | AI291123 | 8619474, 9110174, 1 | 2.8 |
| C15orf48 | chromosome 15 open reading frame 48 | AF228422 | 12209954, 12477932 | 2.79 |
| | | AK022198 | | 2.77 |
| USP53 | ubiquitin specific peptidase 53 | H25097 | 10718198, 12477932 | 2.75 |
| SDPR | serum deprivation response (phosphatidylserine binding protein) | BF982174 | 2390065, 8012384, 8 | 2.71 |
| MAP2 | microtubule-associated protein 2 | BF342661 | 1494913, 1708129, 2 | 2.69 |
| RDH10 | retinol dehydrogenase 10 (all-trans) | AW150720 | 12407145, 12477932 | 2.68 |
| BMP2 | bone morphogenetic protein 2 | AA583044 | 1487246, 2004788, 2 | 2.64 |
| CRYAB | crystalline, alpha B | AF007162 | 838078, 1407707, 15 | 2.64 |
| PAPPA | pregnancy-associated plasma protein A, pappalysin 1 | BG434272 | 1721035, 2422961, 2 | 2.64 |
| USP53 | ubiquitin specific peptidase 53 | AW188464 | 10718198, 12477932 | 2.63 |
| KRTAP1-5 | keratin associated protein 1-5 | AJ406928 | 11279113, 12228244 | 2.63 |
| HSD11B1 | hydroxysteroid (11-beta) dehydrogenase 1 | NM_00525 | 1885595, 3034894, 7 | 2.62 |
| GLS | glutaminase | AB020645 | 3531404, 6682827, 6 | 2.6 |
| ARRDC4 | arrestin domain containing 4 | AV701177 | 12477932, 14702039 | 2.59 |
| CCRL1 | chemokine (C-C motif) receptor-like 1 | NM_016557 | 8125298, 9373149, 9 | 2.58 |
| MAMDC2 | MAM domain containing 2 | AI82120 | 11076863, 11256614 | 2.54 |
| RTN1 | reticulon 1 | NM_021136 | 7515034, 7685762, 7 | 2.52 |
| PAPPA | pregnancy-associated plasma protein A, pappalysin 1 | BG620958 | 1721035, 2422961, 2 | 2.49 |
| FBX032 | F-box protein 32 | BF244402 | 11679633, 11717410 | 2.48 |

This application claims the benefit under 35 U.S.C. § 119(e) to U.S. Provisional Application No. 61/732,746 filed Dec. 3, 2012 and U.S. Provisional Application No. 61/747,653, filed Dec. 31, 2013, which applications are incorporated by reference herein in their entirety.

The various embodiments described above can be combined to provide further embodiments. All the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A method for removing senescent cells that are causing or promoting adverse symptoms in a subject, the method comprising:
    administering to the subject an immunogenic composition that contains a polypeptide or a recombinant expression vector encoding said polypeptide;
    wherein the polypeptide comprises at least 20 contiguous amino acids of a p16INK4a protein that is autologous to the subject;
    wherein the senescent cells are not cancer cells;
    wherein the immunogenic composition evokes an immune response in the subject that is specific for the autologous p16INK4a protein, and
    wherein the immune response is effective in removing at least some of the senescent cells that are causing or promoting the adverse symptoms.

2. The method of claim 1, wherein the protein polypeptide comprises at least 60 contiguous amino acids of the p16INK4a protein.

3. The method of claim 1, wherein the polypeptide comprises a full-length p16INK4a protein.

4. The method of claim 1, wherein the polypeptide is a fusion protein that further comprises at least 20 contiguous amino acids of another senescent cell-associated antigen.

5. The method of claim 4, wherein the other senescent cell-associated antigen is a galactosidase.

6. The method of claim 1, wherein the immunogenic composition comprises an immunological adjuvant.

7. The method of claim 1, further comprising monitoring senescence associated secretory phenotype (SASP) in the subject following administration of the immunogenic composition.

8. A method for evoking an immune response specific for a senescent cell in a subject who does not have cancer, said method comprising administering to the subject an immunogenic composition that includes:
    (a) a pharmaceutically acceptable excipient, and
    (b) an immunogen selected from:
        (i) an immunogenic peptide that contains an isolated senescent cell-associated antigen, wherein the senescent cell-associated antigen is p16;
        (ii) an immunogenic fragment that contains at least 20 contiguous amino acids of p16 protein; or
        (iii) a recombinant expression vector that is a viral vector comprising a polynucleotide that encodes said senescent cell-associated antigen or said immunogenic fragment.

9. The method of claim 8, wherein the immunogen comprises at least 60 contiguous amino acids of p16 protein.

10. The method of claim 8, wherein the immunogen comprises a full-length p16 protein.

11. The method of claim 8, wherein the immunogen is a fusion protein that contains said senescent cell-associated antigen or fragment, and at least 20 contiguous amino acids of another senescent cell-associated antigen.

12. The method of claim 11, wherein the other senescent cell-associated antigen is a galactosidase.

13. The method of claim 8, wherein the immunogenic composition comprises an immunological adjuvant.

14. A method for evoking an immune response specific for a senescent cell in a subject, comprising administering to the subject an immunogenic composition that includes:
    (a) a pharmaceutically acceptable excipient, and
    (b) an immunogen selected from:
        (i) an immunogenic peptide that contains an isolated senescent cell-associated antigen, wherein the senescent cell-associated antigen is p16;
        (ii) an immunogenic fragment that contains at least 20 contiguous amino acids of p16 protein; or
        (iii) a recombinant expression vector that is a viral vector comprising a polynucleotide that encodes said senescent cell-associated antigen or said immunogenic fragment; and
    monitoring senescence associated secretory phenotype (SASP) in the subject following administration of the immunogenic composition.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Linker sequence

<400> SEQUENCE: 1

```
Gly Gly Gly Gly Ser
1               5

<210> SEQ ID NO 2
<211> LENGTH: 11
<212> TYPE: PRT
<213> ORGANISM: Artificial Sequence
<220> FEATURE:
<223> OTHER INFORMATION: Linker sequence

<400> SEQUENCE: 2

Gly Gly Gly Gly Ser Gly Gly Gly Gly Gly Ser
1               5                   10
```